(12) United States Patent
Farady et al.

(10) Patent No.: US 11,208,399 B2
(45) Date of Patent: *Dec. 28, 2021

(54) NLRP3 INFLAMMASOME INHIBITORS

(71) Applicant: Novartis AG, Basel (CH)

(72) Inventors: Christopher Farady, Basel (CH); Nina Gommermann, Lörrach (DE); Philipp Janser, Basel (CH); Angela Mackay, Basel (CH); Henri Mattes, Michelbach le Bas (FR); Nichola Smith, Burlington, MA (US); Catherine Fooks Solovay, Arlington, MA (US); Nikolaus Johannes Stiefl, Lörrach (DE); Eric Vangrevelinghe, Saint-Louis (FR); Juraj Velcicky, Basel (CH); Anette von Matt, Biel-Benken (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,862

(22) Filed: May 15, 2020

(65) Prior Publication Data

US 2020/0361898 A1 Nov. 19, 2020

Related U.S. Application Data

(60) Provisional application No. 62/849,245, filed on May 17, 2019.

(51) Int. Cl.
*C07D 401/12* (2006.01)
*C07D 237/14* (2006.01)
*C07D 237/20* (2006.01)
*C07D 403/12* (2006.01)
*C07D 413/12* (2006.01)
*C07D 451/04* (2006.01)

(52) U.S. Cl.
CPC ......... *C07D 401/12* (2013.01); *C07D 237/14* (2013.01); *C07D 237/20* (2013.01); *C07D 403/12* (2013.01); *C07D 413/12* (2013.01); *C07D 451/04* (2013.01)

(58) Field of Classification Search
CPC .. C07D 401/12; C07D 237/14; C07D 237/20; C07D 403/12; C07D 413/12
See application file for complete search history.

(56) References Cited

U.S. PATENT DOCUMENTS

| 4,514,397 | A | 4/1985 | Biziere et al. |
| 5,276,036 | A | 1/1994 | Bourguignon et al. |
| 8,729,263 | B2 * | 5/2014 | Cheung ............... C07D 471/08 544/238 |

FOREIGN PATENT DOCUMENTS

| CN | 103965169 A | 8/2014 |
| EP | 0072299 B1 | 12/1986 |
| EP | 0382634 B1 | 4/1994 |
| EP | 0514277 B1 | 12/1994 |
| EP | 0429344 B1 | 9/1996 |
| EP | 3272739 B1 | 1/2018 |
| WO | 01/042241 A1 | 6/2001 |
| WO | 2006/004589 A2 | 1/2006 |
| WO | 2008/058064 A1 | 5/2008 |
| WO | 2010/048149 A2 | 4/2010 |
| WO | 2012/016133 A2 | 2/2012 |
| WO | 2012/080729 A2 | 6/2012 |
| WO | 2014/028459 A1 | 2/2014 |
| WO | 2016/022626 A1 | 2/2016 |
| WO | 2016/118638 A1 | 7/2016 |
| WO | 2016/128343 A1 | 8/2016 |
| WO | 2016/138114 A1 | 9/2016 |
| WO | 2017/100726 A1 | 6/2017 |
| WO | 2017/123991 A1 | 7/2017 |
| WO | 2018/232039 A1 | 12/2018 |
| WO | 2019/034690 A1 | 2/2019 |
| WO | 2019/075265 A1 | 4/2019 |
| WO | 2019/092170 A1 | 5/2019 |

(Continued)

OTHER PUBLICATIONS

Cheung et al., "Discovery of Small Molecule Splicing Moderators of Survival Motor Neuron-2 (SMN2) for the Treatment of Spinal Muscular Atrophy (SMA)," Journal of Medicinal Chemistry. 61(24):11021-11036.
Hallot et al., "Synthesis and activity of 6-aryl-3-(hydroxypolymethyleneamino)pyridazines in animal models of epilepsy," Journal of Medicinal Chemistry. 29(3):369-375.
Wermuth et al., "SR 46559 A and related aminopyridazines are potent muscarinic agonists with no cholinergic syndrome," Bioorganic & Medicinal Chemistry Letters. 2(8):833-839.
International Search Report and Written Opinion for PCT/IB2020/054613 dated Jul. 17, 2020 (15 pages).
U.S. Appl. No. 16/874,905.

*Primary Examiner* — Matthew P Coughlin
(74) *Attorney, Agent, or Firm* — Asha K. Nadipuram

(57) ABSTRACT

The present invention relates to novel pyridazin-3-yl phenol compounds of Formula (I):

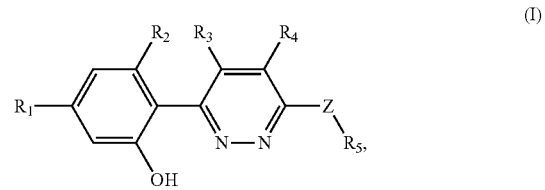

wherein $R^1$, $R^2$, $R^3$, $R^4$, $R^5$ and Z are defined herein, which inhibit NOD-like receptor protein 3 (NLRP3) inflammasome activity. The invention further relates to the processes for their preparation, pharmaceutical compositions and medicaments containing them, and their use in the treatment of diseases and disorders mediated by NLRP3.

19 Claims, No Drawings

(56) References Cited

FOREIGN PATENT DOCUMENTS

WO     2019/199972  A1    10/2019
WO     2019/207538  A1    10/2019

* cited by examiner

NLRP3 INFLAMMASOME INHIBITORS

CROSS REFERENCE TO RELATED APPLICATIONS

This application claims the benefit of U.S. Provisional Application 62/849,245, filed May 17, 2019, the entire content of which is incorporated by reference herein.

FIELD OF THE INVENTION

The present invention relates to novel pyridazin-3-yl phenol compounds that are useful as inhibitors of NOD-like receptor protein 3 (NLRP3) inflammasome pathway. The present invention also relates to processes for the preparation of said compounds, pharmaceutical compositions comprising said compounds, methods of using said compounds in the treatment of various diseases and disorders, and medicaments containing them, and their use in diseases and disorders mediated by NLRP3.

BACKGROUND OF THE INVENTION

The NOD-like receptor protein 3 (NLRP3) is a protein-coding gene: the protein belongs to the family of nucleotide-binding and oligomerization domain-like receptors (NLRs) and is also known as "pyrin domain-containing protein 3" (Inoue et al., Immunology, 2013, 139, 11-18). This gene encodes a protein containing a pyrin domain, a nucleotide-binding site domain (NBD), and a leucine-rich repeat (LRR) motif. In response to sterile inflammatory danger signals, NLRP3 interacts with an adapter protein, apoptosis-associated speck-like protein (ASC) and procaspase-1 to form the NLRP3 inflammasome. NLRP3 inflammasome activation then leads to the release of the inflammatory cytokines IL-1p (interleukin-1p) and IL-18 (interleukin-18), and when dysregulated, can drive pathology in a number of disease settings.

NLRP3 inflammasome activation normally requires two steps. The first step involves a priming signal in which pathogen activated molecular patterns (PAMPs) or danger-activated molecular patterns (DAMPs) are recognized by Toll-like receptors, leading to activation of nuclear factor kappa B (NF-κB)-mediated signaling, which in turn up-regulates transcription of inflammasome-related components, including inactive NLRP3 and proIL-1p (pro-interleukin-1p) (Bauernfeind et al *J. Immunol.* 2009, 183, 787-791; Franchi et al *Nat. Immunol.* 2012, 13, 325-332, Franchi et al *J. Immunol.* 2014, 193, 4214-4222). The second step is the oligomerization of NLRP3 and subsequent assembly of NLRP3, ASC, and procaspase-1 into an inflammasome complex. This triggers the transformation of procaspase-1 to caspase-1, and the production and secretion of mature IL-1p and IL-18 (Kim et al *J. Inflamm.* 2015, 12, 41; Ozaki et al *J. Inflamm. Res.* 2015, 8, 15-27; Rabeony et al. *Eur. J. Immunol.* 2015, 45, 2847-2857).

NLRP3 inflammasome activation has been linked to various inflammasome-related diseases/disorders, immune diseases, inflammatory diseases, auto-immune diseases and auto-inflammatory diseases, for example, autoinflammatory fever syndrome such as cryopyrin-associated periodic syndrome (CAPS) (Mortimer et al *Nature Immunol.* 2016, 17(10), 1176-1188); sickle cell disease; systemic lupus erythematosus (SLE); liver related diseases/disorders such as chronic liver disease, viral hepatitis, non-alcoholic steatohepatitis (NASH), alcoholic steatohepatitis, and alcoholic liver disease (Petrasek et al *J. Clin. Invest.* 2012, 122, 3476-89; Petrasek et al. *Nat. Rev. Gastroenterol. Hepatol.* 2015, 12, 387-400; Mridha et al *J. Hepatol.* 2017, 66, 1037-46); inflammatory arthritis related disorders, such as gout, pseudogout (chondrocalcinosis), osteoarthritis (Ridker et al *N. Engl. J. Med.* 2017, 377, 1119-31), and rheumatoid arthritis (Mathews et al *Ann. Rheum. Dis.* 2014, 73, 1202-10), acute or chronic arthropathy; kidney related diseases such as hyperoxaluria (Knauf et al. *Kidney Int.* 2013, 84, 895-901), lupus nephritis, hypertensive nephropathy (Krishnan et al *Br. J. Pharmacol.* 2016, 173, 752-65), hemodialysis related inflammation and diabetic nephropathy which is a kidney-related complication of diabetes (Type 1, Type 2 and mellitus diabetes), also called diabetic kidney disease (Shahzad et al *Kidney Int.* 2015, 87, 74-84). Emerging studies have revealed the involvement of the increased production of IL-1p and IL-18 by the NLRP3 inflammasome can contribute to the onset and progression of various diseases such as neuroinflammation-related disorders, e.g. brain infection, acute injury, multiple sclerosis, Alzheimer's disease, and neurodegenerative diseases (Shao et al. *Front. Pharmacol.* 2015, 6, 262); cardiovascular/metabolic disorders/diseases, e.g. cardiovascular risk reduction (CvRR), atherosclerosis, type I and type II diabetes and related complications (e.g. nephropathy, retinopathy), peripheral artery disease (PAD), acute heart failure and hypertension (Ridker et al *N. Engl. J. Med.* 2017, 377, 1119-31; Vandanmasgar et al *Nat. Med.* 2011, 17, 179-88; Hu et al *Proc. Natl. Acad. Sci.* 2015, 112, 11318-23; Antonopoulos et al *Curr. Opin. Pharmacol.* 2017, 39, 1-8; Toldo S et al *Nat. Rev. Cardiol.* 2018, 15, 203-214); wound healing and scar formation; inflammatory skin diseases, e.g. acne, hidradenitis suppurativa (Sweeney et al *Br. J. Dermatol.* 2015, 173, 1361), asthma, sarcoidosis, age-related macular degeneration; cancer related diseases/disorders, e.g. myeloproliferative neoplasms, leukemias, myelodysplastic syndromes (MDS), myelofibrosis, lung cancer, colon cancer (Ridker et al *Lancet* 2017, 390, 1833-42; Derangere et al *Cell. Death Differ.* 2014, 21, 1914-24, Gelfo et al *Oncotarget* 2016, 7, 72167-83, Baiorka et al *Blood* 2016, 128, 2960-75; Carey et al *Cell. Rep.* 2017, 18, 3204-18). Those diseases/disorders that are immune or inflammatory in nature usually are difficult to diagnose or treat efficiently. Most treatments include treating of the symptoms, slowing down the progression of the disease/disorder, change in lifestyle and surgery as a last resort (e.g., open heart surgery for advance forms of atherosclerosis). Recent studies have linked mitochondrial dysfunction and NLRP3 activation in neuroinflammation related diseases such as Parkinson's (Sarkar et al npj Parkinson's disease 2017, 3:30; Zhou et al *Nature,* 2011, 469, 221). One of the major problems associated with the mitochondrial modulators is their poor metabolic stability; thus there is a need for selective and stable inhibitors in neuroinflammation of this nature (Lee et al *Eur J. Org. Chem.* 2017, 141, 240).

Therefore, there is a need for inhibitors of the NLRP3 inflammasome pathway to provide new and/or alternative treatments for these inflammasome-related diseases/disorders and others such as autoinflammatory fever syndrome cryopyrin-associated periodic syndrome (e.g. CAPS), sickle cell disease, chronic liver disease, nonalcoholic steatohepatitis (NASH), gout, hyperoxaluria, pseudogout (chondrocalcinosis), Type I/Type II diabetes and related complications (e.g. nephropathy, retinopathy), neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

SUMMARY OF THE INVENTION

The invention provides compounds or pharmaceutically acceptable salts thereof, pharmaceutical compositions thereof, and combination thereof, which compounds inhibit the NLRP3 inflammasome pathway. The invention further provides methods of treating, or preventing, disease and/or disorders related to NLRP3, comprising administering to a subject in need thereof an effective amount of the compounds of the invention, or a pharmaceutically acceptable salt thereof.

Various embodiments of the invention are described herein.

Within certain aspects, provided herein is a compound of formula (I), or a pharmaceutically acceptable salt thereof:

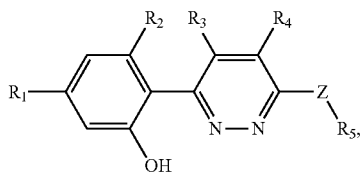

wherein:
$R^1$ is Cl, $CH_3$, —$OCF_3$, or $CF_3$;
$R^2$ is H, halo, $C_1$-$C_4$alkyl, or halo$C_1$-$C_4$alkyl;
$R^3$, $R^4$ are H, CN, $C_1$-$C_4$alkyl, or halo$C_1$-$C_4$alkyl;
Z is —O—, or —NH—$(CH_2)_n$—, wherein n is 0, 1, or 2;
$R^5$ is a mono or bicyclic heterocyclyl, optionally substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2$H; or
$R^5$ is an aryl or heteroaryl, optionally substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl optionally substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —NH($C_1$-$C_4$alkyl), and —N($C_1$-$C_4$alkyl)$_2$.

In another aspect, the invention provides a pharmaceutical composition comprising a therapeutically effective amount of a compound according to the definition of the compound of Formula (I), or subformulae thereof, as disclosed herein, or a pharmaceutically acceptable salt thereof, and one or more pharmaceutically acceptable carriers. The pharmaceutical composition is useful in the treatment of diseases and/or disorders related to the NLRP3 activity.

In another aspect, the invention provides a combination, in particular a pharmaceutical combination, comprising a therapeutically effective amount of a compound according to the definition of compound of formula (I), or subformulae thereof, as disclosed herein, or a pharmaceutically acceptable salt thereof, and one or more therapeutic agents.

In another aspect, the invention provides a combination, in particular a pharmaceutical combination, as disclosed herein, for use as a medicament.

In another aspect, the invention provides a compound of formula (I), or subformulae thereof, as disclosed herein, or a pharmaceutically acceptable salt thereof, for use in the treatment of a disease or disorder in which the NLRP3 signaling contributes to the pathology, and/or symptoms, and/or progression, of said disease or disorder.

In another aspect, the invention provides a method of treating a disease or disorder in which the NLRP3 signaling contributes to the pathology, and/or symptoms, and/or progression, of said disease or disorder, comprising administering a therapeutically effective amount of a compound of formula (I), or subformulae thereof, as disclosed herein, or a pharmaceutically acceptable salt thereof.

In another aspect, the invention provides a method of inhibiting the NLRP3 inflammasome activity in a subject in need thereof, the method comprises administering to the subject in need thereof a therapeutically effective amount of a compound of formula (I), or subformulae thereof, as disclosed herein, or a pharmaceutically acceptable salt thereof.

Another aspect of the invention, relates to the use of a compound of formula (I), or subformulae thereof, as disclosed herein, or a pharmaceutically acceptable salt thereof, as a medicament.

Another aspect of the invention, relates to a compound of formula (I), or subformulae thereof, as disclosed herein, or a pharmaceutically acceptable salt thereof, for use as a medicament.

Another aspect of the invention, also provides a compound of formula (I), or subformulae thereof, as disclosed herein, or a pharmaceutically acceptable salt thereof, for use in the treatment of a disease or disorder selected from inflammasome-related disease/disorders, immune diseases, inflammatory diseases, auto-immune diseases, or auto-inflammatory diseases.

DETAILED DESCRIPTION OF THE INVENTION

The invention therefore provides a compound of Formula (I):

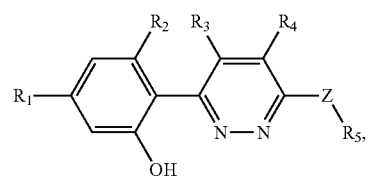

wherein
$R^1$ is Cl, $CH_3$, —$OCF_3$, or $CF_3$;
$R^2$ is H, halo, $C_1$-$C_4$alkyl, or halo$C_1$-$C_4$alkyl;
$R^3$, $R^4$ are H, CN, $C_1$-$C_4$alkyl, or halo$C_1$-$C_4$alkyl;
Z is —O—, or —NH—$(CH_2)_n$—, wherein n is 0, 1, or 2;
$R^5$ is a mono or bicyclic heterocyclyl, optionally substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2$H; or
$R^5$ is an aryl or heteroaryl, optionally substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl optionally substituted with 1 to 3 substituents independently selected from $C_1$-$C_4$alkyl, halo, halo$C_1$-$C_4$alkyl, and —OH; or $R^5$ is $C_2$-$C_6$alkyl substituted with 1 or more substituents independently selected from —OH, $C_1$-$C_4$alkoxy, halo, —$NH_2$, —$NH(C_1$-$C_4$alkyl), and —$N(C_1$-$C_4$alkyl)$_2$.

Definitions

For purpose of interpreting this specification, the following definitions will apply unless specified otherwise and when appropriate, terms used in the singular will also include the plural and vice versa.

It must be noted that as used herein and in the appended claims, the singular forms "a", "an" and "the", and similar terms, used in the context of the present invention (especially in the context of the claims) are to be construed to cover both the singular and the plural referents unless the context clearly dictates otherwise, or clearly contradicted by the context. Thus, for example, reference to "the compound" includes reference to one or more compounds; and so forth.

As used herein, the term "$C_2$-$C_6$alkyl" refers to a straight or branched hydrocarbon chain radical consisting solely of carbon and hydrogen atoms, containing no unsaturation, having from two to six carbon atoms, and which is attached to the rest of the molecule by a single bond. The "$C_2$-$C_6$alkyl" as defined herein, is optionally substituted with 1 or more substituents, preferably with 1 to 13 substituents, more preferably with 1 to 8 substituents. More preferably, up to 7 seven substituents. The term "$C_1$-$C_4$alkyl" is to be construed accordingly. Examples of $C_2$-$C_6$alkyl include, but are not limited to, ethyl, n-propyl, 1-methylethyl (iso-propyl), n-butyl, n-pentyl and 1,1-dimethylethyl (t-butyl).

As used herein, the term "halo$C_1$-$C_4$alkyl" or "halogen$C_1$-$C_4$alkyl" refers to a $C_1$-$C_4$alkyl radical, as defined above, substituted by one or more halo radicals, as defined above.

Examples of halogen$C_1$-$C_4$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "$C_1$-$C_4$alkoxy" refers to a radical of the formula —$OR_a$ where $R_a$ is a $C_1$-$C_4$alkyl radical as generally defined above. Examples of "$C_1$-$C_4$alkoxy" include, but are not limited to, methoxy, ethoxy, propoxy, isopropoxy, butoxy, and isobutoxy.

As used herein, the term "hydroxy$C_1$-$C_4$alkyl" refers to a $C_1$-$C_4$alkyl radical wherein one of the hydrogen atoms of the $C_1$-$C_4$alkyl radical is replaced by OH. Examples of hydroxy$C_1$-$C_4$alkyl include, but are not limited to, hydroxymethyl, 2-hydroxy-ethyl, 2-hydroxy-propyl, 3-hydroxy-propyl and 4-hydroxy-butyl.

As used herein, the term "Halogen" or "Halo" refers to bromo, chloro, fluoro, or iodo.

As used herein, the term "heterocyclyl" or "heterocyclic" refers to a stable 5- or 6-membered non-aromatic monocyclic ring, or a bicyclic ring, or a polycyclic ring radical; which has 3 to 24, preferably 4 to 16, most preferably 5 to 10 ring atoms; wherein one or more, preferably one to four, especially one or two ring atoms are a heteroatom selected from, for example, oxygen, sulphur, and nitrogen (the remaining ring atoms therefore being carbon). The term heterocyclyl excludes heteroaryl. The heterocyclic group can be attached to the rest of the molecule through a heteroatom, selected from, for example, oxygen, sulfur, nitrogen, or a carbon atom. The heterocyclyl can include, for example, fused or bridged rings, as well as spirocyclic rings. For example, the term "heterocyclyl" can refer to a 5-7 monocyclic ring containing 1, 2, or 3 heteroatoms, selected from oxygen, nitrogen and sulfur. Examples of mono heterocyclyl include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, oxapinyl, oxaazepanyl, oxathianyl, thiepanyl, azepanyl, dioxepanyl, and diazepanyl. Preferably, the mono heterocyclyl is morpholino, pyrrolidine or piperidinyl. Examples of bicyclic heterocyclyl include, for example, azabicyclooctanyl, or octahydroindolizinyl. According to the present invention, the term "heterocyclyl" substituted with an "OH" substituent also includes a "heterocyclyl" wherein the heteroatom, e.g. N or S, is oxidized, to obtain, for example, a heterocyclyl N-oxide, heterocyclyl S-oxide, or a heterocyclyl S-dioxide. Examples of heterocyclyl N-oxide, include, pyperidinyl-N-oxide. 1-methylpyrrolidine 1-oxide. Examples of heterocyclyl S-oxide or heterocyclyl S-dioxide, include, tetrahydro-2H-thiopyran-1-oxide, tetrahydro-2H-thiopyran-1,1-dioxide, and tetrahydrothiophene-1-oxide.

As used herein, the term "heteroaryl" refers to a 5- or 6-membered aromatic monocyclic ring radical, which comprises 1, 2, 3 or 4 heteroatoms individually selected from nitrogen, oxygen and sulfur. The heteroaryl radical may be bonded via a carbon atom or heteroatom.

Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "$C_3$-$C_6$cycloalkyl" refers to a stable monocyclic, bicyclic or tricyclic saturated hydrocarbon radical consisting solely of carbon and hydrogen atoms, having from three to ten carbon atoms. The term bicyclic cycloalkyl also includes spiro bicyclic cycloalkyl. Examples of monocyclic $C_3$-$C_6$cycloalkyl include, but are not limited to, cyclopropyl, cyclobutyl, cyclopentyl, and cyclohexyl. Examples of bicyclic $C_3$-$C_{10}$cycloalkyl include but are not limited to, bicyclo[1.1.1]pentane.

As used herein, the term "aryl" refers to an aromatic hydrocarbon group having 6-20 carbon atoms in the ring portion. Typically, aryl is monocyclic, bicyclic or tricyclic aryl having 6-20 carbon atoms. In a preferred embodiment, aryl is phenyl.

Unless specified otherwise, the term "compounds of the present invention" refers to compounds of formula (I), and subformulae thereof (such as Compound of formula (II), Compound of formula (II) or Compound of formula (III-A), as described herein), and salts thereof, as well as all stereoisomers (including diastereoisomers and enantiomers), rotamers, tautomers and isotopically labeled compounds (including deuterium substitutions). The term "compounds of the (present) invention" or "a compound of the (present) invention" refers to a compound as defined in any one of embodiments mentioned below.

Various embodiments of the invention are described herein, it will be recognized that features specified in each embodiment may be combined with other specified features to provide further embodiments of the present invention.

In embodiment 1, the invention provides a compound of formula (I), or a pharmaceutically acceptable salt thereof, as described above.

In embodiment 2, the invention provides a compound of formula (I), or a pharmaceutically acceptable salt thereof, according to embodiment 1, having a formula (II):

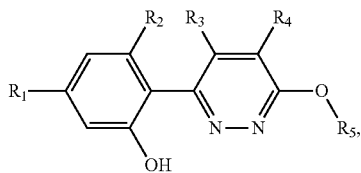
(II)

wherein R¹, R², R³, R⁴, and R⁵ are as defined in embodiment 1.

In embodiment 3, the invention provides a compound of formula (I), or a pharmaceutically acceptable salt thereof, according to embodiment 1, having a formula (II):

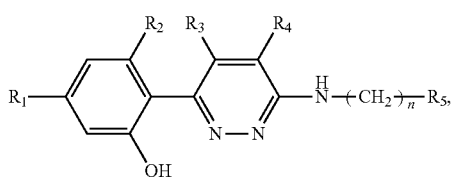
(III)

wherein n is 0, 1, or 2; and R¹, R², R³, R⁴, and R⁵ are as defined in embodiment 1.

In embodiment 3a, and according to embodiment 3, the invention provides a compound of formula (II), or a pharmaceutically acceptable salt thereof, having the formula (III-A):

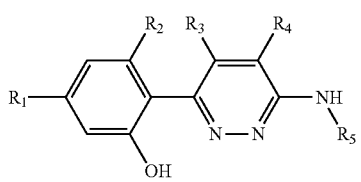
(III-A)

wherein R¹, R², R³, R⁴, and R⁵ are as defined in embodiment 1.

In embodiment 4, the invention provides a compound of any one of the formula (I), (II), (III), and (III-A), or a pharmaceutically acceptable salt thereof, according to embodiment 1, 2, 3, or 3a, wherein R⁵ is a mono or bicyclic heterocyclyl, optionally substituted with 1 to 2 substituents independently selected from $C_1$-$C_4$alkyl, halo$C_1$-$C_4$alkyl, hydroxy$C_1$-$C_4$alkyl, —OH, halo, oxo, and —CO₂H.

In embodiment 5, the invention provides a compound of any one of the formula (I), (II), (III), and (III-A), or a pharmaceutically acceptable salt thereof, according to embodiment 4, wherein R⁵ is selected from the following:

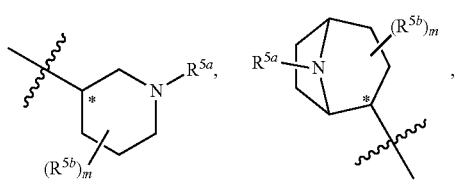

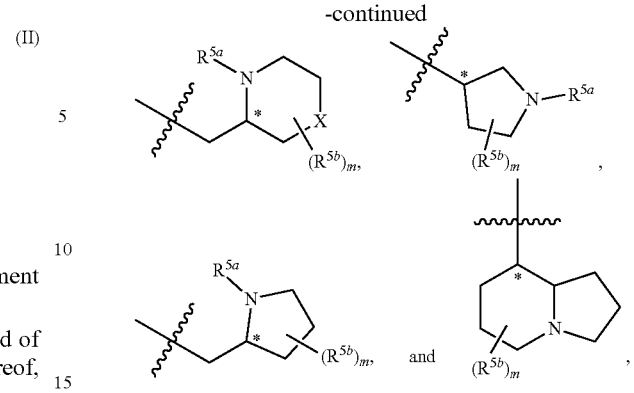

wherein $R^{5a}$ is independently selected from $C_1$-$C_4$alkyl, hydroxy$C_1$-$C_4$alkyl, and H; and $R^{5b}$ is independently selected from —OH, hydroxy$C_1$-$C_4$alkyl, H, halo, oxo, halo$C_1$-$C_4$alkyl, and —CO₂H; X is O or CH₂; and m is 0, or 1.

In embodiment 5a, and according to embodiment 5, the invention provides a compound of any one of formula (I), (II), (III), and (III-A), or a pharmaceutically acceptable salt thereof, wherein R⁵ is selected from the following:

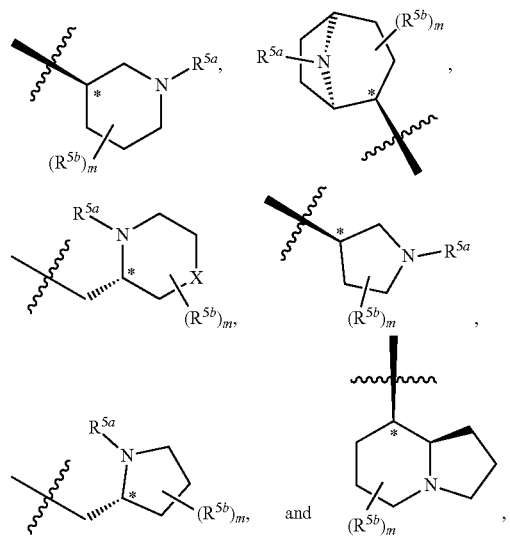

wherein $R^{5a}$ is independently selected from $C_1$-$C_4$alkyl, hydroxy$C_1$-$C_4$alky, and H; and $R^{5b}$ is independently selected from —OH, $C_1$-$C_4$alkyl, hydroxy$C_1$-$C_4$alkyl, H, halo, oxo, halo$C_1$-$C_4$alkyl, and —CO₂H; X is O or CH₂; and m is 0, or 1.

In embodiment 5b, and according to embodiment 5, and 5b, the invention provides a compound of any one of formula (I), (II), (III), and (III-A), or a pharmaceutically acceptable salt thereof, wherein R⁵ is as described herein above and the stereochemistry at the carbon labelled "*" is (R) or (S). Preferably, when Z is —NH—(CH₂)$_n$— with n=1 or 2, the stereochemistry at the carbon labelled "*" is (S). Preferably, Z is —O— or —NH—(CH₂)$_n$— with n=0, the stereochemistry at the carbon labelled "*" is (R).

In embodiment 5c, and according to embodiment 5, 5a, and 5b, the invention provides a compound of any one of the formula (I), (II), (III), and (III-A), or a pharmaceutically acceptable salt thereof, wherein R⁵ is preferably selected from the following structure:

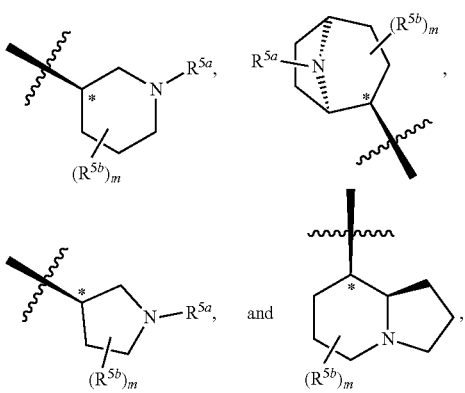

wherein $R^{5a}$ is independently selected from $C_1$-$C_4$alkyl, hydroxy$C_1$-$C_4$alkyl, and H; and $R^{5b}$ is independently selected from —OH, $C_1$-$C_4$alkyl, hydroxy$C_1$-$C_4$alkyl, H, halo, oxo, halo$C_1$-$C_4$alkyl, and —$CO_2$H; and m is 0, or 1.

In embodiment 5d, and according to embodiments 5, 5a, 5b, and 5c, the invention provides a compound of any one of the formula (I), (II), (III), and (III-A), or a pharmaceutically acceptable salt thereof, wherein $R^5$ is preferably selected from the following structure:

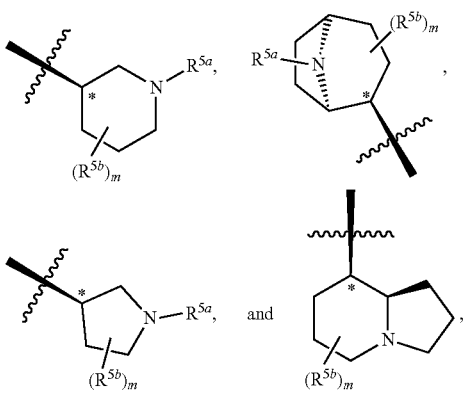

wherein $R^{5a}$ is independently selected from $C_1$-$C_4$alkyl, hydroxy$C_1$-$C_4$alkyl, and H; and $R^{5b}$ is independently selected from —OH, $C_1$-$C_4$alkyl, hydroxy$C_1$-$C_4$alkyl, H, halo, oxo, halo$C_1$-$C_4$alkyl, and —$CO_2$H; and m is 0, or 1.

In embodiment 5e, and according to embodiments 5, 5a, 5b, 5c, and 5d, the invention provides a compound of any one of the formula (I), (II), (III), and (III-A), or a pharmaceutically acceptable salt thereof, wherein $R^5$ is preferably the following structure:

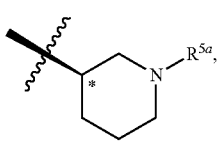

wherein $R^{5a}$ is independently selected from $C_1$-$C_4$alkyl, hydroxy$C_1$-$C_4$alkyl, and H.

In embodiment 6, the invention provides a compound of any one of the formula (I), (II), (III), and (III-A), or a pharmaceutically acceptable salt thereof, according to embodiments 1, 2, 3 or 3a, wherein $R^5$ is an aryl or heteroaryl, optionally substituted with 1 to 2 substituents independently selected from halo, halo$C_1$-$C_4$alkyl, $C_1$-$C_4$alkyl, and —$SO_2NH_2$.

In embodiment 6a, and according to embodiment 6, the invention provides a compound of any one of the formula (I), (II), (III), and (III-A), or a pharmaceutically acceptable salt thereof, wherein $R^5$ is preferably selected from the following structure:

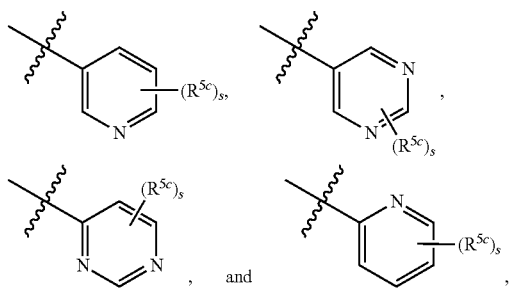

wherein $R^{5c}$ is independently selected from H, $C_1$-$C_4$alkyl, and —$SO_2NH_2$; and s is 0, 1 or 2.

In embodiment 6b, and according to embodiment 6, the invention provides a compound of any one of the formula (I), (II), (III), and (III-A), or a pharmaceutically acceptable salt thereof, wherein $R^5$ is preferably selected from the following structure:

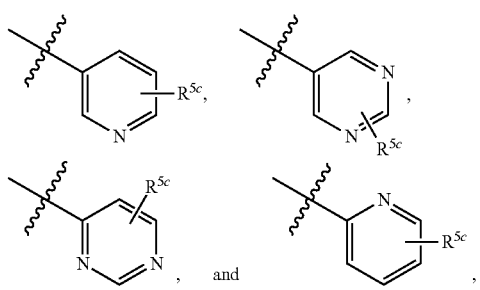

wherein $R^{5c}$ is independently selected from H, $C_1$-$C_4$alkyl, and —$SO_2NH_2$.

In embodiment 6c, and according to embodiments 6, and 6b, the invention provides a compound of any one of the formula (I), (II), (III), and (III-A), or a pharmaceutically acceptable salt thereof, wherein $R^5$ is preferably selected from the following structure:

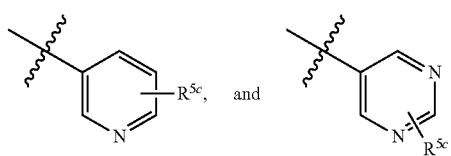

wherein $R^{5c}$ is independently selected from H, and $C_1$-$C_4$alkyl.

In embodiment 7, the invention provides a compound of any one of the formula (I), (II), (III), and (III-A), or a pharmaceutically acceptable salt thereof, according to embodiment 1, 2, 3 or 3a, wherein $R^5$ is $C_3$-$C_6$cycloalkyl optionally substituted with 1 to 3 substituents independently selected from $C_1$-$C_4$alkyl, halo, halo$C_1$-$C_4$alkyl, and —OH.

In embodiment 7a, and according to embodiment 7, the invention provides a compound of any one of the formula (I), (II), (III), and (III-A), or a pharmaceutically acceptable salt thereof, wherein $R^5$ is preferably cyclopropyl, cyclobutyl, cyclopentyl, or cyclohexyl optionally substituted with 1 to 3 substituents independently selected from $C_1$-$C_4$alkyl, halo, halo$C_1$-$C_4$alkyl, and —OH.

In embodiment 7b, and according to embodiment 7, and 7a, the invention provides a compound of any one of the formula (I), (II), (III), and (III-A), or a pharmaceutically acceptable salt thereof, wherein $R^5$ is preferably selected from the following structure:

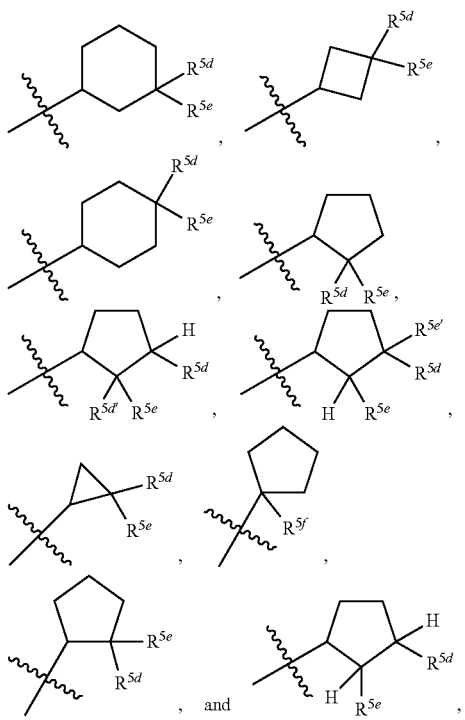

wherein $R^{5e}$, $R^{5e'}$, $R^{5d}$, $R^{5d'}$ and $R^{5f}$ are independently selected from H, $C_1$-$C_4$alkyl, halo, halo$C_1$-$C_4$alkyl, and —OH.

In embodiment 7c, and according to embodiment 7, 7a and 7b, the invention provides a compound of any one of the formula (I), (II), (III), and (III-A), or a pharmaceutically acceptable salt thereof, wherein $R^5$ is preferably selected from the following structure:

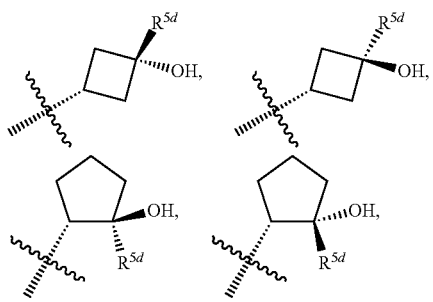

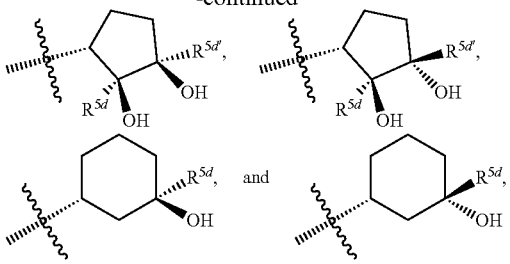

wherein $R^{5d}$, and $R^{5d'}$ are independently selected from H, halo, halo$C_1$-$C_4$alkyl, and $C_1$-$C_4$alkyl.

In embodiment 7d, and according to embodiment 7, 7a, 7b and 7c, the invention provides a compound of any one of the formula (I), (II), (III), and (III-A), or a pharmaceutically acceptable salt thereof, wherein $R^5$ is preferably selected from the following structure:

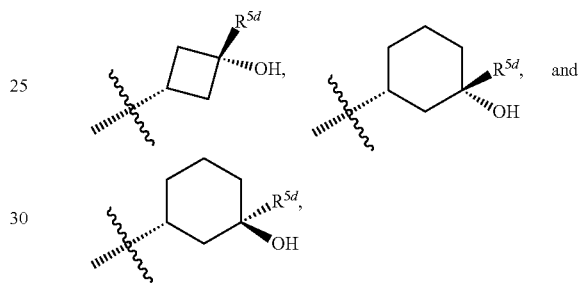

wherein $R^{5d}$, and $R^{5d'}$ are independently selected from H, halo, halo$C_1$-$C_4$alkyl, and $C_1$-$C_4$alkyl.

In embodiment 8, the invention provides a compound of any one of the formula (I), (II), (III), and (III-A), or a pharmaceutically acceptable salt thereof, according to embodiments 1, 2, or 3, wherein $R^5$ is $C_2$-$C_6$alkyl substituted with 1 or more substituents independently selected from —OH, $C_1$-$C_4$alkoxy, halo, —NH$_2$, —NH($C_1$-$C_4$alkyl), and —N($C_1$-$C_4$alkyl)$_2$.

In embodiment 8a, and according to embodiment 8, the invention provides a compound of any one of the formula (I), (II), (III), and (III-A), or a pharmaceutically acceptable salt thereof, wherein $R^5$ is preferably selected from the following structures:

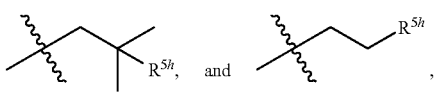

wherein $R^{5h}$ is selected from —NH$_2$, —OH, —NH($C_1$-$C_4$alkyl), and —N($C_1$-$C_4$alkyl)$_2$.

In embodiment 9, the invention provides a compound of any one of the formula (I), (II), (III), and (III-A), or a pharmaceutically acceptable salt thereof, according to any one of embodiments 1, 2, 3, 3a, 4, 5, 5a-5e, 6, 6a-6c, 7, 7a-7d, 8, and 8a, wherein at least one of $R^2$ and $R^3$ is H.

In embodiment 9a, and according to embodiment 9, the invention provides a compound of any one of the formula (I), (II), (III), and (III-A), or a pharmaceutically acceptable salt thereof, wherein $R^2$ is halo, $C_1$-$C_4$alkyl, or halo$C_1$-$C_4$alkyl; and $R^3$ is H.

In embodiment 9b, and according to embodiment 9, the invention provides a compound of any one of the formula (I), (II), (III), and (III-A), or a pharmaceutically acceptable salt thereof, wherein $R^2$ is H; and $R^3$ is CN, $C_1$-$C_4$alkyl, or halo$C_1$-$C_4$alkyl.

In embodiment 10, the invention provides a compound of any one of the formula (I), (II), (III), and (III-A), or a pharmaceutically acceptable salt thereof, according to embodiments 1 to 9, wherein $R^1$ is —OCF$_3$, or —CF$_3$.

In embodiment 10a, and according to embodiment 10, the invention provides a compound of any one of the formula (I), (II), (III), and (III-A), or a pharmaceutically acceptable salt thereof, wherein $R^1$ is CF$_3$.

In embodiment 11, the invention provides a compound of any one of the formula (I), (II), (III) and (III-A), or a pharmaceutically acceptable salt thereof, according to embodiment 1, wherein the compound is selected from:

2-(6-((1-Ethylpiperidin-3-yl)amino)pyridazin-3-yl)-3-methyl-5-(trifluoromethyl)phenol;
(S)-2-(6-((1-Ethylpiperidin-3-yl)amino)pyridazin-3-yl)-3-methyl-5-(trifluoromethyl)phenol;
(R)-2-(6-((1-Ethylpiperidin-3-yl)amino)pyridazin-3-yl)-3-methyl-5-(trifluoromethyl)phenol;
2-(6-((3-Hydroxy-3-methylcyclobutyl)amino)pyridazin-3-yl)-3-methyl-5-(trifluoromethyl)phenol;
2-(6-(((trans)-3-Hydroxy-3-methylcyclobutyl)amino) pyridazin-3-yl)-3-methyl-5-(trifluoromethyl) phenol;
2-(6-(((cis)-3-Hydroxy-3-methylcyclobutyl)amino) pyridazin-3-yl)-3-methyl-5-(trifluoromethyl) phenol;
2-(6-((3-Hydroxycyclohexyl)amino)pyridazin-3-yl)-3-methyl-5-(trifluoromethyl)phenol;
2-(6-(((1S,3S)-3-Hydroxycyclohexyl)amino)pyridazin-3-yl)-3-methyl-5-(trifluoromethyl)phenol;
2-(6-(((1S,3R)-3-Hydroxycyclohexyl)amino)pyridazin-3-yl)-3-methyl-5-(trifluoromethyl)phenol;
2-(6-(((1R,3R)-3-Hydroxycyclohexyl)amino)pyridazin-3-yl)-3-methyl-5-(trifluoromethyl)phenol;
2-(6-(((1R,3S)-3-Hydroxycyclohexyl)amino)pyridazin-3-yl)-3-methyl-5-(trifluoromethyl)phenol;
2-(4-Methyl-6-((1-methylpiperidin-3-yl)amino)pyridazin-3-yl)-5-(trifluoromethyl)phenol;
(S)-2-(4-Methyl-6-((1-methylpiperidin-3-yl)amino) pyridazin-3-yl)-5-(trifluoromethyl)phenol;
(R)-2-(4-Methyl-6-((1-methylpiperidin-3-yl)amino) pyridazin-3-yl)-5-(trifluoromethyl)phenol;
3-Methyl-2-(5-methyl-6-((1-methylpiperidin-3-yl)amino) pyridazin-3-yl)-5-(trifluoromethyl) phenol;
(S)-3-Methyl-2-(5-methyl-6-((1-methylpiperidin-3-yl) amino)pyridazin-3-yl)-5-(trifluoromethyl) phenol;
(R)-3-Methyl-2-(5-methyl-6-((1-methylpiperidin-3-yl) amino)pyridazin-3-yl)-5-(trifluoromethyl) phenol;
2-(6-((1-(2-Hydroxyethyl)piperidin-3-yl)amino)pyridazin-3-yl)-3-methyl-5-(trifluoromethyl) phenol;
(S)-2-(6-((1-(2-Hydroxyethyl)piperidin-3-yl)amino) pyridazin-3-yl)-3-methyl-5-(trifluoromethyl) phenol;
(R)-2-(6-((1-(2-Hydroxyethyl)piperidin-3-yl)amino) pyridazin-3-yl)-3-methyl-5-(trifluoromethyl) phenol;
2-(6-((1-Isopropylpiperidin-3-yl)amino)pyridazin-3-yl)-3-methyl-5-(trifluoromethyl)phenol;
2-(6-(((1-Ethylpyrrolidin-2-yl)methyl)amino)pyridazin-3-yl)-3-methyl-5-(trifluoromethyl)phenol;
(R)-2-(6-(((1-Ethylpyrrolidin-2-yl)methyl)amino)pyridazin-3-yl)-3-methyl-5-(trifluoromethyl) phenol;
(S)-2-(6-(((1-Ethylpyrrolidin-2-yl)methyl)amino)pyridazin-3-yl)-3-methyl-5-(trifluoromethyl) phenol;
2-(6-((5,5-Difluoropiperidin-3-yl)amino)pyridazin-3-yl)-3-methyl-5-(trifluoromethyl)phenol;
3-Methyl-2-(6-((3,3,3-trifluoro-2-hydroxy-2-(trifluoromethyl)propyl)amino)pyridazin-3-yl)-5-(trifluoromethyl) phenol;
3-((1-Ethylpiperidin-3-yl)amino)-6-(2-hydroxy-6-methyl-4-(trifluoromethyl)phenyl) pyridazine-4-carbonitrile;
(S)-3-((1-Ethylpiperidin-3-yl)amino)-6-(2-hydroxy-6-methyl-4-(trifluoromethyl)phenyl) pyridazine-4-carbonitrile;
(R)-3-((1-Ethylpiperidin-3-yl)amino)-6-(2-hydroxy-6-methyl-4-(trifluoromethyl)phenyl) pyridazine-4-carbonitrile;
3-Methyl-2-(6-((1-methylpiperidin-3-yl)amino)pyridazin-3-yl)-5-(trifluoromethyl)phenol;
(S)-3-Methyl-2-(6-((1-methylpiperidin-3-yl)amino) pyridazin-3-yl)-5-(trifluoromethyl)phenol;
(R)-3-Methyl-2-(6-((1-methylpiperidin-3-yl)amino) pyridazin-3-yl)-5-(trifluoromethyl)phenol;
2-(6-((1-(2-Hydroxyethyl)piperidin-3-yl)amino)-5-methylpyridazin-3-yl)-3-methyl-5-(trifluoromethyl)phenol;
(S)-2-(6-((1-(2-Hydroxyethyl)piperidin-3-yl)amino)-5-methylpyridazin-3-yl)-3-methyl-5-(trifluoromethyl)phenol;
(R)-2-(6-((1-(2-Hydroxyethyl)piperidin-3-yl)amino)-5-methylpyridazin-3-yl)-3-methyl-5-(trifluoromethyl)phenol;
3-Methyl-2-(6-((pyrrolidin-2-ylmethyl)amino)pyridazin-3-yl)-5-(trifluoromethyl)phenol;
(S)-3-Methyl-2-(6-((pyrrolidin-2-ylmethyl)amino) pyridazin-3-yl)-5-(trifluoromethyl)phenol;
(R)-3-Methyl-2-(6-((pyrrolidin-2-ylmethyl)amino) pyridazin-3-yl)-5-(trifluoromethyl)phenol;
2-(6-((2-Hydroxy-2-methylpropyl)amino)pyridazin-3-yl)-3-methyl-5-(trifluoromethyl)phenol;
2-(6-((2-(Dimethylamino)-2-methylpropyl)amino) pyridazin-3-yl)-3-methyl-5-(trifluoromethyl) phenol;
(R)-3-Methyl-2-(6-((1-methylpyrrolidin-3-yl)amino) pyridazin-3-yl)-5-(trifluoromethyl)phenol;
3-Methyl-2-(6-((1-methylpyrrolidin-3-yl)amino)pyridazin-3-yl)-5-(trifluoromethyl)phenol; (S)-3-Methyl-2-(6-((1-methylpyrrolidin-3-yl)amino)pyridazin-3-yl)-5-(trifluoromethyl)phenol;
2-(6-(2-Hydroxy-2-methylpropoxy)pyridazin-3-yl)-3-methyl-5-(trifluoromethyl)phenol;
(R)-3-Methyl-2-(6-((piperidin-2-ylmethyl)amino)pyridazin-3-yl)-5-(trifluoromethyl)phenol;
3-Methyl-2-(6-((piperidin-2-ylmethyl)amino)pyridazin-3-yl)-5-(trifluoromethyl)phenol;
(S)-3-Methyl-2-(6-((piperidin-2-ylmethyl)amino)pyridazin-3-yl)-5-(trifluoromethyl)phenol;
(S)-2-(6-(((4,4-Difluoropyrrolidin-2-yl)methyl)amino) pyridazin-3-yl)-3-methyl-5-(trifluoromethyl) phenol;
2-(6-(((4,4-Difluoropyrrolidin-2-yl)methyl)amino) pyridazin-3-yl)-3-methyl-5-(trifluoromethyl) phenol;
(R)-2-(6-(((4,4-Difluoropyrrolidin-2-yl)methyl)amino) pyridazin-3-yl)-3-methyl-5-(trifluoromethyl) phenol;
2-(6-((2-Hydroxycyclopentyl)amino)pyridazin-3-yl)-3-methyl-5-(trifluoromethyl)phenol;
(cis)-2-(6-((2-Hydroxycyclopentyl)amino)pyridazin-3-yl)-3-methyl-5-(trifluoromethyl)phenol;
(trans)-2-(6-((2-Hydroxycyclopentyl)amino)pyridazin-3-yl)-3-methyl-5-(trifluoromethyl)phenol;
3,5-Dichloro-2-(6-((2-hydroxyethyl)amino)pyridazin-3-yl) phenol;
2-(6-((2-Hydroxyethyl)amino)-5-(trifluoromethyl) pyridazin-3-yl)-3-methyl-5-(trifluoromethyl) phenol;
3,5-Dichloro-2-(6-((2,2,2-trifluoroethyl)amino)pyridazin-3-yl)phenol;

3-Methyl-2-(6-((pyridin-2-ylmethyl)amino)pyridazin-3-yl)-5-(trifluoromethyl)phenol;
2-(6-((2-Amino-2-methylpropyl)amino)pyridazin-3-yl)-3-methyl-5-(trifluoromethyl)phenol;
3-Chloro-2-(6-((2-hydroxy-2-methylpropyl)amino) pyridazin-3-yl)-5-(trifluoromethyl)phenol;
3-Chloro-2-(6-((cis-hydroxycyclobutyl)amino)pyridazin-3-yl)-5-(trifluoromethyl)phenol;
3-Chloro-2-(6-((3-hydroxycyclobutyl)amino)pyridazin-3-yl)-5-(trifluoromethyl)phenol;
3-Chloro-2-(6-((trans-3-hydroxycyclobutyl)amino) pyridazin-3-yl)-5-(trifluoromethyl)phenol;
3-Methyl-2-(6-(piperidin-3-ylamino)pyridazin-3-yl)-5-(trifluoromethyl)phenol;
(R)-3-Methyl-2-(6-(piperidin-3-ylamino)pyridazin-3-yl)-5-(trifluoromethyl)phenol;
(S)-3-Methyl-2-(6-(piperidin-3-ylamino)pyridazin-3-yl)-5-(trifluoromethyl)phenol;
3-Chloro-2-(6-(((2-methylpyridin-3-yl)methyl)amino) pyridazin-3-yl)-5-(trifluoromethyl)phenol;
5-Chloro-2-(6-(((2-methylpyridin-3-yl)methyl)amino) pyridazin-3-yl)-3-(trifluoromethyl)phenol;
3-Methyl-2-(6-((1-methyl piperidin-3-yl)amino)pyridazin-3-yl)-5-(trifluoromethyl)phenol;
(R)-3-Methyl-2-(6-((1-methyl piperidin-3-yl)amino) pyridazin-3-yl)-5-(trifluoromethyl)phenol;
(S)-3-Methyl-2-(6-((1-methyl piperidin-3-yl)amino) pyridazin-3-yl)-5-(trifluoromethyl)phenol;
3-Chloro-2-(6-((2-hydroxyethyl)amino)pyridazin-3-yl)-5-(trifluoromethyl)phenol;
5-Chloro-3-fluoro-2-(6-((1-methylpiperidin-3-yl)amino) pyridazin-3-yl)phenol;
10   (S)-5-Chloro-3-fluoro-2-(6-(((1-methylpiperidin-3-yl) amino) pyridazin-3-yl)phenol;
(R)-5-Chloro-3-fluoro-2-(6-(((1-methylpiperidin-3-yl) amino) pyridazin-3-yl)phenol;
5-Chloro-3-fluoro-2-(6-((1-methylpiperidin-3-yl)amino) pyridazin-3-yl)phenolTFA-salt
(S)-5-Chloro-3-fluoro-2-(6-(((1-methylpiperidin-3-yl) amino) pyridazin-3-yl)phenol TFA-salt;
(R)-5-Chloro-3-fluoro-2-(6-(((1-methylpiperidin-3-yl) amino) pyridazin-3-yl)phenol TFA-salt;
2-(6-((1-Methylpiperidin-3-yl)amino)pyridazin-3-yl)-3,5-bis(trifluoromethyl)phenol;
(S)-2-(6-((1-Methylpiperidin-3-yl)amino)pyridazin-3-yl)-3,5-bis(trifluoromethyl)phenol;
(R)-2-(6-((1-Methylpiperidin-3-yl)amino)pyridazin-3-yl)-3,5-bis(trifluoromethyl)phenol;
2-(4,5-Dimethyl-6-((1-methylpiperidin-3-yl)amino) pyridazin-3-yl)-3-methyl-5-(trifluoro methyl)phenol;
2-(4,5-Dimethyl-6-(((S)-1-methylpiperidin-3-yl)amino) pyridazin-3-yl)-3-methyl-5-(trifluoro methyl)phenol;
2-(4,5-Dimethyl-6-(((R)-1-methylpiperidin-3-yl)amino) pyridazin-3-yl)-3-methyl-5-(trifluoro methyl)phenol;
2-(4,5-Dimethyl-6-((1-methylpiperidin-3-yl)amino) pyridazin-3-yl)-3-methyl-5-(trifluoro methyl)phenol TFA-salt;
2-(4,5-Dimethyl-6-(((S)-1-methylpiperidin-3-yl)amino) pyridazin-3-yl)-3-methyl-5-(trifluoro methyl)phenol TFA-salt;
2-(4,5-Dimethyl-6-(((R)-1-methylpiperidin-3-yl)amino) pyridazin-3-yl)-3-methyl-5-(trifluoro methyl)phenol TFA-salt;
5-((6-(2-Hydroxy-6-methyl-4-(trifluoromethyl)phenyl) pyridazin-3-yl)amino)piperidine-2-carboxylic acid;
3-Methyl-2-(6-((1-methylpiperidin-3-yl)oxy)pyridazin-3-yl)-5-(trifluoromethyl)phenol;
(S)-3-Methyl-2-(6-((1-methylpiperidin-3-yl)oxy)pyridazin-3-yl)-5-(trifluoromethyl)phenol;
(R)-3-Methyl-2-(6-((1-methylpiperidin-3-yl)oxy)pyridazin-3-yl)-5-(trifluoromethyl)phenol;
3-Methyl-2-(6-(pyrimidin-5-ylamino)pyridazin-3-yl)-5-(trifluoromethyl)phenol;
3,5-Dichloro-2-(6-(cyclopropylamino)pyridazin-3-yl)phenol;
3,5-Dichloro-2-(6-((1-methyl piperidin-3-yl)amino) pyridazin-3-yl)phenol;
(S)-3,5-Dichloro-2-(6-(((1-methylpiperidin-3-yl)amino) pyridazin-3-yl)phenol;
(R)-3,5-Dichloro-2-(6-(((1-methylpiperidin-3-yl)amino) pyridazin-3-yl)phenol;
3,5-Dichloro-2-(6-(((1-methylpiperidin-3-yl)amino) pyridazin-3-yl)phenolTFA-salt;
(S)-3,5-Dichloro-2-(6-(((1-methylpiperidin-3-yl)amino) pyridazin-3-yl)phenolTFA-salt;
5    (R)-3,5-Dichloro-2-(6-(((1-methylpiperidin-3-yl)amino) pyridazin-3-yl)phenolTFA-salt;
3-Methyl-2-(6-(pyridin-3-ylamino)pyridazin-3-yl)-5-(trifluoromethyl)phenol;
3,5-Dimethyl-2-(6-(((1-methylpiperidin-3-yl)amino) pyridazin-3-yl)phenol;
(S)-3,5-Dimethyl-2-(6-(((1-methylpiperidin-3-yl)amino) pyridazin-3-yl)phenol;
(R)-3,5-Dimethyl-2-(6-(((1-methylpiperidin-3-yl)amino) pyridazin-3-yl)phenol;
2-(4,5-Dimethyl-6-(((1-methylpiperidin-3-yl)amino) pyridazin-3-yl)-5-(trifluoromethyl)phenol;
(S)-2-(4,5-Dimethyl-6-(((1-methylpiperidin-3-yl)amino) pyridazin-3-yl)-5-(trifluoromethyl)phenol;
(R)-2-(4,5-Dimethyl-6-(((1-methylpiperidin-3-yl)amino) pyridazin-3-yl)-5-(trifluoromethyl)phenol;
3-Chloro-2-(6-(((1-methylpiperidin-3-yl)amino)pyridazin-3-yl)-5-(trifluoromethyl)phenol;
(S)-3-Chloro-2-(6-(((1-methylpiperidin-3-yl)amino) pyridazin-3-yl)-5-(trifluoromethyl)phenol;
(R)-3-Chloro-2-(6-(((1-methylpiperidin-3-yl)amino) pyridazin-3-yl)-5-(trifluoromethyl)phenol;
5-Methyl-2-(6-(((1-methylpiperidin-3-yl)amino)-4-(trifluoromethyl)pyridazin-3-yl)phenol;
(S)-5-Methyl-2-(6-(((1-methylpiperidin-3-yl)amino)-4-(trifluoromethyl)pyridazin-3-yl)phenol;
(R)-5-Methyl-2-(6-(((1-methylpiperidin-3-yl)amino)-4-(trifluoromethyl)pyridazin-3-yl)phenol;
5-Chloro-2-(6-(((1-methylpiperidin-3-yl)amino)pyridazin-3-yl)-3-(trifluoromethyl)phenol;
(S)-5-Chloro-2-(6-(((1-methylpiperidin-3-yl)amino) pyridazin-3-yl)-3-(trifluoromethyl)phenol;
(R)-5-Chloro-2-(6-(((1-methylpiperidin-3-yl)amino) pyridazin-3-yl)-3-(trifluoromethyl)phenol;
2-(6-((1,3-Dimethylpiperidin-3-yl)amino)pyridazin-3-yl)-3-methyl-5-(trifluoromethyl)phenol;
2-(6-((1,3-Dimethylpiperidin-3-yl)amino)pyridazin-3-yl)-3-methyl-5-(trifluoromethyl)phenol TFA-salt;
2-(6-((1-Methylpiperidin-3-yl)amino)-4-(trifluoromethyl) pyridazin-3-yl)-5-(trifluoromethyl) phenol;
(S)-2-(6-(((1-Methylpiperidin-3-yl)amino)-4-(trifluoromethyl)pyridazin-3-yl)-5-(trifluoromethyl) phenol;
(R)-2-(6-(((1-Methylpiperidin-3-yl)amino)-4-(trifluoromethyl)pyridazin-3-yl)-5-(trifluoromethyl) phenol;
2-(6-((3-Hydroxy-3-methylcyclobutyl)amino)-5-methylpyridazin-3-yl)-3-methyl-5-(trifluoromethyl)phenol;
2-(6-(((trans)-3-Hydroxy-3-methylcyclobutyl)amino)-5-methylpyridazin-3-yl)-3-methyl-5-(trifluoromethyl)phenol;

2-(6-(((cis)-3-Hydroxy-3-methylcyclobutyl)amino)-5-methylpyridazin-3-yl)-3-methyl-5-(trifluoromethyl)phenol;
2-(6-((3-Hydroxy-3-methylcyclobutyl)amino)-4-methylpyridazin-3-yl)-5-(trifluoromethyl)phenol;
2-(6-(((trans)-3-Hydroxy-3-methylcyclobutyl)amino)-4-methylpyridazin-3-yl)-5-(trifluoromethyl) phenol;
2-(6-(((cis)-3-Hydroxy-3-methylcyclobutyl)amino)-4-methylpyridazin-3-yl)-5-(trifluoromethyl) phenol;
2-(6-((3-Hydroxy-3-methylcyclobutyl)amino)-5-(trifluoromethyl)pyridazin-3-yl)-3-methyl-5-(trifluoromethyl) phenol;
2-(6-(((trans)-3-Hydroxy-3-methylcyclobutyl)amino)-5-(trifluoromethyl)pyridazin-3-yl)-3-methyl-5-(trifluoromethyl)phenol;
2-(6-(((cis)-3-Hydroxy-3-methylcyclobutyl)amino)-5-(trifluoromethyl)pyridazin-3-yl)-3-methyl-5-(trifluoromethyl)phenol;
2-(6-((3-Hydroxycyclohexyl)amino)pyridazin-3-yl)-3-methyl-5-(trifluoromethyl)phenol;
2-(6-(((1S,3S)-3-Hydroxycyclohexyl)amino)pyridazin-3-yl)-3-methyl-5-(trifluoromethyl)phenol;
2-(6-(((1S,3R)-3-Hydroxycyclohexyl)amino)pyridazin-3-yl)-3-methyl-5-(trifluoromethyl)phenol;
2-(6-(((1R,3S)-3-Hydroxycyclohexyl)amino)pyridazin-3-yl)-3-methyl-5-(trifluoromethyl)phenol;
2-(6-(((1R,3R)-3-Hydroxycyclohexyl)amino)pyridazin-3-yl)-3-methyl-5-(trifluoromethyl)phenol;
3-((6-(2-Hydroxy-6-methyl-4-(trifluoromethyl)phenyl)pyridazin-3-yl)amino)-1-methylpiperidin-2-one;
(S)-3-((6-(2-Hydroxy-6-methyl-4-(trifluoromethyl)phenyl)pyridazin-3-yl)amino)-1-methyl piperidin-2-one;
(R)-3-((6-(2-Hydroxy-6-methyl-4-(trifluoromethyl)phenyl)pyridazin-3-yl)amino)-1-methyl piperidin-2-one;
2-(6-((2-Fluoro-3-hydroxy-3-methylbutyl)amino)pyridazin-3-yl)-3-methyl-5-(trifluoromethyl) phenol;
(S)-2-(6-((2-Fluoro-3-hydroxy-3-methylbutyl)amino)pyridazin-3-yl)-3-methyl-5-(trifluoromethyl) phenol;
(R)-2-(6-((2-Fluoro-3-hydroxy-3-methylbutyl)amino)pyridazin-3-yl)-3-methyl-5-(trifluoromethyl) phenol;
5-((6-(2-Hydroxy-6-methyl-4-(trifluoromethyl)phenyl)pyridazin-3-yl)amino)piperidin-2-one;
(S)-5-((6-(2-Hydroxy-6-methyl-4-(trifluoromethyl)phenyl)pyridazin-3-yl)amino)piperidin-2-one;
(R)-5-((6-(2-Hydroxy-6-methyl-4-(trifluoromethyl)phenyl)pyridazin-3-yl)amino)piperidin-2-one;
3-Methyl-5-(trifluoromethyl)-2-(6-((6-(trifluoromethyl)piperidin-3-yl)amino)pyridazin-3-yl) phenol;
3-Methyl-2-(6-((1-(2,2,2-trifluoroethyl)piperidin-3-yl)amino)pyridazin-3-yl)-5-(trifluoromethyl) phenol;
(S)-3-Methyl-2-(6-((1-(2,2,2-trifluoroethyl)piperidin-3-yl)amino)pyridazin-3-yl)-5-(trifluoromethyl) phenol;
(R)-3-Methyl-2-(6-((1-(2,2,2-trifluoroethyl)piperidin-3-yl)amino)pyridazin-3-yl)-5-(trifluoromethyl) phenol;
3-Methyl-2-(6-((1-methylpiperidin-3-yl)amino)-5-(trifluoromethyl)pyridazin-3-yl)-5-(trifluoromethyl)phenol;
(S)-3-Methyl-2-(6-((1-methylpiperidin-3-yl)amino)-5-(trifluoromethyl)pyridazin-3-yl)-5-(trifluoromethyl)phenol;
(R)-3-Methyl-2-(6-((1-methylpiperidin-3-yl)amino)-5-(trifluoromethyl)pyridazin-3-yl)-5-(trifluoromethyl)phenol;
2-(5-Methyl-6-((1-methylpiperidin-3-yl)amino)pyridazin-3-yl)-5-(trifluoromethyl)phenol;
(S)-2-(5-Methyl-6-((1-methylpiperidin-3-yl)amino)pyridazin-3-yl)-5-(trifluoromethyl)phenol;
(R)-2-(5-Methyl-6-((1-methylpiperidin-3-yl)amino)pyridazin-3-yl)-5-(trifluoromethyl)phenol;
2-(6-((3-Hydroxy-3-methylcyclobutyl)amino)-4-(trifluoromethyl)pyridazin-3-yl)-5-(trifluoromethyl)phenol;
2-(6-(((trans)-3-Hydroxy-3-methylcyclobutyl)amino)-4-(trifluoromethyl)pyridazin-3-yl)-5-(trifluoromethyl)phenol;
2-(6-(((cis)-3-Hydroxy-3-methylcyclobutyl)amino)-4-(trifluoromethyl)pyridazin-3-yl)-5-(trifluoromethyl)phenol;
2-(6-((3-Hydroxy-3-(trifluoromethyl)cyclobutyl)amino)pyridazin-3-yl)-3-methyl-5-(trifluoromethyl)phenol;
2-(6-(((trans)-3-Hydroxy-3-(trifluoromethyl)cyclobutyl)amino)pyridazin-3-yl)-3-methyl-5-(trifluoromethyl)phenol;
2-(6-(((cis)-3-Hydroxy-3-(trifluoromethyl)cyclobutyl)amino)pyridazin-3-yl)-3-methyl-5-(trifluoromethyl)phenol;
5-Chloro-2-(6-((3-hydroxy-3-methylcyclobutyl)amino)-4-methylpyridazin-3-yl)phenol;
5-Chloro-2-(6-(((trans)-3-hydroxy-3-methylcyclobutyl)amino)-4-methylpyridazin-3-yl)phenol; 5-Chloro-2-(6-(((cis)-3-hydroxy-3-methylcyclobutyl)amino)-4-methylpyridazin-3-yl)phenol;
5-Chloro-2-(6-((3-hydroxy-3-methylcyclobutyl)amino)-4-(trifluoromethyl)pyridazin-3-yl)phenol;
5-Chloro-2-(6-(((trans)-3-hydroxy-3-methylcyclobutyl)amino)-4-(trifluoromethyl)pyridazin-3-yl)phenol;
5-Chloro-2-(6-(((cis)-3-hydroxy-3-methylcyclobutyl)amino)-4-(trifluoromethyl)pyridazin-3-yl)phenol;
5-Chloro-2-(6-((1-methylpiperidin-3-yl)amino)-4-(trifluoromethyl)pyridazin-3-yl)phenol;
(S)-5-Chloro-2-(6-((1-methylpiperidin-3-yl)amino)-4-(trifluoromethyl)pyridazin-3-yl)phenol;
(R)-5-Chloro-2-(6-((1-methylpiperidin-3-yl)amino)-4-(trifluoromethyl)pyridazin-3-yl)phenol;
5-Chloro-2-(4-methyl-6-((1-methylpiperidin-3-yl)amino)pyridazin-3-yl)phenol;
(S)-5-Chloro-2-(4-methyl-6-((1-methylpiperidin-3-yl)amino) pyridazin-3-yl)phenol;
(R)-5-Chloro-2-(4-methyl-6-((1-methylpiperidin-3-yl)amino) pyridazin-3-yl)phenol;
2-(6-((2-Hydroxy-2-methylpropyl)amino)-5-methylpyridazin-3-yl)-3-methyl-5-(trifluoromethyl) phenol;
2-(6-((2-Hydroxy-2-methylpropyl)amino)-4-methylpyridazin-3-yl)-3-methyl-5-(trifluoromethyl) phenol;
3-Methyl-2-(6-(piperidin-3-ylamino)pyridazin-3-yl)-5-(trifluoromethyl)phenol;
(S)-3-Methyl-2-(6-(piperidin-3-ylamino)pyridazin-3-yl)-5-(trifluoromethyl)phenol;
(R)-3-Methyl-2-(6-(piperidin-3-ylamino)pyridazin-3-yl)-5-(trifluoromethyl)phenol;
2-(6-(((4-Fluoropyrrolidin-2-yl)methyl)amino)pyridazin-3-yl)-3-methyl-5-(trifluoromethyl) phenol;
2-(6-((((2S,4S)-4-Fluoropyrrolidin-2-yl)methyl)amino)pyridazin-3-yl)-3-methyl-5-(trifluoromethyl)phenol;
2-(6-((((2R,4S)-4-Fluoropyrrolidin-2-yl)methyl)amino)pyridazin-3-yl)-3-methyl-5-(trifluoromethyl)phenol;
2-(6-((((2R,4R)-4-Fluoropyrrolidin-2-yl)methyl)amino)pyridazin-3-yl)-3-methyl-5-(trifluoromethyl)phenol;
2-(6-((((2S,4R)-4-Fluoropyrrolidin-2-yl)methyl)amino)pyridazin-3-yl)-3-methyl-5-(trifluoromethyl)phenol;
(S)-3-Methyl-2-(6-(((4-methylmorpholin-3-yl)methyl)amino)pyridazin-3-yl)-5-(trifluoromethyl) phenol;
(R)-3-Methyl-2-(6-(((4-methylmorpholin-3-yl)methyl)amino)pyridazin-3-yl)-5-(trifluoromethyl) phenol;
(rac)-3-Methyl-2-(6-(((4-methylmorpholin-3-yl)methyl)amino)pyridazin-3-yl)-5-(trifluoromethyl) phenol;
3-Methyl-2-(6-((3,3,3-trifluoro-2-hydroxy-2-methylpropyl)amino)pyridazin-3-yl)-5-(trifluoromethyl) phenol;
(S)-3-Methyl-2-(6-((3,3,3-trifluoro-2-hydroxy-2-methylpropyl)amino)pyridazin-3-yl)-5-(trifluoromethyl)phenol;

(R)-3-Methyl-2-(6-((3,3,3-trifluoro-2-hydroxy-2-methyl-propyl)amino)pyridazin-3-yl)-5-(trifluoro methyl)phenol;
3-Methyl-2-(6-((3,3,3-trifluoro-2-hydroxy-2-methylpropyl)amino)pyridazin-3-yl)-5-(trifluoro methyl)phenol HCl-salt;
(R)-3-Methyl-2-(6-((3,3,3-trifluoro-2-hydroxy-2-methyl-propyl)amino)pyridazin-3-yl)-5-(trifluoro methyl)phenol HCl-salt;
(S)-3-Methyl-2-(6-((3,3,3-trifluoro-2-hydroxy-2-methyl-propyl)amino)pyridazin-3-yl)-5-(trifluoro methyl)phenol HCl-salt;
2-(6-((1-Hydroxy-2-methylpropan-2-yl)amino)pyridazin-3-yl)-3-methyl-5-(trifluoromethyl) phenol;
2-(6-((1-(2-Hydroxy-2-methylpropyl)piperidin-3-yl)amino)pyridazin-3-yl)-3-methyl-5-(trifluoromethyl)phenol;
(S)-2-(6-((1-(2-Hydroxy-2-methylpropyl)piperidin-3-yl)amino)pyridazin-3-yl)-3-methyl-5-(trifluoromethyl)phenol;
(R)-2-(6-((1-(2-Hydroxy-2-methylpropyl)piperidin-3-yl)amino)pyridazin-3-yl)-3-methyl-5-(trifluoromethyl)phenol;
2-(6-((3-Hydroxy-3-methylcyclobutyl)amino)-4-methylpyridazin-3-yl)-5-(trifluoromethoxy) phenol;
2-(6-(((trans)-3-Hydroxy-3-methylcyclobutyl)amino)-4-methylpyridazin-3-yl)-5-(trifluoro methoxy)phenol;
2-(6-(((cis)-3-Hydroxy-3-methylcyclobutyl)amino)-4-methylpyridazin-3-yl)-5-(trifluoromethoxy) phenol;
2-(4-Methyl-6-((1-methylpiperidin-3-yl)amino)pyridazin-3-yl)-5-(trifluoromethoxy)phenol;
(S)-2-(4-Methyl-6-((1-methylpiperidin-3-yl)amino)pyridazin-3-yl)-5-(trifluoromethoxy)phenol;
(R)-2-(4-Methyl-6-((1-methylpiperidin-3-yl)amino)pyridazin-3-yl)-5-(trifluoromethoxy)phenol;
3-Methyl-2-(6-((octahydroindolizin-8-yl)amino)pyridazin-3-yl)-5-(trifluoromethyl)phenol;
3-Methyl-2-(6-(((8R,8aR)-octahydroindolizin-8-yl)amino)pyridazin-3-yl)-5-(trifluoromethyl) phenol;
3-Methyl-2-(6-(((8R,8aS)-octahydroindolizin-8-yl)amino)pyridazin-3-yl)-5-(trifluoromethyl) phenol;
3-Methyl-2-(6-(((8S,8aR)-octahydroindolizin-8-yl)amino)pyridazin-3-yl)-5-(trifluoromethyl) phenol;
3-Methyl-2-(6-(((8S,8aS)-octahydroindolizin-8-yl)amino)pyridazin-3-yl)-5-(trifluoromethyl) phenol;
(R)-2-(6-(((1-(2-Hydroxyethyl)piperidin-2-yl)methyl)amino)pyridazin-3-yl)-3-methyl-5-(trifluoro methyl)phenol;
2-(6-(((1-(2-Hydroxyethyl)piperidin-2-yl)methyl)amino)pyridazin-3-yl)-3-methyl-5-(trifluoro methyl)phenol;
(S)-2-(6-(((1-(2-Hydroxyethyl)piperidin-2-yl)methyl)amino)pyridazin-3-yl)-3-methyl-5-(trifluoro methyl)phenol;
3-Methyl-2-(6-((8-methyl-8-azabicyclo[3.2.1]octan-2-yl)amino)pyridazin-3-yl)-5-(trifluoro methyl)phenol;
3-Methyl-2-(6-(((1S,2S,5S)-8-methyl-8-azabicyclo[3.2.1]octan-2-yl)amino)pyridazin-3-yl)-5-(trifluoromethyl) phenol;
3-Methyl-2-(6-(((1S,2R,5S)-8-methyl-8-azabicyclo[3.2.1]octan-2-yl)amino)pyridazin-3-yl)-5-(trifluoromethyl) phenol;
3-Methyl-2-(6-(((1S,2R,5R)-8-methyl-8-azabicyclo[3.2.1]octan-2-yl)amino)pyridazin-3-yl)-5-(trifluoromethyl) phenol;
3-Methyl-2-(6-(((1S,2S,5R)-8-methyl-8-azabicyclo[3.2.1]octan-2-yl)amino)pyridazin-3-yl)-5-(trifluoromethyl) phenol;
3-Methyl-2-(6-(((1R,2R,5S)-8-methyl-8-azabicyclo[3.2.1]octan-2-yl)amino)pyridazin-3-yl)-5-(trifluoromethyl) phenol;
3-Methyl-2-(6-(((1R,2S,5S)-8-methyl-8-azabicyclo[3.2.1]octan-2-yl)amino)pyridazin-3-yl)-5-(trifluoromethyl) phenol;
3-Methyl-2-(6-(((1R,2S,5R)-8-methyl-8-azabicyclo[3.2.1]octan-2-yl)amino)pyridazin-3-yl)-5-(trifluoromethyl) phenol;
3-Methyl-2-(6-(((1R,2R,5R)-8-methyl-8-azabicyclo[3.2.1]octan-2-yl)amino)pyridazin-3-yl)-5-(trifluoromethyl) phenol;
2-(6-((8-(2-Hydroxyethyl)-8-azabicyclo[3.2.1]octan-2-yl)amino)pyridazin-3-yl)-3-methyl-5-(trifluoromethyl)phenol;
2-(6-(((1R,2R,5R)-8-(2-Hydroxyethyl)-8-azabicyclo[3.2.1]octan-2-yl)amino)pyridazin-3-yl)-3-methyl-5-(trifluoromethyl)phenol;
2-(6-(((1R,2S,5S)-8-(2-Hydroxyethyl)-8-azabicyclo[3.2.1]octan-2-yl)amino)pyridazin-3-yl)-3-methyl-5-(trifluoromethyl)phenol;
2-(6-(((1R,2S,5R)-8-(2-Hydroxyethyl)-8-azabicyclo[3.2.1]octan-2-yl)amino)pyridazin-3-yl)-3-methyl-5-(trifluoromethyl)phenol;
2-(6-(((1R,2R,5S)-8-(2-Hydroxyethyl)-8-azabicyclo[3.2.1]octan-2-yl)amino)pyridazin-3-yl)-3-methyl-5-(trifluoromethyl)phenol;
2-(6-(((1S,2S,5R)-8-(2-Hydroxyethyl)-8-azabicyclo[3.2.1]octan-2-yl)amino)pyridazin-3-yl)-3-methyl-5-(trifluoromethyl)phenol;
2-(6-(((1S,2R,5R)-8-(2-Hydroxyethyl)-8-azabicyclo[3.2.1]octan-2-yl)amino)pyridazin-3-yl)-3-methyl-5-(trifluoromethyl)phenol;
2-(6-(((1S,2R,5S)-8-(2-Hydroxyethyl)-8-azabicyclo[3.2.1]octan-2-yl)amino)pyridazin-3-yl)-3-methyl-5-(trifluoromethyl)phenol;
2-(6-(((1S,2S,5S)-8-(2-Hydroxyethyl)-8-azabicyclo[3.2.1]octan-2-yl)amino)pyridazin-3-yl)-3-methyl-5-(trifluoromethyl)phenol;
2-(6-((6-(Hydroxymethyl)-1-methylpiperidin-3-yl)amino)pyridazin-3-yl)-3-methyl-5-(trifluoro methyl)phenol;
2-(6-(((3R,6R)-6-(Hydroxymethyl)-1-methylpiperidin-3-yl)amino)pyridazin-3-yl)-3-methyl-5-(trifluoromethyl)phenol;
2-(6-(((3S,6R)-6-(Hydroxymethyl)-1-methylpiperidin-3-yl)amino)pyridazin-3-yl)-3-methyl-5-(trifluoromethyl)phenol;
2-(6-(((3R,6S)-6-(Hydroxymethyl)-1-methylpiperidin-3-yl)amino)pyridazin-3-yl)-3-methyl-5-(trifluoromethyl)phenol;
2-(6-(((3S,6S)-6-(Hydroxymethyl)-1-methylpiperidin-3-yl)amino)pyridazin-3-yl)-3-methyl-5-(trifluoromethyl)phenol;
(S)-3-((6-(2-Hydroxy-6-methyl-4-(trifluoromethyl)phenyl)pyridazin-3-yl)amino)-2-methyl propane-1,2-diol;
3-((6-(2-Hydroxy-6-methyl-4-(trifluoromethyl)phenyl)pyridazin-3-yl)amino)-2-methylpropane-1,2-diol;
(R)-3-((6-(2-Hydroxy-6-methyl-4-(trifluoromethyl)phenyl)pyridazin-3-yl)amino)-2-methyl propane-1,2-diol;
3-((6-(2-Hydroxy-6-methyl-4-(trifluoromethyl)phenyl)pyridazin-3-yl)amino)cyclopentane-1,2-diol;
(1S,2S,3R)-3-((6-(2-Hydroxy-6-methyl-4-(trifluoromethyl)phenyl)pyridazin-3-yl)amino) cyclopentane-1,2-diol;
(1S,2R,3R)-3-((6-(2-Hydroxy-6-methyl-4-(trifluoromethyl)phenyl)pyridazin-3-yl)amino) cyclopentane-1,2-diol;
(1S,2S,3S)-3-((6-(2-Hydroxy-6-methyl-4-(trifluoromethyl)phenyl)pyridazin-3-yl)amino) cyclopentane-1,2-diol;

(1S,2R,3S)-3-((6-(2-Hydroxy-6-methyl-4-(trifluoromethyl)phenyl)pyridazin-3-yl)amino) cyclopentane-1,2-diol;
(1R,2R,3S)-3-((6-(2-Hydroxy-6-methyl-4-(trifluoromethyl)phenyl)pyridazin-3-yl)amino) cyclopentane-1,2-diol;
(1R,2S,3S)-3-((6-(2-Hydroxy-6-methyl-4-(trifluoromethyl)phenyl)pyridazin-3-yl)amino) cyclopentane-1,2-diol;
(1R,2R,3R)-3-((6-(2-Hydroxy-6-methyl-4-(trifluoromethyl)phenyl)pyridazin-3-yl)amino) cyclopentane-1,2-diol;
(1R,2S,3R)-3-((6-(2-Hydroxy-6-methyl-4-(trifluoromethyl)phenyl)pyridazin-3-yl)amino) cyclopentane-1,2-diol;
(S)-2-(6-((2-Hydroxy-3-methylbutyl)amino)pyridazin-3-yl)-3-methyl-5-(trifluoromethyl)phenol;
2-(6-((2-Hydroxy-3-methylbutyl)amino)pyridazin-3-yl)-3-methyl-5-(trifluoromethyl)phenol;
(R)-2-(6-((2-Hydroxy-3-methylbutyl)amino)pyridazin-3-yl)-3-methyl-5-(trifluoromethyl)phenol;
3-Methyl-2-(6-((2-methylpiperidin-3-yl)amino)pyridazin-3-yl)-5-(trifluoromethyl)phenol; 3-Methyl-2-(6-(((2S,3S)-2-methylpiperidin-3-yl)amino)pyridazin-3-yl)-5-(trifluoromethyl)phenol;
3-Methyl-2-(6-(((2R,3S)-2-methylpiperidin-3-yl)amino)pyridazin-3-yl)-5-(trifluoromethyl)phenol;
3-Methyl-2-(6-(((2S,3R)-2-methylpiperidin-3-yl)amino)pyridazin-3-yl)-5-(trifluoromethyl)phenol;
3-Methyl-2-(6-(((2R,3R)-2-methylpiperidin-3-yl)amino)pyridazin-3-yl)-5-(trifluoromethyl)phenol;
2-(6-((2-Hydroxypropyl)piperidin-3-yl)amino)pyridazin-3-yl)-3-methyl-5-(trifluoromethyl)phenol;
2-(6-(((R)-1-((S)-2-Hydroxypropyl)piperidin-3-yl)amino)pyridazin-3-yl)-3-methyl-5-(trifluoro methyl)phenol;
2-(6-(((S)-1-((R)-2-Hydroxypropyl)piperidin-3-yl)amino)pyridazin-3-yl)-3-methyl-5-(trifluoro methyl)phenol;
2-(6-(((S)-1-((S)-2-Hydroxypropyl)piperidin-3-yl)amino)pyridazin-3-yl)-3-methyl-5-(trifluoro methyl)phenol;
2-(6-(((R)-1-((R)-2-Hydroxypropyl)piperidin-3-yl)amino)pyridazin-3-yl)-3-methyl-5-(trifluoro methyl)phenol;
2-(6-((5-Fluoropiperidin-3-yl)amino)pyridazin-3-yl)-3-methyl-5-(trifluoromethyl)phenol;
2-(6-(((3S,5S)-5-Fluoropiperidin-3-yl)amino)pyridazin-3-yl)-3-methyl-5-(trifluoromethyl)phenol;
2-(6-(((3S,5R)-5-Fluoropiperidin-3-yl)amino)pyridazin-3-yl)-3-methyl-5-(trifluoromethyl)phenol;
2-(6-(((3R,5S)-5-Fluoropiperidin-3-yl)amino)pyridazin-3-yl)-3-methyl-5-(trifluoromethyl)phenol;
2-(6-(((3R,5R)-5-Fluoropiperidin-3-yl)amino)pyridazin-3-yl)-3-methyl-5-(trifluoromethyl)phenol;
2-(6-((5-Fluoro-1-methylpiperidin-3-yl)amino)pyridazin-3-yl)-3-methyl-5-(trifluoromethyl) phenol;
2-(6-(((3S,5S)-5-Fluoro-1-methylpiperidin-3-yl)amino)pyridazin-3-yl)-3-methy-5-(trifluoro methyl)phenol;
2-(6-(((3S,5R)-5-Fluoro-1-methylpiperidin-3-yl)amino)pyridazin-3-yl)-3-methyl-5-(trifluoro methyl)phenol;
2-(6-(((3R,5S)-5-Fluoro-1-methylpiperidin-3-yl)amino)pyridazin-3-yl)-3-methyl-5-(trifluoro methyl)phenol;
2-(6-(((3R,5R)-5-Fluoro-1-methylpiperidin-3-yl)amino)pyridazin-3-yl)-3-methy-5-(trifluoro methyl)phenol;
2-(6-((5-Fluoro-1-methylpiperidin-3-yl)amino)pyridazin-3-yl)-3-methyl-5-(trifluoromethyl) phenol;
2-(6-(((3S,5R)-5-Fluoro-1-methylpiperidin-3-yl)amino)pyridazin-3-yl)-3-methyl-5-(trifluoro methyl)phenol;
2-(6-(((3R,5R)-5-Fluoro-1-methylpiperidin-3-yl)amino)pyridazin-3-yl)-3-methy-5-(trifluoro methyl)phenol;
2-(6-(((3S,5S)-5-Fluoro-1-methylpiperidin-3-yl)amino)pyridazin-3-yl)-3-methy-5-(trifluoro methyl)phenol;
2-(6-(((3R,5S)-5-Fluoro-1-methylpiperidin-3-yl)amino)pyridazin-3-yl)-3-methyl-5-(trifluoro methyl)phenol;
2-(6-((5-Fluoropiperidin-3-yl)amino)pyridazin-3-yl)-3-methyl-5-(trifluoromethyl)phenol;
2-(6-(((3S,5R)-5-Fluoropiperidin-3-yl)amino)pyridazin-3-yl)-3-methyl-5-(trifluoromethyl)phenol;
2-(6-(((3S,5S)-5-Fluoropiperidin-3-yl)amino)pyridazin-3-yl)-3-methyl-5-(trifluoromethyl)phenol;
2-(6-(((3R,5R)-5-Fluoropiperidin-3-yl)amino)pyridazin-3-yl)-3-methyl-5-(trifluoromethyl)phenol;
2-(6-(((3R,5S)-5-Fluoropiperidin-3-yl)amino)pyridazin-3-yl)-3-methyl-5-(trifluoromethyl)phenol;
5-((6-(2-Hydroxy-6-methyl-4-(trifluoromethyl)phenyl)pyridazin-3-yl)amino)-1-methylpiperidin-3-ol;
(3S,5S)-5-((6-(2-Hydroxy-6-methyl-4-(trifluoromethyl)phenyl)pyridazin-3-yl)amino)-1-methyl piperidin-3-ol;
(3R,5S)-5-((6-(2-Hydroxy-6-methyl-4-(trifluoromethyl)phenyl)pyridazin-3-yl)amino)-1-methyl piperidin-3-ol;
(3R,5R)-5-((6-(2-Hydroxy-6-methyl-4-(trifluoromethyl)phenyl)pyridazin-3-yl)amino)-1-methyl piperidin-3-ol;
(3S,5R)-5-((6-(2-Hydroxy-6-methyl-4-(trifluoromethyl)phenyl)pyridazin-3-yl)amino)-1-methyl piperidin-3-ol;
2-(6-(((1-Hydroxycyclopentyl)methyl)amino)pyridazin-3-yl)-3-methyl-5-(trifluoromethyl)phenol;
5-((6-(2-Hydroxy-6-methyl-4-(trifluoromethyl)phenyl)-4-methylpyridazin-3-yl)amino)-1-methyl piperidin-2-one;
3-Methyl-2-(5-methyl-6-(piperidin-3-ylamino)pyridazin-3-yl)-5-(trifluoromethyl)phenol;
(S)-3-Methyl-2-(5-methyl-6-(piperidin-3-ylamino)pyridazin-3-yl)-5-(trifluoromethyl)phenol;
(R)-3-Methyl-2-(5-methyl-6-(piperidin-3-ylamino)pyridazin-3-yl)-5-(trifluoromethyl)phenol;
2-(6-((1-Ethylpiperidin-3-yl)amino)-5-methylpyridazin-3-yl)-3-methyl-5-(trifluoromethyl)-phenol;
(S)-2-(6-((1-Ethylpiperidin-3-yl)amino)-5-methylpyridazin-3-yl)-3-methyl-5-(trifluoromethyl)-phenol;
(R)-2-(6-((1-Ethylpiperidin-3-yl)amino)-5-methylpyridazin-3-yl)-3-methyl-5-(trifluoromethyl)-phenol;
3-((6-(2-Hydroxy-6-methyl-4-(trifluoromethyl)phenyl)-4-methylpyridazin-3-yl)amino)-1-methylpiperidin-2-one;
(S)-3-((6-(2-Hydroxy-6-methyl-4-(trifluoromethyl)phenyl)-4-methylpyridazin-3-yl)amino)-1-methylpiperidin-2-one;
(R)-3-((6-(2-Hydroxy-6-methyl-4-(trifluoromethyl)phenyl)-4-methylpyridazin-3-yl)amino)-1-methylpiperidin-2-one;
4-(2-((6-(2-Hydroxy-4,6-dimethylphenyl)pyridazin-3-yl)amino)ethyl)benzenesulfonamide;
3-((6-(2-Hydroxy-6-methyl-4-(trifluoromethyl)phenyl)-4-methylpyridazin-3-yl)amino)-1-methylpiperidine 1-oxide;
(3S)-3-((6-(2-Hydroxy-6-methyl-4-(trifluoromethyl)phenyl)-4-methylpyridazin-3-yl)amino)-1-methylpiperidine 1-oxide;
(3R)-3-((6-(2-Hydroxy-6-methyl-4-(trifluoromethyl)phenyl)-4-methylpyridazin-3-yl)amino)-1-methylpiperidine 1-oxide:
3-((6-(2-Hydroxy-6-methyl-4-(trifluoromethyl)phenyl)-4-methylpyridazin-3-yl)amino)-1-methylpiperidine 1-oxide TFA-salt;
(3S)-3-((6-(2-Hydroxy-6-methyl-4-(trifluoromethyl)phenyl)-4-methylpyridazin-3-yl)amino)-1-methylpiperidine 1-oxide TFA-salt;
(3R)-3-((6-(2-Hydroxy-6-methyl-4-(trifluoromethyl)phenyl)-4-methylpyridazin-3-yl)amino)-1-methylpiperidine 1-oxide TFA-salt;
or a pharmaceutically acceptable salt thereof.

In embodiment 11a, and according to embodiment 11, the invention provides a compound of any one of the formula (I), (II), (III) and (III-A), or a pharmaceutically acceptable salt thereof, according to embodiment 1, wherein the compound is preferably selected from:

(R)-2-(6-((1-Ethylpiperidin-3-yl)amino)pyridazin-3-yl)-3-methyl-5-(trifluoromethyl)phenol;
2-(6-(((cis)-3-Hydroxy-3-methylcyclobutyl)amino) pyridazin-3-yl)-3-methyl-5-(trifluoromethyl) phenol;
2-(6-(((1R,3S)-3-Hydroxycyclohexyl)amino)pyridazin-3-yl)-3-methyl-5-(trifluoromethyl)phenol;
(R)-2-(4-Methyl-6-((1-methylpiperidin-3-yl)amino) pyridazin-3-yl)-5-(trifluoromethyl)phenol;
(R)-3-Methyl-2-(5-methyl-6-((1-methylpiperidin-3-yl) amino)pyridazin-3-yl)-5-(trifluoromethyl) phenol;
(R)-2-(6-((1-(2-Hydroxyethyl)piperidin-3-yl)amino) pyridazin-3-yl)-3-methyl-5-(trifluoromethyl) phenol;
2-(6-((1-Isopropylpiperidin-3-yl)amino)pyridazin-3-yl)-3-methyl-5-(trifluoromethyl)phenol;
(S)-2-(6-(((1-Ethylpyrrolidin-2-yl)methyl)amino)pyridazin-3-yl)-3-methyl-5-(trifluoromethyl) phenol;
2-(6-((5,5-Difluoropiperidin-3-yl)amino)pyridazin-3-yl)-3-methyl-5-(trifluoromethyl)phenol;
3-Methyl-2-(6-((3,3,3-trifluoro-2-hydroxy-2-(trifluoromethyl)propyl)amino)pyridazin-3-yl)-5-(trifluoromethyl) phenol;
(R)-3-((1-Ethylpiperidin-3-yl)amino)-6-(2-hydroxy-6-methyl-4-(trifluoromethyl)phenyl) pyridazine-4-carbonitrile;
(R)-3-Methyl-2-(6-((1-methylpiperidin-3-yl)amino) pyridazin-3-yl)-5-(trifluoromethyl)phenol;
(R)-2-(6-((1-(2-Hydroxyethyl)piperidin-3-yl)amino)-5-methylpyridazin-3-yl)-3-methyl-5-(trifluoromethyl)phenol;
(R)-3-Methyl-2-(6-((pyrrolidin-2-ylmethyl)amino) pyridazin-3-yl)-5-(trifluoromethyl)phenol;
2-(6-((2-Hydroxy-2-methylpropyl) amino)pyridazin-3-yl)-3-methyl-5-(trifluoromethyl)phenol;
2-(6-((2-(Dimethylamino)-2-methylpropyl)amino) pyridazin-3-yl)-3-methyl-5-(trifluoromethyl) phenol;
(R)-3-Methyl-2-(6-((1-methyl pyrrolidin-3-yl)amino) pyridazin-3-yl)-5-(trifluoromethyl)phenol;
(S)-3-Methyl-2-(6-((1-methyl pyrrolidin-3-yl)amino) pyridazin-3-yl)-5-(trifluoromethyl)phenol;
2-(6-(2-Hydroxy-2-methyl propoxy)pyridazin-3-yl)-3-methyl-5-(trifluoromethyl)phenol;
(R)-3-Methyl-2-(6-((piperidin-2-ylmethyl)amino)pyridazin-3-yl)-5-(trifluoromethyl)phenol;
(S)-3-Methyl-2-(6-((piperidin-2-ylmethyl)amino)pyridazin-3-yl)-5-(trifluoromethyl)phenol;
(S)-2-(6-(((4,4-Difluoropyrrolidin-2-yl)methyl)amino) pyridazin-3-yl)-3-methyl-5-(trifluoromethyl) phenol;
(R)-2-(6-(((4,4-Difluoropyrrolidin-2-yl)methyl)amino) pyridazin-3-yl)-3-methyl-5-(trifluoromethyl) phenol;
(trans)-2-(6-((2-Hydroxycyclopentyl)amino)pyridazin-3-yl)-3-methyl-5-(trifluoromethyl)phenol;
3,5-Dichloro-2-(6-((2-hydroxyethyl)amino)pyridazin-3-yl) phenol;
2-(6-((2-Hydroxyethyl)amino)-5-(trifluoromethyl) pyridazin-3-yl)-3-methyl-5-(trifluoromethyl) phenol;
3,5-Dichloro-2-(6-((2,2,2-trifluoroethyl)amino)pyridazin-3-yl)phenol;
3-Methyl-2-(6-((pyridin-2-ylmethyl)amino)pyridazin-3-yl)-5-(trifluoromethyl)phenol;
2-(6-((2-Amino-2-methylpropyl)amino)pyridazin-3-yl)-3-methyl-5-(trifluoromethyl)phenol;
3-Chloro-2-(6-((2-hydroxy-2-methylpropyl)amino) pyridazin-3-yl)-5-(trifluoromethyl)phenol;
3-Chloro-2-(6-(((cis-3-hydroxycyclobutyl)amino)pyridazin-3-yl)-5-(trifluoromethyl)phenol;
3-Chloro-2-(6-((trans-3-hydroxycyclobutyl)amino) pyridazin-3-yl)-5-(trifluoromethyl)phenol;
(S)-3-Methyl-2-(6-(piperidin-3-ylamino)pyridazin-3-yl)-5-(trifluoromethyl)phenol;
3-Chloro-2-(6-(((2-methylpyridin-3-yl)methyl)amino) pyridazin-3-yl)-5-(trifluoromethyl)phenol;
5-Chloro-2-(6-(((2-methylpyridin-3-yl)methyl)amino) pyridazin-3-yl)-3-(trifluoromethyl)phenol;
(S)-3-Methyl-2-(6-((1-methylpiperidin-3-yl)amino) pyridazin-3-yl)-5-(trifluoromethyl)phenol;
3-Chloro-2-(6-((2-hydroxyethyl)amino)pyridazin-3-yl)-5-(trifluoromethyl)phenol;
(R)-5-Chloro-3-fluoro-2-(6-((1-methylpiperidin-3-yl) amino)pyridazin-3-yl)phenolTFA-salt;
(R)-2-(6-((1-Methylpiperidin-3-yl)amino)pyridazin-3-yl)-3,5-bis(trifluoromethyl)phenol;
2-(4,5-Dimethyl-6-(((R)-1-methylpiperidin-3-yl)amino) pyridazin-3-yl)-3-methyl-5-(trifluoro methyl)phenol TFA-salt;
5-((6-(2-Hydroxy-6-methyl-4-(trifluoromethyl)phenyl) pyridazin-3-yl)amino)piperidine-2-carboxylic acid;
(R)-3-Methyl-2-(6-((1-methylpiperidin-3-yl)oxy)pyridazin-3-yl)-5-(trifluoromethyl)phenol;
3-Methyl-2-(6-(pyrimidin-5-ylamino)pyridazin-3-yl)-5-(trifluoromethyl)phenol;
3,5-Dichloro-2-(6-(cyclopropylamino)pyridazin-3-yl)phenol;
(R)-3,5-Dichloro-2-(6-((1-methyl piperidin-3-yl)amino) pyridazin-3-yl)phenol TFA-salt;
3-Methyl-2-(6-(pyridin-3-ylamino)pyridazin-3-yl)-5-(trifluoromethyl)phenol;
(R)-3,5-Dimethyl-2-(6-((1-methylpiperidin-3-yl)amino) pyridazin-3-yl)phenol;
(R)-2-(4,5-Dimethyl-6-((1-methylpiperidin-3-yl)amino) pyridazin-3-yl)-5-(trifluoromethyl)phenol;
(R)-3-Chloro-2-(6-((1-methylpiperidin-3-yl)amino) pyridazin-3-yl)-5-(trifluoromethyl)phenol;
(R)-5-Methyl-2-(6-((1-methylpiperidin-3-yl)amino)-4-(trifluoromethyl)pyridazin-3-yl)phenol;
(R)-5-Chloro-2-(6-((1-methylpiperidin-3-yl)amino) pyridazin-3-yl)-3-(trifluoromethyl)phenol;
2-(6-((1,3-Dimethylpiperidin-3-yl)amino)pyridazin-3-yl)-3-methyl-5-(trifluoromethyl)phenol TFA-salt;
(R)-2-(6-((1-Methylpiperidin-3-yl)amino)-4-(trifluoromethyl)pyridazin-3-yl)-5-(trifluoromethyl) phenol;
2-(6-(((cis)-3-Hydroxy-3-methylcyclobutyl)amino)-5-methylpyridazin-3-yl)-3-methyl-5-(trifluoromethyl)phenol;
2-(6-(((cis)-3-Hydroxy-3-methylcyclobutyl)amino)-4-methylpyridazin-3-yl)-5-(trifluoromethyl) phenol;
2-(6-(((cis)-3-Hydroxy-3-methylcyclobutyl)amino)-5-(trifluoromethyl)pyridazin-3-yl)-3-methyl-5-(trifluoromethyl)phenol;
2-(6-(((1S,3S)-3-Hydroxycyclohexyl)amino)pyridazin-3-yl)-3-methyl-5-(trifluoromethyl)phenol;
2-(6-(((1R,3R)-3-Hydroxycyclohexyl)amino)pyridazin-3-yl)-3-methyl-5-(trifluoromethyl)phenol;
(R)-3-((6-(2-Hydroxy-6-methyl-4-(trifluoromethyl)phenyl) pyridazin-3-yl)amino)-1-methyl piperidin-2-one;
(R)-2-(6-((2-Fluoro-3-hydroxy-3-methylbutyl)amino) pyridazin-3-yl)-3-methyl-5-(trifluoromethyl) phenol;
(R)-5-((6-(2-Hydroxy-6-methyl-4-(trifluoromethyl)phenyl) pyridazin-3-yl)amino)piperidin-2-one;
3-Methyl-5-(trifluoromethyl)-2-(6-((6-(trifluoromethyl)piperidin-3-yl)amino)pyridazin-3-yl) phenol;
(R)-3-Methyl-2-(6-((1-(2,2,2-trifluoroethyl)piperidin-3-yl) amino)pyridazin-3-yl)-5-(trifluoro methyl)phenol;

(R)-3-Methyl-2-(6-((1-methylpiperidin-3-yl)amino)-5-(trifluoromethyl)pyridazin-3-yl)-5-(trifluoro methyl)phenol;
(R)-2-(5-Methyl-6-((1-methylpiperidin-3-yl)amino) pyridazin-3-yl)-5-(trifluoromethyl)phenol;
2-(6-(((cis)-3-Hydroxy-3-methylcyclobutyl)amino)-4-(trifluoromethyl)pyridazin-3-yl)-5-(trifluoro methyl)phenol;
2-(6-(((cis)-3-Hydroxy-3-(trifluoromethyl)cyclobutyl) amino)pyridazin-3-yl)-3-methyl-5-(trifluoro methyl)phenol;
5-Chloro-2-(6-(((cis)-3-hydroxy-3-methylcyclobutyl) amino)-4-methylpyridazin-3-yl)phenol;
5-Chloro-2-(6-(((cis)-3-hydroxy-3-methylcyclobutyl) amino)-4-(trifluoromethyl)pyridazin-3-yl) phenol;
(R)-5-Chloro-2-(6-((1-methylpiperidin-3-yl)amino)-4-(trifluoromethyl)pyridazin-3-yl)phenol;
(R)-5-Chloro-2-(4-methyl-6-((1-methylpiperidin-3-yl) amino)pyridazin-3-yl)phenol;
2-(6-((2-Hydroxy-2-methylpropyl)amino)-5-methylpyridazin-3-yl)-3-methyl-5-(trifluoromethyl) phenol;
2-(6-((2-Hydroxy-2-methylpropyl)amino)-4-methylpyridazin-3-yl)-3-methyl-5-(trifluoromethyl) phenol;
(R)-3-Methyl-2-(6-(piperidin-3-ylamino)pyridazin-3-yl)-5-(trifluoromethyl)phenol;
2-(6-((((2S,4S)-4-Fluoropyrrolidin-2-yl)methyl)amino) pyridazin-3-yl)-3-methyl-5-(trifluoro methyl)phenol;
2-(6-((((2S,4R)-4-Fluoropyrrolidin-2-yl)methyl)amino) pyridazin-3-yl)-3-methyl-5-(trifluoro methyl)phenol;
(rac)-3-Methyl-2-(6-(((4-methylmorpholin-3-yl)methyl) amino)pyridazin-3-yl)-5-(trifluoromethyl) phenol;
(S)-3-Methyl-2-(6-((3,3,3-trifluoro-2-hydroxy-2-methylpropyl)amino)pyridazin-3-yl)-5-(trifluoro methyl)phenol HCl-salt;
2-(6-((1-Hydroxy-2-methylpropan-2-yl)amino)pyridazin-3-yl)-3-methyl-5-(trifluoromethyl) phenol;
(R)-2-(6-((1-(2-Hydroxy-2-methylpropyl)piperidin-3-yl) amino)pyridazin-3-yl)-3-methyl-5-(trifluoromethyl)phenol;
2-(6-(((cis)-3-Hydroxy-3-methylcyclobutyl)amino)-4-methylpyridazin-3-yl)-5-(trifluoromethoxy) phenol;
(R)-2-(4-Methyl-6-((1-methylpiperidin-3-yl)amino) pyridazin-3-yl)-5-(trifluoromethoxy)phenol;
3-Methyl-2-(6-(((8R,8aR)-octahydroindolizin-8-yl)amino) pyridazin-3-yl)-5-(trifluoromethyl) phenol;
3-Methyl-2-(6-(((8S,8aS)-octahydroindolizin-8-yl)amino) pyridazin-3-yl)-5-(trifluoromethyl) phenol;
(R)-2-(6-(((1-(2-Hydroxyethyl)piperidin-2-yl)methyl) amino)pyridazin-3-yl)-3-methyl-5-(trifluoro methyl)phenol;
(S)-2-(6-(((1-(2-Hydroxyethyl)piperidin-2-yl)methyl) amino)pyridazin-3-yl)-3-methyl-5-(trifluoro methyl)phenol;
3-Methyl-2-(6-(((1S,2S,5S)-8-methyl-8-azabicyclo[3.2.1] octan-2-yl)amino)pyridazin-3-yl)-5-(trifluoromethyl) phenol;
3-Methyl-2-(6-(((1R,2R,5R)-8-methyl-8-azabicyclo[3.2.1] octan-2-yl)amino)pyridazin-3-yl)-5-(trifluoromethyl) phenol;
2-(6-(((1R,2R,5R)-8-(2-Hydroxyethyl)-8-azabicyclo[3.2.1] octan-2-yl)amino)pyridazin-3-yl)-3-methyl-5-(trifluoromethyl)phenol;
2-(6-(((1S,2S,5S)-8-(2-Hydroxyethyl)-8-azabicyclo[3.2.1] octan-2-yl)amino)pyridazin-3-yl)-3-methyl-5-(trifluoromethyl)phenol;
2-(6-(((3R,6R)-6-(Hydroxymethyl)-1-methylpiperidin-3-yl) amino)pyridazin-3-yl)-3-methyl-5-(trifluoromethyl)phenol;
2-(6-(((3S,6S)-6-(Hydroxymethyl)-1-methylpiperidin-3-yl) amino)pyridazin-3-yl)-3-methyl-5-(trifluoromethyl)phenol;
(S)-3-((6-(2-Hydroxy-6-methyl-4-(trifluoromethyl)phenyl) pyridazin-3-yl)amino)-2-methyl propane-1,2-diol;
(R)-3-((6-(2-Hydroxy-6-methyl-4-(trifluoromethyl)phenyl) pyridazin-3-yl)amino)-2-methyl propane-1,2-diol;
(1S,2R,3S)-3-((6-(2-Hydroxy-6-methyl-4-(trifluoromethyl) phenyl)pyridazin-3-yl)amino) cyclopentane-1,2-diol;
(1R,2S,3R)-3-((6-(2-Hydroxy-6-methyl-4-(trifluoromethyl) phenyl)pyridazin-3-yl)amino) cyclopentane-1,2-diol;
(S)-2-(6-((2-Hydroxy-3-methylbutyl)amino)pyridazin-3-yl)-3-methyl-5-(trifluoromethyl)phenol;
(R)-2-(6-((2-Hydroxy-3-methylbutyl)amino)pyridazin-3-yl)-3-methyl-5-(trifluoromethyl)phenol;
3-Methyl-2-(6-(((2S,3S)-2-methylpiperidin-3-yl)amino) pyridazin-3-yl)-5-(trifluoromethyl)phenol;
3-Methyl-2-(6-(((2R,3R)-2-methylpiperidin-3-yl)amino) pyridazin-3-yl)-5-(trifluoromethyl)phenol;
2-(6-(((R)-1-((S)-2-Hydroxypropyl)piperidin-3-yl)amino) pyridazin-3-yl)-3-methyl-5-(trifluoro methyl)phenol;
2-(6-(((R)-1-((R)-2-Hydroxypropyl)piperidin-3-yl)amino) pyridazin-3-yl)-3-methyl-5-(trifluoro methyl)phenol;
2-(6-(((3S,5S)-5-Fluoropiperidin-3-yl)amino)pyridazin-3-yl)-3-methyl-5-(trifluoromethyl)phenol;
2-(6-(((3R,5R)-5-Fluoropiperidin-3-yl)amino)pyridazin-3-yl)-3-methyl-5-(trifluoromethyl)phenol;
2-(6-(((3S,5S)-5-Fluoro-1-methylpiperidin-3-yl)amino) pyridazin-3-yl)-3-methyl-5-(trifluoro methyl)phenol;
2-(6-(((3R,5R)-5-Fluoro-1-methylpiperidin-3-yl)amino) pyridazin-3-yl)-3-methyl-5-(trifluoro methyl)phenol;
2-(6-(((3S,5R)-5-Fluoro-1-methylpiperidin-3-yl)amino) pyridazin-3-yl)-3-methyl-5-(trifluoro methyl)phenol;
2-(6-(((3R,5S)-5-Fluoro-1-methylpiperidin-3-yl)amino) pyridazin-3-yl)-3-methyl-5-(trifluoro methyl)phenol;
2-(6-(((3S,5R)-5-Fluoropiperidin-3-yl)amino)pyridazin-3-yl)-3-methyl-5-(trifluoromethyl)phenol;
2-(6-(((3R,5S)-5-Fluoropiperidin-3-yl)amino)pyridazin-3-yl)-3-methyl-5-(trifluoromethyl)phenol;
(3S,5R)-5-((6-(2-Hydroxy-6-methyl-4-(trifluoromethyl) phenyl)pyridazin-3-yl)amino)-1-methyl piperidin-3-ol;
2-(6-(((1-Hydroxycyclopentyl)methyl)amino)pyridazin-3-yl)-3-methyl-5-(trifluoromethyl)phenol;
5-((6-(2-Hydroxy-6-methyl-4-(trifluoromethyl)phenyl)-4-methylpyridazin-3-yl)amino)-1-methyl piperidin-2-one;
(R)-3-Methyl-2-(5-methyl-6-(piperidin-3-ylamino) pyridazin-3-yl)-5-(trifluoromethyl)phenol;
(R)-2-(6-((1-Ethylpiperidin-3-yl)amino)-5-methylpyridazin-3-yl)-3-methyl-5-(trifluoromethyl)-phenol;
(R)-3-((6-(2-Hydroxy-6-methyl-4-(trifluoromethyl)phenyl)-4-methylpyridazin-3-yl)amino)-1-methylpiperidin-2-one;
4-(2-((6-(2-Hydroxy-4,6-dimethylphenyl)pyridazin-3-yl) amino)ethyl)benzenesulfonamide;
(3R)-3-((6-(2-Hydroxy-6-methyl-4-(trifluoromethyl)phenyl)-4-methylpyridazin-3-yl)amino)-1-methylpiperidine 1-oxide TFA-salt;
or a pharmaceutically acceptable salt thereof.

In embodiment 11b, the invention relates to a compound of formula (I), or a pharmaceutically acceptable salt thereof, according to embodiment 1, wherein the compound is 3-methyl-2-(5-methyl-6-((1-methylpiperidin-3-yl)amino) pyridazin-3-yl)-5-(trifluoromethyl) phenol, or a pharmaceutically acceptable salt thereof. In one example, the compound is (S)-3-methyl-2-(5-methyl-6-((1-methylpiperidin-3-yl)amino)pyridazin-3-yl)-5-(trifluoromethyl)phenol, or a pharmaceutically acceptable salt thereof. In a preferred example, the compound is (R)-3-methyl-2-(5-methyl-6-((1- methylpiperidin-3-yl)amino)pyridazin-3-yl)-5-(trifluoromethyl)phenol, or a pharmaceutically acceptable salt thereof.

In embodiment 11c, the invention relates to a compound of formula (I), or a pharmaceutically acceptable salt thereof, according to embodiment 1, wherein the compound is 2-(4-methyl-6-((1-methylpiperidin-3-yl)amino)pyridazin-3-yl)-5-(trifluoromethyl)phenol, or a pharmaceutically acceptable salt thereof. In one example, the compound is (S)-2-(4-methyl-6-((1-methylpiperidin-3-yl)amino)pyridazin-3-yl)-5-(trifluoromethyl)phenol, or a pharmaceutically acceptable salt thereof. In a preferred example, the compound is (R)-2-(4-methyl-6-((1-methylpiperidin-3-yl)amino)pyridazin-3-yl)-5-(trifluoromethyl)phenol, or a pharmaceutically acceptable salt thereof.

In embodiment 11d, the invention relates to a compound of formula (I), or a pharmaceutically acceptable salt thereof, according to embodiment 1, wherein the compound is 2-(6-((1-ethylpiperidin-3-yl)amino)pyridazin-3-yl)-3-methyl-5-(trifluoromethyl)phenol, or a pharmaceutically acceptable salt thereof. In one example, the compound is (S)-2-(6-((1-ethylpiperidin-3-yl)amino)pyridazin-3-yl)-3-methyl-5-(trifluoromethyl)phenol, or a pharmaceutically acceptable salt thereof. In a preferred example, the compound is (R)-2-(6-((1-ethylpiperidin-3-yl)amino)pyridazin-3-yl)-3-methyl-5-(trifluoromethyl)phenol, or a pharmaceutically acceptable salt thereof.

In embodiment IIe, the invention relates to a compound of formula (I), or a pharmaceutically acceptable salt thereof, according to embodiment 1, wherein the compound is 2-(6-((3-hydroxy-3-methylcyclobutyl)amino)pyridazin-3-yl)-3-methyl-5-(trifluoromethyl) phenol, or a pharmaceutically acceptable salt thereof. In one example, the compound is 2-(6-(((trans)-3-hydroxy-3-methylcyclobutyl)amino)pyridazin-3-yl)-3-methyl-5-(trifluoromethyl) phenol, or a pharmaceutically acceptable salt thereof. In a preferred example, the compound is 2-(6-(((cis)-3-hydroxy-3-methylcyclobutyl)amino)pyridazin-3-yl)-3-methyl-5-(trifluoro methyl) phenol, or a pharmaceutically acceptable salt thereof.

In embodiment 11f, the invention relates to a compound of formula (I), or a pharmaceutically acceptable salt thereof, according to embodiment 1, wherein the compound is 2-(6-((3-hydroxycyclohexyl)amino)pyridazin-3-yl)-3-methyl-5-(trifluoromethyl)phenol, or a pharmaceutically acceptable salt thereof. In one example, the compound is 2-(6-(((1S,3R)-3-hydroxycyclohexyl)amino)pyridazin-3-yl)-3-methyl-5-(trifluoromethyl)phenol, or a pharmaceutically acceptable salt thereof. In one example, the compound is 2-(6-(((1R,3R)-3-hydroxycyclohexyl)amino)pyridazin-3-yl)-3-methyl-5-(trifluoromethyl)phenol, or a pharmaceutically acceptable salt thereof. In one example, the compound is 2-(6-(((1S,3S)-3-hydroxycyclohexyl)amino)pyridazin-3-yl)-3-methyl-5-(trifluoromethyl)phenol, or a pharmaceutically acceptable salt thereof. In a preferred example, the compound is 2-(6-(((1R,3S)-3-hydroxycyclohexyl)amino)pyridazin-3-yl)-3-methyl-5-(trifluoromethyl)phenol, or a pharmaceutically acceptable salt thereof.

In embodiment 11 g, the invention relates to a compound of formula (I), or a pharmaceutically acceptable salt thereof, according to embodiment 1, wherein the compound is 5-((6-(2-hydroxy-6-methyl-4-(trifluoromethyl)phenyl)pyridazin-3-yl)amino)-1-methylpiperidin-3-ol, or a pharmaceutically acceptable salt thereof. In one example, the compound is (3R,5S)-5-((6-(2-hydroxy-6-methyl-4-(trifluoromethyl)phenyl)pyridazin-3-yl)amino)-1-methylpiperidin-3-ol, or a pharmaceutically acceptable salt thereof. In one example, the compound is (3R,5R)-5-((6-(2-hydroxy-6-methyl-4-(trifluoromethyl)phenyl)pyridazin-3-yl)amino)-1-methylpiperidin-3-ol, or a pharmaceutically acceptable salt thereof. In one example, the compound is (3S,5S)-5-((6-(2-hydroxy-6-methyl-4-(trifluoromethyl)phenyl)pyridazin-3-yl)amino)-1-methylpiperidin-3-ol, or a pharmaceutically acceptable salt thereof. In a preferred example, the compound is (3S,5R)-5-((6-(2-hydroxy-6-methyl-4-(trifluoromethyl)phenyl)pyridazin-3-yl)amino)-1-methylpiperidin-3-ol, or a pharmaceutically acceptable salt thereof.

In embodiment 12, the invention relates to a pharmaceutical composition comprising a therapeutically effective amount of a compound of any one of the formula (I), (II), (III), and (III-A), or a pharmaceutically acceptable salt thereof, according to any one of embodiments 1 to 11 g, and one or more pharmaceutically acceptable carriers.

In embodiment 13, the invention relates to a combination comprising a therapeutically effective amount of a compound of any one of formula (I), (II), (III), and (III-A), or a pharmaceutically acceptable salt thereof, according to any one of embodiments 1 to 11 g, and one or more therapeutic agents.

In embodiment 14, the invention relates to a combination comprising a therapeutically effective amount of a compound of any one of formula (I), (II), (III), and (III-A), or a pharmaceutically acceptable salt thereof, according to embodiment 13, wherein one or more therapeutic agents are independently selected from farnesoid X receptor (FXR) agonists; anti-steatotics; anti-fibrotics; JAK inhibitors; checkpoint inhibitors including anti-PD1 inhibitors, anti-LAG-3 inhibitors, anti-TIM-3 inhibitors, or anti-PDL1 inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA) including aspirin; paracetamol; regenerative therapy treatments; cystic fibrosis treatments; or atherosclerotic treatment.

In one embodiment, the invention relates to a method of inhibiting NLRP3 activity in a subject, comprising administering to the subject a therapeutically effective amount of a compound of formula (I), (II), (III), or (III-A), or a pharmaceutically acceptable salt thereof, according to any one of embodiments 1, 2, 3, 3a, 4, 5, 5a-5e, 6, 6a-6c, 7, 7a-7d, 8, 8a, 9, 9a-9b, 10, 10a, 11, 11a-11 g, 12, 13, and 14.

In embodiment 15, the invention relates to a compound of any one of formula (I), (II), (III), and (III-A), or a pharmaceutically acceptable salt thereof, according to any one of embodiments 1 to 11 g, or a combination according to any one of embodiments 13 to 14, for use as a medicament. In particular, the invention relates to a compound of any one of formula (I), (II), (III), and (III-A), or a pharmaceutically acceptable salt thereof, according to any one of embodiments 1 to 11 g, for use as a medicament. In particular, the invention relates to a compound of any one of formula (I), (II), (III), and (III-A), or a pharmaceutically acceptable salt thereof, according to any one of embodiments 1 to 11 g, for use as a medicament for inhibiting NLRP3 pathway. In another particular embodiment, the invention relates to a combination according to any one of embodiments 13 to 14, for use as a medicament.

In embodiment 16, the invention relates to a compound according to any one of formula (I), (II), (III), and (III-A), or a pharmaceutically acceptable salt thereof, according to any one of embodiments 1 to 11 g, for use in the treatment of a disease or disorder in which the NLRP3 signaling contributes to the pathology, and/or symptoms, and/or progression, of said disease or disorder.

In embodiment 17, the invention relates to a method of treating a disease or disorder in which the NLRP3 signaling contributes to the pathology, and/or symptoms, and/or progression, of said disease or disorder, comprising administering a therapeutically effective amount of a compound according to any one of formula (I), (II), (III), and (III-A), or a pharmaceutically acceptable salt thereof, according to any one of embodiments 1 to 11 g.

In embodiment 18, the invention relates to a compound of any one of formula (I), (II), (III), and (III-A), or a pharmaceutically acceptable salt thereof, according to any one of embodiments 1 to 11 g, for use according to embodiment 16, or to the method of treating according to embodiment 17, wherein the disease or disorder is selected from inflammasome-related diseases/disorders, immune diseases, inflammatory diseases, auto-immune diseases, or auto-inflammatory diseases, for example, autoinflammatory fever syndromes (e.g cryopyrin-associated periodic syndrome), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukaemia, myelodysplastic syndromes (MDS), myelofibrosis). In a particular aspect of embodiment 16, the invention relates to a compound of any one of formula (I), (II), (III), and (III-A), or a pharmaceutically acceptable salt thereof, wherein the disease or disorder is preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In one embodiment, the invention relates to a compound of any one of formula (I), (II), (III), and (III-A), or a pharmaceutically acceptable salt thereof, according to any one of embodiments 1 to 11 g, for use in the treatment of a disease or disorder selected from inflammasome-related diseases/disorders, immune diseases, inflammatory diseases, auto-immune diseases, or auto-inflammatory diseases, for example, autoinflammatory fever syndromes (e.g cryopyrin-associated periodic syndrome), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis).

In a particular aspect of embodiment 18, the invention relates to a compound of any one of formula (I), (II), (III), and (III-A), or a pharmaceutically acceptable salt thereof, wherein the disease or disorder is preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In embodiment 19, the invention relates to a method of inhibiting the NLRP3 inflammasome activity in a subject in need thereof, the method comprising administering to a subject in need thereof a therapeutically effective amount of a compound of any one of formula (I), (II), (III), and (III-A), or a pharmaceutically acceptable salt thereof, according to any one of embodiments 1 to 11 g.

In one embodiment, the invention relates to a method of inhibiting NLRP3 activity in a subject, wherein the method comprises administering to the subject a therapeutically effective amount of a compound of any one of formula (I), (II), (III), and (III-A), or a pharmaceutically acceptable salt thereof, according to any one of embodiments 1, 2, 3, 3a, 4, 5, 5a-5e, 6, 6a-6c, 7, 7a-7d, 8, 8a, 9, 9a-9b, 10, 10a, 11, 11a-11 g, 12, 13, and 14.

In one embodiment, the invention relates to a method of treating a disease or disorder selected from inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, acute or chronic arthropathy, kidney related diseases (e.g. hyperoxaluria, lupus nephritis, diabetic nephropathy, hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis), wherein the method comprises administering to the subject a therapeutically effective amount of a compound of any one of formula (I), (II), (III), and (III-A), or a pharmaceutically acceptable salt thereof, according to any one of embodiments 1, 2, 3, 3a, 4, 5, 5a-5e, 6, 6a-6c, 7, 7a-7d, 8, 8a, 9, 9a-9b, 10, 10a, 11, 11a-11 g, 12, 13, and 14. In particular the disease or disorder is preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diastereoisomeric mixtures, and optically pure forms. Optically active (R)- and (S)-stereoisomers may be prepared using chiral synthons or chiral reagents, or resolved using conventional techniques. If the compound contains a disubstituted cycloalkyl, the cycloalkyl substituent may have a cis- or trans-configuration. All tautomeric forms are also intended to be included. The invention is also meant to include any pseudo-asymmetric carbon atom, represented herein as (r)- and (s)-, and which are invariant on reflection in a mirror but are reversed by exchange of any two entities, (PAC 1996, 68, 2193, *Basic terminology of stereochemistry IUPAC recommandations* 1996).

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups, or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of any one of formula (I), (II), (III), and (III-A) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate, or xinafoate salt form.

In another aspect, the present invention provides compounds of any one of formula (I), (II), (III), and (III-A) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

In another aspect, the invention provides a compound of formula (I),

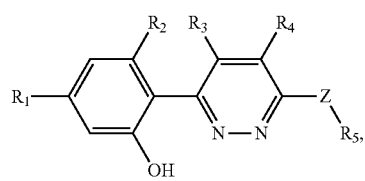

(I)

or a pharmaceutically acceptable salt thereof, as defined herein, wherein when $R^5$ is selected from the following:

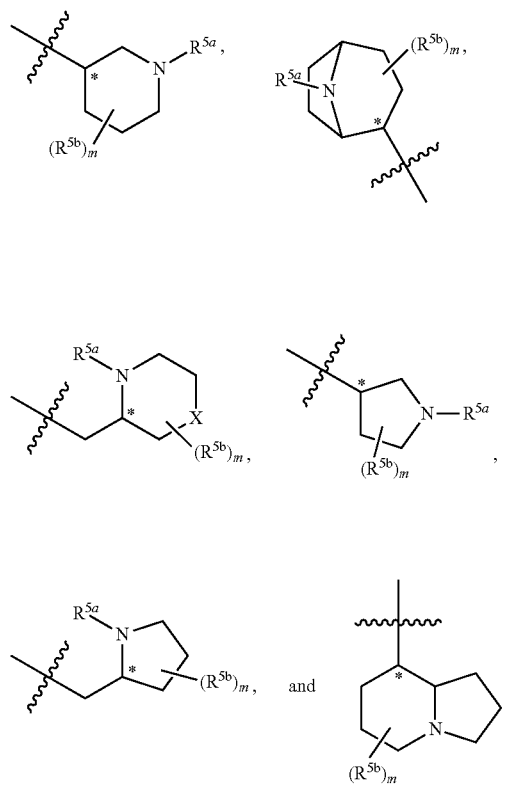

wherein $R^{5a}$, $R^{5b}$, X and m are as defined in embodiment 5, 5a-5e, and one or more hydrogen atoms present in $R^{5a}$ and/or $R^{5b}$ can be replaced with a deuterium atom (including $R^{5a}$ or $R^{5b}$ being a deuterium atom). For example, but not limited to, the deuterium can be incorporated as follows:

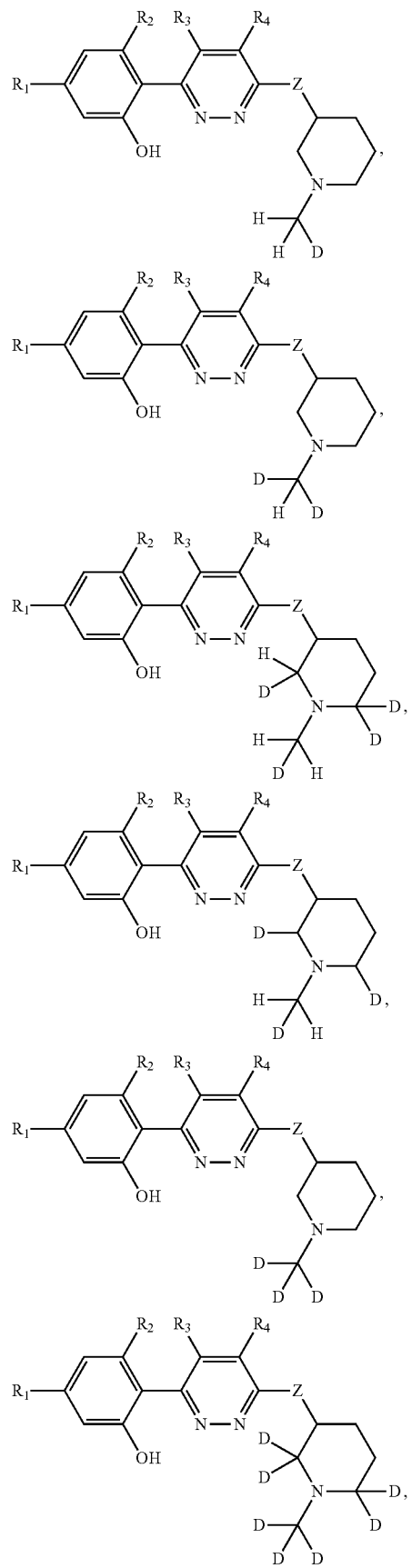

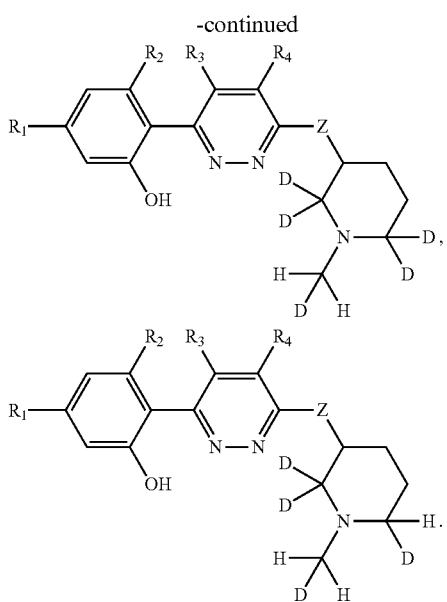

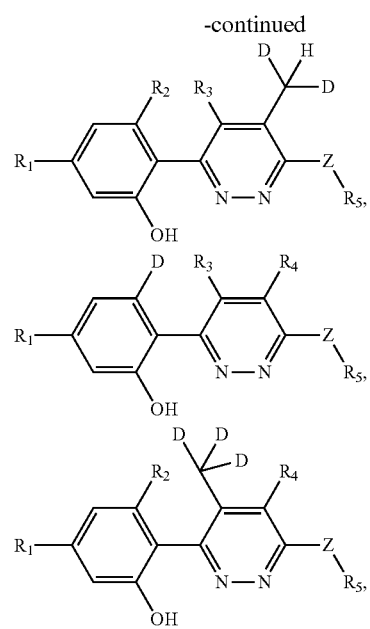

In another aspect, the invention provides a compound of formula (I),

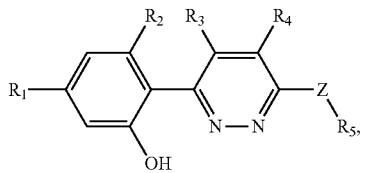

(I)

or a pharmaceutically acceptable salt thereof, as defined herein, wherein when $R^2$, $R^3$, $R^4$ are selected from the following H, $C_1$-$C_4$alkyl, or halo$C_1$-$C_4$alkyl, one or more hydrogen atoms present on said groups can be replaced with a deuterium atom. For example, but not limited to, the deuterium can be incorporated as follows:

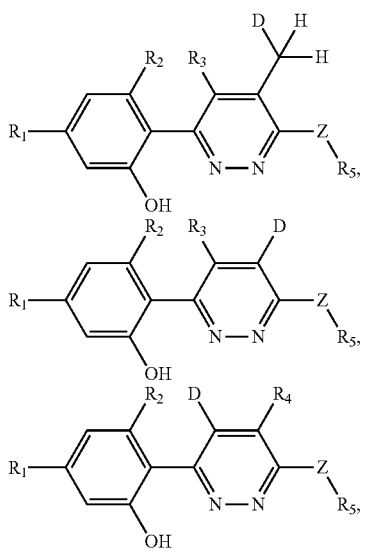

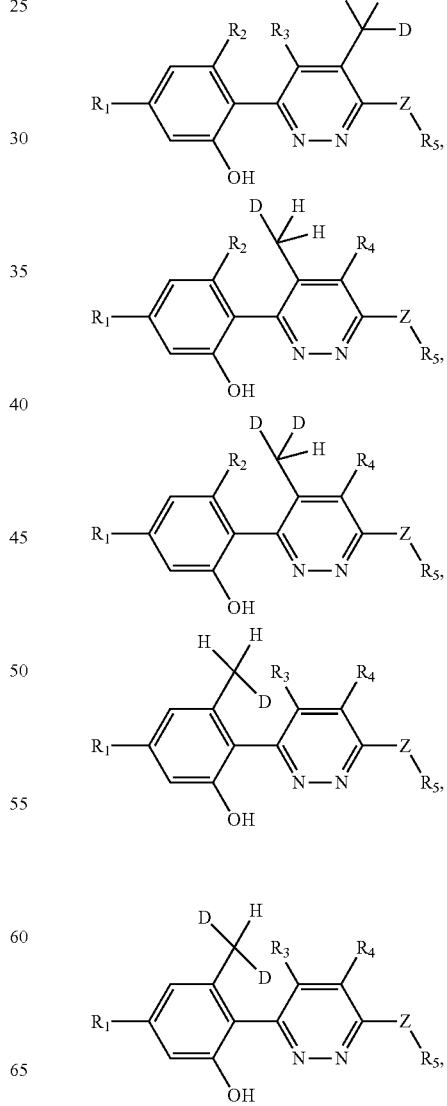

-continued

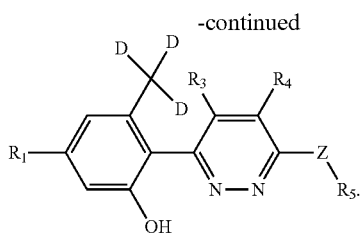

Other examples of isotopes that can be incorporated into compounds of the invention include isotopes of hydrogen, carbon, nitrogen, oxygen, phosphorous, fluorine, chlorine, and iodine, such as $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$, respectively. Accordingly, it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I), or a pharmaceutically acceptable salt thereof, can generally be prepared by conventional techniques known to those skilled in the art or by processes analogous to those described in the accompanying Examples and Preparations using an appropriate isotopically-labeled reagents in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by NLRP3, or (ii) associated with NLRP3 activity, or (iii) characterized by activity (normal or abnormal) of NLRP3; or (2) reduce or inhibit the activity of NLRP3; or (3) reduce or inhibit the expression of NLRP3. In another non-limiting embodiment, the term "a therapeutically effective amount" of a compound of the present invention refers to the amount that when administered to a cell, or a tissue, or a non-cellular biological material, or a medium, is effective to at least partially reduce or inhibit the activity of NLRP3; or at least partially reduce or inhibit the expression of NLRP3.

As used herein, the term "subject" refers to primates (e.g., humans, male or female), dogs, rabbits, guinea pigs, pigs, rats and mice. In certain embodiments, the subject is a primate. In yet another embodiment, the subject is a human.

As used herein, the term "inhibit", "inhibition" or "inhibiting" refers to the reduction or suppression of a given condition, symptom, or disorder, or disease, or a significant decrease in the baseline activity of a biological activity or process. Specifically, inhibiting NLRP3 or inhibiting NLRP3 inflammasome pathway comprises reducing the ability of NLRP3 or NLRP3 inflammasome pathway to induce the production of IL-1 beta and/or IL-18. This can be achieved by mechanisms, including, but not limited to, inactivating, destabilizing, and/or altering distribution of NLRP3.

As used herein, the term "NLRP3" is meant to include, without limitation, nucleic acids, polynucleotides, oligonucleotides, sense and anti-sense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, a subject is "in need of" or "in need thereof" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates, or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) using a chiral adsorbent.

Method of Synthesizing the Compounds of the Invention

The compounds of the present invention may be prepared in accordance to the definition of compound of formula (I), or a pharmaceutically acceptable salt thereof, by the routes described in the following Schemes or the Examples. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. In the following general methods, $R^1$, $R^2$, $R^3$, $R^4$, $R^5$, halo and Z are as previously defined in the above embodiments, or limited to designations in the Schemes. Unless otherwise stated, starting materials are either commercially available or are prepared by known methods.

Reaction Scheme 1

Compounds of the present invention, as described herein, may be prepared by a reaction sequence shown in Scheme 1 (below), whereby an appropriately substituted 3,6-dihalopyridazine (M1) is either reacted with an appropriate amine (M2a) in the presence of a base, e.g. DIPEA, at elevated temperatures, typically between 150° C. and 180° C. (optionally under microwave irradiation), to give 6-halopyridazine-3 amine (M3a), or with an appropriate alcohol (M2b) in the presence of a base, e.g. NaH, at low temperature, typically 0° C., to give 3-halo-6-alkoxypyridazine (M3b). Both intermediates, (M3a) or (M3b) are then subjected to a Suzuki-type cross coupling reaction with the appropriate boronate (M4) in the form of a boronic acid or boronic ester, e.g. 4,4,5,5-tetramethyl-1,3,2-dioxaborolan, using a suitable palladium catalyst, e.g. Pd(PPh$_3$)$_4$, and an aqueous base, typically Na$_2$CO$_3$ or NaHCO$_3$, in a miscible solvent such as DME or dioxane to provide a compound of formula (I), or a pharmaceutically acceptable salt thereof.

Scheme 1

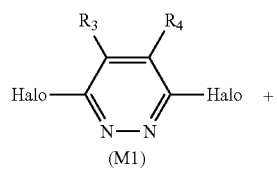

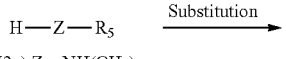

(M2a) Z = NH(CH$_2$)n
(M2b) Z = O

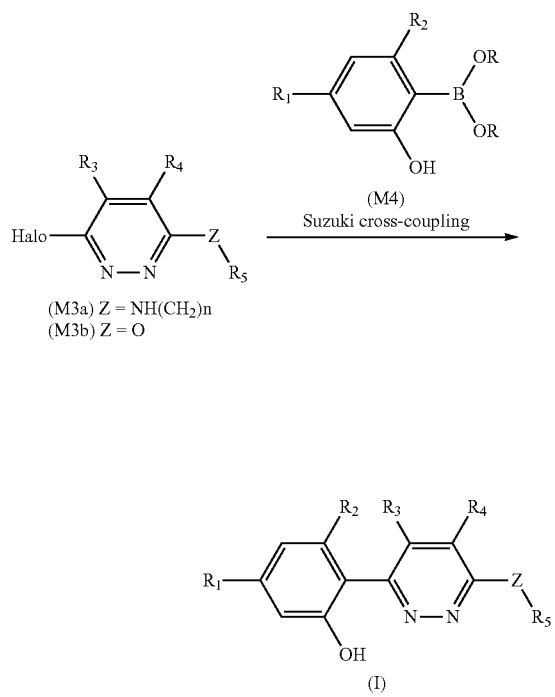

(M3a) Z = NH(CH$_2$)n
(M3b) Z = O (M4)

Reaction Scheme 2

Alternatively, compounds of the present invention, as described herein, may be prepared by a reaction sequence shown in Scheme 2 (below), whereby an appropriately substituted 3,6-dihalopyridazine (M1) is subjected to a Suzuki-type cross coupling reaction with either an appropriate boronate (M4) in the form of boronic acid or boronic ester, e.g. 4,4,5,5-tetramethyl-1,3,2-dioxaborolan (Path A), using a suitable palladium catalyst, e.g. Pd(PPh$_3$)$_4$ or XantPhos-Pd-G2, and an aqueous base, typically Na$_2$CO$_3$ or NaHCO$_3$, in a miscible solvent, such as DME or dioxane, to give 3-halo-pyridazine (M5), or is reacted in the same way with a boronate (M6), carrying a phenol protecting group P, such as methyl or benzyl, (Path B), to provide a compound of formula 3-halo-pyridazine (M7). Intermediate (M5) is then reacted with an appropriate amine (M2a) in the presence of a base, e.g. DIPEA, at elevated temperatures typically, between 150° C. and 180° C. (optionally under microwave irradiation), to provide a compound of formula (I), or a pharmaceutically acceptable salt thereof, whereas intermediate (M7), treated in the same manner, gives the protected form (M8), which is further subjected to typical cleaving treatments, such as BBr$_3$, or catalytic hydrogenation to provide a compound of formula (I), or a pharmaceutically acceptable salt thereof.

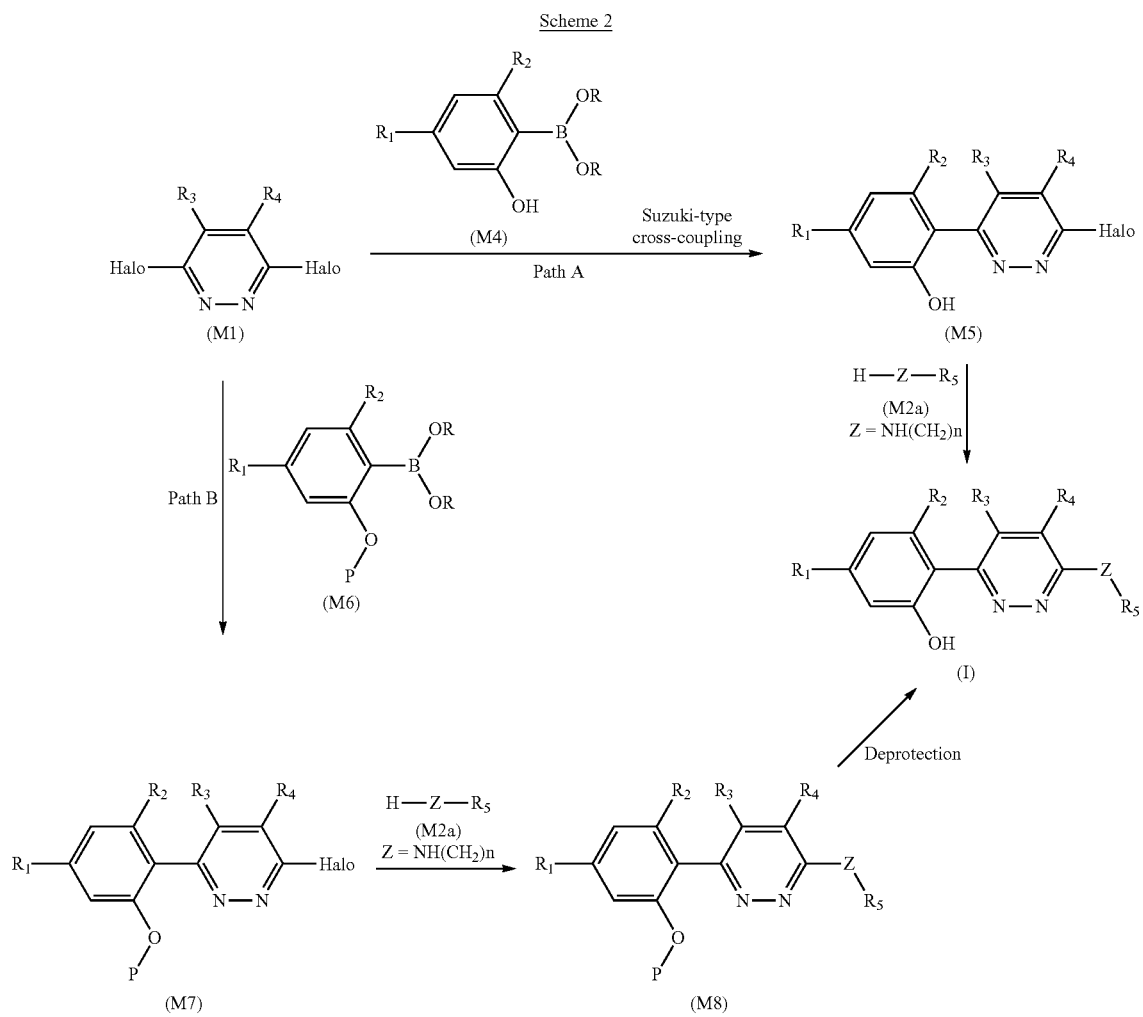

Reaction Scheme 3

Alternatively, compounds of the present invention, as described herein, may be prepared by a reaction sequence shown in Scheme 3 (below), whereby an appropriately substituted intermediate (M5) is subjected to a Buchwald-type amination reaction with an appropriate amine (M2a) in the presence of a suitable palladium catalyst, e.g. $PdCl_2$(dppf), and a base, typically LiOtBu, in a non-protic solvent, such as toluene, to provide a compound of formula (I), or a pharmaceutically acceptable salt thereof.

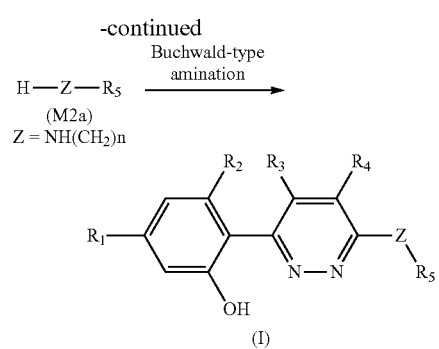

Scheme 3

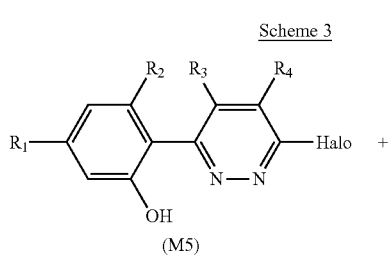

The processes can be extended to prepare a compound of any one of formula (I), (II), (III), and (III-A), or a pharmaceutically acceptable salt thereof, as described herein. Depending on the starting materials and the selected route, as mentioned in Scheme 1, Scheme 2, or Scheme 3, above, a skilled person in the art would know how to prepare compound of formula (I), or a pharmaceutically acceptable salt thereof. Certain variants or alternative processes are described herein below in the experimental section.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) Diluents, e.g., lactose, dextrose, sucrose, mannitol, sorbitol, cellulose and/or glycine;
b) Lubricants, e.g., silica, talcum, stearic acid, its magnesium or calcium salt and/or polyethyleneglycol; for tablets also
c) Binders, e.g., magnesium aluminum silicate, starch paste, gelatin, tragacanth, methylcellulose, sodium carboxymethylcellulose and/or polyvinylpyrrolidone; if desired
d) Disintegrants, e.g., starches, agar, alginic acid or its sodium salt, or effervescent mixtures; and
e) Absorbents, colorants, flavours and sweeteners.

Method of Use of the Invention

There is evidence for a role of NLRP3-induced IL-1 and IL-18 in the inflammatory responses occurring in connection with, or as a result of, a multitude of different disorders (Menu et al, *Clinical and Experimental Immunology*, 2011, 166, 1-15; Strowig et al, *Nature*, 2012, 481, 278-286). NLRP3 mutations have been found to be responsible for a set of rare autoinflammatory diseases known as CAPS (Ozaki et al, *J. Inflammation Research*, 2015, 8, 15-27; Schroder et al, *Cell*, 2010, 140:821-832; Menu et al, *Clinical and Experimental Immunology*, 2011, 166, 1-15). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1 beta. NLRP3 has also been implicated in a number of autoinflammatory diseases, including pyogenic arthritis, pyoderma gangrenosum and acne (PAPA), Sweet's syndrome, chronic nonbacterial osteomyelitis (CNO), and acne vulgaris (Cook et al, *Eur. J. Immunol.*, 2010, 40, 595-653).

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Braddock et al. *Nat. Rev. Drug Disc.* 2004, 3, 1-10; Inoue et al., *Immunology*, 2013, 139, 11-18, Coll et al, *Nat. Med.* 2015, 21(3), 248-55; Scott et al, *Clin. Exp. Rheumatol.* 2016, 34(1), 88-93), systemic lupus erythematosus and its complications such as lupus nephritis (Lu et al, *J. Immunol.*, 2017, 198(3), 1119-29), and systemic sclerosis (Artlett et al, *Arthritis Rheum.* 2011, 63(11), 3563-74). NLRP3 has also been shown to play a role in a number of lung diseases including chronic obstructive pulmonary disorder (COPD), asthma (including steroid-resistant asthma), asbestosis, and silicosis (De Nardo et al, *Am. J. Pathol.*, 2014, 184: 42-54; Kim et al. *Am. J. Respir. Crit. Care Med*, 2017, 196(3), 283-97). NLRP3 has also been suggested to have a role in a number of central nervous system conditions, including Multiple Sclerosis (MS), Parkinson's disease (PD), Alzheimer's disease (AD), dementia, Huntington's disease, cerebral malaria, brain injury from pneumococcal meningitis (Walsh et al, *Nature Reviews*, 2014, 15, 84-97; and Dempsey et al. *Brain. Behav. Immun.* 2017, 61, 306-16), intracranial aneurysms (Zhang et al. *J. Stroke and Cerebrovascular Dis.*, 2015, 24, 5, 972-9), and traumatic brain injury (Ismael et al. *J. Neurotrauma.*, 2018, 35(11), 1294-1303). NRLP3 activity has also been shown to be involved in various metabolic diseases including type 2 diabetes (T2D) and its organ-specific complications, atherosclerosis, obesity, gout, pseudo-gout, metabolic syndrome (Wen et al, *Nature Immunology*, 2012, 13, 352-357; Duewell et al, *Nature*, 2010, 464, 1357-1361; Strowig et al, *Nature*, 2014, 481, 278-286), and non-alcoholic steatohepatitis (Mridha et al. *J. Hepatol.* 2017, 66(5), 1037-46). A role for NLRP3 via IL-1 beta has also been suggested in atherosclerosis, myocardial infarction (van Hout et al. *Eur. Heart J.* 2017, 38(11), 828-36), heart failure (Sano et al. *J. Am. Coll. Cardiol.* 2018, 71(8), 875-66), aortic aneurysm and dissection (Wu et al. *Arterioscler. Thromb. Vasc. Biol.*, 2017, 37(4), 694-706), and other cardiovascular events (Ridker et al., *N. Engl. J. Med.*, 2017, 377(12), 1119-31).

Other diseases in which NLRP3 has been shown to be involved include: ocular diseases such as both wet and dry age-related macular degeneration (Doyle et al. *Nature Medicine*, 2012, 18, 791-798; Tarallo et al. *Cell* 2012, 149(4), 847-59), diabetic retinopathy (Loukovaara et al. *Acta Ophthalmol.*, 2017, 95(8), 803-8), non-infectious uveitis and optic nerve damage (Puyang et al. *Sci. Rep.* 2016, 6, 20998); liver diseases including non-alcoholic steatohepatitis (NASH) and acute alcoholic hepatitis (Henao-Meija et al, *Nature*, 2012, 482, 179-185); inflammatory reactions in the lung and skin (Primiano et al. *J. Immunol.* 2016, 197(6), 2421-33) including contact hypersensitivity (such as bullous pemphigoid (Fang et al. *J Dermatol Sci.* 2016, 83(2), 116-23)), atopic dermatitis (Niebuhr et al. *Allergy*, 2014, 69(8), 1058-67), Hidradenitis suppurativa (Alikhan et al. *J. Am. Acad. Dermatol.*, 2009, 60(4), 539-61), and sarcoidosis (Jager et al. *Am. J. Respir. Crit. Care Med.*, 2015, 191, A5816); inflammatory reactions in the joints (Braddock et al, *Nat. Rev. Drug Disc*, 2004, 3, 1-10); amyotrophic lateral sclerosis (Gugliandolo et al. *Int. J. Mol. Sci.*, 2018, 19(7), E1992); cystic fibrosis (Iannitti et al. *Nat. Commun.*, 2016, 7, 10791); stroke (Walsh et al, *Nature Reviews*, 2014, 15, 84-97); chronic kidney disease (Granata et al. *PLoS One* 2015, 10(3), eoi22272); and inflammatory bowel diseases including ulcerative colitis and Crohn's disease (Braddock et al., *Nat. Rev. Drug Disc*, 2004, 3, 1-10; Neudecker et al.

*J. Exp. Med.* 2017, 214(6), 1737-52; Lazaridis et al. *Dig. Dis. Sci.* 2017, 62(9), 2348-56). The NLRP3 inflammasome has been found to be activated in response to oxidative stress. NLRP3 has also been shown to be involved in inflammatory hyperalgesia (Dolunay et al, *Inflammation,* 2017, 40, 366-86).

Activation of the NLRP3 inflammasome has been shown to potentiate some pathogenic infections such as influenza and Leishmaniasis (Tate et al., *Sci Rep.,* 2016, 10(6), 27912-20; Novias et al., *PLOS Pathogens* 2017, 13(2), e1006196).

NLRP3 has also been implicated in the pathogenesis of many cancers (Menu et al, *Clinical and Experimental Immunology,* 2011, 166,1-15). For example, several previous studies have suggested a role for IL-1 beta in cancer invasiveness, growth and metastasis, and inhibition of IL-1 beta with canakinumab has been shown to reduce the incidence of lung cancer and total cancer mortality in a randomised, double-blind, placebo-controlled trial (Ridker et al. *Lancet.,* 2017, 390(10105), 1833-42). Inhibition of the NLRP3 inflammasome or IL-1 beta has also been shown to inhibit the proliferation and migration of lung cancer cells in vitro (Wang et al. *Oncol Rep.,* 2016, 35(4), 2053-64). A role for the NLRP3 inflammasome has been suggested in myelodysplastic syndromes, myelofibrosis and other myeloproliferative neoplasms, and acute myeloid leukemia (AML) (Basiorka et al. *Blood,* 2016, 128(25), 2960-75.) and also in the carcinogenesis of various other cancers including glioma (Li et al. *Am. J. Cancer Res.* 2015, 5(1), 442-9), inflammation-induced tumors (Allen et al. *J. Exp. Med.* 2010, 207(5), 1045-56; Hu et al. *PNAS.,* 2010, 107(50), 21635-40), multiple myeloma (Li et al. *Hematology,* 2016 21(3), 144-51), and squamous cell carcinoma of the head and neck (Huang et al. *J. Exp. Clin. Cancer Res.,* 2017, 36(1), 116). Activation of the NLRP3 inflammasome has also been shown to mediate chemoresistance of tumor cells to 5-Fluorouracil (Feng et al. *J. Exp. Clin. Cancer Res.,* 2017, 36(1), 81), and activation of NLRP3 inflammasome in peripheral nerve contributes to chemotherapy-induced neuropathic pain (Jia et al. *Mol. Pain.,* 2017, 13, 1-11). NLRP3 has also been shown to be required for the efficient control of viruses, bacteria, and fungi.

The activation of NLRP3 leads to cell pyroptosis and this feature plays an important part in the manifestation of clinical disease (Yan-gang et al., *Cell Death and Disease,* 2017, 8(2), 2579; Alexander et al., *Hepatology,* 2014, 59(3), 898-910; Baldwin et al., *J. Med. Chem.,* 2016, 59(5), 1691-1710; Ozaki et al., *J. Inflammation Research,* 2015, 8, 15-27; Zhen et al., *Neuroimmunology Neuroinflammation,* 2014, 1(2), 60-65; Mattia et al., *J. Med. Chem.,* 2014, 57(24), 10366-82; Satoh et al., *Cell Death and Disease,* 2013, 4, 644). Therefore, it is anticipated that inhibitors of NLRP3 will block pyroptosis, as well as the release of pro-inflammatory cytokines (e.g. IL-1 beta) from the cell.

The compounds of any one of formula (I), (II)(III), and (III-A), or a compound according to any one of the preceding embodiments, or a compound according to any one of the exemplified examples (e.g. Ex 001 to Ex 104 as disclosed herein), in free form or in pharmaceutically acceptable salt form, exhibit valuable pharmacological properties, e.g. NRLP3 inhibiting properties on the NLRP3 pathway, e.g. as indicated by in vitro tests as provided in the next section, and are therefore indicated for therapy or for use as research chemicals, e.g. as tool compounds.

Compounds of the invention may be useful in the treatment of an indication selected from: inflammasome-related disease/disorders, immune diseases, inflammatory diseases, auto-immune diseases, or auto-inflammatory diseases, for example, of diseases, disorders or conditions in which NLRP3 signaling contributes to the pathology, and/or symptoms, and/or progression, and which may be responsive to NLRP3 inhibition and which may be treated or prevented, according to any one of embodiments 1 to 19, or a compound according to any one of the exemplified examples (e.g. Ex 001 to Ex 104 as disclosed herein), of the present invention include:

I. Inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity. Examples of inflammation that may be treated or prevented include inflammatory responses occurring in connection with, or as a result of:

(a) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(b) a joint condition such as osteoarthritis, systemic juvenile idiopathic arthritis, adult-onset Still's disease, relapsing polychondritis, rheumatoid arthritis, juvenile chronic arthritis, crystal induced arthropathy (e.g. pseudo-gout, gout), or a seronegative spondyloarthropathy (e.g. ankylosing spondylitis, psoriatic arthritis or Reiter's disease);

(c) a muscular condition such as polymyositis or myasthenia gravis;

(d) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(e) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(f) a vascular condition such as atherosclerosis, Behcet's disease, vasculitides, or Wegener's granulomatosis;

(g) an immune condition, e.g. autoimmune condition, such as systemic lupus erythematosus (SLE), Sjogren's syndrome, systemic sclerosis, Hashimoto's thyroiditis, type I diabetes, idiopathic thrombocytopenia purpura, or Graves disease;

(h) an ocular condition such as uveitis, allergic conjunctivitis, or vernal conjunctivitis;

(i) a nervous condition such as multiple sclerosis or encephalomyelitis;

(j) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium*

*intracellulare, Pneumocystis carinii* pneumonia, orchitis/epidydimitis, *legionella*, Lyme disease, influenza A, epstein-barr virus, viral encephalitis/aseptic meningitis, or pelvic inflammatory disease;

(k) a renal condition such as mesangial proliferative glomerulonephritis, nephrotic syndrome, nephritis, glomerular nephritis, acute renal failure, uremia, or nephritic syndrome;

(l) a lymphatic condition such as Castleman's disease;

(m) a condition of, or involving, the immune system, such as hyper IgE syndrome, lepromatous leprosy, familial hemophagocytic lymphohistiocytosis, or graft versus host disease;

(n) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(o) a cancer, including those cancers listed herein below;

(p) a burn, wound, trauma, haemorrhage or stroke;

(q) radiation exposure; and/or (r) obesity; and/or (s) pain such as inflammatory hyperalgesia.

II. Inflammatory disease, including inflammation occurring as a result of an inflammatory disorder, e.g. an autoinflammatory disease, such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

III. Immune diseases, e.g. auto-immune diseases, such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjogren's syndrome, systemic sclerosis a systemic connective tissue disorder, Takayasu's arteritis, temporal arteritis, warm autoimmune hemolytic anemia, Wegener's granulomatosis, alopecia universalis, Beliefs disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, giant cell arteritis, vitiligo or vulvodynia;

IV. Cancer including lung cancer, renal cell carcinoma, non-small cell lung carcinoma (NSCLC), Langerhans cell histiocytosis (LCH), myeloproliferative neoplams (MPN), pancreatic cancer, gastric cancer, myelodysplastic syndrome (MDS), leukaemia including acute lymphocytic leukaemia (ALL) and acute myeloid leukaemia (AML), promyelocytic leukemia (APML, or APL), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

V. Infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxyiruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes), and prion infections;

VI. Central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, multiple sclerosis, and amyotrophic lateral sclerosis;

VII. Metabolic diseases such as type 2 diabetes (T2D), atherosclerosis, obesity, gout, and pseudo-gout;

VIII. Cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, cardiovascular risk reduction (CvRR), and pericarditis including Dressler's syndrome;

IX. Respiratory diseases including chronic obstructive pulmonary disorder (COPD), asthma such as allergic asthma and steroid-resistant asthma, asbestosis, silicosis, nanoparticle induced inflammation, cystic fibrosis, and idiopathic pulmonary fibrosis;

X. Liver diseases including non-alcoholic fatty liver disease (NAFLD) and nonalcoholic steatohepatitis (NASH) including advanced fibrosis stages F3 and F4, alcoholic fatty liver disease (AFLD), and alcoholic steatohepatitis (ASH);

XI. Renal diseases including acute kidney disease, hyperoxaluria, chronic kidney disease, oxalate nephropathy, nephrocalcinosis, glomerulonephritis, and diabetic nephropathy;

XII. Ocular diseases including those of the ocular epithelium, age-related macular degeneration (AMD) (dry and wet), uveitis, corneal infection, diabetic retinopathy, optic nerve damage, dry eye, and glaucoma;

XIII. Skin diseases including dermatitis such as contact dermatitis and atopic dermatitis, contact hypersensitivity, sunburn, skin lesions, hidradenitis suppurativa (HS), other cyst-causing skin diseases, and acne conglobata;

XIV. Lymphatic conditions such as lymphangitis, and Castleman's disease;

XV. Psychological disorders such as depression, and psychological stress;

XVI. Graft versus host disease;

XVII. Bone diseases including osteoporosis, osteopetrosis;

XVIII. Blood disease including sickle cell disease;

XVIX. Allodynia including mechanical allodynia; and

XVX. Any disease where an individual has been determined to carry a germline or somatic non-silent mutation in NLRP3.

More specifically the compounds of the invention may be useful in the treatment of an indication selected from: inflammasome-related diasse/disorders, immune diseases, inflammatory diseases, auto-immune diseases, or auto-inflammatory diseases, for example, autoinflammatory fever syndromes (e.g., cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In particular, compounds of the invention, or a pharmaceutically acceptable salt thereof, may be useful in the treatment of a disease or disorder preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides the use of a compound of any one of formula (I), (II), (III), and (III-A), or a compound according to any one of the preceding embodiments (i.e. according to any one of embodiments 1 to 11 g), or a compound according to any one of the exemplified examples (e.g. Ex 001 to Ex 104 as disclosed herein), or a pharmaceutically acceptable salt thereof, in therapy. In a further embodiment, the therapy is selected from a disease, which may be treated by inhibition of NLRP3 inflammasome pathway. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy) hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides a compound of any one of formula (I), (II), (III), and (III-A), or a compound according to any one of the preceding embodiments (i.e. according to any one of embodiments 1 to 11 g), or a compound according to any one of the exemplified examples (e.g. Ex 001 to Ex 104 as disclosed herein), or a pharmaceutically acceptable salt thereof, for use in therapy. In a further embodiment, the therapy is selected from a disease, which may be treated by inhibition of NLRP3 inflammasome pathway. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another aspect, the invention provides a method of treating a disease which is treated by inhibiting NLRP3 comprising administration of a therapeutically effective amount of a compound of any one of formula (I), (II), (III), and (III-A), or a compound according to any one of the preceding embodiments (i.e. according to any one of embodiments 1 to 11 g), or a compound according to any one of the exemplified examples (e.g. Ex 001 to Ex 104 as disclosed herein), or a pharmaceutically acceptable salt thereof. In a further embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In a further aspect, the present invention provides a compound of any one of formula (I), (II), (III), and (III-A), or a compound according to any one of the preceding embodiments (i.e. according to any one of embodiments 1 to 11 g), or a compound according to any one of the exemplified examples (e.g. Ex 001 to Ex 104 as disclosed herein), or a pharmaceutically acceptable salt thereof, useful in the treatment of a disease, disorder or condition substantially or entirely mediated by NLRP3 inflammasome activity, as disclosed herein, and/or NLRP3-induced IL-1 beta, and/or NLRP3-induced IL-18. Some of the diseases, disorders or conditions mentioned herein arise due to mutations in NLRP3, in particular, result in an increased NLRP3 activity.

Thus, as a further aspect, the present invention provides the use of a compound of any one of formula (I), (II), (III), and (III-A), or a compound according to any one of the preceding embodiments (i.e. according to any one of embodiments 1 to 11 g), or a compound according to any one of the exemplified examples (e.g. Ex 001 to Ex 104 as disclosed herein), or a pharmaceutically acceptable salt thereof, for the manufacture of a medicament. In a further embodiment, the medicament is for the treatment of a disease, which is treated by inhibition of NLRP3 inflammasome pathway. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 3-methyl-2-(5-methyl-6-((1-methylpiperidin-3-yl)amino)pyridazin-3-yl)-5-(trifluoromethyl)phenol, or a pharmaceutically acceptable salt thereof, for use in the treatment of a disease or disorder, which is treated by inhibition of the NLRP3 pathway. In another embodiment of the present invention, there is provided (S)-3-methyl-2-(5-methyl-6-((1-methylpiperidin-3-yl)amino)pyridazin-3-yl)-5-(trifluoromethyl)phenol, or a pharmaceutically acceptable salt thereof, for use in the treatment of a disease or disorder, which is treated by inhibition of the NLRP3 pathway. In a preferred embodiment of the invention, there is provided (R)-3-methyl-2-(5-methyl-6-((1-methylpiperidin-3-yl)amino)pyridazin-3-yl)-5-(trifluoromethyl)phenol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In one embodiment of the present invention, there is provided 2-(4-methyl-6-((1-methylpiperidin-3-yl)amino)pyridazin-3-yl)-5-(trifluoromethyl)phenol, or a pharmaceutically acceptable salt thereof, for use in the treatment of a disease or disorder, which is treated by inhibition of the NLRP3 pathway. In another embodiment of the present invention, there is provided (S)-2-(4-methyl-6-((1-methylpiperidin-3-yl)amino)pyridazin-3-yl)-5-(trifluoromethyl) phenol, or a pharmaceutically acceptable salt thereof, for use in the treatment of a disease or disorder, which is treated by inhibition of the NLRP3 pathway. In a preferred embodiment of the invention, there is provided (R)-2-(4-methyl-6-((1-methylpiperidin-3-yl)amino)pyridazin-3-yl)-5-(trifluoromethyl)phenol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(6-((1-ethylpiperidin-3-yl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In another embodiment of the present invention, there is provided (S)-2-(6-((1-ethylpiperidin-3-yl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In a preferred embodiment of the invention, there is provided (R)-2-(6-((1-ethylpiperidin-3-yl)amino)pyridazin-3-yl)-3-methyl-5-(trifluoromethyl) phenol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(6-((3-hydroxy-3-methylcyclobutyl)amino) pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In another embodiment of the present invention, there is provided 2-(6-(((trans)-3-hydroxy-3-methylcyclobutyl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In a preferred embodiment of the invention, there is provided 2-(6-(((cis)-3-hydroxy-3-methylcyclobutyl) amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 2-(6-((3-hydroxycyclohexyl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In another embodiment of the present invention, there is provided 2-(6-(((1S,3R)-3-hydroxycyclohexyl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In another embodiment of the present invention, there is provided 2-(6-(((1R,3R)-3-hydroxycyclohexyl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In another embodiment of the present invention, there is provided 2-(6-(((1S,3S)-3-hydroxycyclohexyl)amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. In a preferred embodiment of the invention, there is provided 2-(6-(((1R,3S)-3-hydroxycyclohexyl) amino)pyridazin-3-yl)-3-methyl-5-(trifluoromethyl)phenol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another embodiment of the present invention, there is provided 5-((6-(2-hydroxy-6-methyl-4-(trifluoromethyl)phenyl)pyridazin-3-yl)amino)-1-methylpiperidin-3-ol, or a pharmaceutically acceptable salt thereof, for use in the treatment of a disease or disorder, which is treated by inhibition of the NLRP3 pathway. In another embodiment of the present invention, there is provided (3R,5S)-5-((6-(2-hydroxy-6-methyl-4-(trifluoromethyl)phenyl)pyridazin-3-yl)amino)-1-methylpiperidin-3-ol, or a pharmaceutically acceptable salt thereof, for use in the treatment of a disease or disorder, which is treated by inhibition of the NLRP3 pathway. In another embodiment of the present invention, there is provided (3R,5R)-5-((6-(2-hydroxy-6-methyl-4-(trifluoromethyl)phenyl)pyridazin-3-yl)amino)-1-methylpiperidin-3-ol, or a pharmaceutically acceptable salt thereof, for use in the treatment of a disease or disorder, which is treated by inhibition of the NLRP3 pathway. In another embodiment of the present invention, there is provided (3S,5S)-5-((6-(2-hydroxy-6-methyl-4-(trifluoromethyl)phenyl)pyridazin-3-yl)amino)-1-methylpiperidin-3-ol, or a pharmaceutically acceptable salt thereof, for use in the treatment of a disease or disorder, which is treated by inhibition of the NLRP3 pathway. In a preferred embodiment of the invention, there is provided (3S,5R)-5-((6-(2-hydroxy-6-methyl-4-(trifluoromethyl)phenyl)pyridazin-3-yl)amino)-1-methylpiperidin-3-ol, or a pharmaceutically acceptable salt thereof, for use in the treatment of a disease or disorder, which is treated by inhibition of the NLRP3 pathway. For example, the disease or disorder is selected from the afore-mentioned list, suitably an inflammasome-related diseases/disorders, immune diseases, inflammatory diseases, auto-immune diseases, or auto-inflammatory diseases, for example, autoinflammatory fever syndromes (e.g cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, compounds of the invention may be useful in treating autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

The pharmaceutical composition or combination of the present invention can be in unit dosage of about 1-1000 mg of active ingredient(s) for a subject of about 50-70 kg, or about 1-500 mg, or about 1-250 mg, or about 1-150 mg, or about 1-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

Combination Product and Combination Therapy of the Invention

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g. powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of any one of formula (I), (II), (III), and (III-A), or a pharmaceutical acceptable salt thereof, and at least one other therapeutic agent as a combined preparation for simultaneous, separate or sequential use in therapy. In one embodiment, the therapy is the treatment of a disease or condition mediated by NLRP3. Products provided as a combined preparation include a composition comprising the compound of any one of formula (I), (II), (III), and (III-A), or a pharmaceutically acceptable salt thereof, and the other therapeutic agent(s) together in the same pharmaceutical composition, or the compound of any one of formula (I), (II), (III), and (III-A), or a pharmaceutically acceptable salt thereof, and the other therapeutic agent(s) in separate form, e.g. in the form of a kit.

In one embodiment, the invention provides a pharmaceutical combination comprising a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formula (I), (II), (III), and (III-A), or a pharmaceutically acceptable salt thereof, for treating a disease or condition mediated by NLRP3, wherein the medicament is prepared for administration with another therapeutic agent. The invention also provides the use of another therapeutic agent for treating a disease or condition mediated by NLRP3 wherein the medicament is administered with a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof.

The invention also provides a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof, for use in a method of treating a disease or condition mediated by NLRP3, wherein the compound of any one of formula (I), (II), (III), and (III-A), or a pharmaceutically acceptable salt thereof, or a compound according to any one of the preceding embodiments (i.e. according to any one of embodiments 1 to 11 g), or pharmaceutical acceptable salt thereof, is prepared for administration with another therapeutic agent. The invention also provides another therapeutic agent for use in a method of treating a disease or condition mediated by NLRP3, wherein the other therapeutic agent is prepared for administration with a compound of any one of formula (I), (II), (III), and (III-A), or a pharmaceutically acceptable salt thereof, or a compound according to any one of the preceding embodiments (i.e. according to any one of embodiments 1 to 11 g), or pharmaceutical acceptable salt thereof. The invention also provides a compound of any one of formula (I), (II), (III), and (III-A), or a pharmaceutically acceptable salt thereof, or a compound according to any one of the preceding embodiments (i.e. according to any one of embodiments 1 to 11 g), or pharmaceutical acceptable salt thereof, for use in a method of treating a disease or condition mediated by NLRP3, wherein the compound of any one of formula (I), (II), (III), and (III-A), or a pharmaceutically acceptable salt thereof, or a compound according to any one of the preceding embodiments (i.e. according to any one of embodiments 1 to 11 g), or pharmaceutical acceptable salt thereof, is administered with another therapeutic agent. The invention also provides another therapeutic agent for use in a method of treating a disease or condition mediated by NLRP3, wherein the other therapeutic agent is administered with a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof.

The invention also provides the use of a compound of any one of formula (I), (II), (III), and (III-A), or a pharmaceutically acceptable salt thereof, or a compound according to any one of the preceding embodiments (i.e. according to any one of embodiments 1 to 11 g), or pharmaceutical acceptable salt thereof, for treating a disease or condition mediated by NLRP3, wherein the patient has previously (e.g. within 24 hours) been treated with another therapeutic agent. The invention also provides the use of another therapeutic agent for treating a disease or condition mediated by NLRP3 inflammasome pathway, wherein the patient has previously (e.g. within 24 hours) been treated with a compound of any one of formula (I), (II), (III), and (III-A), or a pharmaceutically acceptable salt thereof, or a compound according to any one of the preceding embodiments (i.e. according to any one of embodiments 1 to 11 g), or a pharmaceutical acceptable salt thereof.

In one embodiment, the other therapeutic agent is a therapeutic agent useful in the treatment of inflammasome-related diseases/disorders, immune diseases, inflammatory diseases, auto-immune diseases, or auto-inflammatory diseases, as disclosed herein.

In one embodiment, the other therapeutic agent useful in the combination therapy is selected from farnesoid X receptor (FXR) agonists; anti-steatotics; anti-fibrotics; JAK inhibitors; checkpoint inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA) including aspirin; paracetamol; regenerative therapy treatments; cystic fibrosis treatments; and atherosclerotic treatment.

Suitable leukotriene A4 hydrolase (LTA4H) inhibitors for use in the combination include, but are not limited to, compounds disclosed in W2015/092740.

Suitable sodium-dependent glucose transporter 2 (SGLT2) inhibitors for use in the combination include, but are not limited to, compounds disclosed in U.S. Pat. No. 8,163,704, WO2011/048112, WO2011/048148, or in WO2010/128152.

Suitable β2-agonists for use in the combination include, but are not limited to, arformoterol, bambuterol, bitolterol, broxaterol, carbuterol, clenbuterol, dopexamine, fenoterol, formoterol, hexoprenaline, ibuterol, Isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, GSK-159797, GSK-678007, GSK-642444, GSK-159802, HOKU-81, (−)-2-[7 (S)-[2(R)-Hydroxy-2-(4-hydroxyphenyl)ethylamino]-5, 6,7, 8-tetrahydro-2-naphthyloxy]-N,N-di methylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(1-fluoro-4-hydroxyphenyl)-2-[4-(1-benzimidazolyl)-2-methyl-2-butylamino]ethanol, 1-[3-(4-methoxybenzyl amino)-4-hydroxyphenyl]-2-[4(1- benzimidazolyl)-2-methyl-2-butylamino]ethanol, 1-[2H-5-hydroxy-3-oxo-4H-1,4-benzoxazin-8-yl]-2-[3-(4-N,N-dimethyl aminophenyl)-2-methyl-2-propyl amino]ethanol, 1-[2H-5-hydroxy-3-oxo-4H-1,4-benzoxazin-8-yl]-2-[3-(4-methoxyphenyl)-2-methyl-2-propylamino] ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5trifluoromethylphenyl)-2-tert-butylamino) ethanol, 1-(4-ethoxy carbonylamino-3-cyano-5-fluoro phenyl)-2-(tert-butylamino)ethanol, and combinations thereof, each of which is optionally in the form of a racemate, enantiomer, diastereomer, or mixtures thereof, and also optionally in the form of a pharmacologically-compatible acid addition salt.

Suitable cartilage regenerative therapy for use in the combination includes, but are not limited to, ANGPTL3 peptidomimetics disclosed in WO2014/138687, or a chondrogenesis activator disclosed in WO2015/175487.

Suitable checkpoint inhibitors for use in the combination include, but are not limited to, anti-PD1 inhibitors, anti-LAG-3 inhibitors, anti-TIM-3 inhibitors, anti-PDL1 inhibitors. Suitable anti-PD1 inhibitors, include, but are not limited to, an antibody molecule disclosed in WO2015/112900. Suitable anti-LAG-3 inhibitors, include, but are not limited to, an antibody molecule disclosed in WO2015/138920. Suitable anti-TIM-3 inhibitors include, but are not limited to, an antibody molecule disclosed in W2015/117002. Suitable anti-TIM-3 inhibitors include, but are not limited to, an antibody molecule disclosed in WO2015/117002. Suitable anti PDL1 inhibitors include, but are not limited to, an antibody molecule disclosed in WO/2016/061142.

Suitable Toll Like receptor inhibitors (TLR7/8 inhibitors) for use in the combination include, but are not limited to, a compound disclosed in W2018/04081.

Suitable FXR agonists for use in the combination include, but are not limited to, obeticholic acid (so called OCA, Intercept), GS9674, elafibranor (GFT505), GW4064, UPF987, FXR-450, fexaramine, methylcolate, methyl deoxycholate, 5β-cholanic acid, 5β-chloanic acid 7a, 12a diol, NIHS700, marchantin A, marchantin E, MFA-1 INT767 (also called 6α-ethyl-CDCA disclosed in WO2014/085474), MET409 (Metacrine), EDP-305 (Enanta), 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid (also known under the name Tropifexor), or a pharmaceutically acceptable salt thereof, or a compound disclosed in WO 2012/087519, or a compound disclosed in WO 2015/069666.

Suitable JAK inhibitors for use in the combination include, but are not limited to Ruxolitinib.

Suitable NSAIDs for use in the combination include, but are not limited to, Aceclofenac, acemetacin, acetylsalicylic acid, alclofenac, alminoprofen, amfenac, Ampiroxicam, Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac, Enfenaminsaure, Etersalat, etodolac, etofenamate, etoricoxib, Feclobuzon, felbinac, fenbufen, fenclofenac, fenoprofen, fentiazac, Fepradinol, Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

Suitable BTK inhibitors include for example Ibrutinib, Acalabrutinib (ACP-196), Evobrutinib; Fenebrutinib; Tirabrutinib (ONO-4059, GS-4059); Zanubrutinib (BGB-3111), Spebrutinib (CC-292, AVL-292), Poseltinib (HM-71224, LY3337641), Vecabrutinib (SNS-062), BMS-986142; BMS986195; PRN2246; PRN1008, M7583, CT1530, B11B068, AC-0058TA, ARQ-531, TAK-020, TG1701 or a compound described in WO2015/079417, WO2015/083008, WO2015/110923, WO2014/173289, WO2012/021444, WO2013/081016, WO2013/067274, WO2012/170976, WO2011/162515, US2017/119766, WO2016/065226, U.S. Pat. No. 9,688,676, WO2016/201280, WO2017/059702, U.S. Pat. No. 9,630,968, US2014/0256734, WO2017118277, WO2014/039899, WO/16/105531, WO2018/005849, WO2013/185082 or in *J. Med. Chem.*, 2016, 59(19), 9173-9200. Of particular interest, BTK inhibitors include compound of example 31 described in WO2014/039899, compound of the following structure:

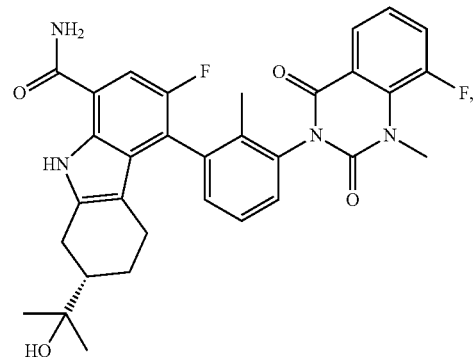 [SMILES: Cc1c(-c2c(F)cc(C(N)=O)c3[nH]c4c(c23)CC[C@H](C(C)(C)O)C4)cccc1-n1c(=O)c2cccc(F)c2n(C)c1=O]

described as compound 14f in *Journal of Medicinal Chemistry*, 2016, 59 (19), 9173-9200; compound of example 2 described in US2017/119766, compound of example 223 described in WO2016/065226 which is:

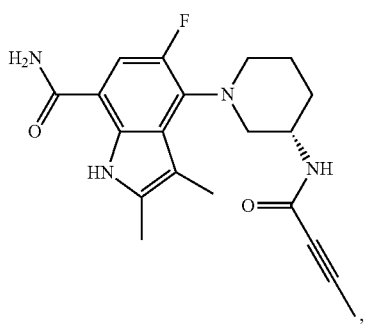 [SMILES: CC#CC(=O)N[C@H]1CCCN(c2c(F)cc(C(N)=O)c3[nH]c(C)c(C)c23)C1]

or compound 1 described in WO2016/201280, compound 1 described in WO2017/059702, or compound 1 described in WO2017/118277; or a pharmaceutically acceptable salt thereof. Of other particular interest, BTK inhibitors include a compound described in WO2015/079417, for example a compound selected from N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluoro benzamide; N-(3-(6-Amino-5-(2-(N-methylbut-2-ynamido)ethoxy) pyrimidin-4-yl)-5-fluoro-2-methylphenyl)-4-cyclopropyl-2-fluorobenzamide; N-(3-(6-Amino-5-(2-(N-ethylacrylamido) ethoxy)pyrimidin-4-yl)-5-fluoro-2-methylphenyl)-4-cyclopropyl-2-fluorobenzamide; N-(3-(6-Amino-5-(2-(N-(2-fluoro ethyl)acrylamido)ethoxy) pyrimidin-4-yl)-5-fluoro-2-methylphenyl)-4-cyclopropyl-2-fluoro benzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclo propyl-2-fluorobenzamide andN-(3-(6-Amino-5-(3-(N-methylacrylamido)propoxy)pyrimidin-4-yl)-5-fluoro-2-methylphenyl)-4-cyclo propyl-2-fluorobenzamide; or a pharmaceutically acceptable salt thereof.

EXAMPLES

Exemplification of the Invention

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof, which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) *Protective Groups in Organic Synthesis,* 5th edition, John Wiley & Sons). These groups are removed at a convenient stage of the compound synthesis using methods that are readily apparent to those skilled in the art.

Unless otherwise noted, reagents and solvents were used as received from commercial suppliers.

The chemical names were generated using ChemBioDraw Ultra v14 from CambridgeSoft.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

AcOH Acetic acid
ASC Apoptosis-associated speck-like protein
BINAP (2,2'-Bis(diphenylphosphino)-1,1'-binaphthyl)
BippyPhos 5-(Di-tert-butylphosphino)-1',3',5'-triphenyl-1'H-1,4-bipyrazole
Boc tert-Butyloxycarbonyl
CAPS Cryopyrin-Associated Periodic Syndromes
DAMPs Danger-activated molecular patterns
DIAD Diisopropyl azodicarboxylate
DIPEA N-Diisopropylethylamine
DME 1,2-Dimethoxyethane
DMF N,N-Dimethylformamide
DMSO Dimethylsulfoxide
dppf 1,1'-Bis(diphenylphosphino)ferrocene
EtOAc Ethyl acetate
EtOH Ethanol
h Hour(s)
HCl Hydrogen chloride
HTRF homogeneous time resolved fluorescence
Hz/MHz Hertz/Mega Hertz
$IC_{50}$ Half maximal inhibitory concentration
IL-1ß Interleukin 1 beta
IR Infrared
LC-MS Liquid chromatography—mass spectrometry
LPS Lipopolysaccharides from *Escherichia coli* O111:B4
LRR Leucine-rich repeat
M Molar
mCPBA 3-Chlorobenzoperoxoic acid
MEK Methyl ethyl ketone; Butan-2-one
MeOH Methanol
min Minute
mL/L Millilitre/Litre
mmol Millimol
NASH Non-alcoholic steatohepatitis
NBD Nucleotide-binding site domain
NLRs NOD-like receptors
NMP 1-Methylpyrrolidin-2-one
NMR Nuclear magnetic resonance
PAD Peripheral artery disease
PAMPs Pathogen activated molecular patterns
Pd/C Palladium on carbon
PMA Phorbol 12-myristate 13-acetate
ppm parts per million
RP Reverse phase
RPMI Roswell Park Memorial Institute
RT Room temperature—in Celsius
Rt Retention time SFC Supercritical fluid chromatography SLE systemic lupus erythematosus

A

TFA Trifluoroacetic acid

THF Tetrahydrofuran

TMEDA N,N,N',N'-Tetramethylethane-1,2-diamine

TMS Tetramethylsilane

TNF-α Tumor necrosis factor-α

UPLC Ultra performance liquid chromatography

XantPhos-Pd-G2 Chloro[(4,5-bis(diphenylphosphino)-9,9-dimethylxanthene)-2-(2'-amino-1,1'-biphenyl)]palladium (II)

Analytical Details

NMR: Measurements were performed on a Bruker Ultrashield™ 400 (400 MHz) or Bruker Ascend™ (400 MHz) or Bruker cryo system (600 MHz) spectrometer using or not tetramethylsilane (TMS) as an internal standard. Chemical shifts (δ) are reported in ppm downfield from TMS, spectra splitting pattern are designated as singlet (s), doublet (d), triplet (t), quartet (q), quintet (quint), septet (sept), multiplet, unresolved or overlapping signals (m), broad signal (br). Deuterated solvents are given in parentheses and have a chemical shifts of dimethyl sulfoxide (δ 2.50 ppm), methanol (δ 3.31 ppm), chloroform (δ 7.26 ppm), or other solvent as indicated in NMR spectral data.

LC-MS: System: Waters Acquity UPLC with Waters SQ detector.

Column: Acquity HSS T3 1.8 μm 2.1×50 mm, column temperature: 60° C.

Gradient: from 5 to 98% B in 1.4 min, A=water+0.05% formic acid+3.75 mM ammonium acetate, B=acetonitrile+0.04% formic acid, flow: 1.0 mL/min.

Mass spectrometry results are reported as the ratio of mass over charge.

Preparative Methods

Flash Column Chromatography System:

System: Teledyne ISCO, CombiFlash Rf.

Columns: pre-packed RediSep Rf cartridges.

Samples were typically adsorbed on Isolute.

Achiral reverse phase (RP) chromatography:

System: Gilson Autopurification LC System

Sunfire C18 5 um 30×100 mm column.

Detection: Gilson UV/VIS 155 Detector

Column temperature: RT

Eluent A: water+0.1% TFA

Eluent B: acetonitrile

Flow: 30 mL/min

Gradient:

| Time [min] | % A (Eluent A) | % B (Eluent B) |
|---|---|---|
| 0.0 | 95 | 5 |
| 2.0 | 95 | 5 |
| 17 | 5 | 95 |
| 18 | 0 | 100 |
| 20 | 0 | 100 |

Chiral Normal Phase Chromatography:

System: Gilson Autopurification LC System

Detection: Gilson UV/VIS-155 Detector

Column temperature: RT

Achiral Supercritical Fluid Chromatography (SFC):

System: Waters SFC-100 SFC System

Detection: Waters 2998 PDA Detector

Waters 3100 Mass Detector

Eluent A: $CO_2$

Eluent B: as described in examples

Chiral Supercritical Fluid Chromatography (SFC):

System: Waters SFC-100 SFC System

Detection: Waters 2998 PDA Detector

Waters 3100 Mass Detector

Eluent A: $CO_2$

Eluent B: as described in examples

All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

Synthesis of Intermediates

Synthesis of Boronate Intermediates

3-Chloro-2-(4,4,5,5-tetramethyl-1,3,2-dioxaborolan-2-yl)-5-(trifluoromethyl)phenol and 5-Chloro-2-(4,4,5,5-tetramethyl-1,3,2-dioxaborolan-2-yl)-3-(trifluoromethyl)phenol, Int B001

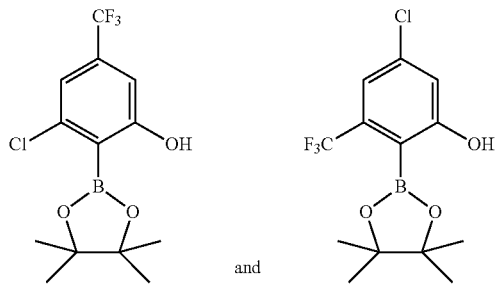 [SMILES: CC1(C)OB(c2c(O)cc(C(F)(F)F)cc2Cl)OC1(C)C ; CC1(C)OB(c2c(O)cc(Cl)cc2C(F)(F)F)OC1(C)C]

(1) 3-Chloro-2-iodo-5-(trifluoromethyl)phenol and 5-Chloro-2-iodo-3-(trifluoromethyl)phenol, Int B002

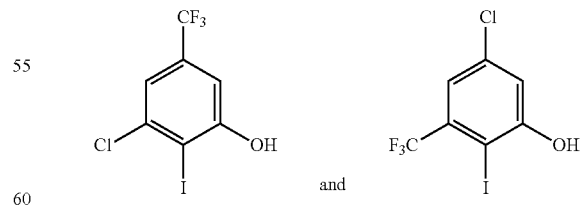

A mixture of 3-chloro-5-(trifluoromethyl)phenol (10 g, 50.9 mmol) and sodium hydride (2.44 g, 102 mmol) in 150 mL of toluene was stirred at 0° C. for 30 min. Iodine (12.9 g, 50.9 mmol) was then added and the solution was stirred at 0° C. for 3 h. The reaction mixture was then acidified with concentrated HCl to give a final pH of 4-5. It was extracted with EtOAc and the organic layer was washed with water and brine, dried over Na$_2$SO$_4$, filtered and evaporated. The crude mixture of regioisomers was used as such in the next step. LC-MS: Rt=1.10 and 1.12 min, MS m/z 320.9 [M–H]–.

(2) 5-Chloro-1-(ethoxymethoxy)-2-iodo-3-(trifluoromethyl)benzene and 1-Chloro-3-(ethoxymethoxy)-2-iodo-5-(trifluoromethyl)benzene, Int B003

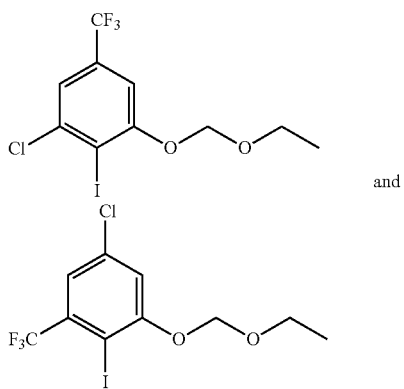

(Chloromethoxy)ethane (7.25 mL, 62.5 mmol) was added to a suspension of Int B002 (16 g, 49.6 mmol) and Cs$_2$CO$_3$ (16.2 g, 49.6 mmol) in 70 mL of DMF. The reaction mixture was stirred at RT for 18 h. More (chloromethoxy)ethane (2.88 mL, 24.8 mmol) was added and stirring was continued for 24 h. The suspension was filtered over celite and the filtrate evaporated to yield the title compound as a mixture of regioisomers which was used without further purification in the next step. LC-MS: Rt=1.37 and 1.38 min.

(3) 2-(2-Chloro-6-(ethoxymethoxy)-4-(trifluoromethyl)phenyl)-4,4,5,5-tetramethyl-1,3,2-dioxaborolane and 2-(4-Chloro-2-(ethoxymethoxy)-6-(trifluoromethyl)phenyl)-4,4,5,5-tetramethyl-1,3,2-dioxaborolane, Int B004

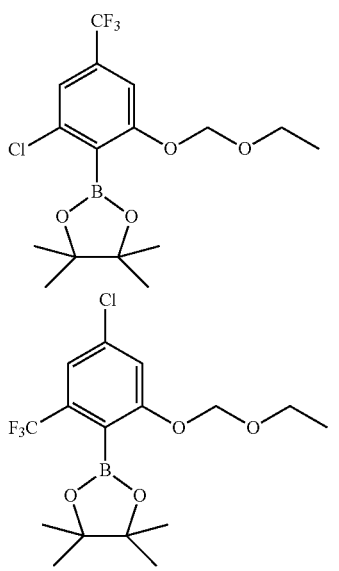

A solution of Int B003 (11.9 g, 31.3 mmol), 4,4,5,5-tetramethyl-[1,3,2]dioxaborolane (9.08 mL, 62.5 mmol) and NEt$_3$ (13.08 mL, 94 mmol) in 60 mL of 1,4-dioxane was purged with nitrogen. Pd(OAc)$_2$ (0.35 g, 1.56 mmol) and biphenyl-2-yl-dicyclohexylphosphane (1.1 g, 3.13 mmol) were added and the resulting mixture was stirred at 80° C. for 3 h. More Pd(OAc)$_2$ (0.35 g, 1.56 mmol) was added and heating continued for 13 h. The reaction was cooled to RT, washed with saturated NH$_4$Cl solution, water and brine to afford an orange oil. The crude product was purified by column chromatography on silica gel using cyclohexane and EtOAc (from 0% to 100%) to afford the title compound as a mixture of regioisomers. LC-MS: Rt=1.43 min.

(4) 3-Chloro-2-(4,4,5,5-tetramethyl-1,3,2-dioxaborolan-2-yl)-5-(trifluoromethyl)phenol and 5-Chloro-2-(4,4,5,5-tetramethyl-1,3,2-dioxaborolan-2-yl)-3-(trifluoromethyl)phenol, Int B001

A solution of Int B004 (8.5 g, 22.34 mmol) and TFA (25.8 mL, 670.2 mmol) in 25 mL of CH$_2$Cl$_2$ was purged with nitrogen and stirred at 0° C. for 1 h. The mixture was washed with saturated NH$_4$Cl solution, water and brine. The organic layer was dried over Na$_2$SO$_4$, filtered and evaporated to afford an orange oil. The crude product was purified by column chromatography on silica gel using cyclohexane and EtOAc (from 0% to 5%) to afford the title compound as a mixture of regioisomers. LC-MS:Rt=1.23 min and 1.28 min; MS m/z Rt 321.1 [M–H]–.

(2-Hydroxy-6-methyl-4-(trifluoromethyl)phenyl)boronic acid, t B005

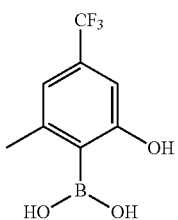

(1) 3-Methyl-5-(trifluoromethyl)phenol, Int B006

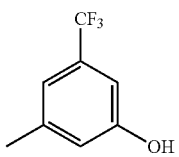

LiOH (26.5 g, 630.33 mmol), Pd$_2$(dba)$_3$ (3.85 g, 4.20 mmol) and BippyPhos (4.25 g, 8.40 mmol) were added to a solution of 1-bromo-3-methyl-5-(trifluoromethyl)benzene (50 g, 210.11 mmol) in 500 mL of 1,4-dioxane and 50 mL of H$_2$O. The reaction mixture was purged with nitrogen and heated at 100° C. for 16 h. The reaction mixture was cooled to RT, filtered through a pad of Celite® and washed with EtOAc. The filtrate was washed with 1.5 M HCl, dried over Na$_2$SO$_4$, filtered and evaporated. The crude material was purified by column chromatography on silica gel using (2) 2-Iodo-3-methyl-5-(trifluoromethyl)phenol, Int B007

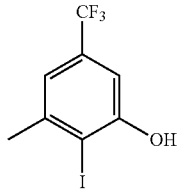

To an ice-cold solution of Int B006 (13.03 g, 74 mmol) in 370 mL of toluene was added NaH (60% dispersion in mineral oil, 5.92 g, 148 mmol). The suspension was stirred at 0° C. for 30 minutes, then iodine (18.77 g, 74 mmol) was slowly added in portions and stirring was continued for 3 h. The mixture was diluted with water, acidified with 2 M HCl to pH=5 and extracted with EtOAc. The organic layer was washed with brine, dried over $Na_2SO_4$, filtered and evaporated.

The crude was purified by column chromatography on silica gel (220 g) using cyclohexane and EtOAc (from 5% to 100%) to afford the title compound as yellow oil. $^1$H NMR (400 MHz, CDCl$_3$) δ (ppm) 7.08-7.04 (m, 2H), 5.74 (s, 1H), 2.50 (s, 3H). LC-MS: Rt=1.11 min; MS m/z 301.0 [M−H]−.

(3) 2-Iodo-1-methoxy-3-methyl-5-(trifluoromethyl) benzene, Int B008

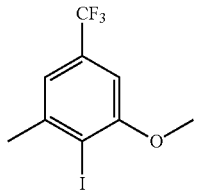

A mixture of $K_2CO_3$ (24 g, 172.22 mmol), methyl iodide (8.1 mL, 129.13 mmol) and Int B007 (26 g, 86.09 mmol) in 300 mL of anhydrous acetone was stirred at RT for 5 h. It was then filtered and the filtrate evaporated. The residue was dissolved in $CH_2Cl_2$, washed with water, dried over $Na_2SO_4$, filtered and evaporated to afford the title compound as an off white solid. $^1$H NMR (400 MHz, CDCl$_3$) δ (ppm) 7.15 (s, 1H), 6.84 (s, 1H), 3.93 (s, 3H), 2.54 (s, 3H).

(4) 2-(2-Methoxy-6-methyl-4-(trifluoromethyl)phenyl)-4,4,5,5-tetramethyl-1,3,2-dioxaborolane, Int B009

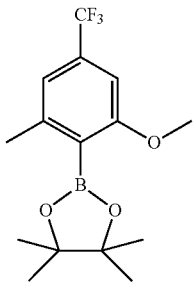

Pinacolborane (50.5 mL, 348.03 mmol), biphenyl-2-yl-dicyclohexylphosphane (2.44 g, 6.96 mmol), Pd(OAc)$_2$ (1.55 g, 6.96 mmol) and NEt$_3$ (48.5 mL, 348.03 mmol) were added to a solution of Int B008 (22 g, 69.61 mmol) in 300 mL of anhydrous 1,4-dioxane (300 mL). The reaction mixture was purged with nitrogen and heated to 100° C. for 16 h. After cooling to RT, it was filtered through a pad of Celite@ and washed with EtOAc. The filtrate was evaporated and the residue was purified by column chromatography on silica gel using petroleum ether and EtOAc (from 0% to 10%) to afford the title compound as an off white solid. H NMR (400 MHz, CDCl$_3$) δ (ppm) 7.02 (s, 1H), 6.85 (s, 1H), 3.84 (s, 3H), 2.40 (s, 3H), 1.40 (s, 9H).

(5) (2-Hydroxy-6-methyl-4-(trifluoromethyl)phenyl) boronic acid, Int B005

BBr$_3$ (1 M in CH$_2$Cl$_2$, 95 mL, 94.86 mmol) was added to a solution of Int B009 (12 g, 37.95 mmol) in 150 mL of anhydrous CH$_2$Cl$_2$ at 0° C. The reaction mixture was stirred at 0° C. for 30 min after which it was carefully poured into ~250 mL of 10% NaOH solution so that the pH is kept at ~9. The resulting mixture was washed with CH$_2$Cl$_2$. The aqueous layer was separated and adjusted to pH 5 with 1.5 M HCl. A solid precipitated which was filtered off, washed with petroleum ether and dried under vacuum to afford the title compound as an off white solid. $^1$H NMR (400 MHz, CD3OD) δ (ppm) 6.94 (s, 1H), 6.82 (s, 1H), 2.29 (s, 3H). MS (ESI): m/z 219.8 [M−H]−

3-Methyl-2-(4,4,5,5-tetramethyl-1,3,2-dioxaborolan-2-yl)-5-(trifluoromethyl)phenol, Int B010

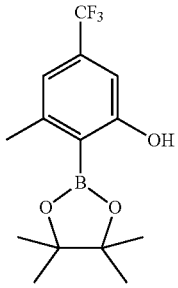 [SMILES: Cc1cc(C(F)(F)F)cc(O)c1B1OC(C)(C)C(C)(C)O1]

(1) 1-(ethoxymethoxy)-2-iodo-3-methyl-5-(trifluoromethyl)benzene, Int B011

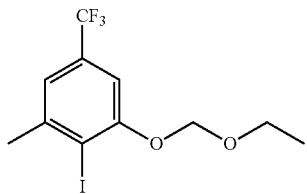 [SMILES: CCOCOc1cc(C(F)(F)F)cc(C)c1I]

(Chloromethoxy)ethane (3.35 g, 35.50 mmol) was added dropwise to a white suspension of Int B007 (8.50 g, 28.10 mmol) and Cs$_2$CO$_3$ (9.17 g, 28.10 mmol) in 30 mL of dry DMF. The reaction mixture was stirred at RT for 2 h before it was evaporated to dryness. The crude was purified by column chromatography on silica gel using cyclohexane and EtOAc (from 0% to 5%) to afford the title compound. LC-MS: Rt=1.39 min.

(2) 2-(2-(Ethoxymethoxy)-6-methyl-4-(trifluoromethyl)phenyl)-4,4,5,5-tetramethyl-1,3,2-dioxaborolane, Int B012

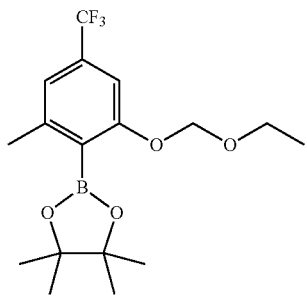 [SMILES: CCOCOc1cc(C(F)(F)F)cc(C)c1B1OC(C)(C)C(C)(C)O1]

A solution of Int B011 (10 g, 27.80 mmol), 4,4,5,5-tetramethyl-[1,3,2]dioxaborolane (20.15 mL, 139 mmol) and NEt$_3$ (28.6 mL, 205 mmol) in 60 mL of 1,4-dioxane was purged with nitrogen. Pd(OAc)$_2$ (0.81 g, 3.61 mmol) and biphenyl-2-yl-dicyclohexylphosphane (2.33 g, 6.66 mmol) were added and the mixture was stirred at 80° C. for 18 h. It was then cooled to RT, diluted with EtOAc and washed with saturated NH$_4$Cl, water and brine. The organic layer was dried over Na$_2$SO$_4$, filtered and evaporated. The crude product was purified by column chromatography on silica gel using cyclohexane and CH$_2$Cl$_2$ (from 0% to 20%) to afford the title compound. LC-MS: Rt=1.40 min.

(3) 3-Methyl-2-(4,4,5,5-tetramethyl-1,3,2-dioxaborolan-2-yl)-5-(trifluoromethyl)phenol, Int B010

TFA (44.9 mL, 583 mmol) was slowly added to a solution of Int B012. (7.00 g, 19.43 mmol) in 250 mL of CH$_2$Cl$_2$ at 0° C. The reaction mixture was stirred at 0° C. for 20 min and then evaporated. The resulting oil was purified by column chromatography on silica gel using cyclohexane and CH$_2$Cl$_2$ (from 0% to 100%) to afford the title compound. $^1$H NMR (400 MHz, DMSO-d$_6$) δ (ppm) 9.80 (s, 1H), 6.92 (s, 1H), 6.82 (s, 1H), 2.30 (s, 3H), 1.30 (s, 12H). LC-MS: Rt=1.38 min: MS m/z 301.1 [M–H]–

3,5-Dimethyl-2-(4,4,5,5-tetramethyl-1,3,2-dioxaborolan-2-yl)phenol, Int B013

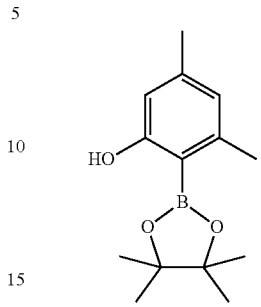

(1) 2-Iodo-3,5-dimethylphenol, Int B014

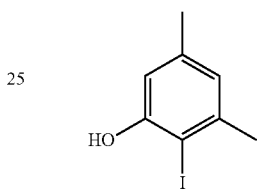

3,5-Dimethylphenol (1 g, 8.2 mmol) was dissolved in 40 mL of toluene and cooled to 0° C. NaH (60% dispersion in mineral oil, 655 mg, 16.4 mmol) was added in portions and the mixture was stirred at 0° C. for 20 min, then at RT for 10 min and finally cooled again to 0° C. Iodine (2.08 g, 8.2 mmol) was then added in portions and stirring was continued for 30 min. The reaction mixture was quenched by addition of 0.5 M HCl and extracted with EtOAc. The combined organic extracts were washed with water and brine, dried over Na$_2$SO$_4$, filtered and evaporated. The crude was purified by column chromatography on silica gel (100 g) using n-heptane and EtOAc (from 0% to 20%), followed by a second (isocratic) run using n-heptane and EtOAc (5%) to afford the title compound as an off-white solid. $^1$H NMR (400 MHz, DMSO-d$_6$) δ (ppm) 10.07 (s, 1H), 6.60 (s, 1H), 6.51 (s, 1H), 2.30 (s, 3H), 2.15 (s, 3H). LC-MS: Rt=1.03 min, MS m/z 246.9 [M–H]–

(2) 1-(Ethoxymethoxy)-2-iodo-3,5-dimethylbenzene, Int B015

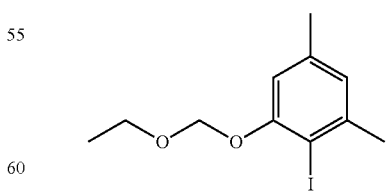

To a solution of Int B014 (660 mg, 2.66 mmol) 6 mL of DMF was added Cs$_2$CO$_3$ (867 mg, 2.66 mmol) followed by (chloromethoxy)ethane (311 µL, 3.35 mmol). The reaction mixture was stirred at RT overnight, then quenched by addition of water and extracted with EtOAc. The combined organic extracts were dried over Na$_2$SO$_4$, filtered and evaporated. The crude was purified by column chromatography on silica gel (50 g) using n-heptane and EtOAc (from 0% to 10%) to afford the title compound as a yellow oil. $^1$H NMR (400 MHz, DMSO-d$_6$) δ (ppm) 6.82 (s, 1H), 6.74 (s, 1H), 5.27 (s, 2H), 3.69 (q, 2H), 2.35 (s, 3H), 2.23 (s, 3H), 1.13 (t, 3H). LC-MS: Rt=1.36 min: MS m/z 307.2 [M+H]+

(3) 2-(2-(Ethoxymethoxy)-4,6-dimethylphenyl)-4,4,5,5-tetramethyl-1,3,2-dioxaborolane, Int B016

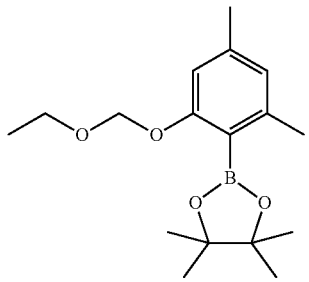 [SMILES: CCOCOc1cc(C)cc(C)c1B1OC(C)(C)C(C)(C)O1]

To a solution of Int B015 (393 mg, 1.28 mmol) in 2.5 mL of 1,4-dioxane was added 4,4,5,5-tetramethyl-1,3,2-dioxaborolane (373 μL, 2.57 mmol) and NEt$_3$ (537 μL, 3.85 mmol) and the vial was purged with nitrogen. Pd(OAc)$_2$ (14.4 mg, 64 μmol) and biphenyl-2-yl-dicyclohexylphosphane (45 mg, 0.128 mmol) were added, the vial was sealed and heated at 80° C. overnight. The reaction mixture was cooled to RT, quenched by addition of water and extracted with EtOAc. The combined organic extracts were dried over Na$_2$SO$_4$, filtered and evaporated. The crude was purified by column chromatography on silica gel (50 g) using n-heptane and EtOAc (from 0% to 20%) to afford the title compound as a colorless oil. $^1$H NMR (400 MHz, DMSO-d$_6$) δ (ppm) 6.63 (s, 1H), 6.60 (s, 1H), 5.13 (s, 2H), 3.64 (q, 2H), 2.23 (s, 3H), 2.20 (s, 3H), 1.29 (s, 12H), 1.12 (t, 3H). LC-MS: Rt=1.36 min; MS m/z 307.2 [M+H]$^+$ (4) 3,5-Dimethyl-2-(4,4,5,5-tetramethyl-1,3,2-dioxaborolan-2-yl)phenol, Int B013

A solution of Int B016 (486 mg, 1.59 mmol) in 25 mL of CH$_2$Cl$_2$ was cooled to −30° C. and TFA (611 μL, 7.94 mmol) was slowly added. After 1 h, the reaction was quenched at −30° C. by addition of water. The mixture was neutralized by addition of 1 M NaHCO$_3$ solution and extracted twice with CH$_2$Cl$_2$. The combined organic extracts were dried over Na$_2$SO$_4$, filtered and evaporated to afford the title compound as a yellow oil which was used without further purification. $^1$H NMR (400 MHz, DMSO-d$_6$) δ (ppm) 8.72 (s, 1H), 6.43 (s, 1H), 6.38 (s, 1H), 2.24 (s, 3H), 2.16 (s, 3H), 1.30 (s, 12H). LC-MS: Rt=1.37 min; MS m/z 249.2 [M+H]$^+$ (2-Methoxy-4,6-dimethylphenyl)boronic acid, Int B017

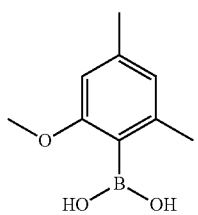

1-Methoxy-3,5-dimethylbenzene (1.04 mL, 7.34 mmol) and TMEDA (2.44 mL, 16.15 mmol) were dissolved in 16 mL of Et$_2$O and cooled to 0-5° C. under nitrogen. n-BuLi (1.6 M in hexane, 10.1 mL, 16.15 mmol) was added dropwise to the colorless solution keeping the temperature below 10° C. The resulting yellow suspension was stirred at RT for 1 h, then it was cooled to −78° C. B(OMe)$_3$ (1.15 mL, 10.28 mmol) was added over a period of about 4 min. keeping the temperature below −70° C. Stirring continued at −78° C. for 20 min, then the reaction mixture was allowed to warm up to RT overnight. It was quenched by addition of water and acidified with 4 M HCl to pH 1. The mixture was extracted 3-times with CH$_2$Cl$_2$ and the combined organic extracts were evaporated. The residue was dissolved in MeOH and washed twice with n-heptane. The lower MeOH layer was evaporated to afford the title compound as a yellow semi-solid. LC-MS: Rt=0.74 min; MS m/z 180.9 [M+H]$^+$ (2,4-Dichloro-6-hydroxyphenyl)boronic acid and 3,5-Dichloro-2-(4,4,5,5-tetramethyl-1,3,2-dioxaborolan-2-yl)phenol, Int B018

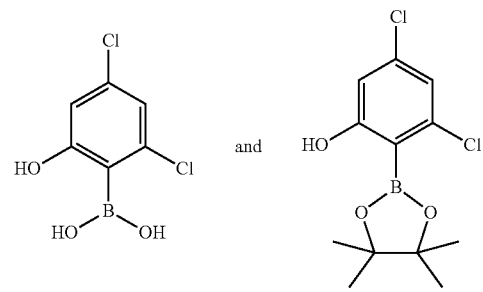 [SMILES: OB(O)c1c(O)cc(Cl)cc1Cl ; CC1(C)OB(c2c(O)cc(Cl)cc2Cl)OC1(C)C]

(1) 3,5-Dichloro-2-iodophenol, Int B019

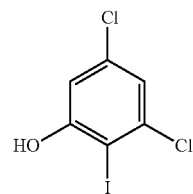

NaH (60% dispersion in mineral oil, 1.472 g, 36.8 mmol) was added in portions to a solution of 3,5-dichlorophenol (2.00 g, 12.27 mmol) in 30 mL of dry toluene at 0° C. under nitrogen. The resulting mixture was allowed to warm to RT and stirred for 30 min. The suspension was then cooled to 0° C. and iodine (2.49 g, 9.82 mmol) was added very slowly. The reaction mixture was stirred for 1.5 h at 0° C., then quenched by addition of 1 M HCl and extracted with CH$_2$Cl$_2$. The organic extract was washed with brine, dried over Na$_2$SO$_4$, filtered and evaporated. The crude was purified by column chromatography on silica gel (50 g) using n-heptane and EtOAc (from 0% to 50%) to afford the title compound as a yellow solid. $^1$H NMR (400 MHz, DMSO-d$_6$) δ (ppm) 11.32 (s, 1H), 7.14 (d, 1H), 6.81 (d, 1H). LC-MS: Rt=1.09 min; MS m/z 287.0 [M−H]−

(2) 1,5-Dichloro-3-(ethoxymethoxy)-2-iodobenzene, Int B020

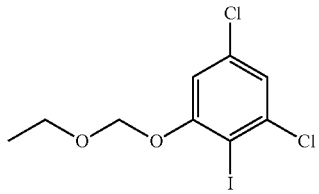

A suspension of (chloromethoxy)ethane (1.004 g, 10.62 mmol), Int B019 (2.8 g, 8.43 mmol) and $Cs_2CO_3$ (2.75 g, 8.43 mmol) in 25 mL of DMF was stirred at RT for 22 h. The reaction mixture was quenched by addition of water and the layers were separated. The aqueous layer was extracted with $CH_2Cl_2$ and the combined organic extracts were dried over $Na_2SO_4$, filtered and evaporated. The crude was purified by column chromatography on silica gel (100 g) using n-heptane and EtOAc (from 0% to 25%) to afford the title compound as a brown solid. $^1H$ NMR (400 MHz, DMSO-$d_6$) δ (ppm) 7.39 (d, 1H), 7.13 (d, 1H), 5.39 (s, 2H), 3.69 (q, 2H), 1.14 (t, 3H).

(3) 2-(2,4-Dichloro-6-(ethoxymethoxy)phenyl)-4,4,5,5-tetramethyl-1,3,2-dioxaborolane, Int B021

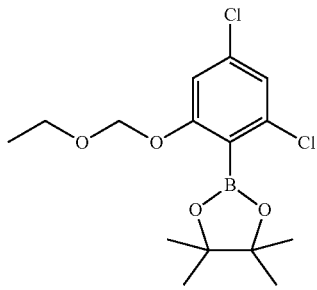 [SMILES: CCOCOc1cc(Cl)cc(Cl)c1B1OC(C)(C)C(C)(C)O1]

A solution of Int B020 (2.7 g, 7.78 mmol), 4,4,5,5-tetramethyl-[1,3,2]dioxaborolane (1M in THF, 15.56 mL, 15.56 mmol) and $NEt_3$ (3.25 mL, 23.34 mmol) in 15 mL of 1,4-dioxane was purged with nitrogen for 30 min. Then, $Pd(OAc)_2$ (87 mg, 0.389 mmol) and biphenyl-2-yl-dicyclohexylphosphane (273 mg, 0.778 mmol) were added and the mixture stirred at 80° C. for 20 h. The reaction mixture was quenched by addition of saturated $NH_4Cl$ and the layers separated. The organic layer was washed with water and brine then evaporated to afford an orange oil. The crude was purified by column chromatography on silica gel (100 g) using n-heptane and EtOAc (from 0% to 20%) followed by a second chromatography on silica gel (50 g) using n-heptane and EtOAc (from 0% to 5%) to afford the title compound as a pale yellow solid. $^1H$ NMR (400 MHz, DMSO-$d_6$) δ (ppm) 7.17 (d, 1H), 7.11 (d, 1H), 5.26 (s, 2H), 3.64 (q, 2H), 1.31 (s, 12H), 1.12 (t, 3H).

(4) (2,4-Dichloro-6-hydroxyphenyl)boronic acid and 3,5-Dichloro-2-(4,4,5,5-tetramethyl-1,3,2-dioxaborolan-2-yl)Phenol, Int B018

A solution of Int B021 (880 mg, 2.54 mmol) in 10 mL of $CH_2Cl_2$ was cooled to 0° C. TFA (3.91 mL, 50.7 mmol) was added and the reaction mixture was stirred at 0° C. for 1 h. The mixture was quenched by addition of saturated $NH_4Cl$. The layers were separated and the organic extract washed with water and brine. The solvent was evaporated to afford the title compounds as a mixture which was used without purification. LC-MS: Rt=0.76 min and 1.32 min, MS m/z 205.0 [M–H]– and 289.0 [M+H]+

3-Chloro-5-fluoro-2-(4,4,5,5-tetramethyl-1,3,2-dioxaborolan-2-yl)phenol and 5-Chloro-3-fluoro-2-(4,4,5,5-tetramethyl-1,3,2-dioxaborolan-2-yl)phenol, Int B022

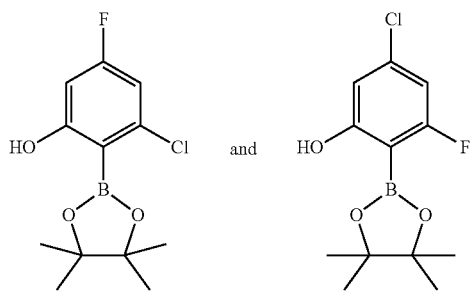 [SMILES: CC1(C)OB(c2c(O)cc(F)cc2Cl)OC1(C)C ; CC1(C)OB(c2c(O)cc(Cl)cc2F)OC1(C)C]

The mixture of regioisomers was synthesized analogous to Int B018 as described above starting from 3-chloro-5-fluorophenol. LC-MS: Rt=1.25 min.

(2-Hydroxy-4,6-bis(trifluoromethyl)phenyl)boronic acid, Int B023

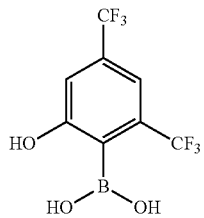

To a solution of (2-methoxy-4,6-bis(trifluoromethyl)phenyl)boronic acid (500 mg, 1.736 mmol) in 10 mL of $CH_2Cl_2$ was added dropwise $BBr_3$ (1 M in $CH_2Cl_2$, 8.68 mL, 8.68 mmol) at 0° C. under nitrogen. The resulting pale orange solution was allowed to warm to RT and was stirred for 17 h. The reaction mixture was poured into ice-water (~30 mL) and the pH was adjusted to 10 by addition of 2 M NaOH. The aqueous layer was separated, acidified to pH 1 by addition of 2 M HCl and extracted with $CH_2Cl_2$ followed by EtOAc. The combined organic extracts were dried over $Na_2SO_4$, filtered and evaporated. The crude was purified by column chromatography on silica gel (25 g) using $CH_2Cl_2$ and MeOH (from 0% to 5%) to afford the title compound as a beige solid. LC-MS: Rt=0.81 min, MS m/z 273.1 [M–H]–

Synthesis of 6-HALO-PYRIDAZINE-3-AMINE Intermediates (R)-6-Chloro-N-(1-ethylpiperidin-3-yl)pyridazin-3-amine, Int P024

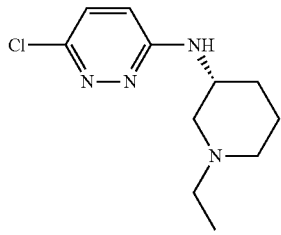 [SMILES: CCN1CCC[C@@H](Nc2ccc(Cl)nn2)C1]

To a solution of 3,6-dichloropyridazine (3 g, 20.13 mmol) and (R)-1-ethylpiperidin-3-amine (5.24 g, 22.15 mmol) in 80 mL of NMP was added DIPEA (17.59 mL, 101 mmol) and the reaction mixture was stirred at 150° C. for 48 h. It was then cooled to RT, poured into water and extracted twice with EtOAc. The combined organic layers were washed with brine, dried over $Na_2SO_4$, filtered and evaporated. The crude was purified by column chromatography on silica gel using $CH_2Cl_2$ and MeOH (from 0% to 10%) to provide the title compound. LC-MS: Rt=0.42 min; MS m/z 241.2 [M+H]$^+$ (R)-6-Chloro-N-(1-methylpiperidin-3-yl)pyridazin-3-amine, Int P025

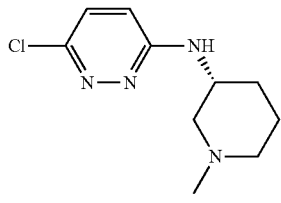

A mixture of 3,6-dichloropyridazine (500 mg, 3.26 mmol), (R)-1-methylpiperidin-3-amine (379 mg, 3.32 mmol) and DIPEA (505 mg, 3.91 mmol) in 4 mL of NMP was heated at 150° C. for 4 h. The reaction was cooled to RT and evaporated to dryness. The residue was dissolved in EtOAc and washed with a saturated solution of $Na_2CO_3$. The aqueous layer was extracted 3 more times with EtOAc. The combined organic extracts were dried over $Na_2SO_4$, filtered and evaporated to give a dark orange oil which was purified by column chromatography on silica gel (50 g) using $CH_2Cl_2$ and MeOH containing 5% of $NH_4OH$ (from 0% to 10%) to afford the title compound. $^1$H NMR (600 MHz, DMSO-$d_6$) δ (ppm) 7.34 (d, 1H), 7.00 (d, 1H), 6.92 (d, 1H), 4.03-3.93 (m, 1H), 2.90-2.70 (m, 1H), 2.58-2.51 (m, 1H) overlapping with DMSO signal, 2.19 (s, 3H), 2.12-1.87 (m, 2H), 1.84-1.75 (m, 1H), 1.74-1.64 (m, 1H), 1.57-1.47 (m, 1H), 1.37-1.23 (m, 1H). LC-MS: Rt=0.34 min; MS m/z 227.2 [M+H]+

(R)-6-Chloro-N-(1-methylpiperidin-3-yl)-4-(trifluoromethyl)pyridazin-3-amine, Int P026 and (R)-6-Chloro-N-(1-methylpiperidin-3-yl)-5-(trifluoromethyl)pyridazin-3-amine, Int P027

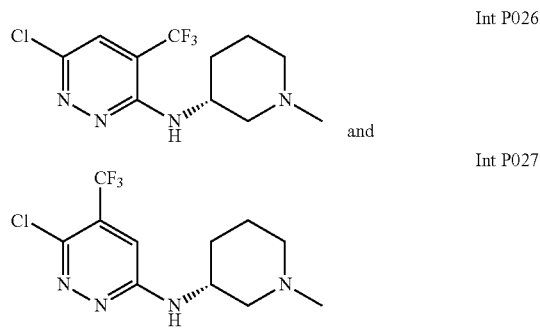

A solution of 3,6-dichloro-4-(trifluoromethyl)pyridazine (3.4 g, 15.67 mmol), (R)-1-methylpiperidin-3-amine (2.468 mL, 18.80 mmol) and DIPEA (8.21 mL, 47.0 mmol) in 5 mL of 1-butanol was heated at 110° C. for 20 h. The reaction mixture was evaporated and the crude was purified and separated by column chromatography on silica gel (220 g) using $CH_2Cl_2$ and MeOH (from 0% to 10%). The fractions containing Int P026 (first eluting) or Int P027 (second eluting) were combined separately and evaporated. Both products were then individually partitioned between $CH_2Cl_2$ and 1 M NaOH. The organic extracts were dried over $Na_2SO_4$, filtered and evaporated to give the title compounds Int P026 as a brown oil and Int P027 as a pale yellow solid, respectively.

Int P026 (first eluting): $^1$H-NMR (400 MHz, DMSO-$d_6$) δ (ppm) 7.91 (s, 1H), 6.22 (d, 1H), 4.44-4.27 (m, 1H), 2.69-2.55 (m, 1H), 2.42-2.28 (m, 1H), 2.18 (s, 3H, overlapping with m, 2H), 1.71-1.58 (m, 3H), 1.56-1.43 (m, 1H). LC-MS: Rt=0.52 min; MS m/z 295.1 [M+H]$^+$ Int P027 (second eluting): $^1$H NMR (400 MHz, DMSO-$d_6$) δ (ppm) 7.50 (d, 1H), 7.39 (s, 1H), 4.12-4.02 (m, 1H), 2.79-2.64 (m, 1H), 2.46-2.37 (m, 1H), 2.17 (s, 3H, overlapping with m, 1H), 2.08-1.98 (m, 1H), 1.81-1.63 (m, 2H), 1.58-1.46 (m, 1H), 1.43-1.30 (m, 1H). LC-MS: Rt=0.59 min; MS m/z 295.1 [M+H]$^+$ cis-3-((6-Chloro-4-(trifluoromethyl)pyridazin-3-yl)amino)-1-methylcyclobutan-1-ol, Int P028 and cis-3-((6-Chloro-5-(trifluoromethyl)pyridazin-3-yl)amino)-1-methylcyclobutan-1-ol, Int P029

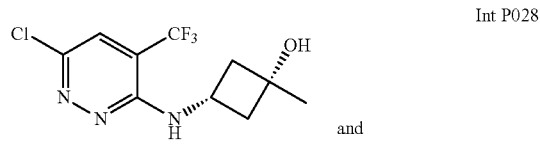

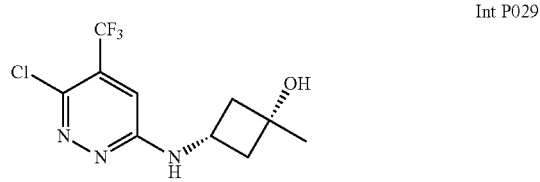

A solution of 3,6-dichloro-4-(trifluoromethyl)pyridazine (1 g, 4.61 mmol), cis-3-amino-1-methylcyclobutan-1-ol hydrochloride (0.698 g, 5.07 mmol) and DIPEA (2.415 mL, 13.83 mmol) in 5 mL of 1-butanol was heated at 180° C. for 1 h in a microwave apparatus. The reaction mixture was partitioned between EtOAc and 10% NaHCO₃ solution. The organic extract was washed with brine, dried over Na₂SO₄, filtered and evaporated. The crude was purified and separated by column chromatography on silica gel (40 g) using CH₂Cl₂ and MeOH (from 0% to 10%). The product-containing fractions were combined separately and evaporated to give the title compounds Int P028 (first eluting) as a brownish oil and Int P029 (second eluting) as a pale yellow solid, respectively.

Int P028 (first eluting): ¹H-NMR (400 MHz, DMSO-d₆) δ (ppm) 7.87 (s, 1H), 6.91 (d, 1H), 4.94 (s, 1H), 4.19-4.01 (m, 1H), 2.44-2.35 (m, 2H), 2.19-2.10 (m, 2H), 1.27 (s, 3H). LC-MS: Rt=0.82 min; MS m/z 282.1 [M+H]⁺

Int P029 (second eluting): ¹H NMR (400 MHz, DMSO-d₆) δ (ppm) 7.83 (d, 1H), 7.24 (s, 1H), 5.06 (s, 1H), 4.02-3.87 (m, 1H), 2.46-2.37 (m, 2H), 1.99-1.88 (m, 2H), 1.27 (s, 3H). LC-MS: Rt=0.82 min; MS m/z 282.1 [M+H]⁺

(R)-6-Chloro-4-methyl-N-(1-methylpiperidin-3-yl)pyridazin-3-amine, Int P030 and (R)-6-Chloro-5-methyl-N-(1-methylpiperidin-3-yl)pyridazin-3-amine, Int P031

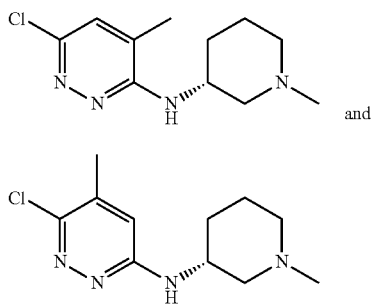

Int P030 and

Int P031

A solution of 3,6-dichloro-4-methylpyridazine (1.02 g, 6.26 mmol), (R)-1-methylpiperidin-3-amine (0.986 mL, 7.51 mmol) and DIPEA (3.28 mL, 18.77 mmol) in 5 mL of NMP was heated at 180° C. for 2 h under microwave irradiation. The reaction mixture was mostly evaporated and the residue was partitioned between CH₂Cl₂ and 1 M NaOH. The organic layer was washed with brine, dried over Na₂SO₄, filtered and evaporated. The crude was purified by column chromatography on silica gel (40 g) using CH₂Cl₂ and MeOH (from 0% to 20%) to yield the title compounds as a ~1:3 mixture of regioisomers. This mixture was further purified and separated by chiral SFC (Column: ChiralPak AY, 250×30 mm, 5 μm; at 38° C., Eluent B: 35% EtOH+ 0.1% NH₄OH, Flow: 50 mL/min, pressure: 100 bar, cycle time: 8 min.) to provide the title compounds Int P030 (first eluting) as an orange oil and Int P031 (second eluting) as a brown solid, respectively.

Int P030 (first eluting): ¹H-NMR (400 MHz, CDCl₃) δ (ppm) 6.99 (s, 1H), 4.97 (br s, 1H), 4.50-4.42 (m, 1H), 2.69-2.38 (m, 3H), 2.25 (s, 3H), 2.18-2.25 (m, 1H) overlapping with 2.13 (s, 3H), 1.89-1.77 (m, 1H), 1.74-1.67 (m, 1H), 1.61-1.51 (m, 2H). LC-MS: Rt=0.40 min; MS m/z 241.1 [M+H]⁺

Int P031 (second eluting): ¹H NMR (400 MHz, CDCl₃) δ (ppm) 6.52 (s, 1H), 5.13 (br s, 1H), 4.08-3.97 (m, 1H), 2.65-2.33 (m, 3H), 2.32-2.24 (m, 1H) overlapping with 2.26 (s, 3H) and 2.25 (s, 3H), 1.75-1.69 (m, 1H), 1.69-1.52 (m, 3H). LC-MS: Rt=0.43 min; MS m/z 241.1 [M+H]⁺

Alternatively, substituted pyridazine intermediate Int P030 was prepared using a regioselective route described below:

(R)-6-Chloro-4-methyl-N-(1-methylpiperidin-3-yl)pyridazin-3-amine, Int P030

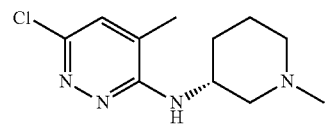 [SMILES: Cc1cc(Cl)nnc1N[C@@H]1CCCN(C)C1]

(1) 6-Chloro-2-(4-methoxybenzyl)-5-methylpyridazin-3(2H)-one, Int P032

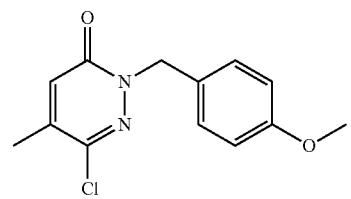

6-chloro-4-methylpyridazin-3(2H)-one (25 g, 173 mmol), 1-(bromomethyl)-4-methoxybenzene (36.5 g, 182 mmol), K₂CO₃ (47.8 g, 346 mmol) and Bu₄NBr (2.79 g, 8.65 mmol) were dissolved in 300 mL of acetonitrile. The mixture was heated to 90° C. and stirred for 2.25 h. The mixture was cooled to RT and filtered over a pad of Celite@. The filtrate was evaporated to dryness under reduced pressure to afford the title compound as a brown oil which was used in the next step without further purification. LC-MS: Rt=0.98 min; MS m/z 265.1 [M+H]⁺

(2) (R)-2-(4-Methoxybenzyl)-5-methyl-6-((1-methylpiperidin-3-yl)amino)pyridazin-3(2H)-one, Int P033

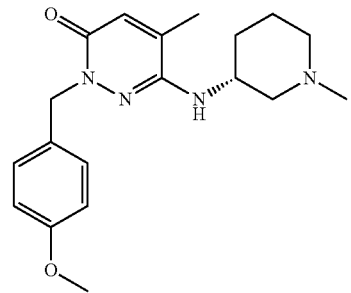 [SMILES: COc1ccc(Cn2nc(N[C@@H]3CCCN(C)C3)c(C)cc2=O)cc1]

A mixture of Int P032 (30.5 g, 115.3 mmol), (R)-1-methylpiperidin-3-amine (15 g, 131 mmol) and Cs₂CO₃ (75 g, 231 mmol) in 300 mL of dry toluene was purged with nitrogen for 5 min. Then, Pd(OAc)₂ (1.3 g, 5.79 mmol) and BINAP (8 g, 12.85 mmol) were added successively and the reaction mixture was stirred under reflux for 3 h. It was then cooled to RT and filtered over a pad of Celite@. The filter cake was washed with toluene. The filtrate was evaporated to dryness under reduced pressure to afford the title compound as a brown oil, which was used without further purification. LC-MS: Rt=0.51 min; MS m/z 343.5 [M+H]⁺

(3) (R)-5-Methyl-6-((1-methylpiperidin-3-yl)amino)pyridazin-3(2H)-one, Int P034

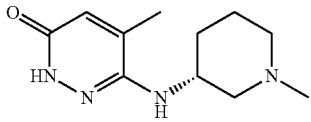 [SMILES: Cc1cc(=O)[nH]nc1N[C@@H]1CCCN(C)C1]

Int P033 (39.4 g, 115 mmol) was dissolved in 250 mL of TFA. The dark brown mixture was stirred under reflux for 2 days. The reaction mixture was evaporated to dryness. The residue was dissolved in 200 mL of acetonitrile and 5 mL of water and evaporated to dryness again. The resulting black oil was triturated with Et₂O. The supernatant was removed and the remaining brown oil was dried under high vacuum to afford the title compound which was used without further purification. LC-MS: Rt=0.19/0.25 min (injection peaks); MS m/z 223.2 [M+H]⁺

(4) (R)-6-Chloro-4-methyl-N-(1-methylpiperidin-3-yl)pyridazin-3-amine, Int P030

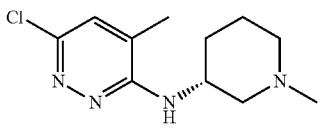 [SMILES: Cc1cc(Cl)nnc1N[C@@H]1CCCN(C)C1]

POCl₃ (250 mL) was added to a solution of Int P034 (38.7 g, 115 mmol) in 250 mL of dry acetonitrile and the mixture was heated under reflux for 2.5 days. The reaction mixture was cooled to RT and evaporated to dryness. The black oily residue was dissolved in 200 mL of acetonitrile. This solution was added dropwise (strongly exothermic) to an ice cold saturated solution of Na₂CO₃. The pH was adjusted to >12 by addition of 30% NaOH. This black mixture was evaporated to dryness, then treated with a 1:1 mixture of CH₂Cl₂ and MeOH. This black suspension was stirred for 30 min at RT. It was then filtered through a pad of Celite® and the filter cake was washed with more of the 1:1 mixture of CH₂Cl₂ and MeOH (~500 mL). The filtrate was evaporated to dryness, affording the title compound as a black solid which was used without further purification. LC-MS: Rt=0.43 min; MS m/z 241.1 [M+H]+ cis-3-((6-Chloro-4-methylpyridazin-3-yl)amino)-1-methylcyclobutan-1-ol, Int P035 and cis-3-((6-Chloro-5-methylpyridazin-3-yl)amino)-1-methylcyclobutan-1-ol, Int P036

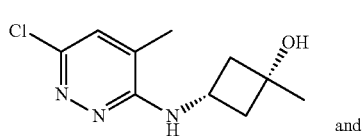

and

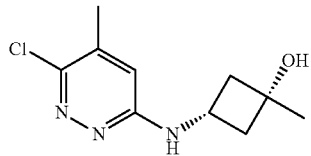

A solution of cis-3-amino-1-methylcyclobutan-1-ol (309 mg, 2.392 mmol), 3,6-dichloro-4-methylpyridazine (300 mg, 1.840 mmol) and DIPEA (1.3 mL, 7.36 mmol) in 1.9 mL of 1-butanol was heated at 180° C. for 90 minutes in a microwave apparatus. The reaction mixture was evaporated and the crude orange oil was partitioned between EtOAc and 2 M Na₂CO₃ solution. The organic extract was washed with brine, dried over Na₂SO₄, filtered and evaporated. The crude was purified and separated by column chromatography on silica gel (40 g) using CH₂Cl₂ and MeOH (from 0% to 5%). The product-containing fractions were combined separately and evaporated to give the title compounds Int P035 (first eluting) as a beige solid and Int P036 (second eluting) as a white solid, respectively.

Int P035 (first eluting): ¹H-NMR (400 MHz, CDCl₃) δ (ppm) 7.02 (s, 1H), 4.38 (br s, 1H), 4.32-4.20 (m, 1H), 2.77-2.63 (m, 2H), 2.11 (s, 3H), 2.09-2.00 (m, 2H), 1.96 (s, 1H), 1.45 (s, 3H). LC-MS: Rt=0.58 min; MS m/z 228.1 [M+H]⁺

Int P036 (second eluting): ¹H NMR (400 MHz, CDCl₃) δ (ppm) 6.52-6.47 (m, 1H), 5.81-5.69 (m, 1H), 3.91-3.76 (m, 1H), 2.76 (s, 1H), 2.72-2.63 (m, 2H), 2.29 (d, 3H), 2.18-2.08 (m, 2H), 1.43 (s. 3H). LC-MS: Rt=0.58 min: MS m/z 228.1 [M+H]⁺ cis-3-((6-Chloropyridazin-3-yl)amino)-1-methylcyclobutan-1-ol, Int P037

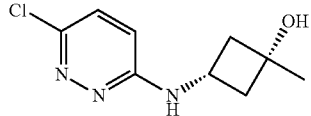

A solution of 3,6-dichloropyridazine (1 g, 6.71 mmol), cis-3-amino-1-methylcyclobutan-1-ol (0.970 g, 7.05 mmol) and DIPEA (4.1 mL, 23.49 mmol) in 8 mL of 1-butanol was heated at 180° C. for 1 h under microwave irradiation. The reaction mixture was poured onto water and extracted 3-times with EtOAc. The combined organic extracts were washed with brine, dried over Na₂SO₄, filtered and evaporated. The crude was triturated with acetonitrile for 20 min, filtered off and washed once more with acetonitrile to give the title compound as beige solid. ¹H-NMR (400 MHz, DMSO-$d_6$) δ (ppm) 7.33 (overlapping d, 1H and br s, 1H), 6.84 (d, 1H), 4.98 (s, 1H), 3.91-3.78 (m, 1H), 2.42-2.34 (m, 2H), 1.96-1.86 (m, 2H), 1.26 (s, 3H). LC-MS: Rt=0.53 min; MS m/z 214.1 [M+H]$^+$ (1S,3R)-3-((6-Chloropyridazin-3-yl)amino)cyclohexan-1-ol, Int P038

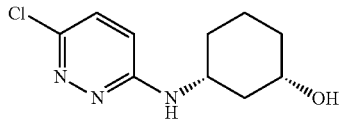

A solution of 3,6-dichloropyridazine (100 mg, 0.671 mmol), (1S,3R)-3-aminocyclohexan-1-ol (102 mg, 0.671 mmol) and DIPEA (0.352 mL, 2.014 mmol) was heated at 180° C. in a microwave apparatus for 1 hour. The residue was dissolved in EtOAc and washed with saturated NaHCO$_3$ and brine, dried over Na$_2$SO$_4$, filtered and evaporated. Column chromatography on silica gel (12 g) using CH$_2$Cl$_2$ and MeOH (from 0% to 10%) provided the title compound as sticky solid. LC-MS: Rt=0.55 min; MS m/z 228.1 [M+H]$^+$ (R)-3-Chloro-6-((1-methylpiperidin-3-yl)oxy)pyridazine, Int P039

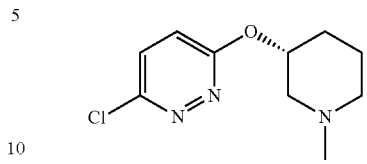

To an ice-cold mixture of 3,6-dichloropyridazine (150 mg, 1.0 mmol) and (R)-3-hydroxy-1-methylpiperidine (128 mg, 1.1 mmol) in 1 mL of 1,4-dioxane was slowly added NaH (60% in mineral oil, 161 mg, 4.0 mmol) and the suspension was stirred at 0° C. for 1 h. It was then quenched by careful addition of water and acidified with 1 M HCl. The aqueous layer was separated and washed with EtOAc, then made basic by addition of saturated Na$_2$CO$_3$ solution and extracted with EtOAc. The organic extract was evaporated and the crude was purified by column chromatography on silica gel (25 g) using CH$_2$Cl$_2$ and MeOH (from 0% to 20%) to afford the title compound as a colorless oil. $^1$H NMR (400 MHz, DMSO-$d_6$) δ (ppm) 7.76 (d, 1H). 7.31 (d, 1H), 522-514 (m, 1H),2.90-2.82 (m, 1H), 2.48-2.43 (m, 1H) overlapping with DMSO-signal, 2.24-2.19 (m, 1H), 2.17 (s, 3H), 2.14-2.05 (m, 1H), 2.02-1.92 (m, 1H), 1.79-1.72 (m, 1H), 1.55-1.50 (m, 2H). LC-MS: Rt=0.36 min; MS m/z 228.2 [M+H]$^+$ The following pyridazine intermediates (IntP) were prepared analogous to the above procedures using the corresponding 3,6-dihalopyridazines and the appropriate amines, optionally followed by a deprotection step:

| Int No. | Structure | Name | LC-MS (min; m/z) |
|---|---|---|---|
| Int P040 | 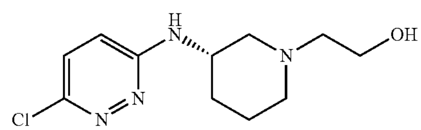 [SMILES: OCCN1CCC[C@H](Nc2ccc(Cl)nn2)C1] | (S)-2-(3-((6-Chloropyridazin-3-yl)amino)piperidin-1-yl)ethan-1-ol | Rt = 0.32; 257.2 [M + H]+ |
| Int P041 | 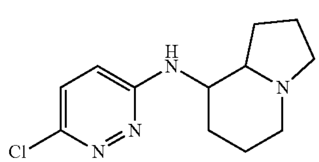 [SMILES: Clc1ccc(NC2CCCN3CCCC23)nn1] | (rac)-(8r,8ar)-N-(6-Chloropyridazin-3-yl)octahydroindolizin-8-amine | Rt = 0.38; 253.2 [M + H]+ |
| Int P042 | 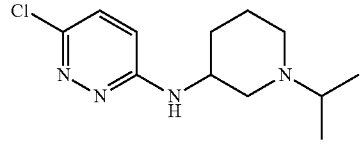 [SMILES: CC(C)N1CCCC(Nc2ccc(Cl)nn2)C1] | (rac)-6-Chloro-N-(1-isopropylpiperidin-3-yl)pyridazin-3-amine | Rt = 0.35; 255.3 [M + H]+ |
| Int P043 | 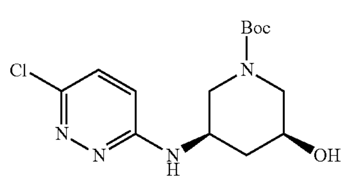 [SMILES: CC(C)(C)OC(=O)N1C[C@@H](O)C[C@@H](Nc2ccc(Cl)nn2)C1] | tert-Butyl (3R,5S)-3-((6-chloropyridazin-3-yl)amino)-5-hydroxypiperidine-1-carboxylate | Rt = 0.78; 329.2 [M + H]+ |

| Int No. | Structure | Name | LC-MS (min; m/z) |
|---|---|---|---|
| Int P044 | 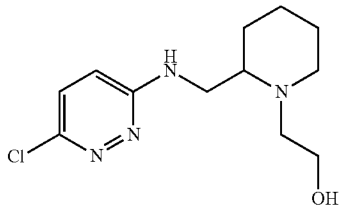 [SMILES: OCCN1CCCCC1CNc1ccc(Cl)nn1] | (rac)-2-(2-(((6-Chloropyridazin-3-yl)amino)methyl)piperidin-1-yl)ethan-1-ol) | Rt = 0.34; 271.2 [M + H]+ |
| Int P045 | 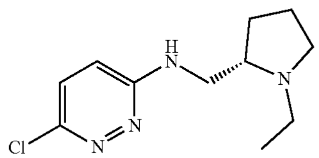 [SMILES: CCN1CCC[C@H]1CNc1ccc(Cl)nn1] | (S)-6-Chloro-N-((1-ethylpyrrolidin-2-yl)methyl)pyridazin-3-amine | Rt = 0.38; 241.2 [M + H]+ |
| Int P046 | 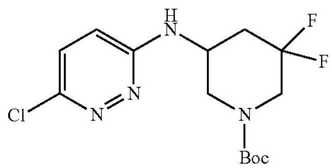 [SMILES: CC(C)(C)OC(=O)N1CC(Nc2ccc(Cl)nn2)CC(F)(F)C1] | (rac)-tert-Butyl 5-((6-chloropyridazin-3-yl)amino)-3,3-difluoropiperidine-1-carboxylate | Rt = 0.98; 349.2 [M + H]+ |
| Int P047 | 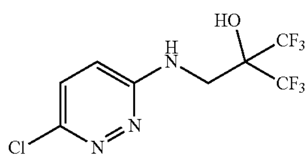 [SMILES: OC(CNc1ccc(Cl)nn1)(C(F)(F)F)C(F)(F)F] | 2-(((6-Chloropyridazin-3-yl)amino)methyl)-1,1,1,3,3,3-hexafluoropropan-2-ol | Rt = 0.92; 310.1 [M + H]+ |
| Int P048 | 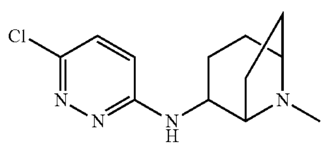 [SMILES: CN1C2CCC(Nc3ccc(Cl)nn3)C1CC2] | (rac)-(1s,2s,5s)-N-(6-Chloropyridazin-3-yl)-8-methyl-8-azabicyclo[3.2.1]octan-2-amine | Rt = 0.37; 253.2 [M + H]+ |
| Int P049 | 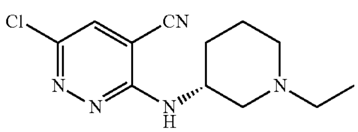 [SMILES: CCN1CCC[C@@H](Nc2nnc(Cl)cc2C#N)C1] | (R)-6-Chloro-3-((1-ethylpiperidin-3-yl)amino)pyridazine-4-carbonitrile | Rt = 0.44; 266.3 [M + H]+ |
| Int P050 | 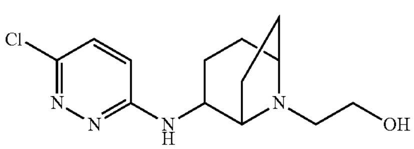 [SMILES: OCCN1C2CCC(Nc3ccc(Cl)nn3)C1CC2] | (rac)-2-((1s,2s,5s)-2-((6-Chloropyridazin-3-yl)amino)-8-azabicyclo[3.2.1]octan-8-yl)ethan-1-ol | Rt = 0.39; 284.2 [M + H]+ |
| Int P051 | 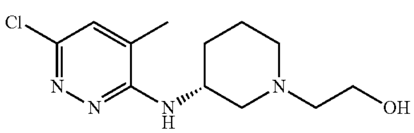 [SMILES: Cc1cc(Cl)nnc1N[C@@H]1CCCN(CCO)C1] | (R)-2-(3-((6-Chloro-4-methylpyridazin-3-yl)amino)piperidin-1-yl)ethan-1-ol | Rt = 0.42; 271.3 [M + H]+ |
| Int P052 | 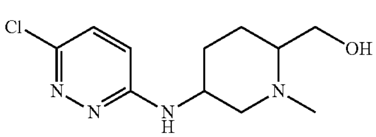 [SMILES: CN1CC(Nc2ccc(Cl)nn2)CCC1CO] | (rac)-((cis)-5-((6-Chloropyridazin-3-yl)amino)-1-methylpiperidin-2-yl)methanol | Rt = 0.34; 257.2 [M + H]+ |
| Int P053 | 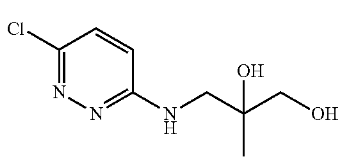 | (rac)-3-((6-Chloropyridazin-3-yl)amino)-2-methylpropane-1,2-diol | Rt = 0.39; 218.1 [M + H]+ |

-continued

| Int No. | Structure | Name | LC-MS (min; m/z) |
|---|---|---|---|
| Int P054 | 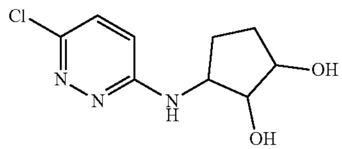 [SMILES: OC1CCC(Nc2ccc(Cl)nn2)C1O] | (rac)-(1s,2r,3s)-3-((6-Chloropyridazin-3-yl)amino)cyclopentane-1,2-diol | Rt = 0.43; 230.1 [M + H]+ |
| Int P055 | 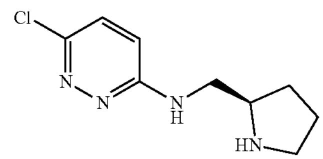 [SMILES: Clc1ccc(NC[C@H]2CCCN2)nn1] | (R)-6-Chloro-N-(pyrrolidin-2-ylmethyl)pyridazin-3-amine | Rt = 0.33; 213.2 [M + H]+ |
| Int P056 | 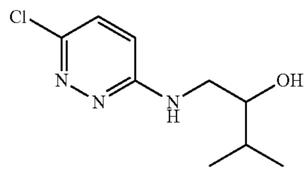 | (rac)-1-((6-Chloropyridazin-3-yl)amino)-3-methylbutan-2-ol | Rt = 0.62; 216.2 [M + H]+ |
| Int P057 | 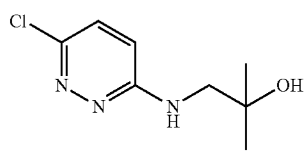 | 1-((6-Chloropyridazin-3-yl)amino)-2-methylpropan-2-ol | Rt = 0.49; 202.1 [M + H]+ |
| Int P058 | 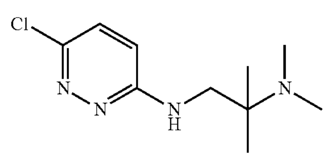 | N1-(6-Chloropyridazin-3-yl)-N2,N2,2-trimethylpropane-1,2-diamine | Rt = 0.36; 229.2 [M + H]+ |
| Int P059 | 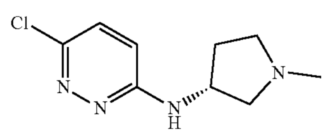 | (R)-Chloro-N-(1-methylpyrrolidin-3-yl)pyridazin-3-amine | Rt = 0.32; 213.1 [M + H]+ |
| Int P060 | 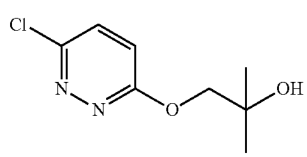 | 1-((6-Chloropyridazin-3-yl)oxy)-2-methylpropan-2-ol | Rt = 0.58; 203.1 [M + H]+ |
| Int P061 | 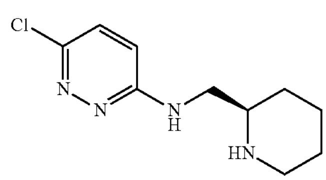 [SMILES: Clc1ccc(NC[C@H]2CCCCN2)nn1] | (R)-6-Chloro-N-(piperidin-2-ylmethyl)pyridazin-3-amine | Rt = 0.37; 227.1 [M + H]+ |
| Int P062 | 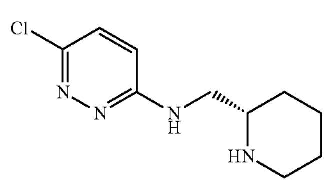 [SMILES: Clc1ccc(NC[C@@H]2CCCCN2)nn1] | (S)-6-Chloro-N-(piperidin-2-ylmethyl)pyridazin-3-amine | Rt = 0.37; 227.1 [M + H]+ |

| Int No. | Structure | Name | LC-MS (min; m/z) |
|---|---|---|---|
| Int P063 | 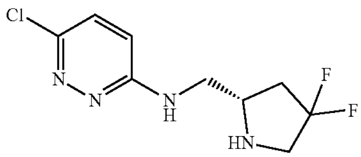 [SMILES: FC1(F)CN[C@H](CNc2ccc(Cl)nn2)C1] | (S)-6-Chloro-N-((4,4-difluoropyrrolidin-2-yl)methyl)pyridazin-3-amine | Rt = 0.37; 249.1 [M + H]+ |
| Int P064 | 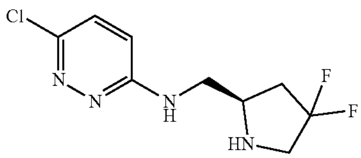 [SMILES: FC1(F)CN[C@@H](CNc2ccc(Cl)nn2)C1] | (R)-6-Chloro-N-((4,4-difluoropyrrolidin-2-yl)methyl)pyridazin-3-amine | Rt = 0.37; 249.1 [M + H]+ |
| Int P065 | 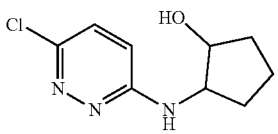 [SMILES: OC1CCCC1Nc1ccc(Cl)nn1] | (rac)-trans-2-((6-Chloropyridazin-3-yl)amino)cyclopentanol | Rt = 0.55; 214.2 [M + H]+ |
| Int P066 | 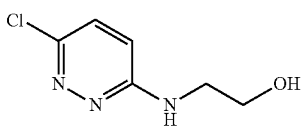 [SMILES: OCCNc1ccc(Cl)nn1] | 2-((6-Chloropyridazin-3-yl)amino)ethanol | Rt = 0.36; 174.0 [M + H]+ |
| Int P067 | 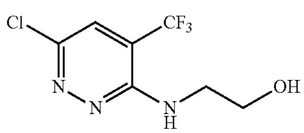 [SMILES: OCCNc1nnc(Cl)cc1C(F)(F)F] | 2-((6-Chloro-4-(trifluoromethyl)pyridazin-3-yl)amino)ethanol | Rt = 0.65; 242.1 [M + H]+ |
| Int P068 | 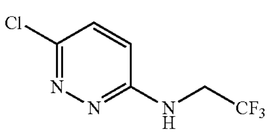 [SMILES: FC(F)(F)CNc1ccc(Cl)nn1] | 6-Chloro-N-(2,2,2-trifluoroethyl)pyridazin-3-amine | Rt = 0.33; 212.1 [M + H]+ |
| Int P069 | 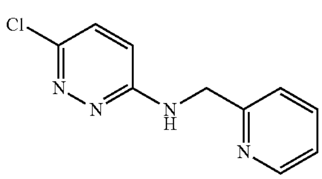 [SMILES: Clc1ccc(NCc2ccccn2)nn1] | 6-Chloro-N-(pyridin-2-ylmethyl)pyridazin-3-amine | Rt = 0.45; 221.1 [M + H]+ |
| Int P070 | 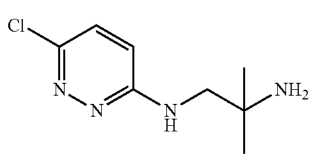 | N1-(6-Chloropyridazin-3-yl)-2-methylpropane-1,2-diamine | Rt = 0.33; 201.1 [M + H]+ |
| Int P071 | 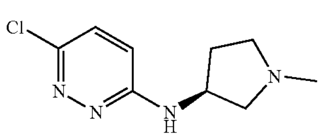 | (S)-3-Methyl-2-(6-((1-methyl pyrrolidin-3-yl)amino) pyridazin-3-yl)-5-(trifluoromethyl) phenol | Rt = 0.68; 353.2 [M + H]+ |
| Int P072 | 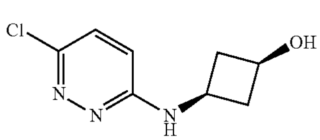 [SMILES: O[C@H]1C[C@@H](Nc2ccc(Cl)nn2)C1] | cis-3-((6-Chloropyriddazin-3-yl)amino)cyclobutan-1-ol | Rt = 0.41; 200.1 [M + H]+ |

| Int No. | Structure | Name | LC-MS (min; m/z) |
|---|---|---|---|
| Int P073 | 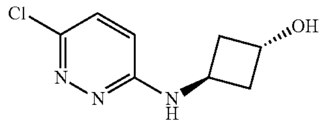 [SMILES: O[C@H]1C[C@H](Nc2ccc(Cl)nn2)C1] | trans-3-((6-Chloropyridazin-3-yl)amino)cyclobutan-1-ol | Rt = 0.43; 200.1 [M + H]+ |
| Int P074 | 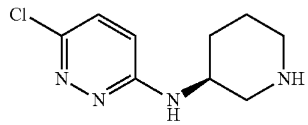 [SMILES: Clc1ccc(N[C@H]2CCCNC2)nn1] | (S)-6-Chloro-N-(piperidin-3-yl)pyridazin-3-amine | Rt = 0.35; 213.2 [M + H]+ |
| Int P075 | 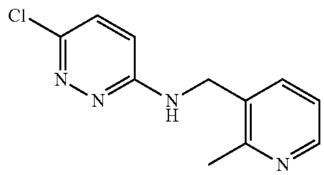 [SMILES: Cc1ncccc1CNc1ccc(Cl)nn1] | 6-Chloro-N-((2-methylpyridin-3-yl)methyl)pyridazin-3-amine | Rt = 0.37; 235.1 [M + H]+ |
| Int P076 | 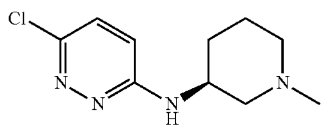 | (S)-6-Chloro-N-(1-methylpiperidin-3-yl)pyridazin-3-amine | Rt = 0.33; 227.2 [M + H]+ |
| Int P077 | 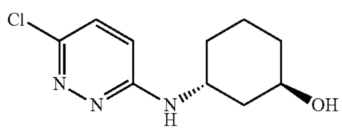 [SMILES: O[C@@H]1CCC[C@@H](Nc2ccc(Cl)nn2)C1] | (1R,3R)-3-((6-Chloropyridazin-3-yl)amino)cyclohexan-1-ol | Rt = 0.57; 228.1 [M + H]+ |
| Int P078 | 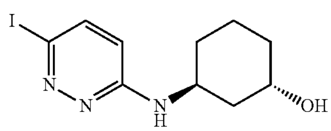 [SMILES: O[C@H]1CCC[C@H](Nc2ccc(I)nn2)C1] | (1S,3S)-3-((6-Iodopyridazin-3-yl)amino)cyclohexan-1-ol | Rt = 0.61; 320.1 [M + H]+ |
| Int P079 | 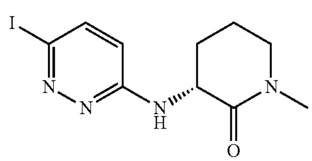 [SMILES: CN1CCC[C@@H](Nc2ccc(I)nn2)C1=O] | (R)-3-((6-Iodopyridazin-3-yl)amino)-1-methylpiperidin-2-one | Rt = 0.59; 333.0 [M + H]+ |
| Int P080 | 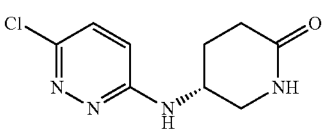 [SMILES: O=C1CC[C@@H](Nc2ccc(Cl)nn2)CN1] | (R)-5-((6-Chloropyridazin-3-yl)amino)piperidin-2-one | Rt = 0.45; 227.1 [M + H]+ |
| Int P081 | 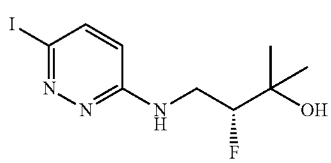 | (R)-3-Fluoro-4-((6-iodopyridazin-3-yl)amino)-2-methylbutan-2-ol | Rt = 0.63; 326.0 [M + H]+ |
| Int P082 | 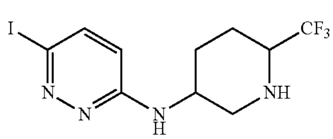 [SMILES: FC(F)(F)C1CCC(Nc2ccc(I)nn2)CN1] | 6-Iodo-N-(6-(trifluoromethyl)piperidin-3-yl)pyridazin-3-amine | Rt = 0.68; 373.1 [M + H]+ |

| Int No. | Structure | Name | LC-MS (min; m/z) |
|---|---|---|---|
| Int P083 | 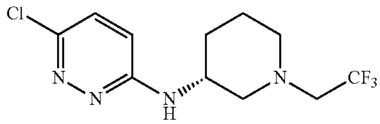 [SMILES: FC(F)(F)CN1CCC[C@@H](Nc2ccc(Cl)nn2)C1] | (R)-6-Chloro-N-(1-(2,2,2-trifluoroethyl)piperidin-3-yl)pyridazin-3-amine | Rt = 0.91; 295.1 [M + H]+ |
| Int P084 | 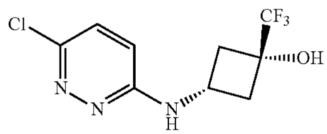 [SMILES: O[C@]1(C(F)(F)F)C[C@H](Nc2ccc(Cl)nn2)C1] | cis-3-((6-Chloropyridazin-3-yl)amino)-1-(trifluoromethyl)cyclobutan-1-ol | Rt = 0.68; 268.0 [M + H]+ |
| Int P085 | 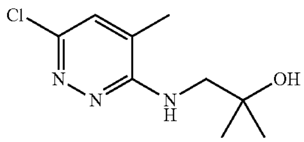 | 1-((6-Chloro-4-methylpyridazin-3-yl)amino)-2-methylpropan-2-ol | Rt = 0.59; 216.1 [M + H]+ |
| Int P086 | 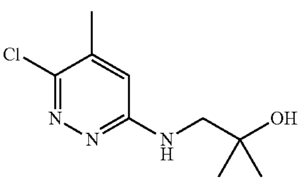 | 1-((6-Chloro-5-methylpyridazin-3-yl)amino)-2-methylpropan-2-ol | Rt = 0.57; 216.1 [M + H]+ |
| Int P087 | 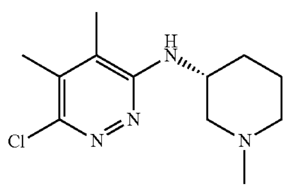 [SMILES: Cc1c(Cl)nnc(N[C@@H]2CCCN(C)C2)c1C] | (R)-6-Chloro-4,5-dimethyl-N-(1-methylpiperidin-3-yl)pyridazin-3-amine | Rt = 0.51 255.3 [M + H]+ |
| Int P088 | 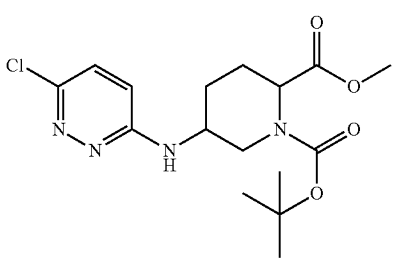 [SMILES: COC(=O)C1CCC(Nc2ccc(Cl)nn2)CN1C(=O)OC(C)(C)C] | 1-(tert-Butyl) 2-methyl 5-((6-chloropyridazin-3-yl)amino)piperidine-1,2-dicarboxylate | Rt = 0.95 371.4 [M + H]+ |
| Int P089 | 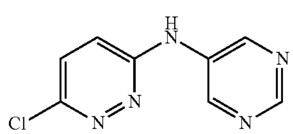 [SMILES: Clc1ccc(Nc2cncnc2)nn1] | 6-Chloro-N-(pyrimidin-5-yl)pyridazin-3-amine | Rt = 0.51 208.1 [M + H]+ |
| Int P090 | 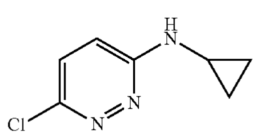 [SMILES: Clc1ccc(NC2CC2)nn1] | 6-Chloro-N-cyclopropylpyridazin-3-amine | Rt = 0.53 170.1 [M + H]+ |
| Int P091 | 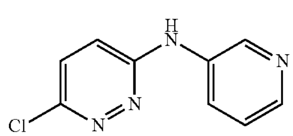 [SMILES: Clc1ccc(Nc2cccnc2)nn1] | 6-Chloro-N-(pyridin-3-yl)pyridazin-3-amine | Rt = 0.44 207.1 [M + H]+ |

| Int No. | Structure | Name | LC-MS (min; m/z) |
|---|---|---|---|
| Int P092 | 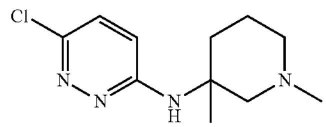 [SMILES: CN1CCCC(C)(Nc2ccc(Cl)nn2)C1] | (rac)-6-Chloro-N-(1,3-dimethylpiperidin-3-yl)pyridazin-3-amine | Rt = 0.43 241.1 [M + H]+ |
| Int P093 | 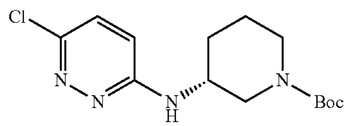 [SMILES: CC(C)(C)OC(=O)N1CCC[C@@H](Nc2ccc(Cl)nn2)C1] | tert-Butyl (R)-3-((6-chloropyridazin-3-yl)amino)piperidine-1-carboxylate | Rt = 0.98; 313.3 [M + H]+ |
| Int P094 | 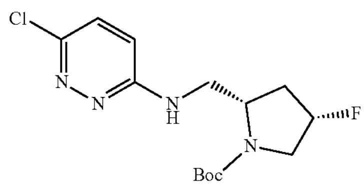 [SMILES: CC(C)(C)OC(=O)N1C[C@@H](F)C[C@H]1CNc1ccc(Cl)nn1] | tert-Butyl (2S,4S)-2-(((6-chloropyridazin-3-yl)amino)methyl)-4-fluoropyrrolidine-1-carboxylate | Rt = 0.97; 331.2 [M + H]+ |
| Int P095 | 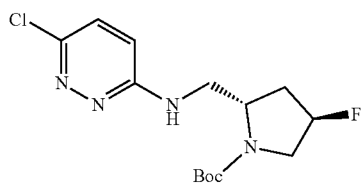 [SMILES: CC(C)(C)OC(=O)N1C[C@H](F)C[C@H]1CNc1ccc(Cl)nn1] | tert-Butyl (2S,4R)-2-(((6-chloropyridazin-3-yl)amino)methyl)-4-fluoropyrrolidine-1-carboxylate | Rt = 0.98; 331.3 [M + H]+ |
| Int P096 | 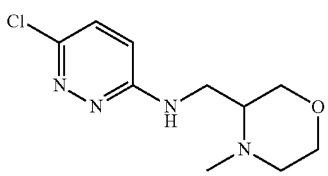 [SMILES: CN1CCOCC1CNc1ccc(Cl)nn1] | (rac)-6-Chloro-N-((4-methylmorpholin-3-yl)methyl)pyridazin-3-amine | Rt = 0.39; 243.3 [M + H]+ |
| Int P097 | 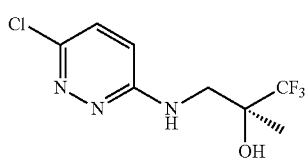 [SMILES: C[C@](O)(CNc1ccc(Cl)nn1)C(F)(F)F] | (S)-3-((6-Chloropyridazin-3-yl)amino)-1,1,1-trifluoro-2-methylpropan-2-ol | Rt = 0.75; 256.1 [M + H]+ |
| Int P098 | 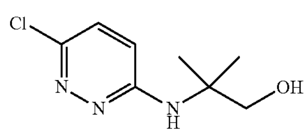 | 2-((6-Chloropyridazin-3-yl)amino)-2-methylpropan-1-ol | Rt = 0.61; 202.0 [M + H]+ |
| Int P099 | 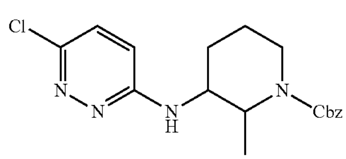 [SMILES: CC1C(Nc2ccc(Cl)nn2)CCCN1C(=O)OCc1ccccc1] | (rac)-Benzyl (cis)-3-((6-chloropyridazin-3-yl)amino)-2-methylpiperidine-1-carboxylate | Rt = 1.07; 361.2 [M + H]+ |
| Int P100 | 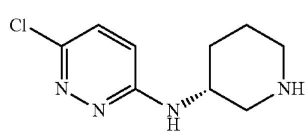 [SMILES: Clc1ccc(N[C@@H]2CCCNC2)nn1] | (R)-6-chloro-N-(piperidin-3-yl)pyridazin-3-amine | Rt = 0.39; 213.1 [M + H]+ |
| Int P101 | 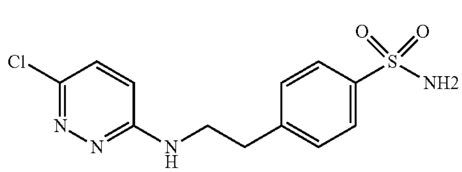 [SMILES: NS(=O)(=O)c1ccc(CCNc2ccc(Cl)nn2)cc1] | 4-(2-((6-Chloropyridazin-3-yl)amino)ethyl)benzenesulfonamide | Rt = 0.63; 313.3 [M + H]+ |

| Int No. | Structure | Name | LC-MS (min; m/z) |
|---|---|---|---|
| Int P102 | 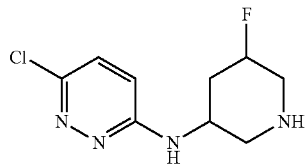 [SMILES: FC1CNCC(Nc2ccc(Cl)nn2)C1] | (rac)-trans-6-Chloro-N-(5-fluoropiperidin-3-yl)pyridazin-3-amine | Rt = 0.38; 231.1 [M + H]+ |
| Int P103 | 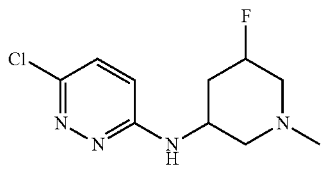 [SMILES: CN1CC(F)CC(Nc2ccc(Cl)nn2)C1] | (rac)-cis-6-Chloro-N-(5-fluoro-1-methylpiperidin-3-yl)pyridazin-3-amine | Rt = 0.32; 245.1 [M + H]+ |
| Int P104 | 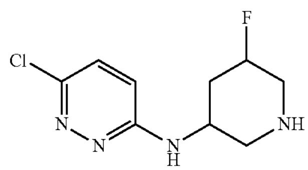 [SMILES: FC1CNCC(Nc2ccc(Cl)nn2)C1] | (rac)-cis-6-Chloro-N-(5-fluoropiperidin-3-yl)pyridazin-3-amine | Rt = 0.33; 231.1 [M + H]+ |

Further modifications of piperazine intermediates:

1-((R)-3-((6-Chloropyridazin-3-yl)amino)piperidin-1-yl)propan-2-ol, Int P105

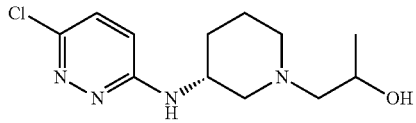 [SMILES: CC(O)CN1CCC[C@@H](Nc2ccc(Cl)nn2)C1]

Int P100 (200 mg, 0.621 mmol) was dissolved in 2 mL of DMF before adding K$_2$CO$_3$ (429 mg, 3.11 mmol) and 1-chloropropan-2-ol (0.23 mL, 1.86 mmol). The yellow suspension was stirred at 100° C. for 4.5 hours and then at 120° C. for 1.5 hours. The mixture was cooled to RT, diluted with a small amount of water and purified by achiral reverse phase HPLC to give the title compound as a pale yellow solid. LC-MS: Rt=0.40 min; MS m/z 271.2 [M+H]$^+$ (R)-1-(3-((6-Chloropyridazin-3-yl)amino)piperidin-1-yl)-2-methylpropan-2-ol, Int P106

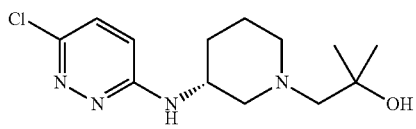 [SMILES: CC(C)(O)CN1CCC[C@@H](Nc2ccc(Cl)nn2)C1]

The title compound was synthesized analogous to the procedure described above for Int P105 using Int P100 and 1-chloro-2-methylpropan-2-ol. LC-MS: Rt=0.47 min; MS m/z 285.3 [M+H]$^+$ Synthesis of Selected Amines for the Above Intermediates (R)-2-(3-Aminopiperidin-1-yl)ethan-1-ol dihydrochloride, Int A107

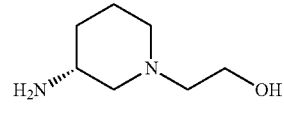

(1) tert-Butyl (R)-(1-(2-hydroxyethyl)piperidin-3-yl)carbamate, Int A108

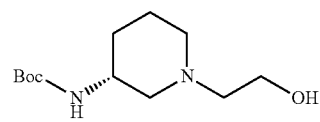 [SMILES: CC(C)(C)OC(=O)N[C@@H]1CCCN(CCO)C1]

A suspension of tert-butyl (R)-piperidin-3-ylcarbamate (10 g, 49.9 mmol), 2-bromoethan-1-ol (6.24 g, 49.9 mmol) and Na$_2$CO$_3$ (10.58 g, 100 mmol) in 100 mL of acetonitrile was stirred at RT for 2 days. The suspension was filtered and the solid was washed several times with acetonitrile. The combined filtrates were evaporated. The residue was purified by column chromatography on silica gel using CH$_2$Cl$_2$ and MeOH (from 0% to 10%) to afford the title compound. LC-MS: Rt=0.40 min; MS m/z 245.1 [M+H]$^+$ (2) (R)-2-(3-Aminopiperidin-1-yl)ethan-1-ol dihydrochloride, Int A107

A solution of Int A108 (10.0 g, 40.9 mmol) in 20 mL of CH$_2$Cl$_2$ was treated with 4 M HCl in 1,4-dioxane (40.9 mL, 164 mmol). The mixture was stirred at RT for 3 h. The precipitated was filtered off, washed several times with 1,4-dioxane and dried overnight at 60° C. under high vacuum to provide the title compound. LC-MS: Rt=0.15 min; MS m/z 145.2 [M+H]$^+$ 1-(tert-Butyl) 2-methyl 5-aminopiperidine-1,2-dicarboxylate, Int A109

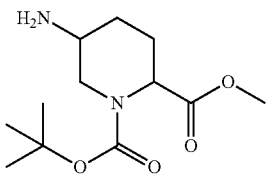

(1) 1-(tert-Butyl) 2-methyl 5-hydroxypiperidine-1,2-dicarboxylate, Int A110

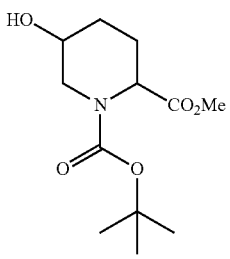 [SMILES: COC(=O)C1CCC(O)CN1C(=O)OC(C)(C)C]

1-tert-Butyl-2-methyl 5-oxopiperidine-1,2-dicarboxylate (500 mg, 1.943 mmol) was dissolved in 15 mL of MeOH and cooled to 0° C. NaBH$_4$ (73.5 mg, 19.43 mmol) was added in portions. After stirring for 3 h, half of the MeOH was removed under reduced pressure. The residue was diluted with EtOAc and washed subsequently with 0.5 M HCl, 0.5 M NaOH and brine. The organic extract was dried over Na$_2$SO$_4$, filtered and evaporated to afford the title compound as a colorless oil. The mixture of diastereomers was used without further purification. $^1$H-NMR (400 MHz, DMSO-d$_6$) δ (ppm) 4.95 (d, 1H), 4.70-4.54 (m, 1H), 3.97-3.84 (m, 1H), 3.68 and 3.67 (2 s (diastereomers), 3H), 3.42-3.29 (m, 2H), 2.11-2.05 (m, 1H), 1.85-1.72 (m, 1H), 1.72-1.58 (m, 1H), 1.41 and 1.36 (2 s (diastereomers), 9H), 1.04-0.94 (m, 1H).

(2) 1-(tert-Butyl) 2-methyl 5-azidopiperidine-1,2-dicarboxylate, Int A111

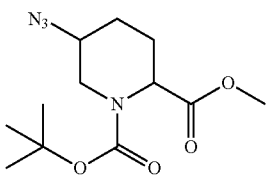

Int A110 (526 mg, 1.927 mmol) was dissolved in 10 mL of toluene and treated at RT with PPh$_3$ (1.064 g, 4.06 mmol) and Zn(N$_3$)$_2$ (468 mg, 1.521 mmol). To this mixture, DIAD (0.789 mL, 4.06 mmol) was then added dropwise. After stirring at RT for 4 h, the reaction mixture was filtered through Hyflo and washed with EtOAc. The filtrate was evaporated and the crude was purified by column chromatography on silica gel (50 g) using n-heptane and EtOAc (from 10% to 80%), to afford the title compound as a mixture of diastereomers. $^1$H-NMR (400 MHz, DMSO-d$_6$) δ (ppm) 4.88-4.63 (m, 1H), 4.05-3.90 (m, 2H), 3.68 (s, 3H), 3.19-2.97 (m, 1H), 1.99-1.78 (m, 2H), 1.72-1.63 (m, 1H), 1.55-1.47 (m, 1H), 1.41 and 1.39 (2 s (diastereomers), 9H).

(3) 1-(tert-Butyl) 2-methyl 5-aminopiperidine-1,2-dicarboxylate, IntA109

To a suspension of Pd/C (159 mg, 0.15 mmol, 10% Pd content) in 10 mL of MeOH was added a solution of Int A111 (426 mg, 1.498 mmol) in 30 mL of MeOH. The mixture was hydrogenated under atmospheric pressure at RT for 1 h. The mixture was filtered through a pad of Celite® and washed with EtOAc. The filtrate was evaporated to afford the title compound as mixture of diastereomers and was used without further purification. $^1$H-NMR (400 MHz, DMSO-d$_6$) δ (ppm) 4.75-4.5 (m, 1H), 3.65 (s, 3H), 3.59-3.52 (m, 1H), 3.31 (s, 2H), 3.15-2.86 (m, 2H), 2.16-2.02 (m, 1H), 1.82-1.71 (m, 1H), 1.49-1.40 (m, 2H) overlapping with 1.38 (s, 9H).

SYNTHESIS OF EXAMPLES

Example Ex 001

(R)-2-(6-((1-Ethylpiperidin-3-yl)amino)pyridazin-3-yl)-3-methyl-5-(trifluoromethyl)phenol

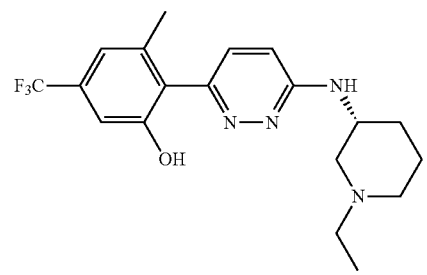 [SMILES: CCN1CCC[C@@H](Nc2ccc(-c3c(C)cc(C(F)(F)F)cc3O)nn2)C1]

Int P024 (770 mg, 1.663 mmol) and Int B010 (754 mg, 2.495 mmol) were dissolved in 8 mL of 1,4-dioxane and 2M Na$_2$CO$_3$ (0.25 mL, 0.499 mmol) added. Then, Pd(Ph$_3$P)$_4$ (96 mg, 0.083 mmol) was added and the reaction mixture was purged with nitrogen for 5 min and then stirred at 120° C. for 1 h under microwave irradiation. The reaction mixture was poured into water and extracted twice with EtOAc. The combined organic extracts were evaporated and the residue was purified by column chromatography on silica gel using CH$_2$Cl$_2$ and MeOH (from 0% to 10%) to provide the title compound. $^1$H NMR (600 MHz, DMSO-d$_6$) δ (ppm) 10.14 (s, 1H), 7.22 (d, 1H), 7.10 (d, 1H), 7.04 (d, 1H), 6.88 (d, 1H), 6.75 (d, 1H), 4.07 (s, 1H), 2.97 (s, 1H), 2.37 (s, 3H), 2.13 (s, 3H), 2.08-1.83 (m, 3H), 1.78-1.67 (m, 1H), 1.60-1.48 (m, 1H), 1.39-1.27 (m, 1H), 1.01 (t, 3H). LC-MS: Rt=0.42 min; MS m/z 241.3 [M+H]$^+$

Example Ex 002

2-(6-(((cis)-3-Hydroxy-3-methylcyclobutyl)amino)pyridazin-3-yl)-3-methyl-5-(trifluoromethyl)phenol

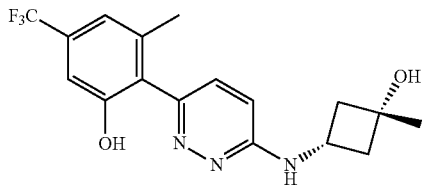 [SMILES: Cc1cc(C(F)(F)F)cc(O)c1-c1ccc(N[C@H]2C[C@@](C)(O)C2)nn1]

A mixture of Int P037 (50 mg, 0.145 mmol), Int B005 (35.1 mg, 0.160 mmol) and 2 M Na₂CO₃ (0.218 mL, 0.435 mmol) in 1 mL of DME and 1 mL of water was purged with argon for 3 min. Then, Pd(PPh₃)₄ (8.38 mg, 7.25 µmol) was added and the mixture was heated at 140° C. for 30 min under microwave irradiation. The reaction mixture was evaporated and purified by column chromatography on silica gel (4 g) using CH₂Cl₂ and MeOH (from 0% to 4%) to provide the title compound as pale yellow solid. ¹H-NMR (400 MHz, DMSO-d₆) δ (ppm) 10.13 (s, 1H), 7.22 (d, 1H), 7.13 (d, 1H), 7.10 (s, 1H), 7.04 (s, 1H), 6.81 (d, 1H), 4.99 (s, 1H), 4.03-3.90 (m, 1H), 2.45-2.38 (m, 2H), 2.12 (s, 3H), 2.00-1.92 (m, 2H), 1.29 (s, 3H). LC-MS: Rt=0.80 min; MS m/z 354.1 [M+H]⁺

Example Ex 003

2-(6-(((1R,3S)-3-Hydroxycyclohexyl)amino)pyridazin-3-yl)-3-methyl-5-(trifluoromethyl)phenol

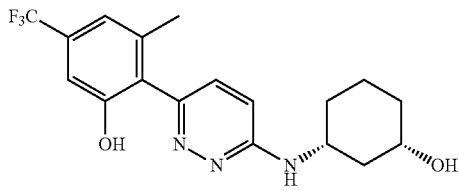 [SMILES: Cc1cc(C(F)(F)F)cc(O)c1-c1ccc(N[C@@H]2CCC[C@H](O)C2)nn1]

A mixture of Int P038 (50 mg, 0.220 mmol), Int B010 (73.0 mg, 0.242 mmol) and 2 M Na₂CO₃ (0.329 mL, 0.659 mmol) in 5 mL of 1,4-dioxane and was purged with argon for 3 min. Then, Pd(PPh₃)₄ (7.61 mg, 6.59 µmol) was added and the mixture was stirred at 120° C. for 6 h. Another portion of Int B010 (50.0 mg, 0.166 mmol) was added together with more Pd(PPh₃)₄ (5 mg, 4.33 µmol) and heating continued for 24 h. The reaction mixture was allowed to cool to RT. It was diluted with water and extracted with EtOAc. The organic layer was washed with water and brine, dried over Na₂SO₄, filtered and evaporated. The crude was purified by SFC (Column: Waters TORUS 2-PIC 130A, 250×30 mm, 5 µm; 35° C., Eluent B: 17-25% MeOH in 10 min., Flow: 100 mL/min, pressure: 120 bar) to give the title compound as white solid. ¹H-NMR (400 MHz, DMSO-d₆) δ (ppm) 10.14 (s, 1H), 7.21 (d, 1H), 7.10 (s, 1H), 7.04 (s, 1H), 6.84-6.76 (m, 2H), 4.65 (d, 1H), 3.93-3.80 (m, 1H), 3.54-3.45 (m, 1H), 2.27-2.18 (m, 1H), 2.13 (s, 3H), 2.02-1.92 (m, 1H), 1.87-1.79 (m, 1H), 1.76-1.65 (m, 1H), 1.37-1.22 (m, 1H), 1.18-1.00 (m, 3H). LC-MS: Rt=0.78 min; MS m/z 368.2 [M+H]⁺

Example Ex 004

(R)-2-(4-Methyl-6-((1-methylpiperidin-3-yl)amino)pyridazin-3-yl)-5-(trifluoromethyl)phenol

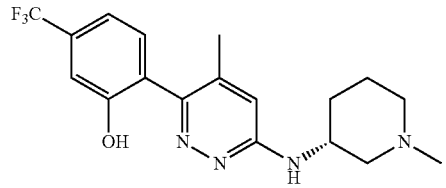 [SMILES: Cc1cc(N[C@@H]2CCCN(C)C2)nnc1-c1ccc(C(F)(F)F)cc1O]

A mixture of Int P031 (438 mg, 1.819 mmol), commercially available (2-hydroxy-4-(trifluoromethyl)phenyl)boronic acid (CAS 1072951-50-8, 412 mg, 2.001 mmol), Pd(PPh₃)₄ (63.1 mg, 0.055 mmol) and 1.2 M NaHCO₃ (4.55 mL, 5.46 mmol) in 9 mL of 1,4-dioxane was heated at 105° C. overnight. To complete the conversion, another portion of (2-hydroxy-4-(trifluoromethyl)phenyl)boronic acid (187 mg, 0.909 mmol) was added and the mixture was heated at 180° C. for 30 min under microwave irradiation. The reaction mixture was diluted with water and extracted twice with CH₂Cl₂. The combined organic extracts were dried over Na₂SO₄, filtered and evaporated. The crude was purified by column chromatography on silica gel (40 g) using CH₂Cl₂ and MeOH (from 0% to 20%). The product containing fractions were evaporated and triturated with CH₂Cl₂ to give the title compound as white solid. ¹H-NMR (400 MHz, DMSO-d₆) δ (ppm) 10.45 (s, 1H), 7.39 (d, 1H), 7.26-7.16 (m, 2H), 6.70 (s, 1H), 6.63 (d, 1H), 4.11-3.98 (m, 1H), 2.89-2.82 (m, 1H), 2.18 (s, 3H), 2.01 (s, 3H, overlapping with m, 1H), 1.94-1.78 (m, 3H), 1.75-1.66 (m, 1H), 1.59-1.48 (m, 1H), 1.35-1.24 (m, 1H). LC-MS: Rt=0.67 min; MS m/z 367.3 [M+H]⁺

Example Ex 005

(R)-3-Methyl-2-(5-methyl-6-((1-methylpiperidin-3-yl)amino)pyridazin-3-yl)-5-(trifluoromethyl)phenol

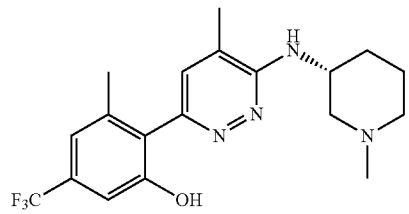 [SMILES: Cc1cc(-c2c(C)cc(C(F)(F)F)cc2O)nnc1N[C@@H]1CCCN(C)C1]

A mixture of amine Int P030 (76 mg, 0.316 mmol), boronate Int B010 (124 mg, 0.410 mmol) and aqueous 2 M Na₂CO₃ (0.474 mL, 0.947 mmol) in 2 mL of 1,4-dioxane was purged with argon for 3 minutes. Then, Pd(Ph₃P)₄ (10.9 mg, 9.4 µmol) was added and the mixture was heated at 120° C. for 2 hours. Another portion of Int B010 (50 mg, 0.166 mmol) and Pd(Ph₃P)₄ (10.9 mg, 9.4 µmol) was added and heating continued overnight. The reaction mixture was allowed to cool to RT, diluted with water and extracted with ethyl acetate. The organic layer was washed with water and brine, dried over Na₂SO₄, filtered and evaporated. The crude was purified by SFC (Column: Waters Viridis 2-EP 130A, 250×30 mm, 5 μm; 35° C., Eluent B: 16-24% MeOH in 10 min. Flow: 100 mL/min, pressure: 120 bar) to provide the title compound as white solid. ¹H NMR (400 MHz, DMSO-$d_6$) δ (ppm) 10.12 (s, 1H), 7.13-7.11 (m, 1H), 7.09 (br s, 1H), 7.05 (br s, 1H), 5.80 (d, 1H), 4.33-4.22 (m, 1H), 3.00-2.89 (m, 1H), 2.69-2.59 (m, 1H), 2.21 (s, 3H), 2.12 (br s, 3+3H), 2.04-1.92 (m, 2H), 1.92-1.84 (m, 1H), 1.77-1.66 (m, 1H), 1.63-1.51 (m, 1H), 1.49-1.36 (m, 1H). LC-MS: Rt=0.74 min; MS m/z 381.3 [M+H]⁺

The following examples were synthesized analogous to the above procedures, using the appropriate halo-pyridazine intermediates (Int P) and the corresponding boronic acids or boronate intermediates (Int B) or commercially available boronic acids (BCA), respectively, optionally followed by deprotection steps:

| Ex No. | Structure and Name | ¹H NMR | LC-MS (min; m/z) | IntP & IntB |
|---|---|---|---|---|
| Ex 006 | (R)-2-(6-((1-(2-Hydroxyethyl)piperidin-3-yl)amino)pyridazin-3-yl)-3-methyl-5-(trifluoromethyl)phenol | (600 MHz, DMSO-$d_6$) δ (ppm) 10.15 (s, 1H), 7.22 (d, 1H), 7.10 (s, 1H), 7.04 (s, 1H), 6.87 (d, 1H), 6.78 (d, 1H), 4.45-4.34 (m, 1H), 4.19-4.01 (m, 1H), 3.50 (q, 2H), 3.00-2.88 (m, 1H), 2.75-2.59 (m, 1H), 2.47-2.35 (m, 2H), 2.13 (s, 3H), 2.18-1.98 (m, 1H), 1.90-1.80 (m, 1H), 1.76-1.65 (m, 1H), 1.61-1.46 (m, 1H), 1.39-1.27 (m, 1H). | Rt = 0.70; 397.2 [M + H]+ | Int P040 & Int B010 |
| Ex 007 | 2-(6-((1-Isopropylpiperidin-3-yl)amino)pyridazin-3-yl)-3-methyl-5-(trifluoromethyl)phenol | (600 MHz, DMSO-$d_6$) δ (ppm) 10.18 (s, 1H), 7.28 (d, 1H), 7.11 (s, 1H), 7.05 (s, 1H), 6.90 (d, 1H), 4.11 (q, 1H), 3.16 (d, 2H), 2.12 (s, 3H), 2.06-1.34 (m, 5H), 1.33-0.89 (m, 8H). | Rt = 0.71; 395.4 [M + H]+ | Int P042 & Int B010 |
| Ex 008 | (S)-2-(6-(((1-Ethylpyrrolidin-2-yl)methyl)amino)pyridazin-3-yl)-3-methyl-5-(trifluoromethyl)phenol | (600 MHz, DMSO-$d_6$) δ (ppm) 10.18 (s, 1H), 7.24 (d, 1H), 7.10 (s, 1H), 7.05 (s, 1H), 6.95 (d, 1H), 6.80 (broad s, 1H), 3.72-3.61 (m, 1H), 3.26-3.07 (s, 2H), 3.03-2.84 (m, 1H), 2.12 (s, 3H), 2.01-1.86 (m, 1H), 1.82-1.53 (m, 3H), 1.18-1.01 (m, 3H). | Rt = 0.70; 381.4 [M + H]+ | Int P045 & Int B010 |
| Ex 009 | 2-(6-((5,5-Difluoropiperidin-3-yl)amino)pyridazin-3-yl)-3-methyl-5-(trifluoromethyl)phenol | (600 MHz, DMSO-$d_6$) δ (ppm) 10.19 (s, 1H), 7.31 (d, 1H), 7.13 (s, 1H), 7.12 (s, 1H), 7.06 (s, 1H), 6.91 (d, 1H), 4.44-4.33 (m, 1H), 4.18-4.08 (m, 2H), 3.54-3.21 (d, 2H), 2.75-2.64 (m, 1H), 2.63-2.54 (m, 1H), 2.12 (s, 3H). | Rt = 0.71; 389.3 [M + H]+ | Int P046 & Int B010 |

| Ex No. | Structure and Name | ¹H NMR | LC-MS (min; m/z) | IntP & IntB |
|---|---|---|---|---|
| Ex 010 | 3-Methyl-2-(6-((3,3,3-trifluoro-2-hydroxy-2-(trifluoromethyl)propyl)amino)pyridazin-3-yl)-5-(trifluoromethyl)phenol | (600 MHz, DMSO-$d_6$) δ (ppm) 10.29 (bs, 1H), 10.00 (bs, 1H), 7.66 (m, 1H), 7.43 (d, 1H), 7.19 (d, 1H), 7.12 (s, 1H), 7.06 (s, 1H), 4.07 (d, 2H), 2.12 (s, 3H). | Rt = 1.13; 450.2 [M + H]+ | Int P047 & Int B010 |
| Ex 011 | (R)-3-((1-Ethylpiperidin-3-yl)amino)-6-(2-hydroxy-6-methyl-4-(trifluoromethyl)phenyl)pyridazine-4-carbonitrile | (600 MHz, DMSO-$d_6$) δ (ppm) 10.30 (s, 1H), 7.92 (s, 1H), 7.15 (s, 1H), 7.08 (s, 1H), 4.38 (s, 1H), 3.10-2.58 (m, 2H), 2.46-2.31 (m, 2H), 2.25-2.00 (m, 1H), 2.15 (s, 3H), 1.96-1.44 (m, 5H), 1.20-1.00 (m, 3H). | Rt = 0.77; 406.3 [M + H]+ | Int P049 & Int B010 |
| Ex 012 | (R)-3-Methyl-2-(6-((1-methylpiperidin-3-yl)amino)pyridazin-3-yl)-5-(trifluoromethyl)phenol | (600 MHz, DMSO-$d_6$) δ (ppm) 10.17 (s, 1H), 7.23 (d, 1H), 7.10 (s, 1H), 7.05 (d, 1H), 6.89 (d, 1H), 4.17-4.05 (m, 1H), 2.35-2.21 (m, 3H), 2.12 (s, 3H), 1.92-1.83 (m, 2H), 1.81-1.72 (m, 1H), 1.64-1.52 (m, 1H), 1.40-1.29 (m, 1H). | Rt = 0.69; 367 [M + H]+ | Int P025 & Int B010 |
| Ex 013 | (R)-2-(6-((1-(2-Hydroxyethyl)piperidin-3-yl)amino)-5-methylpyridazin-3-yl)-3-methyl-5-(trifluoromethyl)phenol | (400 MHz, DMSO-$d_6$) δ (ppm) 10.17 (s, 1H), 9.67 (s, 1H), 7.19 (d, 1H), 7.11 (d, 1H), 7.07 (s, 1H), 6.26 (s, 1H), 5.39-5.23 (m, 1H), 4.77-4.51 (m, 1H), 3.84-3.62 (m, 2H), 3.25-3.14 (m, 1H), 2.20-2.11 (m, 2H), 2.11 (s, 3H), 2.15-1.50 (m, 6H). | Rt = 0.71; 411 [M + H]+ | Int P051 & Int B010 |
| Ex 014 | (R)-3-Methyl-2-(6-((pyrrolidin-2-ylmethyl)amino)pyridazin-3-yl)-5-(trifluoromethyl)phenol | (600 MHz, DMSO-$d_6$) δ (ppm) 7.26 (d, 1H), 7.11 (s, 1H), 7.07-7.01 (m, 2H), 6.93 (d, 1H), 3.54-3.46 (m, 2H), 3.45-3.39 (m, 1H), 3.03-2.97 (m, 1H), 2.96-2.89 (m, 1H), 1.99-1.89 (m, 1H), 1.84-1.77 (m, 1H), 1.76-1.70 (m, 1H), 1.57-1.47 (m, 1H). | Rt = 0.68; 353 [M + H]+ | Int P055 & Int B010 |

-continued

| Ex No. | Structure and Name | ¹H NMR | LC-MS (min; m/z) | IntP & IntB |
|---|---|---|---|---|
| Ex 015 | 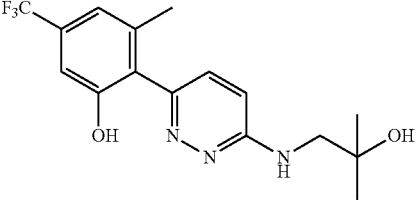 [SMILES: Cc1cc(C(F)(F)F)cc(O)c1-c1ccc(NCC(C)(C)O)nn1]<br>2-(6-((2-Hydroxy-2-methylpropyl)amino)pyridazin-3-yl)-3-methyl-5-(trifluoromethyl)phenol | (600 MHz, DMSO-d$_6$) δ (ppm) 10.16 (s, 1H), 7.22 (d, 1H), 7.10 (s, 1H), 7.04 (s, 1H), 7.02 (d, 1H), 6.76 (t, 1H), 4.72 (s, 1H), 3.38 (d, 2H), 2.12 (s, 3H), 1.18 (s, 6H). | Rt = 0.77; 342 [M + H]+ | Int P057 & Int B010 |
| Ex 016 | 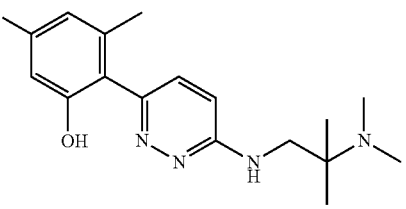<br>2-(6-((2-(Dimethylamino)-2-methylpropyl)amino)pyridazin-3-yl)-3-methyl-5-(trifluoromethyl)phenol | (600 MHz, DMSO-d$_6$) δ (ppm) 10.17 (s, 1H), 7.30-7.18 (m, 1H), 7.15-7.03 (m, 3H), 6.61-6.33 (m, 1H), 3.48-3.36 (m, 2H), 2.22 (s, 6H), 2.12 (s, 3H), 1.08 (s, 6H). | Rt = 0.69; 369 [M + H]+ | Int P058 & Int B010 |
| Ex 017 | 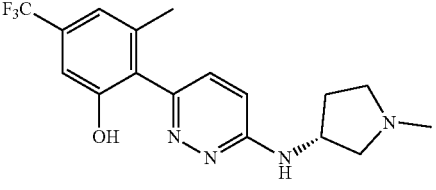 [SMILES: Cc1cc(C(F)(F)F)cc(O)c1-c1ccc(N[C@@H]2CCN(C)C2)nn1]<br>(R)-3-Methyl-2-(6-((1-methylpyrrolidin-3-yl)amino)pyridazin-3-yl)-5-(trifluoromethyl)phenol | (600 MHz, DMSO-d$_6$) δ (ppm) 10.18 (s, 1H), 7.27 (d, 1H), 7.21 (d, 1H), 7.11 (s, 1H), 7.06 (s, 1H), 6.90 (d, 1H), 4.61-4.46 (m, 1H), 3.28-3.16 (m, 1H), 3.13-3.01 (m, 1H), 2.96-2.79 (m, 2H), 2.65-2.54 (m, 3H), 2.41-2.33 (m, 1H), 2.12 (s, 3H), 1.89-1.80 (m, 1H). | Rt = 0.65; 353 [M + H]+ | Int P059 & Int B010 |
| Ex 018 | 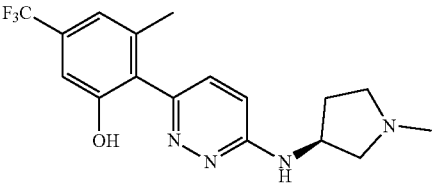 [SMILES: Cc1cc(C(F)(F)F)cc(O)c1-c1ccc(N[C@H]2CCN(C)C2)nn1]<br>(S)-3-Methyl-2-(6-((1-methylpyrrolidin-3-yl)amino)pyridazin-3-yl)-5-(trifluoromethyl)phenol | (600 MHz, DMSO-d$_6$) δ (ppm) 10.15 (s, 1H), 7.22 (d, 1H), 7.13-7.06 (m, 2H), 7.04 (s, 1H), 6.86 (d, 1H), 4.53-4.39 (m, 1H), 2.85-2.74 (m, 1H), 2.73-2.65 (m, 1H), 2.49-2.45 (m, 1H), 2.45-2.40 (m, 1H), 2.34-2.22 (m, 4H), 2.12 (s, 3H), 1.71-1.63 (m, 1H). | Rt = 0.68; 353 [M + H]+ | Int P071 & Int B010 |
| Ex 019 | 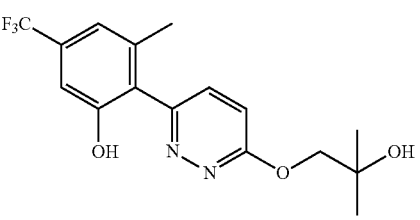 [SMILES: Cc1cc(C(F)(F)F)cc(O)c1-c1ccc(OCC(C)(C)O)nn1]<br>2-(6-(2-Hydroxy-2-methylpropoxy)pyridazin-3-yl)-3-methyl-5-(trifluoromethyl)phenol | (600 MHz, DMSO-d$_6$) δ (ppm) 10.27 (s, 1H), 7.61 (d, 1H), 7.28 (d, 1H), 7.14 (s, 1H), 7.07 (d, 1H), 4.73 (s, 1H), 4.24 (s, 2H), 2.10 (s, 3H), 1.24 (s, 6H). | Rt = 0.94; 343 [M + H]+ | Int P060 & Int B010 |

| Ex No. | Structure and Name | ¹H NMR | LC-MS (min; m/z) | IntP & IntB |
|---|---|---|---|---|
| Ex 020 | (R)-3-Methyl-2-(6-((piperidin-2-ylmethyl)amino)pyridazin-3-yl)-5-(trifluoromethyl)phenol | (600 MHz, DMSO-$d_6$) δ (ppm) 9.99 (br s, 1H), 7.22 (d, 1H), 7.10 (s, 1H), 7.04 (s, 1H), 6.93-6.84 (m, 2H), 3.37-3.32 (m, 2H) overlapping with water signal, 3.28-3.21 (m, 1H), 3.00-2.91 (m, 1H), 2.74-2.64 (m, 1H), 2.55-2.51 (m, 1H), overlapping with DMSO signal, 2.12 (s, 3H), 1.80-1.72 (m, 1H), 1.70-1.62 (m, 1H), 1.55-1.45 (m, 1H), 1.38-1.26 (m, 2H), 1.13-1.04 (m, 1H). | Rt = 0.68; 367.3 [M + H]+ | Int P061 & Int B010 |
| Ex 021 | (S)-3-Methyl-2-(6-((piperidin-2-ylmethyl)amino)pyridazin-3-yl)-5-(trifluoromethyl)phenol | (400 MHz, DMSO-$d_6$) δ (ppm) 7.22 (d, 1H), 7.10 (s, 1H), 7.04 (br s, 1H), 6.92-6.85 (m, 2H), 3.40-3.22 (m, 3H) overlapping with water signal, 3.00-2.93 (m, 1H), 2.77-2.65 (m, 1H), 2.55-2.51 (m, 1H) overlapping with DMSO signal, 2.13 (s, 3H), 1.80-1.72 (m, 1H), 1.70-1.62 (m, 1H), 1.56-1.47 (m, 1H), 1.37-1.25 (m, 2H), 1.16-1.02 (m, 1H), phenolic proton not observed. | Rt = 0.7; 367.3 [M + H]+ | Int P062 & Int B010 |
| Ex 022 | (S)-2-(6-(((4,4-Difluoropyrrolidin-2-yl)methyl)amino)pyridazin-3-yl)-3-methyl-5-(trifluoromethyl)phenol | (600 MHz, DMSO-$d_6$) δ (ppm) 10.19 (s, 1H), 7.24 (d, 1H), 7.10 (s, 1H), 7.04 (s, 1H), 6.97 (t, 1H), 6.90 (d, 1H), 3.58-3.50 (m, 1H), 3.49-3.42 (m, 2H), 3.28-3.14 (m, 1H), 3.14-3.04 (m, 1H), 3.04-2.88 (m, 1H), 2.42-2.30 (m, 1H), 2.06-1.91 (m, 1H). | Rt = 0.71; 389 [M + H]+ | Int P063 & Int B010 |
| Ex 023 | (R)-2-(6-(((4,4-Difluoropyrrolidin-2-yl)methyl)amino)pyridazin-3-yl)-3-methyl-5-(trifluoromethyl)phenol | (600 MHz, DMSO-$d_6$) δ (ppm) 10.16 (s, 1H), 7.26 (d, 1H), 7.11 (s, 1H), 7.07-7.01 (m, 2H), 6.92 (d, 1H), 3.70-3.59 (m, 1H), 3.54-3.46 (m, 2H), 3.31-3.28 (m, 1H), 3.25-3.12 (m, 1H), 2.47-2.39 (m, 1H), 2.10-1.98 (m, 1H). | Rt = 0.73; 389 [M + H]+ | Int P064 & Int B010 |

| Ex No. | Structure and Name | ¹H NMR | LC-MS (min; m/z) | IntP & IntB |
|---|---|---|---|---|
| Ex 024 | (trans)-2-(6-((2-Hydroxycyclopentyl)amino)pyridazin-3-yl)-3-methyl-5-(trifluoromethyl)phenol | (600 MHz, DMSO-$d_6$) δ (ppm) 10.16 (s, 1H), 7.24 (d, 1H), 7.11 (s, 1H), 7.05 (s, 1H), 6.97-6.91 (m, 1H), 6.89 (d, 1H), 5.11 (s, 1H), 4.04-3.87 (m, 2H), 1.94-1.82 (m, 1H), 1.77-1.62 (m, 2H), 1.57-1.44 (m, 2H). | Rt = 0.80; 354 [M + H]+ | Int P065 & Int B010 |
| Ex 025 | 3,5-Dichloro-2-(6-((2-hydroxyethyl)amino)pyridazin-3-yl)phenol | (600 MHz, DMSO-$d_6$) δ (ppm) 10.57 (s, 1H), 7.21 (d, 1H), 7.13 (s, 1H), 7.02-6.96 (m, 1H), 6.95 (s, 1H), 6.90 (d, 1H), 4.89-4.73 (m, 1H), 3.65-3.54 (m, 2H), 3.51-3.41 (m, 2H). | Rt = 0.60; 300 [M + H]+ | Int P066 & Int B018 |
| Ex 026 | 2-(6-((2-Hydroxyethyl)amino)-5-(trifluoromethyl)pyridazin-3-yl)-3-methyl-5-(trifluoromethyl)phenol | (600 MHz, DMSO-$d_6$) δ (ppm) 10.27 (s, 1H), 7.66 (s, 1H), 7.15 (s, 1H), 7.08 (s, 1H), 6.78-6.70 (m, 1H), 4.88-4.80 (m, 1H), 3.72-3.60 (m, 4H), 2.16 (s, 3H). | Rt = 0.95; 382 [M + H]+ | Int P067 & Int B010 |
| Ex 027 | 3,5-Dichloro-2-(6-((2,2,2-trifluoroethyl)amino)pyridazin-3-yl)phenol | (600 MHz, DMSO-$d_6$) δ (ppm) 10.58 (s, 1H), 7.61-7.54 (m, 1H), 7.33 (d, 1H), 7.16-7.13 (m, 1H), 7.02 (d, 1H), 6.98-6.93 (m, 1H), 4.42-4.27 (m, 2H). | Rt = 1.02; 338 [M + H]+ | Int P068 & Int B018 |
| Ex 028 | 3-Methyl-2-(6-((pyridin-2-ylmethyl)amino)pyridazin-3-yl)-5-(trifluoromethyl)phenol | (600 MHz, DMSO-$d_6$) δ (ppm) 10.16 (s, 1H), 8.60-8.50 (m, 1H), 7.82-7.70 (m, 1H), 7.58-7.50 (m, 1H), 7.41 (d, 1H), 7.31-7.23 (m, 2H), 7.10 (s, 1H), 7.04 (s, 1H), 7.00 (d, 1H), 4.71 (d, 2H), 2.11 (s, 3H). | Rt = 0.83; 361 [M + H]+ | Int P069 & Int B010 |

| Ex No. | Structure and Name | ¹H NMR | LC-MS (min; m/z) | IntP & IntB |
|---|---|---|---|---|
| Ex 029 | 2-(6-((2-Amino-2-methylpropyl) amino)pyridazin-3-yl)-3-methyl-5-(trifluoromethyl)phenol | (600 MHz, DMSO-$d_6$) δ (ppm) 7.31 (d, 1H), 7.19-7.13 (m, 1H), 7.12 (s, 1H), 7.06 (s, 1H), 6.99 (d, 1H), 3.59 (d, 2H), 2.14 (s, 3H), 1.27 (s, 6H). | Rt = 0.67; 341 [M + H]+ | Int P070 & Int B010 |
| Ex 030 | 3-Chloro-2-(6-((2-hydroxy-2-methylpropyl)amino)pyridazin-3-yl)-5-(trifluoromethyl)phenol | (600 MHz, DMSO-$d_6$) δ (ppm) 10.79 (s, 1H), 7.37 (s, 1H), 7.26 (d, 1H), 7.19 (s, 1H), 7.04 (d, 1H), 6.88-6.83 (m, 1H), 4.70 (s, 1H), 3.42-3.35 (m, 2H), 1.18 (s, 6H). | Rt = 0.88; 362 [M + H]+ | Int P057 & Int B001 |
| Ex 031 | 3-Chloro-2-(6-((cis-3-hydroxy cyclobutyl)amino)pyridazin-3-yl)-5-(trifluoromethyl)phenol | (600 MHz, DMSO-$d_6$) δ (ppm) 10.79 (s, 1H), 7.37 (s, 1H), 7.31-7.22 (m, 2H), 7.18 (s, 1H), 6.81 (d, 1H), 5.12 (d, 1H), 4.03-3.78 (m, 2H), 2.78-2.63 (m, 2H), 1.94-1.63 (m, 2H). | Rt = 0.83; 360 [M + H]+ | Int P072 & Int B001 |
| Ex 032 | 3-Chloro-2-(6-((trans-3-hydroxy cyclobutyl)amino)pyridazin-3-yl)-5-(trifluoromethyl)phenol | (600 MHz, DMSO-$d_6$) δ (ppm) 10.78 (s, 1H), 7.37 (s, 1H), 7.31 (d, 1H), 7.27 (d, 1H), 7.18 (d, 1H), 6.80 (d, 1H), 5.07 (d, 1H), 4.44-4.26 (m, 2H), 2.30-2.10 (m, 4H). | Rt = 0.81; 360 [M + H]+ | Int P073 & Int B001 |
| Ex 033 | (S)-3-Methyl-2-(6-(piperidin-3-ylamino)pyridazin-3-yl)-5-(trifluoromethyl)phenol | (600 MHz, DMSO-$d_6$) δ (ppm) 7.19 (d, 1H), 6.83-6.67 (m, 2H), 6.68-6.48 (m, 2H), 4.03-3.78 (m, 1H), 3.16-3.04 (m, 1H), 2.87-2.69 (m, 1H), 2.48-2.44 (m, 1H), 2.41-2.30 (m, 1H), 1.99-1.90 (m, 1H), 1.70-1.60 (m, 1H), 1.48-1.31 (m, 2H). | Rt = 0.66; 353 [M + H]+ | Int P074 & Int B010 |

| Ex No. | Structure and Name | $^1$H NMR | LC-MS (min; m/z) | IntP & IntB |
|---|---|---|---|---|
| Ex 034 | 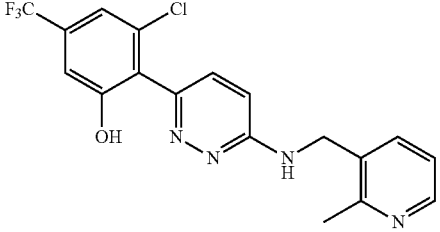 [SMILES: Cc1ncccc1CNc1ccc(-c2c(O)cc(C(F)(F)F)cc2Cl)nn1]<br>3-Chloro-2-(6-(((2-methylpyridin-3-yl)methyl)amino)pyridazin-3-yl)-5-(trifluoromethyl)phenol | (600 MHz, DMSO-d$_6$) δ (ppm) 10.78 (s, 1H), 8.34 (d, 1H), 7.68 (d, 1H), 7.56-7.46 (m, 1H), 7.37 (s, 1H), 7.31 (d, 1H), 7.24-7.17 (m, 2H), 6.96 (d, 1H), 4.61 (d, 2H), 2.56 (s, 3H). | Rt = 0.79; 395 [M + H]+ | Int P075 & Int B001 |
| Ex 035 | 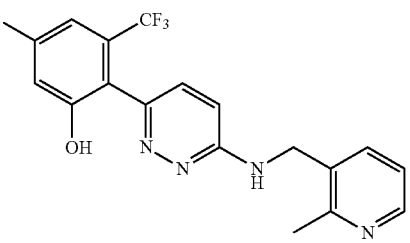<br>5-Chloro-2-(6-(((2-methylpyridin-3-yl)methyl)amino)pyridazin-3-yl)-3-(trifluoromethyl)phenol | (600 MHz, DMSO-d$_6$) δ (ppm) 10.69 (s, 1H), 8.41-8.26 (m, 1H), 7.66 (d, 1H), 7.43-7.39 (m, 1H), 7.30 (s, 1H), 7.27-7.17 (m, 3H), 6.92 (d, 1H), 4.60 (d, 2H), 2.55 (s, 3H). | Rt = 0.73; 395 [M + H]+ | Int P075 & Int B001 |
| Ex 036 | 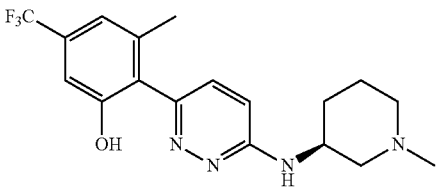 [SMILES: Cc1cc(C(F)(F)F)cc(O)c1-c1ccc(N[C@H]2CCCN(C)C2)nn1]<br>(S)-3-Methyl-2-(6-((1-methyl piperidin-3-yl)amino)pyridazin-3-yl)-5-(trifluoromethyl)phenol | (600 MHz, DMSO-d$_6$) δ (ppm) 10.17 (s, 1H), 7.23 (d, 1H), 7.10 (s, 1H), 7.05 (d, 1H), 6.89 (d, 1H), 4.17-4.05 (m, 1H), 2.35-2.21 (m, 3H), 2.12 (s, 3H), 1.92-1.83 (m, 2H), 1.81-1.72 (m, 1H), 1.64-1.52 (m, 1H), 1.40-1.29 (m, 1H). | Rt = 0.67; 367 [M + H]+ | Int P076 & Int B010 |
| Ex 037 | 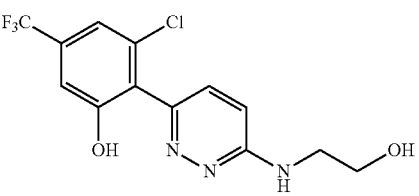 [SMILES: OCCNc1ccc(-c2c(O)cc(C(F)(F)F)cc2Cl)nn1]<br>3-Chloro-2-(6-((2-hydroxyethyl)amino)pyridazin-3-yl)-5-(trifluoromethyl)phenol | (600 MHz, DMSO-d$_6$) δ (ppm) 10.79 (s, 1H), 7.37 (d, 1H), 7.26 (d, 1H), 7.19 (d, 1H), 7.03 (t, 1H), 6.92 (d, 1H), 4.81 (t, 1H), 3.61 (q, 2H), 3.47 (q, 2H). | Rt = 0.78; 334 [M + H]+ | Int P066 & Int B001 |
| Ex 038 | 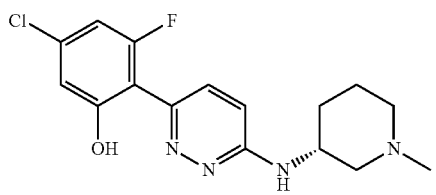 [SMILES: CN1CCC[C@@H](Nc2ccc(-c3c(O)cc(Cl)cc3F)nn2)C1]<br>(R)-5-Chloro-3-fluoro-2-(6-((1-methylpiperidin-3-yl)amino)pyridazin-3-yl)phenol TFA-salt | (400 MHz, DMSO-d$_6$) δ (ppm) (ppm) 9.66 (s, 1H), 7.74 (d, 1H), 7.50 (d, 1H), 7.06 (d, 1H), 6.98 (dd, 1H), 6.92-6.85 (m, 1H), 4.34-4.24 (m, 1H), 3.72 (d, 1H), 3.22 (d, 1H), 2.91 (d, 1H), 2.84 (d, 3H), 2.78 (s, 1H), 2.75-2.63 (m, 1H), 1.88-1.67 (m, 2H), 1.55-1.40 (m, 1H). | Rt = 0.76; 337.2 [M + H]+ | Int P025 & Int B022 |

| Ex No. | Structure and Name | ¹H NMR | LC-MS (min; m/z) | IntP & IntB |
|---|---|---|---|---|
| Ex 039 | 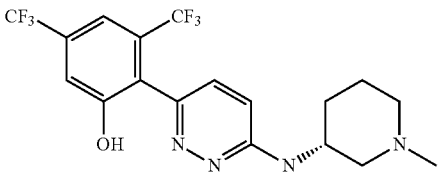<br>(R)-2-(6-((1-Methylpiperidin-3-yl)amino)pyridazin-3-yl)-3,5-bis(trifluoromethyl)phenol | (400 MHz, DMSO-d$_6$) δ (ppm) 10.98 (s, 1H), 7.57-7.45 (m, 2H), 7.24 (d, 1H), 6.89 (d, 1H), 6.84 (d, 1H), 4.09 (s br, 1H), 2.86 (d, 1H), 2.58-2.55 (m, 1H), 2.19 (s, 3H), 2.10-2.03 (m, 1H), 1.99-1.94 (m, 1H), 1.88-1.82 (m, 1H), 1.77-1.70 (m, 1H), 1.59-1.51 (m, 1H), 1.37-1.28 (m, 1H). | Rt = 0.75; 424.4 [M + H]+ | Int P025 & Int B023 |
| Ex 040 | 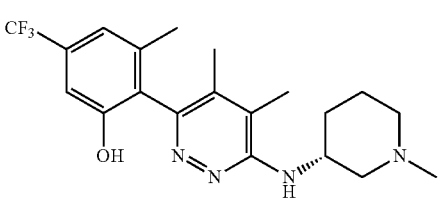 [SMILES: Cc1cc(C(F)(F)F)cc(O)c1-c1nnc(N[C@@H]2CCCN(C)C2)c(C)c1C]<br>2-(4,5-Dimethyl-6-(((R)-1-methylpiperidin-3-yl)amino)pyridazin-3-yl)-3-methyl-5-(trifluoromethyl)phenol TFA-salt | (400 MHz, DMSO-d$_6$) δ (ppm) 10.52 (s, 1H), 9.96-9.64 (m, 1H), 7.20 (s, 1H), 7.10 (s, 1H), 6.61 (s br, 1H), 4.53-4.39 (m, 1H), 3.68-3.60 (m, 1H), 3.49-3.42 (m, 1H), 2.93-2.76 (m, 5H), 2.25 (s, 3H), 2.08-1.92 (m, 8H), 1.86-1.60 (m, 2H). | Rt = 0.72 and 0.76 (atropisomers); 395.3 [M + H]+ | Int P087 & Int B010 |
| Ex 041 | 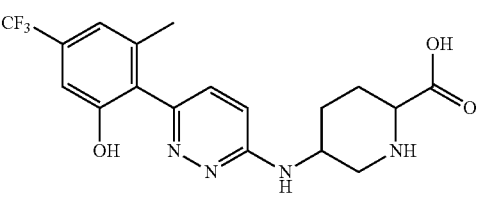 [SMILES: Cc1cc(C(F)(F)F)cc(O)c1-c1ccc(NC2CCC(C(=O)O)NC2)nn1]<br>5-((6-(2-Hydroxy-6-methyl-4-(trifluoromethyl)phenyl)pyridazin-3-yl)amino)piperidine-2-carboxylic acid | (400 MHz, DMSO-d$_6$) δ (ppm) 10.17 (s, 1H), 7.26 (d, 1H), 7.10 (d, 1H), 7.05 (d, 1H), 6.91 (d, 1H), 6.86 (d, 1H), 4.15 (s, 1H), 3.42 (s, 1H), 3.15 (d, 1H), 2.63-2.57 (m, 1H), 2.25-2.12 (m, 5H), 1.54 (dp, 2H). | Rt = 0.70; 397.3 [M + H]+ | Int P088 & Int B010 |
| Ex 042 | 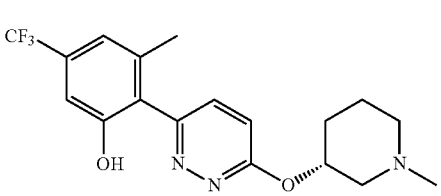 [SMILES: Cc1cc(C(F)(F)F)cc(O)c1-c1ccc(O[C@@H]2CCCN(C)C2)nn1]<br>(R)-3-Methyl-2-(6-((1-methylpiperidin-3-yl)oxy)pyridazin-3-yl)-5-(trifluoromethyl)phenol | (400 MHz, DMSO-d$_6$) δ (ppm) 10.23 (s, 1H), 7.60 (d, 1H), 7.23 (d, 1H), 7.15 (s, 1H), 7.08 (d, 1H), 5.29 (tt, 1H), 2.99-2.90 (m, 1H), 2.57-2.53 (m, 1H), 2.25-2.18 (m, 1H), 2.21 (s, 3H), 2.11 (s, 3H), 2.07-1.99 (m, 1H), 1.81-1.72 (m, 1H), 1.64-1.45 (m, 2H). | Rt = 0.71; 368.4 [M + H]+ | Int P039 & Int B010 |
| Ex 043 | 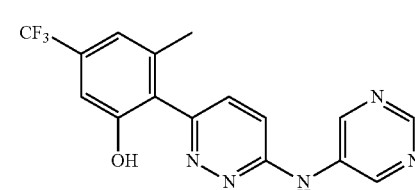<br>3-Methyl-2-(6-(pyrimidin-5-ylamino)pyridazin-3-yl)-5-(trifluoromethyl)phenol | (400 MHz, DMSO-d$_6$) δ (ppm) 10.27 (s, 1H), 9.77 (s, 1H), 9.26 (s, 2H), 8.80 (s, 1H), 7.55 (d, 1H), 7.29 (d, 1H), 7.14 (d, 1H), 7.08 (d, 1H), 2.15 (s, 3H). | Rt = 0.84; 348.3 [M + H]+ | Int P089 & Int B010 |

-continued

| Ex No. | Structure and Name | ¹H NMR | LC-MS (min; m/z) | IntP & IntB |
|---|---|---|---|---|
| Ex 044 | 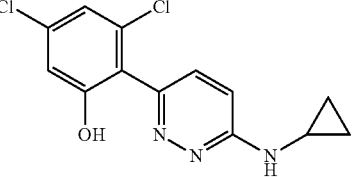<br>3,5-Dichloro-2-(6-(cyclopropylamino)pyridazin-3-yl)phenol | (400 MHz, DMSO-$d_6$) δ (ppm) 10.56 (s, 1H), 7.38 (d, 1H), 7.30 (d, 1H), 7.14 (d, 1H), 6.99-6.90 (m, 2H), 2.68-2.60 (m, 1H), 0.75 (dt, 2H), 0.55-0.37 (m, 2H). | Rt = 0.84; 296.1 [M + H]+ | Int P090 & Int B018 |
| Ex 045 | 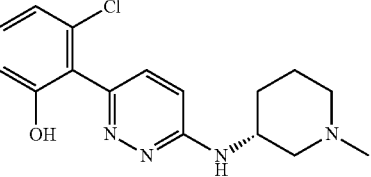<br>(R)-3,5-Dichloro-2-(6-((1-methyl piperidin-3-yl)amino)pyridazin-3-yl)phenol TFA-salt | (400 MHz, DMSO-$d_6$) δ (ppm) 10.60 (s, 1H), 7.21 (d, 1H), 7.11 (d, 1H), 6.95 (d, 1H), 6.88 (d, 1H), 6.82 (d, 1H), 4.07 (s br, 1H), 2.88-2.83 (m, 1H), 2.56-2.53 (m, 1H), 2.08-1.98 (m, 1H), 1.97-1.90 (m, 1H), 1.88-1.78 (m, 1H), 1.75-1.68 (m, 1H), 1.59-1.49 (m, 1H), 1.39-1.25 (m, 1H). | Rt = 0.66; 353.2 [M + H]+ | Int P025 & Int B018 |
| Ex 046 | 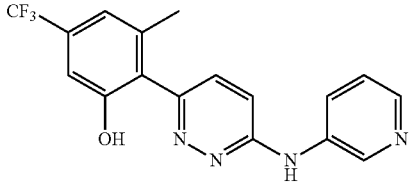 [SMILES: Cc1cc(C(F)(F)F)cc(O)c1-c1ccc(Nc2cccnc2)nn1]<br>3-Methyl-2-(6-(pyridin-3-ylamino)pyridazin-3-yl)-5-(trifluoromethyl)phenol | (400 MHz, DMSO-$d_6$) δ (ppm) 10.24 (s, 1H), 9.56 (s, 1H), 8.88 (d, 1H), 8.36 (ddd, 1H), 8.18 (dd, 1H), 7.50 (d, 1H), 7.37 (dd, 1H), 7.24 (d, 1H), 7.13 (s, 1H), 7.07 (s, 1H), 2.15 (s, 3H). | Rt = 0.80; 346.9 [M + H]+ | Int P091 & Int B010 |
| Ex 047 | 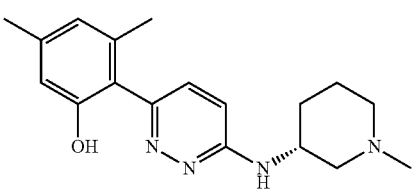<br>(R)-3,5-Dimethyl-2-(6-((1-methylpiperidin-3-yl)amino)pyridazin-3-yl)phenol | (400 MHz, DMSO-$d_6$) δ (ppm) 9.43 (s, 1H), 7.21 (d, 1H), 6.86 (d, 1H), 6.79 (s br, 1H), 6.56 (s, 1H), 6.55 (s, 1H), 4.29 (s br, 1H), 3.32-3.29 (m, 4H), 2.21 (s, 3H), 2.03 (s, 3H), 1.95-1.81 (m, 2H), 1.71-1.58 (m, 1H), 1.46-1.35 (m, 1H). | Rt = 0.56; 313.3 [M + H]+ | Int P025 & Int B013 |
| Ex 048 | 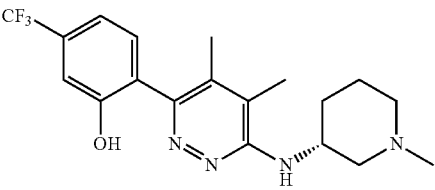 [SMILES: Cc1c(N[C@@H]2CCCN(C)C2)nnc(-c2ccc(C(F)(F)F)cc2O)c1C]<br>(R)-2-(4,5-Dimethyl-6-((1-methylpiperidin-3-yl)amino)pyridazin-3-yl)-5-(trifluoromethyl)phenol | (400 MHz, DMSO-$d_6$) δ (ppm) 10.34 (s, 1H), 7.37 (d, 1H), 7.26-7.16 (m, 2H), 5.65 (d, 1H), 4.29-4.20 (m, 1H), 2.93-2.89 (m, 1H), 2.64-2.56 (m, 1H), 2.18 (s, 3H), 2.06 (s, 3H), 1.97 (s, 3H), 1.95-1.82 (m, 4H), 1.74-1.66 (m, 1H), 1.60-1.50 (m, 1H), 1.50-1.34 (m, 1H). | Rt = 0.71; 381.3 [M + H]+ | Int P087 & BCA |

| Ex No. | Structure and Name | ¹H NMR | LC-MS (min; m/z) | IntP & IntB |
|---|---|---|---|---|
| Ex 049 | 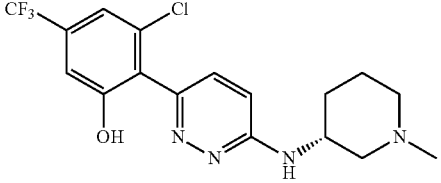 [SMILES: CN1CCC[C@@H](Nc2ccc(-c3c(O)cc(C(F)(F)F)cc3Cl)nn2)C1]<br>(R)-3-Chloro-2-(6-((1-methylpiperidin-3-yl)amino)pyridazin-3-yl)-5-(trifluoromethyl)phenol | (400 MHz, DMSO-$d_6$) δ (ppm) 10.78 (s, 1H), 7.37 (s, 1H), 7.27 (d, 1H), 7.20 (s, 1H), 6.94 (s br, 1H), 6.92 (d, 1H), 4.13 (s br, 1H), 3.08-2.89 (m, 1H), 2.36-2.22 (m, 4H), 1.90-1.84 (m, 1H), 1.81-1.74 (m, 1H), 1.66-1.49 (m, 1H), 1.42-1.33 (m, 1H). | Rt = 0.72; 387.2 [M + H]+ | Int P025 & Int B001 |
| Ex 050 | 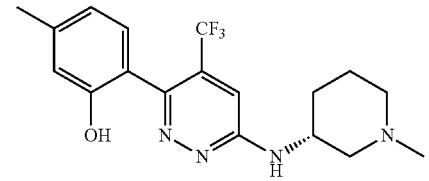<br>(R)-5-Methyl-2-(6-((1-methylpiperidin-3-yl)amino)-4-(trifluoromethyl)pyridazin-3-yl)phenol | (400 MHz, DMSO-$d_6$) δ (ppm) 9.32 (s, 1H), 7.26 (s, 1H), 7.24 (s, 1H), 6.97 (d, 1H), 6.70 (s, 1H), 6.66 (d, 1H), 4.18 (s, 1H), 2.91 (s, 1H), 2.59 (s, 1H), 2.27 (s, 6 H), 2.11 (s, 2H), 1.84 (s, 1H), 1.75 (s, 1H), 1.63-1.57 (m, 1H), 1.43-1.35 (m, 1H). | Rt = 0.66; 367.2 [M + H]+ | Int P027 & com |
| Ex 051 | 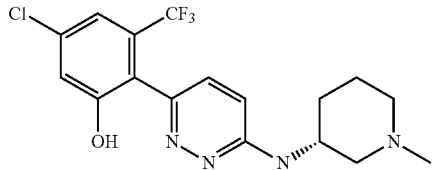<br>(R)-5-Chloro-2-(6-((1-methylpiperidin-3-yl)amino)pyridazin-3-yl)-3-(trifluoromethyl)phenol | (400 MHz, DMSO-$d_6$) δ (ppm) 7.07 (d, 1H), 6.74 (d, 1H), 6.58 (s, 1H), 6.49 (d, 2H), 4.07-3.99 (m, 1H), 2.89-2.83 (m, 1H), 2.58-2.54 (m, 1H), 2.17 (s, 3H), 2.04-1.97 (m, 1H), 1.92-1.79 (m, 2H), 1.73-1.67 (m, 1H), 1.58-1.49 (m, 1H), 1.33-1.24 (m, 1H). | Rt = 0.70; 387.3 [M + H]+ | Int P025 & Int B001 |
| Ex 052 | 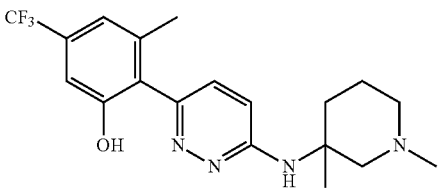 [SMILES: Cc1cc(C(F)(F)F)cc(O)c1-c1ccc(NC2(C)CCCN(C)C2)nn1]<br>2-(6-((1,3-Dimethylpiperidin-3-yl)amino)pyridazin-3-yl)-3-methyl-5-(trifluoromethyl)phenol TFA-salt | (400 MHz, DMSO-$d_6$) δ (ppm) 10.19 (s, 1H), 9.11 (s, 1H), 7.30 (s, 1H), 7.12 (s, 1H), 7.06 (s, 1H), 7.00 (d, 1H), 6.57 (s br, 1H), 4.66 (s, 1H), 3.09-2.58 (m, 4H), 2.14 (s, 3H), 2.10-2.03 (m, 1H), 1.84-1.73 (m, 1H), 1.63-1.53 (m, 2H), 1.47 (s, 3H). | Rt = 0.73; 381.2 [M + H]+ | Int P092 & Int B005 |
| Ex 053 | 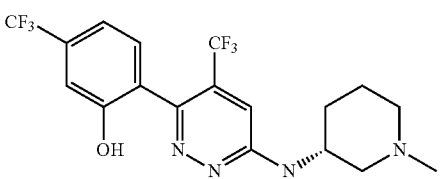<br>(R)-2-(6-((1-Methylpiperidin-3-yl)amino)-4-(trifluoromethyl)pyridazin-3-yl)-5-(trifluoromethyl)phenol | (400 MHz, DMSO-$d_6$) δ (ppm) 10.28 (s, 1H), 7.37 (d, 1H), 7.34 (d, 1H), 7.29 (s, 1H), 7.24-7.16 (m, 2H), 4.23-4.12 (m, 1H), 2.87-2.75 (m, 1H), 2.47 (m, 1H, overlapping with DMSO-signal), 2.20 (s, 3H), 2.17-2.00 (m, 2H), 1.88-1.68 (m, 2H), 1.62-1.50 (m, 1H), 1.45-1.33 (m, 1H) | Rt = 0.73; 421.1 [M + H]+ | Int P027 & BCA |

| Ex No. | Structure and Name | ¹H NMR | LC-MS (min; m/z) | IntP & IntB |
|---|---|---|---|---|
| Ex 054 | 2-(6-(((cis)-3-Hydroxy-3-methylcyclobutyl)amino)-5-methylpyridazin-3-yl)-3-methyl-5-(trifluoromethyl)phenol | (400 MHz, DMSO-$d_6$) δ (ppm) 10.13 (br s, 1H), 7.13-7.06 (m, 2H), 7.04 (s, 1H), 6.33 (d, 1H), 4.93 (br s, 1H), 4.20-4.05 (m, 1H), 2.45-2.36 (m, 2H), 2.13 (s, 3H), 2.11 (s, 3H), 2.10-2.04 (m, 2H), 1.31 (s, 3H). | Rt = 0.80; 368.2 [M + H]+ | Int P035 & Int B010 |
| Ex 055 | 2-(6-(((cis)-3-Hydroxy-3-methylcyclobutyl)amino)-4-methylpyridazin-3-yl)-5-(trifluoromethyl)phenol | (400 MHz, DMSO-$d_6$) δ (ppm) 10.44 (s, 1H), 7.39 (d, 1H), 7.30-7.14 (m, 2H), 7.01 (d, 1H), 6.33 (s, 1H), 4.98 (s, 1H), 3.99-3.85 (m, 1H), 2.45-2.37 (m, 2H), 2.02 (s, 3H), 1.99-1.90 (m, 2H), 1.29 (s, 3H). | Rt = 0.74; 354.2 [M + H]+ | Int P036 & BCA |
| Ex 056 | 2-(6-(((cis)-3-Hydroxy-3-methylcyclobutyl)amino)-5-(trifluoromethyl)pyridazin-3-yl)-3-methyl-5-(trifluoromethyl)phenol | (400 MHz, DMSO-$d_6$) δ (ppm) 10.26 (br s, 1H), 7.65 (s, 1H), 7.14 (s, 1H), 7.07 (s, 1H), 6.73 (d, 1H), 4.95 (s, 1H), 4.32-4.21 (m, 1H), 2.47-2.39 (m, 2H), 2.23-2.16 (m, 2H), 2.15 (s, 3H), 1.30 (s, 3H). | Rt = 1.05; 422.2 [M + H]+ | Int P028 & Int B010 |
| Ex 057 | 2-(6-(((1S,3S)-3-Hydroxycyclohexyl)amino)pyridazin-3-yl)-3-methyl-5-(trifluoromethyl)phenol | (400 MHz, DMSO-$d_6$) δ (ppm) 10.16 (s, 1H), 7.21 (d, 1H), 7.10 (s, 1H), 7.04 (s, 1H), 6.84 (d, 1H), 6.71 (br d, 1H), 4.48 (br d, 1H), 4.32-4.23 (m, 1H), 3.94 (br s, 1H), 2.13 (s, 3H), 1.87-1.74 (m, 2H), 1.73-1.65 (m, 1H), 1.64-1.57 (m, 1H), 1.56-1.44 (m, 3H), 1.38-1.30 (m, 1H). | Rt = 0.79; 368.2 [M + H]+ | Int P078 & Int B010 |
| Ex 058 | 2-(6-(((1R,3R)-3-Hydroxycyclohexyl)amino)pyridazin-3-yl)-3-methyl-5-(trifluoromethyl)phenol | (400 MHz, DMSO-$d_6$) δ (ppm) 10.15 (s, 1H), 7.21 (d, 1H), 7.10 (br s, 1H), 7.04 (br s, 1H), 6.84 (d, 1H), 6.70 (br d, 1H), 4.46 (br d, 1H), 4.33-4.23 (m, 1H), 3.95 (br s, 1H), 2.13 (s, 3H), 1.94-1.27 (m, 8H). | Rt = 0.79; 368.2 [M + H]+ | Int P077 & Int B010 |

| Ex No. | Structure and Name | ¹H NMR | LC-MS (min; m/z) | IntP & IntB |
|---|---|---|---|---|
| Ex 059 | 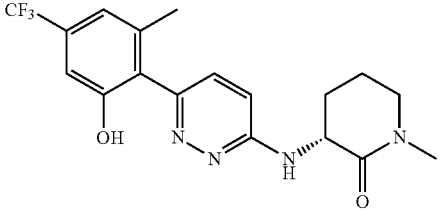 [SMILES: Cc1cc(C(F)(F)F)cc(O)c1-c1ccc(N[C@@H]2CCCN(C)C2=O)nn1]<br>(R)-3-((6-(2-Hydroxy-6-methyl-4-(trifluoromethyl)phenyl)pyridazin-3-yl)amino)-1-methylpiperidin-2-one | (400 MHz, DMSO-$d_6$) δ (ppm) 10.17 (br s, 1H) 7.25 (d, 1H), 7.10 (br s, 1H), 7.08 (d, 1H), 7.05 (br s, 1H), 6.99 (d, 1H), 4.63-4.53 (m, 1H), 3.34 (s, 2H), overlapping with water signal), 2.87 (s, 3H), 2.34-2.24 (m, 1H), 2.13 (s, 3H), 1.95-1.86 (m, 2H), 1.81-1.69 (m, 1H). | Rt = 0.83; 381.2 [M + H]+ | Int P079 & Int B010 |
| Ex 060 | 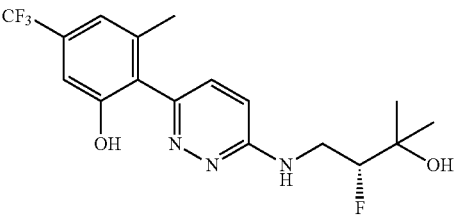 [SMILES: Cc1cc(C(F)(F)F)cc(O)c1-c1ccc(NC[C@@H](F)C(C)(C)O)nn1]<br>(R)-2-(6-((2-Fluoro-3-hydroxy-3-methylbutyl)amino)pyridazin-3-yl)-3-methyl-5-(trifluoromethyl)phenol | (400 MHz, DMSO-$d_6$) δ (ppm) 10.13 (br s, 1H), 7.25 (d, 1H), 7.19-7.01 (m, 3H), 6.93 (d, 1H), 4.84 (s, 1H), 4.59-4.27 (m, 1H), 4.06-3.87 (m, 1H), 3.59-3.39 (m, 1H), 2.12 (s, 3H), 1.20 (s, 3H), 1.18 (s, 3H). | Rt = 0.85; 374.2 [M + H]+ | Int P081 & Int B010 |
| Ex 061 | 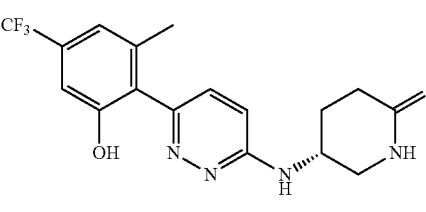<br>(R)-5-((6-(2-Hydroxy-6-methyl-4-(trifluoromethyl)phenyl)pyridazin-3-yl)amino)piperidin-2-one | (400 MHz, DMSO-$d_6$) δ (ppm) 10.15 (s, 1H), 7.73 (s, 1H), 7.25 (d, 1H), 7.10 (br s, 1H), 7.05 (br s, 1H), 7.00 (br t, 1H), 6.90 (d, 1H), 3.87-3.78 (m, 1H), 3.56-3.47 (m, 1H), 3.43-3.37 (m, 1H, overlapping with water signal), 2.25-2.09 (m, 3H) overlapping with 2.12 (s, 3H), 1.91-1.72 (m, 1H). | Rt = 0.74; 367.2 [M + H]+ | Int P080 & Int B010 |
| Ex 062 | 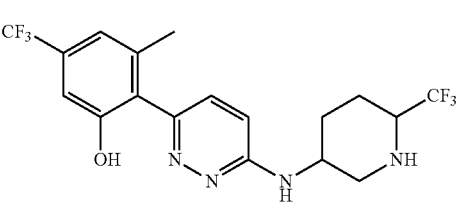 [SMILES: Cc1cc(C(F)(F)F)cc(O)c1-c1ccc(NC2CCC(C(F)(F)F)NC2)nn1]<br>3-Methyl-5-(trifluoromethyl)-2-(6-((6-(trifluoromethyl)piperidin-3-yl)amino)pyridazin-3-yl)phenol | (400 MHz, DMSO-$d_6$) mixture of isomers δ (ppm) 10.2 (br s, 1H), 7.69-7.49 (m, 2H), 7.23 (br d, 1H), 7.09 (s, 1H), 7.04 (s, 1H), 7.00-6.85 (m, 2H), 4.05 (br s, 1H), 3.11-2.77 (m, 2H), 2.13 (s, 3H), 2.07-1.56 (m, 4H). | Rt = 0.94; 421.3 [M + H]+ | Int P082 & Int B010 |
| Ex 063 | 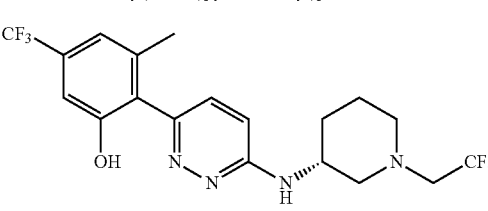<br>(R)-3-Methyl-2-(6-((1-(2,2,2-trifluoroethyl)piperidin-3-yl)amino)pyridazin-3-yl)-5-(trifluoromethyl)phenol | (400 MHz, DMSO-$d_6$) δ (ppm) 10.15 (br s, 1H), 7.23 (d, 1H), 7.09 (br s, 1H), 7.05 (br s, 1H), 6.86 (d, 1H), 6.77 (d, 1H), 4.12-4.00 (m, 1H), 3.28-3.14 (m, 3H), 2.88-2.81 (m, 1H), 2.43-2.34 (m, 1H), 2.31-2.22 (m, 1H), 2.13 (s, 3H), 1.97-1.89 (m, 1H), 1.77-1.66 (m, 1H), 1.64-1.50 (m, 1H), 1.35-1.22 (m, 1H). | Rt = 1.09; 435.2 [M + H]+ | Int P083 & Int B010 |

| Ex No. | Structure and Name | ¹H NMR | LC-MS (min; m/z) | IntP & IntB |
|---|---|---|---|---|
| Ex 064 | 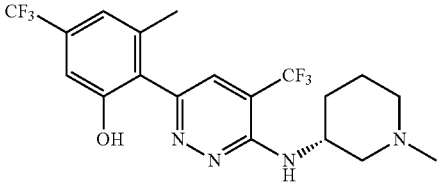 [SMILES: Cc1cc(C(F)(F)F)cc(O)c1-c1cc(C(F)(F)F)c(N[C@@H]2CCCN(C)C2)nn1]<br>(R)-3-Methyl-2-(6-((1-methylpiperidin-3-yl)amino)-5-(trifluoromethyl)pyridazin-3-yl)-5-(trifluoromethyl)phenol | (400 MHz, DMSO-d$_6$) δ (ppm) 10.35 (br s, 1H), 7.67 (s, 1H), 7.14 (s, 1H), 7.07 (s, 1H), 6.14 (br d, 1H), 4.50 (br s, 1H), 2.67 (br s, 1H), 2.40-2.08 (m, 3H) overlapping with 2.21 (s, 3H) and 2.15 (s, 3H), 1.76-1.47 (m, 4H). | Rt = 0.81; 435.3 [M + H]+ | Int P026 & Int B010 |
| Ex 065 | 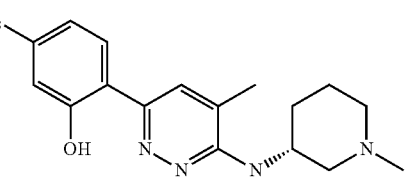<br>(R)-2-(5-Methyl-6-((1-methylpiperidin-3-yl)amino)pyridazin-3-yl)-5-(trifluoromethyl)phenol | (400 MHz, DMSO-d$_6$) δ (ppm) 14.53 (s, 1H), 8.14 (s, 1H), 8.08 (d, 1H), 7.25-7.19 (overlapping d, 1H and s, 1H), 6.30 (d, 1H), 4.29-4.19 (m, 1H), 2.97-2.88 (m, 1H), 2.68-2.60 (m, 1H), 2.24 (s, 3H), 2.20 (s, 3H), 2.01-1.82 (m, 3H), 1.75-1.66 (m, 1H), 1.63-1.50 (m, 1H), 1.49-1.38 (m, 1H). | Rt = 0.81; 367.3 [M + H]+ | Int P030 & BCA |
| Ex 066 | 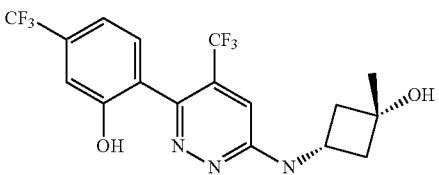<br>2-(6-(((cis)-3-Hydroxy-3-methylcyclobutyl)amino)-4-(trifluoromethyl)pyridazin-3-yl)-5-(trifluoromethyl)phenol | (400 MHz, DMSO-d$_6$) very broad signals δ (ppm) 10.29 (s, 1H), 7.67 (s, 1H), 7.37 (s, 1H), 7.30-7.03 (m, 3H), 5.06 (s, 1H), 4.15-3.87 (m, 1H), 2.47-2.36 (m, 2H, overlapping with DMSO signal), 2.09-1.86 (m, 2H), 1.30 (s, 3H). | Rt = 0.94; 408.2 [M + H]+ | Int P029 & BCA |
| Ex 067 | 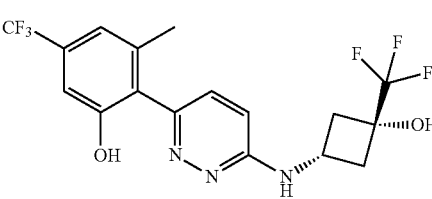<br>2-(6-(((cis)-3-Hydroxy-3-(trifluoromethyl)cyclobutyl)amino)pyridazin-3-yl)-3-methyl-5-(trifluoromethyl)phenol | (400 MHz, DMSO-d$_6$) δ (ppm) 10.14 (s, 1H), 7.36 (d, 1H), 7.26 (d, 1H), 7.10 (s, 1H), 7.05 (s, 1H), 6.84 (d, 1H), 6.65 (s, 1H), 4.24-4.11 (m, 1H), 2.95-2.85 (m, 2H), 2.24-2.15 (m, 2H), 2.11 (s, 3H). | Rt = 0.94; 408.2 [M + H]+ | Int P084 & Int B005 |
| Ex 068 | 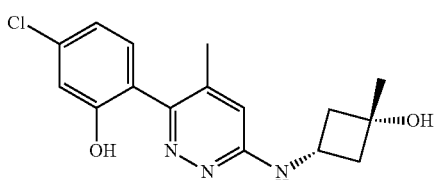<br>5-Chloro-2-(6-(((cis)-3-hydroxy-3-methylcyclobutyl)amino)-4-methylpyridazin-3-yl)phenol | (400 MHz, DMSO-d$_6$) δ (ppm) 10.29 (s, 1H), 7.18 (d, 1H), 7.02-6.85 (m, 3H), 6.60 (s, 1H), 4.97 (s, 1H), 4.05-3.73 (m, 1H), 2.40 (dd, 2H), 2.02 (s, 3H), 1.94 (dd, 2H), 1.28 (s, 3H). | Rt = 0.66; 320.1 [M + H]+ | Int P036 & BCA |

| Ex No. | Structure and Name | $^1$H NMR | LC-MS (min; m/z) | IntP & IntB |
|---|---|---|---|---|
| Ex 069 | 5-Chloro-2-(6-(((cis)-3-hydroxy-3-methylcyclobutyl)amino)-4-(trifluoromethyl)pyridazin-3-yl)phenol | (400 MHz, DMSO-$d_6$) δ (ppm) 10.03 (s, 1H), 7.62 (d, 1H), 7.18-7.09 (m, 2H), 6.96-6.84 (m, 2H), 5.04 (s, 1H), 4.10-3.94 (m, 1H), 2.48-2.39 (m, 2H), 2.03-1.92 (m, 2H), 1.30 (s, 3H). | Rt = 0.88; 374.1 [M + H]+ | Int P029 & BCA |
| Ex 070 | (R)-5-Chloro-2-(6-((1-methylpiperidin-3-yl)amino)-4-(trifluoromethyl)pyridazin-3-yl)phenol | (400 MHz, DMSO-$d_6$) δ (ppm) 10.03 (s, 1H), 7.39-7.22 (m, 2H), 7.14 (d, 1H), 7.01-6.83 (m, 2H), 4.23-4.09 (m, 1H), 2.86-2.73 (m, 1H), 2.47-2.43 (m, 1H, overlapping with DMSO-signal), 2.19 (s, 3H), 2.16-2.08 (m, 1H), 2.07-1.95 (m, 1H), 1.88-1.78 (m, 1H), 1.77-1.66 (m, 1H), 1.62-1.48 (m, 1H), 1.45-1.31 (m, 1H). | Rt = 0.72; 387.2 [M + H]+ | Int P027 & BCA |
| Ex 071 | (R)-5-Chloro-2-(4-methyl-6-((1-methylpiperidin-3-yl)amino)pyridazin-3-yl)phenol | (400 MHz, DMSO-$d_6$) δ (ppm) 10.29 (s, 1H), 7.18 (d, 1H), 6.97-6.90 (m, 2H), 6.68 (s, 1H), 6.59 (d, 1H), 4.09-3.97 (m, 1H), 2.92-2.80 (m, 1H), 2.60-2.52 (m, 1H), 2.18 (s, 3H), 2.01 (s, 3H), 2.00-1.96 (m, 1H), 1.94-1.87 (m, 1H), 1.86-1.78 (m, 1H), 1.76-1.65 (m, 1H), 1.61-1.46 (m, 1H), 1.36-1.21 (m, 1H). | Rt = 0.60; 333.2 [M + H]+ | Int P031 & BCA |
| Ex 072 | 2-(6-((2-Hydroxy-2-methylpropyl)amino)-5-methylpyridazin-3-yl)-3-methyl-5-(trifluoromethyl)phenol | (400 MHz, DMSO-$d_6$) δ (ppm) 10.13 (s, 1H), 7.15 (s, 1H), 7.09 (s, 1H), 7.05 (s, 1H), 5.94 (t, 1H), 5.10 (s, 1H), 3.51 (d, 2H), 2.17 (s, 3H), 2.11 (s, 3H), 1.17 (s, 6H). | Rt = 0.81; 356.2 [M + H]+ | Int P085 & Int B010 |
| Ex 073 | 2-(6-((2-Hydroxy-2-methylpropyl)amino)-4-methylpyridazin-3-yl)-3-methyl-5-(trifluoromethyl)phenol | (400 MHz, CDCl$_3$) δ (ppm) 7.03 (s, 1H), 6.96 (s, 1H), 6.65 (s, 1H), 5.50 (s, 1H), 3.39 (d, 2H), 2.04 (s, 3H), 1.97 (s, 3H), 1.29 (s, 3H), 1.29 (s, 3H). | Rt = 0.73; 356.3 [M + H]+ | Int P086 & Int B005 |

-continued

| Ex No. | Structure and Name | ¹H NMR | LC-MS (min; m/z) | IntP & IntB |
|---|---|---|---|---|
| Ex 074 | (R)-3-Methyl-2-(6-(piperidin-3-ylamino)pyridazin-3-yl)-5-(trifluoromethyl)phenol | (400 MHz, DMSO-d$_6$ + TFA) δ (ppm) 9.14 (br s, 1H), 8.89 (br s, 1H), 8.73-8.52 (br s, 1H), 7.97 (d, 1H), 7.66 (d, 1H), 7.20 (s, 1H), 7.13 (s, 1H), 4.13-4.03 (m, 1H), 3.48-3.41 (m, 1H), 3.26-3.15 (m, 1H), 3.07-2.92 (m, 2H), 2.22 (s, 3H), 2.15-2.07 (m, 1H), 2.02-1.91 (m, 1H), 1.82-1.57 (m, 2H) | Rt = 0.71; 353.3 [M + H]+ | Int P093 & Int B010 |
| Ex 075 | 2-(6-((((2S,4S)-4-Fluoropyrrolidin-2-yl)methyl)amino)pyridazin-3-yl)-3-methyl-5-(trifluoromethyl)phenol | (400 MHz, CD$_3$OD) δ (ppm) 7.34 (d, 1H), 7.08 (s, 1H), 7.03-6.96 (m, 2H), 5.34-5.13 (m, 1H), 3.68-3.60 (m, 2H), 3.58-3.49 (m, 1H), 3.30-3.21 (m, 1H), 2.93 (ddd, 1H), 2.40-2.23 (m, 1H), 2.20 (s, 3H), 1.97-1.79 (m, 1H). | Rt = 0.73; 371.3 [M + H]+ | Int P094 & Int B010 |
| Ex 076 | 2-(6-((((2S,4R)-4-Fluoropyrrolidin-2-yl)methyl)amino)pyridazin-3-yl)-3-methyl-5-(trifluoromethyl)phenol | (400 MHz, CD$_3$OD) δ (ppm) 7.35 (d, 1H), 7.11-7.07 (s, 1H), 7.04-6.98 (m, 2H), 5.35-5.18 (m, 1H), 3.81-3.69 (m, 1H), 3.62 (dd, 1H), 3.53 (dd, 1H), 3.29-3.09 (m, 2H), 2.36-2.22 (m, 1H), 2.20 (s, 3H), 1.86-1.67 (m, 1H). | Rt = 0.71; 371.3 [M + H]+ | Int P095 & Int B010 |
| Ex 077 | (rac)-3-Methyl-2-(6-(((4-methylmorpholin-3-yl)methyl)amino)pyridazin-3-yl)-5-(trifluoromethyl)phenol | (400 MHz, DMSO-d$_6$) δ (ppm) 10.13 (s, 1H), 7.23 (d, 1H), 7.10 (s, 1H), 7.05 (s, 1H), 6.94 (d, 1H), 6.77 (t, 1H), 3.83-3.76 (m, 1H), 3.74-3.64 (m, 2H), 3.56-3.47 (m, 1H), 3.39-3.25 (m, 2H), 2.71-2.66 (m, 1H), 2.32 (s, 3H), overlapping with m, 1H), 2.28-2.18 (m, 1H), 2.12 (s, 3H). | Rt = 0.72; 383.3 [M + H]+ | Int P096 & Int B010 |

| Ex No. | Structure and Name | ¹H NMR | LC-MS (min; m/z) | IntP & IntB |
|---|---|---|---|---|
| Ex 078 | (S)-3-Methyl-2-(6-((3,3,3-trifluoro-2-hydroxy-2-methylpropyl)amino)pyridazin-3-yl)-5-(trifluoromethyl)phenol HCl-salt | (400 MHz, CD₃OD) δ (ppm) 7.92 (d, 1H), 7.75 (d, 1H), 7.17 (s, 1H), 7.08 (s, 1H), 3.88-3.71 (m, 2H), 2.30 (s, 3H), 1.50 (s, 3H). | Rt = 1.03; 396.3 [M + H]+ | Int P097 & Int B010 |
| Ex 079 | 2-(6-((1-Hydroxy-2-methylpropan-2-yl)amino)pyridazin-3-yl)-3-methyl-5-(trifluoromethyl)phenol | (400 MHz, DMSO-d₆) δ (ppm) 10.18 (s, 1H), 7.22 (d, 1H), 7.11 (s, 1H), 7.05 (d, 1H), 6.94 (d, 1H), 6.48 (s, 1H), 5.38 (t, 1H), 3.60 (d, 2H), 2.15 (s, 3H), 1.38 (s, 6H). | Rt = 0.88; 342.3 [M + H]+ | Int P098 & Int B010 |
| Ex 080 | (R)-2-(6-((1-(2-Hydroxy-2-methylpropyl)piperidin-3-yl)amino)pyridazin-3-yl)-3-methyl-5-(trifluoromethyl)phenol | (400 MHz, DMSO-d₆) δ (ppm) 10.13 (s, 1H), 7.22 (d, 1H), 7.10 (s, 1H), 7.04 (s, 1H), 6.87 (d, 1H), 6.72 (d, 1H), 4.13-4.01 (m, 1H), 3.07-2.98 (m, 1H), 2.78-2.71 (m, 1H), 2.29-2.16 (m, 4H), 2.12 (s, 3H), 1.89-1.80 (m, 1H), 1.72-1.66 (m, 1H), 1.59-1.52 (m, 1H), 1.32-1.23 (m, 1H), 1.08 (s, 6H). | Rt = 0.78; 425.3 [M + H]+ | Int P103 & Int B010 |
| Ex 081 | 2-(6-(((cis)-3-Hydroxy-3-methylcyclobutyl)amino)-4-methylpyridazin-3-yl)-5-(trifluoromethoxy)phenol | (400 MHz, DMSO-d6) δ (ppm) 10.46 (s, 1H), 7.28 (d, 1H), 7.17-7.04 (m, 1H), 6.90-6.84 (m, 2H), 6.65 (s, 1H), 4.98 (s, 1H), 3.98-3.81 (m, 1H), 2.47-2.36 (m, 2H), 2.03 (s, 3H), 1.95 (td, 2H), 1.28 (s, 3H). | Rt = 0.89; 370.1 [M + H]+ | Int P036 & BCA |
| Ex 082 | (R)-2-(4-Methyl-6-((1-methylpiperidin-3-yl)amino)pyridazin-3-yl)-5-(trifluoromethoxy)phenol | (400 MHz, DMSO-d6) δ (ppm) 10.43 (s, 1H), 7.28 (d, 1H), 6.86 (s, 2H), 6.69 (s, 1H), 6.60 (d, 1H), 4.14-3.93 (m, 1H), 2.96-2.77 (m, 1H), 2.61-2.51 (m, 1H), 2.18 (s, 3H), 2.01 (s, 3H), 1.98 (s, 1H), 1.94-1.78 (m, 2H), 1.75-1.65 (m, 1H), 1.61-1.45 (m, 1H), 1.36-1.21 (m, 1H). | Rt = 0.84; 383.1 [M + H]+ | Int P031 & BCA |

The following Examples Ex 083(A/B) to Ex096 (A/B) were prepared as racemates following analogous procedures as in Example Ex 001 using the corresponding amine and bororate, as defined herein, followed by achiral chromatography separation step.

Example Ex 083A and Ex 083B

3-Methyl-2-(6-(((8R,8aR)-octahydroindolizin-8-yl) amino)pyridazin-3-yl)-5-(trifluoro methyl) phenol and 3-Methyl-2-(6-(((8S,8aS)-octahydroindolizin-8-yl)amino)pyridazin-3-yl)-5-(trifluoro methyl) phenol Racemate (rac)-3-methyl-2-(6-(((8r,8ar)-octahydroindolizin-8-yl)amino)pyridazin-3-yl)-5-(trifluoromethyl)phenol (prepared as described for Example Ex 001 starting from Int P041 and Int B010) was separated by chiral normal phase chromatography (Column: Chiralpak AD, 250×30 mm, 5 μm; RT, Eluent: n-heptane:EtOH=90:10+0.05% DEA; Flow: 20 mL/min; Cycle time:15 min) to provide the two enantiomers Ex 083A (first eluting, Rt=25 min) and Ex 083B (second eluting, Rt=31 min) respectively.

Ex 083A $^1$H NMR (400 MHz, DMSO-$d_6$) δ 10.14 (m, 1H), 7.21 (d, 1H), 7.12-7.08 (m, 1H), 7.07-7.02 (m, 1H), 6.88-6.75 (m, 2H), 3.96-3.77 (n, 1H), 3.29-3.20 (m, 2H), 3.13-2.93 (n, 2H), 2.16-2.09 (m, 4H), 2.05-1.88 (m, 2H), 1.72-1.45 (m, 5H), 1.17-1.04 (m, 1H). LC-MS: Rt=0.73 min; MS m/z 393.2 [M+H]$^+$ Ex 083B $^1$H NMR (600 MHz, DMSO-$d_6$) δ 10.19 (s, 1H), 7.23 (d, 1H), 7.11 (s, 1H), 7.06 (s, 1H), 6.96-6.76 (m, 2H), 3.99-3.82 (m, 1H), 3.34-3.28 (m, 2H), 3.17-3.02 (m, 2H), 2.19-2.11 (m, 4H), 2.03-1.87 (m, 2H), 1.77-1.49 (m, 5H), 1.20-1.13 (m, 1H). LC-MS: Rt=0.73 min; MS m/z 393.2 [M+H]$^+$ Example Ex 084A and Ex 084B (R)-2-(6-(((1-(2-Hydroxyethyl)piperidin-2-yl) methyl)amino)pyridazin-3-yl)-3-methyl-5-(trifluoro 10 methyl)phenol and (S)-2-(6-(((1-(2-Hydroxyethyl)piperidin-2-yl)methyl)amino) pyridazin-3-yl)-3-methyl-5-(trifluoromethyl)phenol Racemate 2-(6-(((1-(2-Hydroxyethyl)piperidin-2-yl)methyl)amino)pyridazin-3-yl)-3-methyl-5-(trifluoromethyl)phenol (prepared as described for Example Ex 001 starting from Int P044 and Int B010) was separated by chiral normal phase chromatography (Column: Chiralpak AD, 250×30 mm, 5 μm; RT, Eluent: n-heptane:EtOH=80:20+0.05% DEA; Flow: 20 mL/min; Cycle time: 30 min) to provide the two enantiomers Ex 084A (first eluting, Rt=15 min) and Ex 084B (second eluting, Rt=23.5 min) respectively.

Ex 084A' H NMR (600 MHz, DMSO-$d_6$) δ (ppm) 10.15 (s, 1H), 7.22 (d, 1H), 7.10 (s, 1H), 7.04 (s, 1H), 6.93 (d, 1H), 6.70 (s, 1H), 4.51-4.38 (m, 1H), 3.68-3.57 (m, 2H), 3.56-3.47 (m, 2H), 3.44-3.34 (m, 1H), 2.97-2.77 (m, 2H), 2.37-2.23 (m, 1H), 2.13 (s, 3H), 1.70-1.62 (m, 2H), 1.57-1.41 (m, 4H). LC-MS: Rt=0.72 min; MS m/z 411.3 [M+H]$^+$ Ex 084 B $^1$H NMR (600 MHz, DMSO-$d_6$) δ (ppm) 10.15 (s, 1H), 7.22 (d, 1H), 7.10 (s, 1H), 7.04 (s, 1H), 6.93 (d, 1H), 6.70 (s, 1H), 4.51-4.38 (m, 1H), 3.68-3.57 (m, 2H), 3.56-3.47 (m, 2H), 3.44-3.34 (m, 1H), 2.97-2.77 (m, 2H), 2.37-2.23 (m, 1H), 2.13 (s, 3H), 1.70-1.62 (m, 2H), 1.57-1.41 (m, 4H). LC-MS: Rt=0.72 min; MS m/z 411.3 [M+H]$^+$ Example Ex 085A and Ex 085B 3-Methyl-2-(6-(((1S,2S,5S)-8-methyl-8-azabicyclo [3.2.1]octan-2-yl)amino)pyridazin-3-yl)-5-(trifluoromethyl)phenol (Ex 085A) and 3-Methyl-2-(6-(((1R,2R,5R)-8-methyl-8-azabicyclo [3.2.1]octan-2-yl)amino)pyridazin-3-yl)-5-(trifluoromethyl)phenol (Ex 085B)

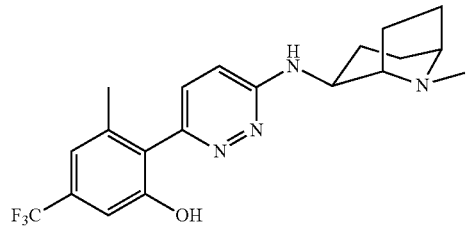
(85A)

, and

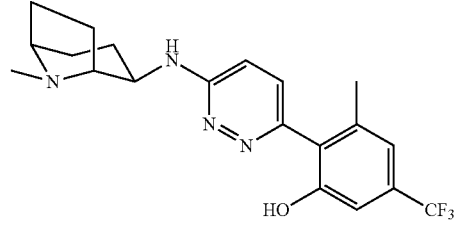
(85B)

The racemate product (prepared as described for Example Ex 001 starting from Int P048 and Int B010) was separated by chiral normal phase chromatography (Column: Chiralpak IG, 250 x 30 mm, 5 μm; 40° C., Eluent: n-heptane:i-PrOH=70:30+0.1% ammonia; Flow: 80 mL/min; Pressure: 120 bar, Cycle time: 20 min) to provide the two enantiomers Ex 085A (first eluting, Rt=7 min) and Ex 085B (second eluting, Rt=11.9 min) respectively. Stereochemistry was assigned by X-ray crystallography.

Ex 085A' H NMR (600 MHz, DMSO-$d_6$) δ (ppm) 10.16 (s, 1H), 7.21 (d, 1H), 7.10 (s, 1H), 7.04 (s, 1H), 6.82 (d, 1H), 6.75 (br d, 1H), 4.13-4.04 (m, 1H), 3.28-3.21 (m, 1H), 3.06-3.0 (m, 1H), 2.20 (s, 3H), 2.13 (s, 3H), 2.05-1.94 (m, 1H), 1.86-1.61 (m, 4H), 1.55-1.29 (m, 3H). LC-MS: Rt=0.71 min; MS m/z 393.2 [M+H]$^+$ Ex 085B $^1$H NMR (600 MHz, DMSO-$d_6$) δ (ppm) 10.21 (s, 1H), 7.21 (d, 1H), 7.10 (s, 1H), 7.04 (s, 1H), 6.82 (d, 1H), 6.75 (br d, 1H), 4.12-4.04 (m, 1H), 3.26-3.22 (m, 1H), 3.06-3.0 (m, 1H), 2.20 (s, 3H), 2.13 (s, 3H), 2.01-1.92 (m, 1H), 1.80-1.61 (m, 4H), 1.48-1.28 (m, 3H).

LC-MS: Rt=0.71 min; MS m/z 393.2 [M+H]$^+$

Example Ex 086A and Ex 086B 2-(6-(((1R,2R,5R)-8-(2-Hydroxyethyl)-8-azabicyclo[3.2.1]octan-2-yl)amino)pyridazin-3-yl)-3-methyl-5-(trifluoromethyl)phenol (Ex 086B) and 2-(6-(((1S,2S,5S)-8-(2-Hydroxyethyl)-8-azabicyclo[3.2.1] octan-2-yl)amino)pyridazin-3-yl)-3-methyl-5-(trifluoromethyl)phenol (Ex 086A)

(86A)

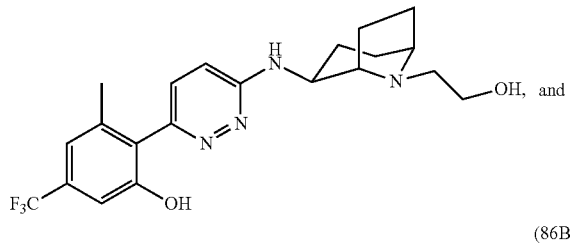

(86B)

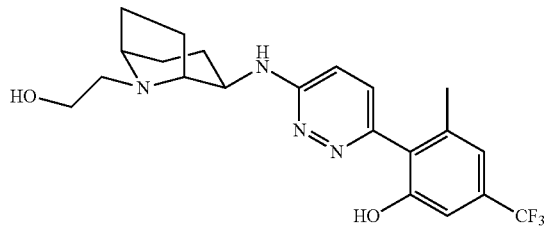

The racemate 2-(6-((-8-(2-Hydroxyethyl)-8-azabicyclo[3.2.1]octan-2-yl)amino)pyridazin-3-yl)-3-methyl-5-(trifluoromethyl)phenol (prepared as described for Example Ex 001 starting from Int P050 and Int B010) was separated by chiral SFC (Column: Chiralpak IG, 250×30 mm, 5 μm, 40° C., Eluent B: i-PrOH 35%+0.1% ammonia; Flow: 70 mL/min; Pressure: 110 bar, Cycle time: 6 min) to provide the two enantiomers Ex 086A (first eluting, Rt=5.2 min) and Ex 086B (second eluting, Rt=6.5 min) respectively. Stereochemistry was assigned by ROESY NMR.

Ex 086A $^1$H NMR (600 MHz, DMSO-$d_6$) δ 10.17 (s, 1H), 7.21 (d, 1H), 7.11 (s, 1H), 7.05 (s, 1H), 6.83 (d, 1H), 6.75 (d, 1H), 4.41-4.30 (m, 1H), 4.16-4.04 (m, 1H), 3.52-3.43 (m, 2H), 3.33-3.29 (m, 1H), 3.23-3.15 (m, 1H), 2.47-2.36 (m, 2H), 2.13 (s, 3H), 1.94-1.85 (m, 1H), 1.80-1.61 (m, 4H), 1.49-1.30 (m, 3H). LC-MS: Rt=0.71 min; MS m/z 423.3 [M+H]$^+$ Ex 086B $^1$H NMR (600 MHz, DMSO-$d_6$) δ 10.17 (s, 1H), 7.21 (d, 1H), 7.11 (s, 1H), 7.05 (s, 1H), 6.83 (d, 1H), 6.75 (d, 1H), 4.41-4.30 (m, 1H), 4.16-4.04 (m, 1H), 3.52-3.43 (m, 2H), 3.33-3.29 (m, 1H), 3.23-3.15 (m, 1H), 2.47-2.36 (m, 2H), 2.13 (s, 3H), 1.94-1.85 (m, 1H), 1.80-1.61 (m 4H), 1.49-1.30 (m 3H). LC-MS: Rt=0.71 min: MS m/z 423.3 [M+H]$^+$

Example Ex 087A and Ex 087B 2-(6-(((3R,6R)-6-(Hydroxymethyl)-1-methylpiperidin-3-yl)amino)pyridazin-3-yl)-3-methyl-5-(trifluoromethyl)phenol and 2-(6-(((3S,6S)-6-(Hydroxymethyl)-1-methylpiperidin-3-yl)amino) pyridazin-3-yl)-3-methyl-5-(trifluoromethyl)phenol The racemate 2-(6-((-6-(hydroxymethyl)-1-methylpiperidin-3-yl)amino)pyridazin-3-yl)-3-methyl-5-(trifluoromethyl)phenol (prepared as described for Example Ex 001 starting from Int P052 and Int B010) was separated by chiral SFC (Column: Chiralpak IG-LL, 250×30 mm, 5 μm, 40° C., Eluent B: MeOH 22%+0.1% ammonia; Flow: 80 mL/min; Pressure: 120 bar, Cycle time: 20 min) to provide the two diastereoisomers Ex 087A (first eluting, Rt=8.2 min) and Ex 087B (second eluting, Rt=11.3 min) respectively.

Ex 087A $^1$H NMR (600 MHz, DMSO-$d_6$) δ 10.19 (s, 1H), 7.22 (d, 1H), 7.10 (s, 1H), 7.04 (s, 1H), 7.02 (d, 1H), 6.72 (d, 1H), 4.44-4.34 (m, 1H), 4.27-4.17 (m, 1H), 3.64-3.56 (m, 1H), 3.48-3.40 (m, 1H), 2.80-2.73 (m, 1H), 2.44-2.37 (m, 1H), 2.27 (s, 3H), 2.13 (s, 3H), 2.07-1.98 (m, 1H), 1.86-1.78 (m, 1H), 1.66-1.52 (m, 3H). LC-MS: Rt=0.71 min; MS m/z 423.3 [M+H]$^+$ Ex 087B $^1$H NMR (600 MHz, DMSO-$d_6$) δ 10.19 (s, 1H), 7.22 (d, 1H), 7.10 (s, 1H), 7.04 (s, 1H), 7.02 (d, 1H), 6.72 (d, 1H), 4.45-4.33 (m, 1H), 4.26-4.15 (m, 1H), 3.64-3.55 (m, 1H), 3.50-3.40 (m, 1H), 2.81-2.72 (m, 1H), 2.44-2.36 (m, 1H), 2.27 (s, 3H), 2.13 (s, 3H), 2.07-1.99 (m, 1H), 1.86-1.78 (m, 1H), 1.68-1.51 (m, 3H). LC-MS: Rt=0.71 min; MS m/z 423.3 [M+H]$^+$

Example Ex 088A and Ex 088B (S)-3-((6-(2-Hydroxy-6-methyl-4-(trifluoromethyl)phenyl)pyridazin-3-yl)amino)-2-methylpropane-1,2-diol and (R)-3-((6-(2-Hydroxy-6-methyl-4-(trifluoromethyl)phenyl)pyridazin-3-yl)amino)-2-methylpropane-1,2-diol Racemate 3-((6-(2-Hydroxy-6-methyl-4-(trifluoromethyl)phenyl)pyridazin-3-yl)amino)-2-methyl propane-1,2-diol (prepared as described for Example Ex 001 starting from Int P053 and Int B010) was separated by chiral SFC (Column: Chiralpak IG, 250×30 mm, 5 μm, 40° C., Eluent B: MeOH 25%+0.1% ammonia; Flow: 80 mL/min; Pressure: 120 bar, Cycle time: 20 min) to provide the two enantiomers Ex 088A (first eluting, Rt=8.7 min) and Ex 088B (second eluting, Rt=13.8 min) respectively.

Ex 088A $^1$H NMR (600 MHz, DMSO-$d_6$) δ (ppm) 10.19 (s, 1H), 7.24 (d, 1H), 7.10 (s, 1H), 7.04 (s, 1H), 7.02 (d, 1H), 6.88-6.83 (m, 1H), 4.99-4.92 (m, 1H), 4.77 (s, 1H), 3.44-3.37 (m, 2H), 3.32-3.27 (m, 1H), 3.24-3.18 (m, 1H), 2.12 (s, 3H), 1.11 (s, 3H). LC-MS: Rt=0.7 min; MS m/z 358.1 [M+H]$^+$ Ex 088B $^1$H NMR (600 MHz, DMSO-$d_6$) δ (ppm) 10.17 (s, 1H), 7.24 (d, 1H), 7.10 (s, 1H), 7.04 (s, 1H), 7.02 (d, 1H), 6.90-6.82 (m, 1H), 4.99-4.92 (m, 1H), 4.77 (s, 1H), 3.43-3.37 (m, 2H), 3.32-3.26 (m, 1H), 3.24-3.18 (m, 1H), 2.12 (s, 3H), 1.11 (s, 3H). LC-MS: Rt=0.7 min; MS m/z 358.1 [M+H]$^+$

Example Ex 089A and Ex 089B (1S,2R,3S)-3-((6-(2-Hydroxy-6-methyl-4-(trifluoromethyl)phenyl)pyridazin-3-yl)amino) cyclopentane-1,2-diol and (1R,2S,3R)-3-((6-(2-Hydroxy-6-methyl-4-(trifluoromethyl)phenyl) pyridazin-3-yl)amino)cyclopentane-1,2-diol Racemate 3-((6-(2-hydroxy-6-methyl-4-(trifluoromethyl)phenyl)pyridazin-3-yl)amino)cyclo pentane-1,2-diol (prepared as described for Example Ex 001 starting from Int P054 and Int B010) was separated by chiral SFC (Column: i-LuxCel (IC), 250×30 mm, 5 μm; Eluent B: MeOH 15%+0.1% ammonia; Flow: 80 mL/min; Cycle time: 30 min) to provide the two diastereoisomers Ex 089A (first eluting, Rt=14.3 min) and Ex 089B (second eluting, Rt=22.2 min) respectively.

Ex 089A' H NMR (600 MHz, DMSO-d$_6$) δ (ppm) 10.18 (s, 1H), 7.24 (d, 1H), 7.10 (s, 1H), 7.04 (s, 1H), 7.02 (d, 1H), 6.89 (d, 1H), 5.11 (d, 1H), 4.43 (d, 1H), 4.19-4.05 (m, 1H), 3.98-3.91 (m, 1H), 3.74-3.66 (m, 1H), 2.29-2.19 (m, 1H), 2.13 (s, 3H), 1.95-1.83 (m, 1H), 1.63-1.52 (m, 1H), 1.42-1.32 (m, 1H). LC-MS: Rt=0.7 min; MS m/z 370.3 [M+H]$^+$ Ex 089 B $^1$H NMR (600 MHz, DMSO-d$_6$) δ (ppm) 10.19 (s, 1H), 7.24 (d, 1H), 7.10 (s, 1H), 7.06-6.98 (m, 2H), 6.89 (d, 1H), 5.11 (d, 1H), 4.43 (d, 1H), 4.16-4.05 (m, 1H), 3.98-3.90 (m, 1H), 3.76-3.68 (m, 1H), 2.28-2.18 (m, 1H), 2.13 (s, 3H), 1.95-1.85 (m, 1H), 1.63-1.52 (m, 1H), 1.42-1.32 (m, 1H). LC-MS: Rt=0.7 min; MS m/z 370.3 [M+H]$^+$ Example Ex 090A and Ex 090B (S)-2-(6-((2-Hydroxy-3-methylbutyl)amino) pyridazin-3-yl)-3-methyl-5-(trifluoromethyl)phenol and (R)-2-(6-((2-Hydroxy-3-methylbutyl)amino) pyridazin-3-yl)-3-methyl-5-(trifluoromethyl) phenol Racemate 2-(6-((2-hydroxy-3-methylbutyl)amino) pyridazin-3-yl)-3-methyl-5-(trifluoromethyl) phenol (prepared as described for Example Ex 001 starting from Int P056 and Int B010) was separated by chiral SFC (Column: Chiralpak IB-N, 250×30 mm, 5 μm, 40° C., Eluent B: i-PrOH 23%+0.1% ammonia; Flow: 80 mL/min; Pressure: 120 bar, Cycle time: 20 min) to provide the two enantiomers Ex 090A (first eluting, Rt=9.6 min) and Ex 090B (second eluting, Rt=13 min) respectively.

Ex 090A' H NMR (600 MHz, DMSO-d$_6$) δ (ppm) 10.18 (s, 1H), 7.22 (d, 1H), 7.10 (s, 1H), 7.04 (s, 1H), 6.94 (d, 1H), 6.83 (t, 1H), 4.82 (d, 1H), 3.59-3.52 (m, 1H), 3.49-3.43 (m, 1H), 3.27-3.21 (m, 1H), 2.12 (s, 3H), 1.76-1.66 (m, 1H), 0.96-0.89 (m, 6H). LC-MS: Rt=0.85 min; MS m/z 356.2 [M+H]$^+$ Ex 090 B $^1$H NMR (600 MHz, DMSO-d$_6$) δ (ppm) 10.17 (s, 1H), 7.22 (d, 1H), 7.10 (s, 1H), 7.04 (s, 1H), 6.94 (d, 1H), 6.83 (t, 1H), 4.82 (d, 1H), 3.58-3.50 (m, 1H), 3.50-3.42 (m, 1H), 3.28-3.21 (m, 1H), 2.12 (s, 3H), 1.77-1.67 (m, 1H), 0.96-0.89 (m, 6H). LC-MS: Rt=0.85 min; MS m/z 356.2 [M+H]$^+$ Example Ex 091A and Ex 091B 3-Methyl-2-(6-(((2S,3S)-2-methylpiperidin-3-yl) amino)pyridazin-3-yl)-5-(trifluoromethyl)phenol and 3-Methyl-2-(6-(((2R,3R)-2-methylpiperidin-3-yl) amino)pyridazin-3-yl)-5-(trifluoromethyl) phenol Racemate 3-methyl-2-(6-((2-methylpiperidin-3-yl) amino)pyridazin-3-yl)-5-(trifluoromethyl) phenol (prepared as described for Example Ex 001 starting from Int P099 and Int B010) was separated by chiral SFC (Column: Lux i-Cellulose 5, 250×30 mm, 5 μm, 40° C., Eluent B: MeOH 23%+0.1% NH3, Flow: 80 mL/min, pressure: 120 bar, cycle time: 20 min) to provide the title compounds Ex 091A (first eluting, Rt=9.17 min) and Ex 091B (second eluting, Rt=12.01 min) respectively.

Ex 091A $^1$H NMR (400 MHz, CD$_3$OD) δ (ppm) 7.34 (d, 1H), 7.08 (s, 1H), 7.01-7.03 (m, 2H), 4.27-4.22 (m, 1H), 3.18-3.12 (m, 1H), 3.10-3.03 (m, 1H), 2.81-2.73 (m, 1H), 2.21 (s, 3H), 2.08-2.01 (m, 1H), 1.75-1.70 (m, 2H), 1.59-1.53 (m, 1H), 1.15 (d, 3H). LC-MS: Rt=0.73 min; m/z 367.1 [M+H]$^+$ Ex 091B $^1$H NMR (400 MHz, CD$_3$OD) δ (ppm) 7.35 (d, 1H), 7.07 (s, 1H), 7.05-7.01 (m, 2H), 4.27-4.21 (m, 1H), 3.18-3.12 (m, 1H), 3.11-3.02 (m, 1H), 2.81-2.72 (m, 1H), 2.21 (s, 3H), 2.10-1.99 (m, 1H), 1.78-1.68 (m, 2H), 1.61-1.51 (m, 1H), 1.16 (d, 3H) LC-MS: Rt=0.73 min; MS m/z 367.1 [M+H]$^+$ Example Ex 092A and Ex 092B 2-(6-(((R)-1-((S)-2-Hydroxypropyl)piperidin-3-yl) amino)pyridazin-3-yl)-3-methyl-5-(trifluoromethyl) phenol and 2-(6-(((R)-1-((R)-2-Hydroxypropyl)piperidin-3-yl)amino)pyridazin-3-yl)-3-methyl-5-(trifluoromethyl)phenol The diastereomeric mixture of 2-(6-(((3R)-1-(2-hydroxypropyl)piperidin-3-yl)amino)pyridazin-3-yl)-3-methyl-5-(trifluoromethyl)phenol (prepared as described for Example Ex 001 starting from Int P105 and Int B010) was separated by chiral SFC (Column: ChiralPak AD, 250×30 mm, 5 μm, 40° C., Eluent B: EtOH 25%+0.1% NH3, Flow: 80 mL/min, pressure: 120 bar, cycle time: 20 min) to provide the title compounds Ex 092A (first eluting, Rt=8.7 min) and Ex 092B (second eluting, Rt=12.0 min) respectively.

Ex 092A' H NMR (400 MHz, DMSO-d$_6$) δ (ppm) 10.14 (s, 1H), 7.22 (d, 1H), 7.10 (s, 1H), 7.05 (s, 1H), 6.88 (d, 1H), 6.79 (d, 1H), 4.32-4.26 (m, 1H), 4.14-4.06 (m, 1H), 3.80-3.72 (m, 1H), 3.48-3.40 (m, 1H), 2.95-2.87 (m, 1H), 2.28-2.16 (m, 3H), 2.12 (s, 3H), 1.86-1.78 (m, 1H), 1.76-1.67 (m, 1H), 1.58-1.47 (m, 1H), 1.43-1.34 (m, 1H), 1.03 (d, 3H). LC-MS: Rt=0.73 min: MS m/z 411.2 [M+H]$^+$ Ex 092 B $^1$H NMR (400 MHz, DMSO-d$_6$) δ (ppm) 10.14 (s, 1H), 7.22 (d, 1H), 7.10 (s, 1H), 7.05 (s, 1H), 6.88 (d, 1H), 6.79 (d, 1H), 4.29-4.24 (m, 1H), 4.14-4.06 (m, 1H), 3.80-3.72 (m, 1H), 3.48-3.40 (m, 1H), 2.95-2.87 (m, 1H), 2.29-2.16 (m, 3H), 2.13 (s, 3H), 1.88-1.78 (m, 1H), 1.76-1.67 (m, 1H), 1.61-1.48 (m, 1H), 1.42-1.31 (m, 1H), 1.04 (d, 3H) LC-MS: Rt=0.73 min; MS m/z 411.2 [M+H]$^+$ Example Ex 093A and Ex 093B 2-(6-(((3S,5S)-5-Fluoropiperidin-3-yl)amino) pyridazin-3-yl)-3-methyl-5-(trifluoromethyl)phenol and 2-(6-(((3R,5R)-5-Fluoropiperidin-3-yl)amino) pyridazin-3-yl)-3-methyl-5-(trifluoromethyl) phenol The diastereomeric mixture of 2-(6-((5-fluoropiperidin-3-yl)amino)pyridazin-3-yl)-3-methyl-5-(trifluoromethyl) phenol (prepared as described for Example Ex 003 starting from Int P102 and Int B005) was separated by chiral SFC (Column: Lux i-Cellulose-5, 250×30 mm, 5 μm, 40° C., Eluent B: 33% [iPrOH+0.1% NH$_3$], Flow: 80 mL/min, pressure: 120 bar, cycle time: 20 min) to provide the title compounds Ex 093A (first eluting, Rt=6.9 min) and Ex 093B (second eluting, Rt=11.5 min) respectively.

Ex 093A' H NMR (400 MHz, DMSO-d$_6$) δ (ppm) 10.17 (s, 1H), 7.23 (d, 1H), 7.10 (s, 1H), 7.04 (s, 1H), 6.85 (d, 1H), 6.81 (d, 1H), 4.89-4.72 (m, 1H), 4.25-4.15 (m, 1H), 3.12-3.05 (m, 1H), 2.94-2.84 (m, 1H), 2.82-2.68 (m, 1H), 2.44-2.35 (m, 2H), 2.24-2.13 (m, 1H), 2.13 (s, 3H), 1.86-1.68 (m, 1H); LC-MS: Rt=0.85 min; MS m/z 371.2 [M+H]$^+$ Ex 093 B $^1$H NMR (400 MHz, DMSO-d$_6$) δ (ppm) 10.14 (s, 1H), 7.24 (d, 1H), 7.10 (s, 1H), 7.05 (s, 1H), 6.85 (d, 1H), 6.82 (d, 1H), 4.93-4.75 (m, 1H), 4.28-4.18 (m, 1H), 3.16-3.10 (m, 1H), 2.99-2.90 (m, 1H), 2.86-2.71 (m, 1H), 2.49-

2.40 (m, 2H), 2.26-2.15 (m, 1H), 2.13 (s, 3H), 1.88-1.70 (m, 1H); LC-MS: Rt=0.85 min; MS m/z 371.2 [M+H]+

Example Ex 094A and Ex 094B 2-(6-(((3S, 5S)-5-Fluoro-1-methylpiperidin-3-yl) amino)pyridazin-3-yl)-3-methyl-5-(trifluoro methyl) phenol and 2-(6-(((3R, 5R)-5-Fluoro-1-methylpiperidin-3-yl)amino)pyridazin-3-yl)-3-methyl-5-(trifluoromethyl)phenol The diastereomeric mixture of 2-(6-((5-fluoro-1-methylpiperidin-3-yl)amino)pyridazin-3-yl)-3-methyl-5-(trifluoromethyl)phenol was prepared as follows: rac-Ex 093A/B (40 mg, 0.10 mmol) was dissolved in THF and formaldehyde (0.038 mL, 0.51 mmol, 37% in water) was added. NaBH(OAc)₃ (43 mg, 0.205 mmol) was added and the resulting mixture stirred at RT for 1 h. Further formaldehyde (0.038 mL, 0.51 mmol, 37% in water), NaBH(OAc)₃ (43 mg, 0.205 mmol) and AcOH (1 drop) were added. After stirring for a further 2 h the reaction was quenched by addition of NaHCO₃ solution and extracted with EtOAc. The combined organics were washed with brine, dried over Na₂SO₄, filtered and concentrated in vacuo. The residue was purified by achiral RP chromatography. Fractions containing the pure product were combined and taken to pH 8-9 using saturated NaHCO₃ solution then extracted twice with EtOAc. The organics were dried over Na₂SO₄, filtered and concentrated in vacuo. The distereomeric products were separated by chiral SFC (Column: Lux i-Cellulose-5, 250×30 mm, 5 µm, 40° C., Eluent B: 33% [iPrOH+0.1% NH3], Flow: 80 mL/min, pressure: 120 bar, cycle time: 20 min) to provide the title compounds Ex 094A (first eluting, Rt=3.99 min) and Ex 094B (second eluting, Rt=4.52 min) respectively.

Ex 094A ¹H NMR (400 MHz, DMSO-d₆) δ (ppm) 10.18 (s, 1H), 7.24 (d, 1H), 7.10 (s, 1H), 7.04 (s, 1H), 6.88-6.84 (m, 1H), 5.02-4.84 (m, 1H), 4.42-4.33 (m, 1H), 2.93-2.86 (m, 1H), 2.80-2.70 (m, 1H), 2.37-2.24 (m, 1H), 2.22 (s, 3H), 2.12 (s, 3H), 2.12-2.03 (m, 1H), 2.01-1.93 (m, 1H), 1.77-1.58 (m, 1H). LC-MS: Rt=0.86 min; MS m/z 385.2 [M+H]+

Ex 094 B ¹H NMR (400 MHz, DMSO-d₆) δ (ppm) 10.19 (s, 1H), 7.24 (d, 1H), 7.10 (s, 1H), 7.04 (s, 1H), 6.88-6.84 (m, 1H), 5.02-4.84 (m, 1H), 4.42-4.33 (m, 1H), 2.93-2.86 (m, 1H), 2.80-2.70 (m, 1H), 2.37-2.24 (m, 1H), 2.22 (s, 3H), 2.12 (s, 3H), 2.12-2.03 (m, 1H), 2.01-1.93 (m, 1H), 1.77-1.58 (m, 1H). LC-MS: Rt=0.86 min; MS m/z 385.2 [M+H]+

Example Ex 095A and Ex 095B 2-(6-(((3S, 5R)-5-Fluoro-1-methylpiperidin-3-yl) amino)pyridazin-3-yl)-3-methyl-5-(trifluoromethyl) phenol and 2-(6-(((3R, 5S)-5-Fluoro-1-methylpiperidin-3-yl)amino)pyridazin-3-yl)-3-methyl-5-(trifluoromethyl)phenol The diastereomeric mixture of 2-(6-((5-fluoro-1-methylpiperidin-3-yl)amino)pyridazin-3-yl)-3-methyl-5-(trifluoromethyl)phenol (prepared as described for Example Ex 001 starting from Int P103 and Int B005) was separated by chiral SFC (Column: Lux Amylose-1, 250×30 mm, 5 µm, 40° C., Eluent B: 17% [iPrOH+0.1% NH3], Flow: 80 mL/min, pressure: 120 bar, cycle time: 20 min) to provide the title compounds Ex 095A (first eluting, Rt=13.58 min) and Ex 095B (second eluting, Rt=15.01 min) respectively.

Ex 095A ¹H NMR (400 MHz, DMSO-d₆) δ (ppm) 10.16 (br s, 1H), 7.24 (d, 1H), 7.09 (s, 1H), 7.04 (s, 1H), 6.88 (d, 1H), 6.82 (d, 1H), 4.84-4.63 (m, 1H), 4.20-4.09 (m, 1H), 3.01-2.91 (m, 2H), 2.39-2.30 (m, 1H), 2.26 (s, 3H), 2.12 (s, 3H), 2.10-2.04 (m, 1H), 1.91-1.84 (m, 1H), 1.56-1.44 (m, 1H). LC-MS: Rt=0.83 min; MS m/z 385.3 [M+H]+

Ex 095B ¹H NMR (400 MHz, DMSO-d₆) δ (ppm) 10.17 (br s, 1H), 7.24 (d, 1H), 7.09 (s, 1H), 7.04 (s, 1H), 6.89 (d, 1H), 6.82 (d, 1H), 4.84-4.63 (m, 1H), 4.20-4.10 (m, 1H), 3.01-2.91 (m, 2H), 2.39-2.32 (m, 1H), 2.26 (s, 3H), 2.12 (s, 3H), 2.10-2.04 (m, 1H), 1.91-1.84 (m, 1H), 1.56-1.44 (m, 1H). LC-MS: Rt=0.83 min; MS m/z 385.2 [M+H]+

Example Ex 096A and Ex 096B 2-(6-(((3S, 5R)-5-Fluoropiperidin-3-yl)amino) pyridazin-3-yl)-3-methyl-5-(trifluoromethyl)phenol and 2-(6-(((3R, 5S)-5-Fluoropiperidin-3-yl)amino) pyridazin-3-yl)-3-methyl-5-(trifluoromethyl) phenol The diastereomeric mixture of 2-(6-((5-fluoropiperidin-3-yl)amino)pyridazin-3-yl)-3-methyl-5-(trifluoromethyl) phenol (prepared as described for Example Ex 001 starting from Int P104 and Int B005) was separated by chiral SFC (Column: Lux Amylose-1, 250×30 mm, 5 µm, 40° C., Eluent B: 40% [MeOH+0.1% NH3], Flow: 80 mL/min, pressure: 120 bar, cycle time: 20 min) to provide the title compounds Ex 096A (first eluting, Rt=4.79 min) and Ex 096B (second eluting, Rt=9.34 min) respectively.

Ex 096A ¹H NMR (400 MHz, DMSO-d₆) δ (ppm) 10.16 (br s, 1H), 7.24 (d, 1H), 7.09 (s, 1H), 7.04 (s, 1H), 6.87-6.82 (m, 2H), 4.67-4.46 (m, 1H), 4.04-3.96 (m, 1H), 3.17-3.08 (m, 2H), 2.47-2.37 (m, 2H), 2.25-2.18 (m, 1H), 2.13 (s, 3H), 1.60-1.49 (m, 1H). LC-MS: Rt=0.82 min; MS m/z 371.2 [M+H]+

Ex 096B ¹H NMR (400 MHz, DMSO-d₆) δ (ppm) 10.17 (br s, 1H), 7.24 (d, 1H), 7.10 (s, 1H), 7.04 (s, 1H), 6.87-6.82 (m, 2H), 4.67-4.46 (m, 1H), 4.04-3.96 (m, 1H), 3.17-3.08 (m, 2H), 2.47-2.37 (m, 2H), 2.25-2.18 (m, 1H), 2.13 (s, 3H), 1.60-1.49 (m, 1H). LC-MS: Rt=0.82 min; MS m/z 371.2 [M+H]+

Example Ex 097

(3S,5R)-5-((6-(2-Hydroxy-6-methyl-4-(trifluoromethyl)phenyl)pyridazin-3-yl)amino)-1-methylpiperidin-3-ol

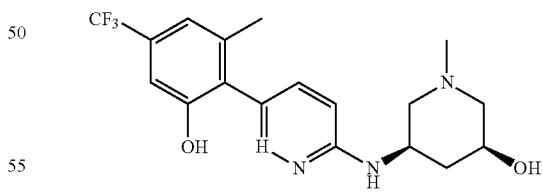

A solution of crude tert-butyl (3S,5R)-3-hydroxy-5-((6-(2-hydroxy-6-methyl-4-(trifluoromethyl)phenyl)pyridazin-3-yl)amino)piperidine-1-carboxylate (660 mg, 1.409 mmol), prepared analogous to Example Ex 002 using intermediate Int P043 and boronic acid Int B005, in 3 mL of CH₂Cl₂ was treated with 4 M HCl in 1,4-dioxane (4.23 mL, 16.91 mmol) at RT for 2 h. The reaction mixture was evaporated. The resulting solid was dissolved in a mixture of 2 mL of DMSO and 2 mL of CH₂Cl₂ and treated with paraformaldehyde (76 mg, 2.52 mmol). After 1 h, NaBH(OAc) (534 mg, 2.52 mmol) was added and stirring at RT continued for 18 h. The reaction mixture was evaporated and the crude purified by column chromatography on silica gel using CH$_2$Cl$_2$ and MeOH containing 5% of ammonia (from 0% to 30%) to provide the title compound as an off-white solid. $^1$H NMR (600 MHz, DMSO-d$_6$) δ (ppm) 10.17 (s, 2H), 7.26 (d, 1H), 7.11 (s. 1H), 7.06 (s. 1H), 6.96-6.89 (m 1H), 6.86 (d, 1H), 4.20-4.09 (m 1H), 3.76-3.65 (m, 1H), 3.41-3.29 (m, 1H), 3.37 (s, 3H), 3.26-3.15 (m, 1H), 3.07-2.94 (m, 1H), 2.46-2.32 (s, 3H). LC-MS: Rt=0.61 min; MS m/z 383.2 [M+H]$^+$.

Example Ex 098

2-(6-(((1-Hydroxycyclopentyl)methyl)amino)pyridazin-3-yl)-3-methyl-5-(trifluoromethyl)phenol

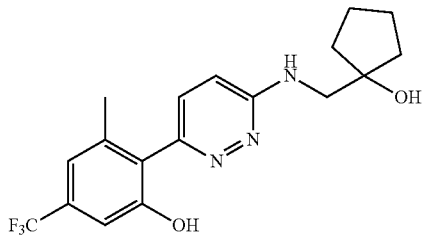 [SMILES: Cc1cc(C(F)(F)F)cc(O)c1-c1ccc(NCC2(O)CCCC2)nn1]

(1) 2-(6-Chloropyridazin-3-yl)-3-methyl-5-(trifluoromethyl)phenol, Int X109

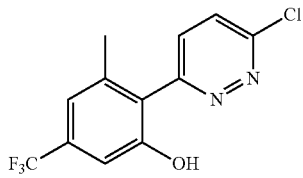 [SMILES: Cc1cc(C(F)(F)F)cc(O)c1-c1ccc(Cl)nn1]

A mixture of Int B010 (150 mg, 0.497 mmol), 3,6-dichloropyridazine (89 mg, 0.596 mmol), Pd(Ph$_3$P)$_4$ (28.7 mg, 0.025 mmol) and 2 M Na$_2$CO$_3$ (0.75 mL, 1.5 mmol) in 3.9 mL of 1,4-dioxane was purged with nitrogen. The vial was sealed and heated at 120° C. under microwave irradiation for 1 h. The reaction mixture was diluted with brine and extracted 3-times with AcOEt. The combined organic layers were dried over Na$_2$SO$_4$, filtered and evaporated. The crude was purified by column chromatography on silica gel (25 g) using cyclohexane and EtOAc (from 0% to 50%) to provide the title compound. $^1$H NMR (600 MHz, DMSO-d$_6$) δ (ppm) 10.43 (s, 1H), 8.02 (d, 1H), 7.85 (d, 1H), 7.19 (s, 1H), 7.10 (s, 1H), 2.11 (s, 3H). LC-MS: Rt=0.95 min; MS m/z 289.1 [M+H]$^+$ (2) 2-(6-(((1-Hydroxycyclopentyl)methyl)amino)pyridazin-3-yl)-3-methyl-5-(trifluoromethyl)phenol A mixture of Int X109 (95 mg, 0.214 mmol), 1-(aminomethyl)cyclopentanol (73.9 mg, 0.642 mmol) and DIPEA (0.112 mL, 0.642 mmol) in 5 mL of NMP was heated at 150° C. for 18 h. The reaction mixture was evaporated and purified by SFC (Column: Reprospher PEI 100A, 250×30 mm, 5 μm, 40° C., Eluent B: 25-35% MeOH in 10 min, Flow: 100 mL/min, Pressure: 120 bar) to provide the title compound. $^1$H NMR (400 MHz, DMSO-d$_6$) δ (ppm) 8.37 (s, 1H), 7.22 (d, 1H), 7.09 (s, 1H), 7.05 (s, 1H), 7.01 (d, 1H), 6.81-6.71 (m, 1H), 4.66 (s, 1H), 3.49 (d, 2H), 2.13 (s, 3H), 1.79-1.54 (m 8H). LC-MS: Rt=0.84 min: MS m/z 368.2 [M+H]$^+$ Example Ex 099

5-((6-(2-Hydroxy-6-methyl-4-(trifluoromethyl)phenyl)-4-methylpyridazin-3-yl)amino)-1-methylpiperidin-2-one

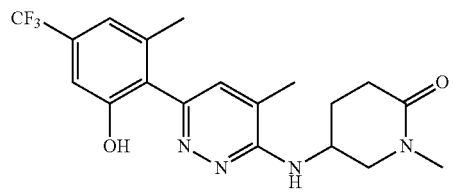 [SMILES: Cc1cc(-c2c(C)cc(C(F)(F)F)cc2O)nnc1NC1CCC(=O)N(C)C1]

(1) 2-(6-Chloro-5-methylpyridazin-3-yl)-3-methyl-5-(trifluoromethyl)phenol, Int X110

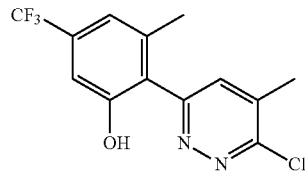 [SMILES: Cc1cc(-c2c(C)cc(C(F)(F)F)cc2O)nnc1Cl]

A mixture of 3,6-dichloro-4-methylpyridazine (1.60 g, 9.52 mmol), (2-hydroxy-6-methyl-4-(trifluoromethyl)phenyl)boronic acid (2.09 g, 9.52 mmol) and 2 M Na$_2$CO$_3$ (14.28 mL, 28.6 mmol) in 95 mL of 1,4-dioxane was purged with argon for 5 min. Then, Pd(PPh$_3$)$_4$ (0.66 g, 0.57 mmol) was added and the mixture was stirred under an argon atmosphere at 120° C. for 1 h. The reaction mixture was quenched with water and brine (50 mL each) and extracted with EtOAc (2×150 mL). The combined organic extracts were dried over Na$_2$SO$_4$, filtered and evaporated. The crude product was triturated with 5 mL of CH$_2$Cl$_2$ overnight. The resulting solid was collected by filtration, washed with little CH$_2$Cl$_2$ and dried to provide the title compound as a white solid. $^1$H NMR (400 MHz, DMSO-d$_6$) δ 10.36 (s, 1H), 7.80 (d, 1H), 7.17 (s, 1H), 7.11 (s, 1H), 2.45 (s, 3H), 2.09 (s, 3H). LC-MS: Rt=1.07 min, MS m/z 303.0 [M+H]$^+$ (2) 5-((6-(2-Hydroxy-6-methyl-4-(trifluoromethyl)phenyl)-4-methylpyridazin-3-yl)amino)-1-methylpiperidin-2-one To a suspension of Int X110 (100 mg, 0.330 mmol) and 5-amino-1-methylpiperidin-2-one (63.5 mg, 0.496 mmol) in 2 mL of toluene was added LiOtBu (167 mg, 1.982 mmol) and PdCl2 (dppf) (12.09 mg, 0.017 mmol). The vial was closed and heated at 105° C. overnight. After cooling to RT, the reaction mixture was poured into water (30 mL) and extracted with EtOAc (3×50 mL). The combined organic extracts were dried over Na$_2$SO$_4$, filtered and evaporated. The crude was purified by column chromatography on silica gel (25 g) using first n-heptane and EtOAc (from 0% to 100%), then CH₂Cl₂ and MeOH (from 0% to 30%) to afford the title compound as a brown solid. ¹H NMR (400 MHz, DMSO-d₆) δ 10.14 (s, 1H), 7.18-7.15 (m, 1H), 7.10 (s, 1H), 7.06 (s, 1H), 6.16 (d, 1H), 4.68-4.51 (m, 1H), 3.63 (dd, 1H), 3.31-3.25 (m, 1H), 2.83 (s, 3H), 2.42-2.35 (m, 2H), 2.16 (s, 3H), 2.11 (s, 3H), 2.09-1.94 (m, 2H). LC-MS: Rt=0.93 min, MS m/z 395.3 [M+H]⁺

Example Ex 100

(R)-3-Methyl-2-(5-methyl-6-(piperidin-3-ylamino)pyridazin-3-yl)-5-(trifluoromethyl)phenol

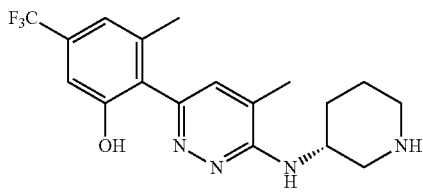

The compound was synthesized analogous to the procedure described for Example Ex 099 using tert-butyl (R)-3-aminopiperidine-1-carboxylate in step (2), followed by TFA-mediated Boc-cleavage and extraction with NaHCO₃ to provide the title compound as off-white solid. ¹H NMR (400 MHz, DMSO-d₆) δ (ppm) 7.10 (s, 1H), 7.05 (s, 1H), 7.02 (s, 1H), 5.75 (d, 1H), 4.16-4.09 (m, 1H), 3.12 (d, 1H), 2.81 (d, 1H), 2.12 (s, 6H), 1.99-1.91 (m, 1H), 1.70-1.43 (m, 3H), 1.27-1.20 (m, 2H). LC-MS: Rt=0.86 min; MS m/z 367.1 [M+H]⁺.

Example Ex 101

(R)-2-(6-((1-Ethylpiperidin-3-yl)amino)-5-methylpyridazin-3-yl)-3-methyl-5-(trifluoromethyl)-phenol

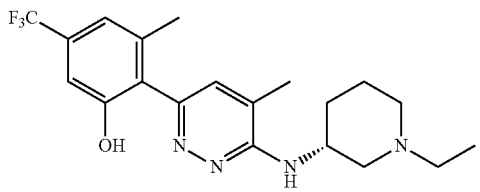 [SMILES: CCN1CCC[C@@H](Nc2nnc(-c3c(C)cc(C(F)(F)F)cc3O)cc2C)C1]

The compound was synthesized analogous to the procedure described for Example Ex 099 using (R)-1-ethylpiperidin-3-amine in step (2), to provide the title compound as off-white solid. ¹H NMR (400 MHz, MeOH-d₄) δ (ppm) 7.26 (s, 1H), 7.09 (s, 1H), 7.02 (s, 1H), 4.56 (s br, 1H), 3.67 (s, 1H), 3.10-3.00 (m, 2H), 2.88-2.66 (m, 2H), 2.26 (s, 3H), 2.17 (s, 3H), 2.12-2.05 (m, 2H), 1.96-1.73 (m, 3H), 1.31 (t, 3H). LC-MS: Rt=0.87 min; MS m/z 395.2 [M+H]⁺

Example Ex 102

(R)-3-((6-(2-Hydroxy-6-methyl-4-(trifluoromethyl)phenyl)-4-methylpyridazin-3-yl)amino)-1-methylpiperidin-2-one

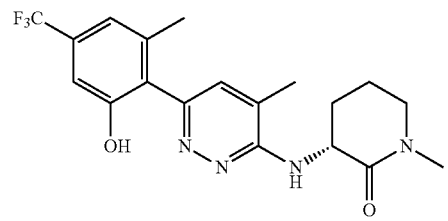 [SMILES: Cc1cc(-c2c(C)cc(C(F)(F)F)cc2O)nnc1N[C@@H]1CCCN(C)C1=O]

The compound was synthesized analogous to the procedure described for Example Ex 099 using (R)-3-amino-1-methylpiperidin-2-one hydrochloride in step (2), to provide the title compound as off-white solid. ¹H NMR (400 MHz, DMSO-d₆) δ (ppm) 7.15 (s, 1H), 6.92 (s, 1H), 6.85 (s, 1H), 6.25 (d, 1H), 4.73-4.66 (m, 1H), 3.37-3.34 (m, 2H), 2.88 (s, 3H), 2.37-2.30 (m, 1H), 2.10 (s, 3H), 2.08 (s, 3H), 1.96-1.90 (m, 2H), 1.88-1.78 (m, 1H). LC-MS: Rt=0.87 min; MS m/z 395.2 [M+H]⁺

Example Ex 103

4-(2-((6-(2-Hydroxy-4,6-dimethylphenyl)pyridazin-3-yl)amino)ethyl)benzenesulfonamide

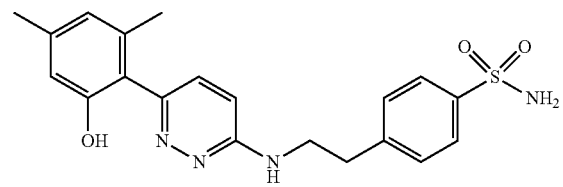 [SMILES: Cc1cc(C)c(-c2ccc(NCCc3ccc(S(N)(=O)=O)cc3)nn2)c(O)c1]

(1) 4-(2-((6-(2-Methoxy-4,6-dimethylphenyl)pyridazin-3-yl)amino)ethyl), Int X111

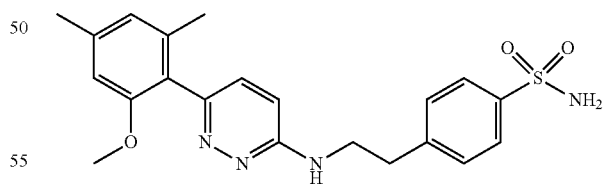

Int P101 (400 mg, 1.279 mmol), Int B017 (493 mg, 1.918 mmol) and Pd(Ph₃P)₄ (148 mg, 0.128 mmol) were dissolved in 10 mL of DME. 2 M Na₂CO₃ (1.92 mL, 3.84 mmol) was added and the reaction mixture was stirred at 90° C. for 22 h. The reaction mixture was poured into water and extracted 3-times with EtOAc. The combined organic extracts were washed with brine and evaporated to dryness. The crude was purified by column chromatography on silica gel (12 g) using CH₂Cl₂ and MeOH (from 0% to 10%). The product containing fractions were evaporated to dryness and triturated with MeOH to provide the title compound as an off-white solid. LC-MS: Rt=0.80 min; MS m/z 413.2 [M+H]+

(2) 4-(2-((6-(2-Hydroxy-4,6-dimethylphenyl) pyridazin-3-yl)amino)ethyl) benzenesulfonamide Int X111 (65 mg, 0.137 mmol) was suspended in 5 mL of CH$_2$Cl$_2$, then BBr$_3$ (1 M in CH$_2$Cl$_2$, 0.206 mL, 0.206 mmol) was added. The resulting orange suspension was stirred at RT for 3 h. The reaction mixture was evaporated to dryness and the residue was purified by achiral RP chromatography. Fractions containing the pure product were combined and taken to pH 8-9 using saturated NaHCO$_3$ solution then extracted twice with CH$_2$Cl$_2$. The combined organic extracts were evaporated to afford the title compound as a beige solid. $^1$H NMR (400 MHz, DMSO-d$_6$) δ (ppm) 9.46 (s, 1H), 7.78 (d, 2H), 7.49 (d, 2H), 7.31 (s, 2H), 7.20 (d, 1H), 6.96-6.91 (m, 1H), 6.84 (d, 1H), 6.60-6.55 (m, 2H), 3.74-3.57 (m, 2H), 3.07-2.94 (m, 2H), 2.22 (s, 3H), 2.05 (s, 3H). LC-MS: Rt=0.71 min: MS m/z 399.2 [M+H]1

Example Ex 104

(3R)-3-((6-(2-Hydroxy-6-methyl-4-(trifluoromethyl) phenyl)-4-methylpyridazin-3-yl)amino)-1-methylpiperidine 1-oxide TFA-salt

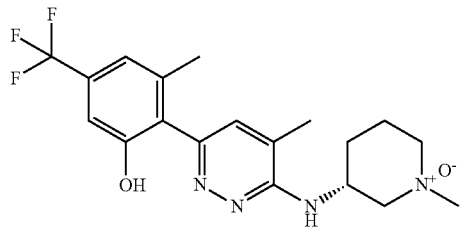

A solution of Example Ex 005 (27 mg, 0.071 mmol) in 1 mL of CH$_2$Cl$_2$ was treated with mCPBA (13.6 mg, 0.079 mmol) and stirred at RT for 90 min. The reaction mixture was quenched with saturated NaHCO$_3$ solution and extracted with CH$_2$Cl$_2$. The crude was purified by achiral RP chromatography to provide the title compound as white solid. $^1$H NMR (400 MHz, DMSO-d$_6$) δ (ppm) 12.63 (s, 1H), 10.27 (s, 1H), 7.36 (s, 1H), 7.14 (s, 1H), 7.08 (s, 1H), 4.84-4.69 (m, 1H), 4.08-3.92 (m, 1H), 3.88-3.80 (m, 1H), 3.63-3.52 (m, 5H), 2.20 (s, 3H), 2.26-2.10 (m, 1H), 2.13 (s, 3H), 2.08-1.96 (m, 2H), 1.85-1.70 (m, 1H). LC-MS: Rt=0.86 min; MS m/z 397.2 [M+H]+

Biological Assays and Data

The activity of a compound according to the present invention can be assessed by the following in vitro methods. A compound of formula (I), or a pharmaceutically acceptable salt thereof, exhibits valuable pharmacological properties, e.g. properties susceptible to inhibit NLRP3 activity, e.g. as indicated in tests as provided in the next sections, and are therefore indicated for therapy related to NLRP3 inflammasome activity.

IL-1 Secretion Assay:

Monocytic THP-1 cells (ATCC: TIB-202) were maintained according to providers' instructions in RPMI media (RPMI/Hepes+10% fetal bovine serum+Sodium Pyruvate+ 0.05 mM Beta-mercaptoethanol (1000× stock)+Pen-Strep). Cells were differentiated in bulk with 0.5 µM phorbol 12-myristate 13-acetate (PMA; Sigma #P8139) for 3 hours, media was exchanged, and cells were plated at 50,000 cells per well in a 384-well flat-bottom cell culture plates (Greiner, #781986), and allowed to differentiate overnight. Compound in a 1:3.16 serial dilution series in DMSO was added 1:100 to the cells and incubated for 1 hour. The NLRP3 inflammasome was activated with the addition of 15 µM (final concentration) Nigericin (Enzo Life Sciences, #BML-CA421-0005), and cells were incubated for 3 hours. 10 µL supernatant was removed, and IL-1p levels were monitored using an HTRF assay (CisBio, #621L1PEC) according to manufacturers' instructions. Viability and pyroptosis was monitored with the addition of PrestoBlue cell viability reagent (Life Technologies, #A13261) directly to the cell culture plate.

TNF-α Secretion Assay:

Monocytic THP-1 cells were maintained according to providers' instructions in RPMI media as described above. Undifferentiated cells were plated at 50,000 cells per well in a 384-well flat-bottom cell culture plates (Greiner, #781986), and allowed to rest overnight. Experimental compounds were prepared and added as described above. TNF-α secretion was triggered by the addition of either 1 µg/mL LPS (Sigma, #L4391) or 100 ng/mL Pam3CSK4 (Invivogen, #tlrl-pms) depending on the experiment, and cells were incubated for 3 hours. 10 µL supernatant was removed, and TNF-α levels were monitored using an HTRF assay (CisBio, #62TNFPEC) according to manufacturers' instructions. Viability was monitored as described above.

Data Interpretation:

IC$_{50}$ values were calculated from the plot of percentage of inhibition versus the inhibitor concentration by a logistics fit according to:

$$y=A2+(A1-A2)/(1+(x/IC_{50})^p)$$

where y is the %-inhibition at the inhibitor concentration, x. A1 is the lowest inhibition value, i.e. 0%, and A2 the maximum inhibition value, i.e. 100%. The exponent, p, is the Hill coefficient. The curve fitting was conducted with an internally developed software suite.

NLRP3-dependent IL-1β secretion was stimulated in PMA-differentiated THP-1 cells by the addition of nigericin, and cytokines were measured in the serum after 3 hours. As discussed above, activation of the NLRP3 inflammasome requires both an NF-kB-dependent priming step and the addition of a NLRP3 activator. To ensure that the inhibitors did not interfere with the priming step, Pam3CSK4-stimulated, NF-kB-dependent TNF-α secretion was monitored as a counter screen. Data for the inhibitory effect (IC$_{50}$) of the compounds of the invention for both assays are given in the table below.

| Ex. No. | IL-1β IC$_{50}$ [µM] | TNF-α IC$_{50}$ [µM] |
| --- | --- | --- |
| 1 | 0.0008 | >100 |
| 2 | 0.0102 | >100 |
| 3 | 0.0255 | >100 |
| 4 | 0.0004 | >100 |
| 5 | 0.0030 | >33 |
| 6 | 0.0009 | >100 |
| 7 | 0.0019 | >100 |
| 8 | 0.0241 | >100 |
| 9 | 0.0931 | >100 |
| 10 | 0.3490 | >33 |
| 11 | 0.0013 | >100 |
| 12 | 0.0006 | >100 |
| 13 | 0.0012 | >100 |

| Ex. No. | IL-1β IC$_{50}$ [μM] | TNF-α IC$_{50}$ [μM] |
|---|---|---|
| 14 | 0.0857 | >100 |
| 15 | 0.0859 | >100 |
| 16 | 0.0363 | >100 |
| 17 | 0.0331 | >33 |
| 18 | 0.1652 | >100 |
| 19 | 0.0936 | >100 |
| 20 | 0.0823 | >100 |
| 21 | 0.0484 | >100 |
| 22 | 0.0807 | >100 |
| 23 | 0.0934 | >100 |
| 24 | 0.1199 | 37 |
| 25 | 0.1769 | 35 |
| 26 | 0.1653 | >100 |
| 27 | 0.1809 | >100 |
| 28 | 0.2884 | >100 |
| 29 | 0.1689 | >100 |
| 30 | 0.2144 | >100 |
| 31 | 0.1667 | >100 |
| 32 | 0.2184 | 85 |
| 33 | 0.0565 | >100 |
| 34 | 0.4956 | >100 |
| 35 | 0.2428 | >100 |
| 36 | 0.3783 | >100 |
| 37 | 0.3807 | >100 |
| 38 | — | — |
| 39 | 0.0032 | >100 |
| 40 | 0.0068 | >33 |
| 41 | 0.0030 | |
| 42 | 0.0253 | >100 |
| 43 | 0.2814 | 25 |
| 44 | 0.4216 | >100 |
| 45 | 0.0032 | >100 |
| 46 | 0.0936 | >100 |
| 47 | 0.0008 | >100 |
| 48 | 0.0008 | >100 |
| 49 | 0.0016 | >100 |
| 50 | 0.0023 | >100 |
| 51 | 0.0026 | >100 |
| 52 | 0.1856 | >100 |
| 53 | 0.0004 | >33 |
| 54 | 0.0118 | 35 |
| 55 | 0.0458 | 45 |
| 56 | 0.0083 | >100 |
| 57 | 0.2235 | 84 |
| 58 | 0.0584 | >100 |
| 59 | 0.0359 | >100 |
| 60 | 0.1395 | >100 |
| 61 | 0.0658 | >100 |
| 62 | 0.1620 | >100 |
| 63 | 0.0227 | 32 |
| 64 | 0.0059 | >100 |
| 65 | 0.0074 | >33 |
| 66 | 0.1871 | >33 |
| 67 | 0.0401 | 46 |
| 68 | 0.0893 | >100 |
| 69 | 0.4308 | >33 |
| 70 | 0.0035 | >100 |
| 71 | 0.0008 | >100 |
| 72 | 0.0449 | >100 |
| 73 | 0.1538 | 55 |
| 74 | 0.0026 | >100 |
| 75 | 0.0183 | >100 |
| 76 | 0.0897 | >100 |
| 77 | 0.0619 | >100 |
| 78 | 0.1977 | >100 |
| 79 | 0.3704 | >100 |
| 80 | 0.0047 | >33 |
| 81 | 0.1299 | >100 |
| 82 | 0.0007 | >100 |
| 83a | 0.0008 | >100 |
| 83b | 0.0694 | >100 |
| 84a | 0.0425 | >100 |
| 84b | 0.0533 | >33 |
| 85a | 0.1476 | >100 |
| 85b | 0.0013 | >100 |
| 86a | 0.1746 | >100 |
| 86b | 0.0018 | >100 |
| 87a | 0.0063 | >100 |
| 87b | 0.5069 | 77 |
| 88a | 0.0623 | 41 |
| 88b | 0.0605 | >100 |
| 89a | 0.0597 | >100 |
| 89b | 0.1816 | >100 |
| 90a | 0.0642 | >33 |
| 90b | 0.1150 | >100 |
| 91a | 2.2236 | >100 |
| 91b | 0.1811 | >100 |
| 92a | 0.0033 | >100 |
| 92b | 0.0036 | 45 |
| 93a | 0.0066 | |
| 93b | 0.440 | |
| 94a | 0.0016 | |
| 94b | 0.730 | |
| 95a | 0.013 | |
| 95b | 0.92 | |
| 96a | 0.470 | |
| 96b | 0.026 | |
| 97 | 0.0076 | >100 |
| 98 | 0.1150 | >100 |
| 99 | 0.0750 | >100 |
| 100 | 0.0060 | >100 |
| 101 | 0.0019 | >100 |
| 102 | 0.049 | |
| 103 | 0.1359 | 16 |
| 104 | 0.0590 | >100 |

The invention claimed is:

1. A compound or pharmaceutically acceptable salt thereof, selected from the group consisting of:

2-(6-((1-Ethylpiperidin-3-yl)amino)pyridazin-3-yl)-3-methyl-5-(trifluoromethyl)phenol;

(S)-2-(6-((1-Ethylpiperidin-3-yl)amino)pyridazin-3-yl)-3-methyl-5-(trifluoromethyl)phenol;

(R)-2-(6-((1-Ethylpiperidin-3-yl)amino)pyridazin-3-yl)-3-methyl-5-(trifluoromethyl)phenol;

2-(6-((3-Hydroxycyclohexyl)amino)pyridazin-3-yl)-3-methyl-5-(trifluoromethyl)phenol;

2-(6-(((1S,3S)-3-Hydroxycyclohexyl)amino)pyridazin-3-yl)-3-methyl-5-(trifluoromethyl)phenol;

2-(6-(((1S,3R)-3-Hydroxycyclohexyl)amino)pyridazin-3-yl)-3-methyl-5-(trifluoromethyl)phenol;

2-(6-(((1 R,3R)-3-Hydroxycyclohexyl)amino)pyridazin-3-yl)-3-methyl-5-(trifluoromethyl)phenol;

2-(6-(((1 R,3S)-3-Hydroxycyclohexyl)amino)pyridazin-3-yl)-3-methyl-5-(trifluoromethyl)phenol;

3-Methyl-2-(5-methyl-6((1-methylpiperidin-3-yl)amino)pyridazin-3-yl)-5-(trifluoromethyl) phenol;

(S)-3-Methyl-2-(5-methyl-6((1-methylpiperidin-3-yl)amino)pyridazin-3-yl)-5-(trifluoromethyl) phenol;

(R)-3-Methyl-2-(5-methyl-6((1-methylpiperidin-3-yl)amino)pyridazin-3-yl)-5-(trifluoromethyl) phenol;

2-(6-((1-(2-Hydroxyethyl)piperidin-3-yl)amino)pyridazin-3-yl)-3-methyl-5-(trifluoromethyl) phenol;

(R)-2-(6-((1-(2-Hydroxyethyl)piperidin-3-yl)amino)pyridazin-3-yl)-3-methyl-5-(trifluoromethyl) phenol (S)-2-(6-((1-(2-Hydroxyethyl)piperidin-3-yl)amino)pyridazin-3-yl)-3-methyl-5-(trifluoromethyl)phenol;

2-(6-((1-(2-Hydroxyethyl)piperidin-3-yl)amino)pyridazin-3-yl)-3-methyl-5-(trifluoromethyl)phenol;

(S)-2-(6-((1-(2-Hydroxyethyl)piperidin-3-yl)amino)pyridazin-3-yl)-3-methyl-5-(trifluoromethyl)phenol;

(R)-2-(6-((1-(2-Hydroxyethyl)piperidin-3-yl)amino)pyridazin-3-yl)-3-methyl-5-(trifluoromethyl) phenol;

2-(6(1-isopropylpiperidin-3-yl)amino)pyridazin-3-yl)-3-methyl-5-(trifluoromethyl)phenol;

3-((1-Ethylpiperidin-3-yl)amino)-6-(2-hydroxy-6-methyl-4-(trifluoromethyl)phenyl) pyridazine-4-carbonitrile;

(S)-3-((1-Ethylpiperidin-3-yl)amino)-6-(2-hydroxy-6-methyl-4-(trifluoromethyl)phenyl) pyridazine-4-carbonitrile;

(R)-3-((1-Ethylpiperidin-3-yl)amino)-6-(2-hydroxy-6-methyl-4-(trifluoromethyl)phenyl) pyridazine-4-carbonitrile;

2-(6-((3-Hydroxy-3-methylcyclobutyl)amino)pyridazin-3-yl)-3-methyl-5-(trifluoromethyl)phenol;

2-(6-(((trans)-3-Hydroxy-3-methylcyclobutyl)amino) pyridazin-3-yl)-3-methyl-5-(trifluoromethyl)phenol;

2-(6-(((cis)-3-Hydroxy-3-methylcyclobutyl)amino) pyridazin-3-yl)-3-methyl-5-(trifluoromethyl)phenol;

2-(6-((3-Hydroxycyclohexyl)amino)pyridazin-3-yl)-3-methyl-5-(trifluoromethyl)phenol;

2-(6-(((1S,3S)-3-Hydroxycyclohexyl)amino)pyridazin-3-yl)-3-methyl-5-(trifluoromethyl)phenol;

2-(6-(((1S,3R)-3-Hydroxycyclohexyl)amino)pyridazin-3-yl)-3-methyl-5-(trifluoromethyl)phenol;

2-(6-(((1R,3R)-3-Hydroxycyclohexyl)amino)pyridazin-3-yl)-3-methyl-5-(trifluoromethyl)phenol;

2-(6-(((1R,3S)-3-Hydroxycyclohexyl)amino)pyridazin-3-yl)-3-methyl-5-(trifluoromethyl)phenol; 2-(6-(((1-Ethylpyrrolidin-2-yl)methyl)amino)pyridazin-3-yl)-3-methyl-5-(trifluoromethyl) phenol;

(R)-2-(6-(((1-Ethylpyrrolidin-2-yl)methyl)amino) pyridazin-3-yl)-3-methyl-5-(trifluoromethyl) phenol;

(S)-2-(6-(((1-Ethylpyrrolidin-2-yl)methyl)amino) pyridazin-3-yl)-3-methyl-5-(trifluoromethyl) phenol;

3-Methyl-2-(6-((1-methylpiperidin-3-yl)amino)-5-(trifluoromethyl)pyridazin-3-yl)-5-(trifluoromethyl)phenol;

(R)-3-Methyl-2-(6-((1-methylpiperidin-3-yl)amino)-5-(trifluoromethyl)pyridazin-3-yl)-5-(trifluoromethyl) phenol; and (S)-3-Methyl-2-(6-((1-methylpiperidin-3-yl)amino)-5-(trifluoromethyl)pyridazin-3-yl)-5-(trifluoromethyl) phenol.

2. The compound or pharmaceutically acceptable salt thereof according to claim 1, selected from the group consisting of:

2-(6-((1-Ethylpiperidin-3-yl)amino)pyridazin-3-yl)-3-methyl-5-(trifluoromethyl)phenol;

(S)-2-(6-((1-Ethylpiperidin-3-yl)amino)pyridazin-3-yl)-3-methyl-5-(trifluoromethyl)phenol;

(R)-2-(6-((1-Ethylpiperidin-3-yl)amino)pyridazin-3-yl)-3-methyl-5-(trifluoromethyl)phenol;

2-(6-((3-Hydroxycyclohexyl)amino)pyridazin-3-yl)-3-methyl-5-(trifluoromethyl)phenol;

2-(6-(((1S,3S)-3-Hydroxycyclohexyl)amino)pyridazin-3-yl)-3-methyl-5-(trifluoromethyl)phenol;

2-(6-(((1S,3R)-3-Hydroxycyclohexyl)amino)pyridazin-3-yl)-3-methyl-5-(trifluoromethyl)phenol;

2-(6-(((1R,3R)-3-Hydroxycyclohexyl)amino)pyridazin-3-yl)-3-methyl-5-(trifluoromethyl)phenol;

2-(6-(((1R,3S)-3-Hydroxycyclohexyl)amino)pyridazin-3-yl)-3-methyl-5-(trifluoromethyl)phenol;

3-Methyl-2-(5-methyl-6-((1-methylpiperidin-3-yl)amino) pyridazin-3-yl)-5-(trifluoromethyl) phenol;

(S)-3-Methyl-2-(5-methyl-6((1-methylpiperidin-3-yl-) amino)pyridazin-3-yl)-5-(trifluoromethyl) phenol;

(R)-3-Methyl-2-(5-methyl-6((1-methylpiperidin-3-yl) amino)pyridazin-3-yl)-5-(trifluoromethyl) phenol;

2-(6-((1-(2-Hydroxyethyl)piperidin-3-yl)amino) pyridazin-3-yl)-3-methyl-5-(trifluoromethyl) phenol;

(R)-2-(6-((1-(2-Hydroxyethyl)piperidin-3-yl)amino) pyridazin-3-yl)-3-methyl-5-(trifluoromethyl) phenol;

(S)-2-(6-((1-(2-Hydroxyethyl)piperidin-3-yl)amino) pyridazin-3-yl)-3-methyl-5-(trifluoromethyl) phenol;

2-(6-((1-(2-Hydroxyethyl)piperidin-3-yl)amino) pyridazin-3-yl)-3-methyl-5-(trifluoromethyl) phenol;

(S)-2-(6-((1-(2-Hydroxyethyl)piperidin-3-yl)amino) pyridazin-3-yl)-3-methyl-5-(trifluoromethyl) phenol;

(R)-2-(6-((1-(2-Hydroxyethyl)piperidin-3-yl)amino) pyridazin-3-yl)-3-methyl-5-(trifluoromethyl) phenol;

2-(6((1-isopropylpiperidin-3-yl)amino)pyridazin-3-yl)-3-methyl-5-(trifluoromethyl)phenol;

3-((1-Ethylpiperidin-3-yl)amino)-6-(2-hydroxy-6-methyl-4-(trifluoromethyl)phenyl) pyridazine-4-carbonitrile;

(S)-3-((1-Ethylpiperidin-3-yl)amino)-6-(2-hydroxy-6-methyl-4-(trifluoromethyl)phenyl) pyridazine-4-carbonitrile; and (R)-3-((1-Ethylpiperidin-3-yl)amino)-6-(2-hydroxy-6-methyl-4-(trifluoromethyl)phenyl) pyridazine-4-carbonitrile.

3. The compound or pharmaceutically acceptable salt thereof according to claim 1, selected from the group consisting of:

2-(6-((1-(2-Hydroxyethyl)piperidin-3-yl)amino) pyridazin-3-yl)-3-methyl-5-(trifluoromethyl) phenol;

(R)-2-(6-((1-(2-Hydroxyethyl)piperidin-3-yl)amino) pyridazin-3-yl)-3-methyl-5-(trifluoromethyl) phenol; and (S)-2-(6-((1-(2-Hydroxyethyl)piperidin-3-yl)amino) pyridazin-3-yl)-3-methyl-5-(trifluoromethyl) phenol.

4. The compound or pharmaceutically acceptable salt thereof according to claim 1, selected from the group consisting of:

2-(6-((3-Hydroxy-3-methylcyclobutyl)amino)pyridazin-3-yl)-3-methyl-5-(trifluoromethyl)phenol;

2-(6-(((trans)-3-Hydroxy-3-methylcyclobutyl)amino) pyridazin-3-yl)-3-methyl-5-(trifluoromethyl)phenol; and 2-(6-(((cis)-3-Hydroxy-3-methylcyclobutyl)amino) pyridazin-3-yl)-3-methyl-5-(trifluoromethyl)phenol.

5. The compound or pharmaceutically acceptable salt thereof according to claim 1, selected from the group consisting of:

2-(6-((3-Hydroxycyclohexyl)amino)pyridazin-3-yl)-3-methyl-5-(trifluoromethyl)phenol;

2-(6-(((1S,3S)-3-Hydroxycyclohexyl)amino)pyridazin-3-yl)-3-methyl-5-(trifluoromethyl)phenol;

2-(6-(((1S,3R)-3-Hydroxycyclohexyl)amino)pyridazin-3-yl)-3-methyl-5-(trifluoromethyl)phenol;

2-(6-(((1R,3R)-3-Hydroxycyclohexyl)amino)pyridazin-3-yl)-3-methyl-5-(trifluoromethyl)phenol; and 2-(6-(((1R,3S)-3-Hydroxycyclohexyl)amino)pyridazin-3-yl)-3-methyl-5-(trifluoromethyl)phenol.

6. The compound or pharmaceutically acceptable salt thereof according to claim 1, selected from the group consisting of:

2-(6-(((1-Ethylpyrrolidin-2-yl)methyl)amino)pyridazin-3-yl)-3-methyl-5-(trifluoromethyl) phenol;

(R)-2-(6-(((1-Ethylpyrrolidin-2-yl)methyl)amino) pyridazin-3-yl)-3-methyl-5-(trifluoromethyl) phenol; and (S)-2-(6-(((1-Ethylpyrrolidin-2-yl)methyl)amino) pyridazin-3-yl)-3-methyl-5-(trifluoromethyl) phenol.

7. A pharmaceutical composition comprising a therapeutically effective amount of a compound or a pharmaceutically acceptable salt thereof according to claim 1, and one or more pharmaceutically acceptable carriers.

8. A combination comprising a therapeutically effective amount of a compound or a pharmaceutically acceptable salt thereof according to claim 1, and one or more therapeutic agents.

9. The combination according to claim 8, wherein one or more therapeutic agents are independently selected from the group consisting of farnesoid X receptor (FXR) agonists; anti-steatotics; anti-fibrotics; JAK inhibitors; checkpoint inhibitors; complement inhibitors; Bruton's tyrosine Kinase inhibitors (BTK inhibitors); Toll Like receptor inhibitors anti-hypertensive agents; cholesterol lowering agents; leukotriene A4 hydrolase (LTAH4) inhibitors; SGLT2 inhibitors; β2-agonists; anti-inflammatory agents; and acetylsalicylic acid (ASA).

10. A method of treating a disease or disorder in which the NLRP3 signaling contributes to the pathology, and/or symptoms, and/or progression, of said disease or disorder, comprising administering to a subject in need thereof a therapeutically effective amount of a compound or a pharmaceutically acceptable salt thereof according to claim 1.

11. A method of inhibiting NLRP3 inflammasome activity in a subject in need thereof, the method comprising administering to a subject in need thereof a therapeutically effective amount of a compound or a pharmaceutically acceptable salt thereof according to claim 1.

12. A method of inhibiting NLRP3 inflammasome activity in a subject in need thereof, the method comprising administering to a subject in need thereof a therapeutically effective amount of a compound or a pharmaceutically acceptable salt thereof according to claim 2.

13. A method of inhibiting NLRP3 inflammasome activity in a subject in need thereof, the method comprising administering to a subject in need thereof a therapeutically effective amount of a compound or a pharmaceutically acceptable salt thereof according to claim 3.

14. A method of inhibiting NLRP3 inflammasome activity in a subject in need thereof, the method comprising administering to a subject in need thereof a therapeutically effective amount of a compound or a pharmaceutically acceptable salt thereof according to claim 4.

15. A method of inhibiting NLRP3 inflammasome activity in a subject in need thereof, the method comprising administering to a subject in need thereof a therapeutically effective amount of a compound or a pharmaceutically acceptable salt thereof according to claim 5.

16. A method of treating a disease or disorder in which the NLRP3 signaling contributes to the pathology, and/or symptoms, and/or progression, of said disease or disorder, comprising administering to a subject in need thereof a therapeutically effective amount of a compound or a pharmaceutically acceptable salt thereof according to claim 2.

17. A method of treating a disease or disorder in which the NLRP3 signaling contributes to the pathology, and/or symptoms, and/or progression, of said disease or disorder, comprising administering to a subject in need thereof a therapeutically effective amount of a compound or a pharmaceutically acceptable salt thereof according to claim 3.

18. A method of treating a disease or disorder in which the NLRP3 signaling contributes to the pathology, and/or symptoms, and/or progression, of said disease or disorder, comprising administering to a subject in need thereof a therapeutically effective amount of a compound or a pharmaceutically acceptable salt thereof according to claim 4.

19. A method of treating a disease or disorder in which the NLRP3 signaling contributes to the pathology, and/or symptoms, and/or progression, of said disease or disorder, comprising administering to a subject in need thereof a therapeutically effective amount of a compound or a pharmaceutically acceptable salt thereof according to claim 5.

* * * * *